(12) United States Patent
Ziesche

(10) Patent No.: US 10,526,656 B2
(45) Date of Patent: *Jan. 7, 2020

(54) METHODS OF DIAGNOSING CHRONIC OBSTRUCTIVE PULMONARY DISEASE (COPD) USING NOVEL MOLECULAR BIOMARKERS

(71) Applicant: Transgenion—International Institute for Regenerative Translational Medicine GmbH, Vienna (AT)

(72) Inventor: Rolf Ziesche, Neusiedl am See (AT)

(73) Assignee: Transgenion—International Institute for Regenerative Translational Medicine GmbH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 15/316,202

(22) PCT Filed: Jun. 3, 2015

(86) PCT No.: PCT/EP2015/062426
§ 371 (c)(1),
(2) Date: Dec. 5, 2016

(87) PCT Pub. No.: WO2015/185653
PCT Pub. Date: Dec. 10, 2015

(65) Prior Publication Data
US 2017/0349947 A1    Dec. 7, 2017

(30) Foreign Application Priority Data

Jun. 5, 2014 (EP) .................................... 14171390

(51) Int. Cl.
*C12Q 1/6883* (2018.01)
*A61K 31/44* (2006.01)

(52) U.S. Cl.
CPC ............ *C12Q 1/6883* (2013.01); *A61K 31/44* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2005/0208496 A1 | 9/2005 | Ohtani et al. |
| 2013/0165343 A1 | 6/2013 | Robinson et al. |
| 2013/0324428 A1 | 12/2013 | Ryu et al. |
| 2017/0107574 A1 | 4/2017 | Ziesche |
| 2017/0335393 A1 | 11/2017 | Ziesche |

FOREIGN PATENT DOCUMENTS

| | | |
|---|---|---|
| JP | 2013-35871 | 2/2013 |
| WO | WO 2008/003701 | 1/2008 |
| WO | WO 2010/064702 | 6/2010 |
| WO | WO 2013/104990 | 7/2013 |
| WO | WO 2013/177060 | 11/2013 |
| WO | WO 2013/190092 | 12/2013 |

(Continued)

OTHER PUBLICATIONS

Banyard et al (Genes Chromosomes Cancer. Jun. 2009. 48(6): 502-509 (Year: 2009).*

(Continued)

*Primary Examiner* — Carla J Myers
(74) *Attorney, Agent, or Firm* — Parker Highlander PLLC

(57) ABSTRACT

The present invention relates to in vitro methods for the diagnosis of chronic obstructive pulmonary disease (COPD), wherein the expression of the marker gene TMSB15A is determined. In particular, the invention relates to an in vitro diagnostic method of assessing the susceptibility of a subject to develop progressive COPD involving the appearance of irreversible lung damage, wherein the expression of the marker gene TMSB15A and optionally one or more further marker genes selected from DMBT1, KIAA1 T99, DPP6, SLC51 B, NUDT1 1, ELF5, AZGP1, PRRX1, AQP3, SFN, GPR1 10, GDF15, RASGRF2, RND1, PLA1A, FGG, CEACAM5, HYAL2, AHRR, CXCL3, CYP1A1, CYP1 B1, CYP1A2, CST6, NTRK2, COMP, ITGA10, CTHRC1, TAL1, FIBIN, BEX5, BEX1, ESM1 and GHRL is determined. The invention also relates to an in vitro method of diagnosing stable COPD or assessing the susceptibility of a subject to develop stable COPD, wherein the expression of TMSB15A and optionally one or more further marker genes selected from DMBT1, KIAA1 199, DPP6, SLC51 B, NUDT1 1, ELF5, AZGP1, PRRX1, AQP3, SFN, GPR1 10, GDF15, RASGRF2, RND1, PLA1A, FGG, CEACAM5, HYAL2, AHRR, CXCL3, CYP1A1, CYP1 B1, CYP1A2, CST6, NTRK2, COMP, ITGA10, CTHRC1, TAL1, FIBIN, BEX5, BEX1, ESM1 and GHRL is determined. Furthermore, the invention relates to the use of primers for transcripts of the aforementioned marker genes, the use of nucleic acid probes to transcripts of these marker genes, the use of microarrays comprising nucleic acid probes to transcripts of these marker genes, and the use of antibodies against the proteins expressed from these marker genes in corresponding in vitro methods. In vitro methods of monitoring the progression of COPD are also provided, in which the expression of marker genes according to the invention is determined.

19 Claims, 28 Drawing Sheets

Figure 1:
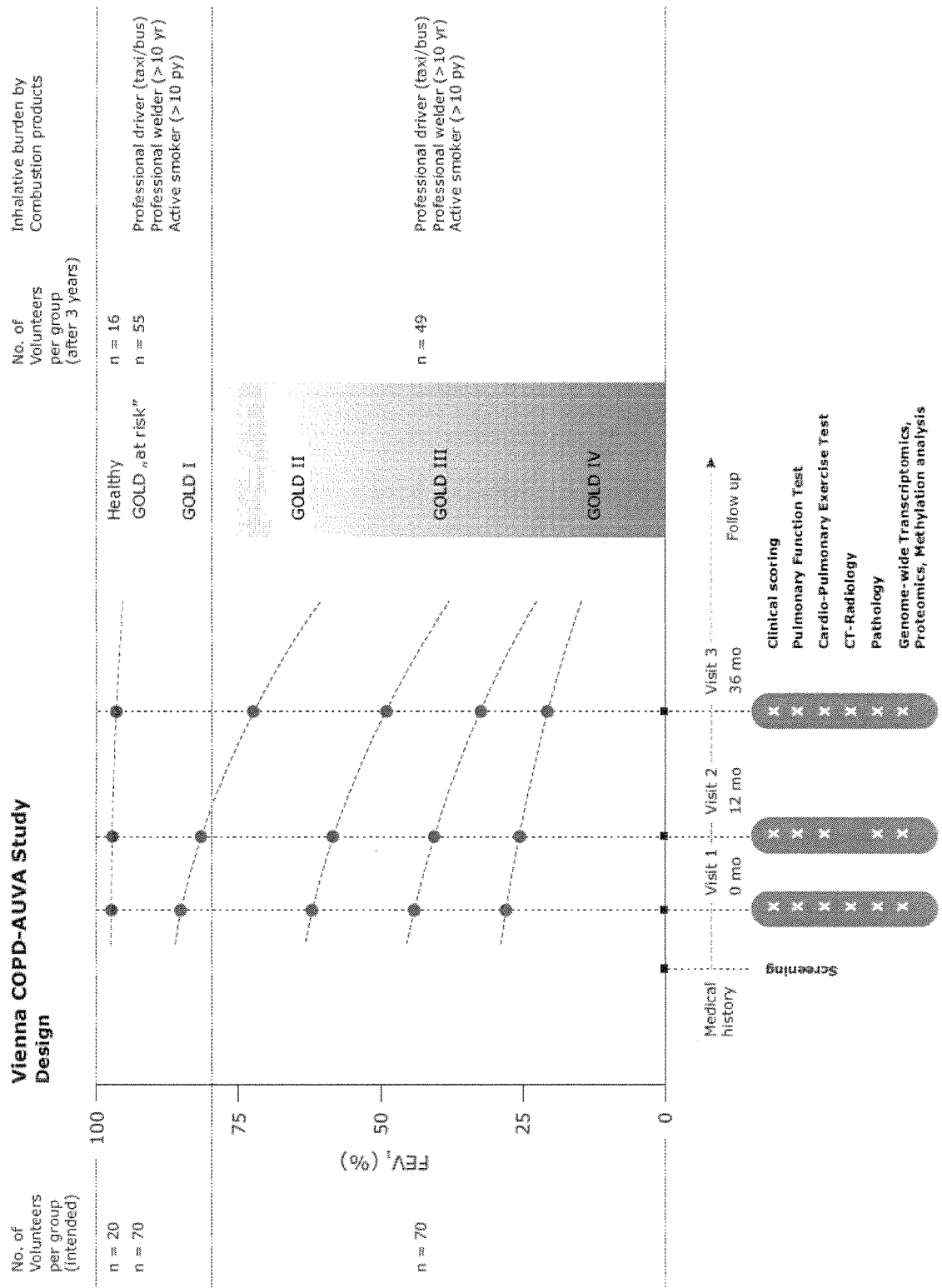

Specification includes a Sequence Listing.

(56) References Cited

FOREIGN PATENT DOCUMENTS

| WO | WO 2015/185656 | 12/2015 |
|---|---|---|
| WO | WO 2015/185658 | 12/2015 |

OTHER PUBLICATIONS

Liu et al Clinical Immunology. 2004. 112: 225-230.*
Coleman, R. (Drug Discovery Today. 2003. 8: 233-235.*
Palmer BMC Genomics. 2006. 7:115.*
Min et al BMC Genomics. 2010. 11:96.*
Haynes et al Electrophoresis. 1998. 19: 1862-1871.*
Chen et al Molecular & Cellular Proteomics. 2002. 1: 304-313.*
Vogel et al Nature Review Genet. Mar. 2012. 13(4): 227-232.*
Bhattacharya et al American J Respir Cell and Molec Biology. 2009. 40: 359-367.*
Bhattacharya et al., "Molecular biomarkers for quantitative and discrete COPD phenotypes," *American Journal of Respiratory and Cell and Molecular Biology*, 40(3):359-367, 2009.
Gosselink et al., "Differential expression of tissue repair genes in the pathogenesis of chronic obstructive pulmonary disease," *American Journal of Respiratory and Critical Care Medicine*, 181(12):1329-1335, 2010.
PCT International Preliminary Report on Patentability issued in International Application No. PCT/EP2015/062426, dated Dec. 15, 2016.
PCT International Search Report and Written Opinion issued in International Application No. PCT/EP2015/062426, dated Dec. 18, 2015.
Savarimuthu Francis et al., "Genes and gene ontologies common to airflow obstruction and emphysema in the lungs of patients with COPD," *PLOS ONE*, 6(3):e17442, 2011.
Steiling et al., "A dynamic bronchial airway gene expression signature of chronic obstructive pulmonary disease and lung function impairment," *American Journal of Respiratory and Critical Care Medicine*, 187(9):933-942, 2013.
Office Action issued in Japanese Application No. 2017-516196, dated Jun. 4, 2019.
Office Action issued in Japanese Application No. 2017-516198, dated Jun. 4, 2019.
Affymetrix Inc. Human Genome U95 Set. GeneChip® Human Genome U95 Set, available via URL: <tools.thermofisher.com/content/sfs/brochures/hgu95_datasheet.pdf>, 2001-2003, printed on Jan. 8, 2019, pp. 1-2.
Affymetrix NetAffx. Expression Probeset Details for Human Genome U95 Sets for the KIA 1199, TMSB15A, and DMBT1 genes, available via URL: <affymetrix.com/analysis/netaffx/xmlquery.affx?netaffx=netaffx4_annot>, printed on Jan. 8, 2019, 14 pages.
Bahr et al., "Peripheral blood mononuclear cell gene expression in chronic obstructive pulmonary disease", *Am. J. Respir. Cell Mol. Biol.*, 49:316-323, 2013.
Baye et al., "Roflumilast (Daliresp) A Novel Phosphodiesterase-4 Inhibitor for the Treatment of Severe Chronic Obstructive Pulmonary Disease", *Pharm. Ther.*, 37(3):149-150, 157-161, 2012.
Calverley et al., "Effect of 1-year treatment with roflumilast in severe chronic obstructive pulmonary disease", *Am. J. Respir. Crit. Care Med.*, 176:154-161, 2007.
Calverley et al., "Roflumilast in symptomatic chronic obstructive pulmonary disease: two randomised clinical trials", *Lancet*, 374:685-694, 2009.
Chan et al., "Integrating transcriptomics and proteomics", *G &P Magazine*, 6(3):20-26, 2006.
Hoshikawa et al., "Hypoxia induces different genes in the lungs of rats when compared with mice", *Phys. Genomics*, 12:209-219, 2003.
Kendrick et al., "A gene's mRNA level does not usually predict its protein level", *Kendrick Labs, Inc.*, Sep. 25, 2014.
Llinas et al., "Similar gene expression profiles in smokers and patients with moderate COPD", *Pulm. Pharmacol. Ther.*, 24:32-41, 2011.
Maier et al., "Correlation of mRNA and protein in complex biological samples", *FEBS Lett.*, 583:3966-3973, 2009.
Pascal et al., "Correlation of mRNA and protein levels: cell type-specific gene expression of cluster designation antigens in the prostate", *BMC Genomics*, 9:246, 2008.
Rabe et al., "Roflumilast—an oral anti-inflammatory treatment of chronic obstructive pulmonary disease: a randomised controlled trial", *Lancet*, 366:563-571, 2005.
Renner et al., "DMBT1 confers mucosal protection in vivo and a deletion variant is associated with Crohn's disease", *Gastroenterol.*, 133:1499-1509, 2007.
Richens et al., "Systems biology coupled with label-free high-throughput detection as a novel approach for diagnosis of chronic obstructive pulmonary disease," *Respiratory Research*, 10(1):29, 2009.
Saito-Hisaminato et al., "Genome-wide profiling of gene expression in 29 normal human tissues with a cDNA microarray", *DNA Res.*, 9:35-45, 2002.
Spira et al., "Gene expression profiling of human lung tissue from smokers with severe emphysema", *Am. J. Respir. Care Mol. Biol.*, 31:601-610, 2004.
Steiling et al., "Personalized Management of Chronic Obstructive Pulmonary Disease via Transcriptomic Profiling of the Airway and Lung", *Ann. Am. Thorac.*, 10(Suppl.):S190-S196, 2013.
van den Berge et al., "Airway gene expression in COPD is dynamic with inhaled corticosteroid treatment and reflects biological pathways associated with disease activity", *Thorax*, 69:14-23, 2014.
Whitehead et al., "Variation in tissue-specific gene expression among natural populations", *Genome Biol.*, 6:R13, 2005.

* cited by examiner

Fig. 3

A)

Healthy participants

| Initials | Gender | ID | Clinical strata / Healthy controls | Age | GOLD V1 | GOLD V2 | GOLD V3 | Bronchitis & Phlegm V1 | Bronchitis & Phlegm V2 | Bronchitis & Phlegm V3 | Pack Years Total | Smoking habits V1 | Smoking habits V2 | Smoking habits V3 |
|---|---|---|---|---|---|---|---|---|---|---|---|---|---|---|
| AC | F | 145 | Healthy | 40.2 | 0 | 0 | 0 | n.a. | n.a. | n.a. | n.a. | -1 | -1 | -1 |
| BR | M | 24 | Healthy | 48.3 | 0 | 0 | 0 | n.a. | n.a. | n.a. | n.a. | -1 | -1 | -1 |
| GI | F | 159 | Healthy | 24.2 | 0 | 0 | 0 | n.a. | n.a. | n.a. | n.a. | -1 | -1 | -1 |
| HD | F | 44 | Healthy | 33.0 | 0 | 0 | 0 | n.a. | n.a. | n.a. | n.a. | -1 | -1 | -1 |
| KH | M | 35 | Healthy | 62.7 | 0 | 0 | 0 | n.a. | n.a. | n.a. | n.a. | -1 | -1 | -1 |
| LH | F | 161 | Healthy | 33.3 | 0 | 0 | 0 | n.a. | n.a. | n.a. | n.a. | -1 | -1 | -1 |
| MA | F | 158 | Healthy | 24.2 | 0 | 0 | 0 | n.a. | n.a. | n.a. | n.a. | -1 | -1 | -1 |
| MO | F | 31 | Healthy | 41.5 | 0 | 0 | 0 | n.a. | n.a. | n.a. | n.a. | -1 | -1 | -1 |
| SE | M | 57 | Healthy | 35.6 | 0 | 0 | 0 | n.a. | n.a. | n.a. | n.a. | -1 | -1 | -1 |
| SH | M | 23 | Healthy | 45.2 | 0 | 0 | 0 | n.a. | n.a. | n.a. | n.a. | -1 | -1 | -1 |
| SS | M | 34 | Healthy | 27.2 | 0 | 0 | 0 | n.a. | n.a. | n.a. | n.a. | -1 | -1 | -1 |
| TK | F | 163 | Healthy | 24.6 | 0 | 0 | 0 | n.a. | n.a. | n.a. | n.a. | -1 | -1 | -1 |
| TT | M | 50 | Healthy | 58.9 | 0 | 0 | 0 | n.a. | n.a. | n.a. | n.a. | -1 | -1 | -1 |
| WH | M | 123 | Healthy | 27.0 | 0 | 0 | 0 | n.a. | n.a. | n.a. | n.a. | -1 | -1 | -1 |
| WW | M | 155 | Healthy | 28.2 | 0 | 0 | 0 | n.a. | n.a. | n.a. | n.a. | -1 | -1 | -1 |
| ZB | M | 128 | Healthy | 28.0 | 0 | 0 | 0 | n.a. | n.a. | n.a. | n.a. | -1 | -1 | -1 |
| | n | 16 | Age (yrs, mean) | 36.4 | | | | | | | | | | |

Fig. 3 (cont.)

B)

COPD „at risk" at Visit 1 (GOLD 0)

| Initials | Gender | ID | Clinical strata COPD "at risk" | Age | GOLD V1 | GOLD V2 | GOLD V3 | Intensity of Bronchitis V1 | Intensity of Bronchitis V2 | Intensity of Bronchitis V3 | Pack Years Total | Smoking habits V1 | Smoking habits V2 | Smoking habits V3 |
|---|---|---|---|---|---|---|---|---|---|---|---|---|---|---|
| AA | M | 1 | Car/Bus driver COPD "0 | 42.0 | 0 | 0 | 0 | 2 | 2 | 2 | 30 | 4 | 4 | 4 |
| BH | M | 140 | Welder COPD "0 | 31.2 | 0 | 0 | 0 | 1 | 2 | 3 | 16 | 5 | 5 | 5 |
| BM | M | 106 | Welder COPD "0 | 40.2 | 0 | 0 | 0 | 3 | 0 | 0 | 10 | 3 | 0 | 0 |
| BR | M | 166 | Welder COPD "0 | 37.7 | 0 | 0 | 0 | 3 | 1 | 1 | 15 | 3 | 3 | 2 |
| DA | M | 84 | Welder COPD "0 | 46.4 | 0 | 2 | 0 | 0 | 0 | 0 | 13 | 2 | 2 | 1 |
| DM | F | 88 | Car/Bus driver COPD "0 | 50.2 | 0 | 1 | 1 | 0 | 0 | 1 | 70 | 3 | 2 | 2 |
| DE | M | 103 | Welder COPD "0 | 33.0 | 0 | 0 | n.d. | 3 | 1 | n.d. | 6 | 1 | 2 | n.d. |
| ER | M | 165 | Welder COPD "0 | 40.7 | 0 | 0 | n.d. | 0 | -1 | n.d. | 30 | 2 | 2 | n.d. |
| EF | M | 25 | Car/Bus driver COPD "0 | 53.0 | 0 | 0 | 0 | 1 | 1 | 0 | 25 | 0 | 0 | 0 |
| ES | M | 39 | Car/Bus driver COPD "0 | 67.7 | 0 | 0 | 0 | 0 | 2 | 2 | 150 | 6 | 5 | 5 |
| FE | F | 131 | Car/Bus driver COPD "0 | 64.7 | 0 | 0 | 0 | 1 | 1 | 0 | 8 | 0 | 0 | 0 |
| GT | M | 134 | Car/Bus driver COPD "0 | 47.5 | 0 | 2 | 1 | 2 | 2 | 0 | 45 | 5 | 4 | 4 |
| HI | M | 20 | Car/Bus driver COPD "0 | 50.4 | 0 | 0 | 0 | 3 | 3 | 3 | 15 | 2 | 2 | 2 |
| HA | F | 72 | Car/Bus driver COPD "0 | 49.2 | 0 | 0 | 0 | 0 | 0 | 0 | 14 | 2 | 2 | 2 |
| HK | M | 97 | Car/Bus driver COPD "0 | 52.1 | 0 | 0 | 0 | 3 | 3 | 2 | 40 | 2 | n.d. | n.d. |
| JW | M | 40 | Car/Bus driver COPD "0 | 68.8 | 0 | 0 | 0 | 1 | 1 | 1 | 20 | 5 | 5 | 5 |
| JS | F | 32 | Car/Bus driver COPD "0 | 46.5 | 0 | 0 | 0 | 0 | 0 | 1 | 10 | 1 | 1 | 1 |
| KR | M | 86 | Car/Bus driver COPD "0 | 49.5 | 0 | 0 | 0 | 0 | 0 | 0 | 30 | 3 | 3 | 3 |
| KE | M | 176 | Welder COPD "0 | 50.7 | 0 | 2 | n.d. | 2 | 2 | n.d. | 55 | 5 | 3 | n.d. |
| KJ | M | 168 | Welder COPD "0 | 32.1 | 0 | 0 | 0 | 2 | 2 | 1 | 10 | 3 | 0 | 1 |
| KG | M | 16 | Car/Bus driver COPD "0 | 43.8 | 0 | 0 | 0 | 0 | 0 | 0 | 20 | 3 | 3 | 3 |
| KEM | F | 101 | Car/Bus driver COPD "0 | 65.2 | 0 | 0 | 0 | 2 | 2 | 3 | 40 | 3 | 4 | 4 |
| KJ | M | 13 | Car/Bus driver COPD "0 | 54.2 | 0 | 0 | 0 | 0 | 0 | -1 | 35 | 5 | 0 | 0 |
| KH | M | 47 | Car/Bus driver COPD "0 | 65.5 | 0 | 0 | 0 | 0 | -1 | -1 | 50 | 3 | 5 | 3 |
| LI | M | 4 | Car/Bus driver COPD "0 | 56.3 | 0 | 1 | n.d. | 0 | 0 | n.d. | 40 | 0 | 0 | n.d. |
| MT | M | 154 | Welder COPD "0 | 37.6 | 0 | 0 | 2 | 2 | 3 | 1 | 20 | 3 | 2 | 2 |
| MW | M | 58 | Car/Bus driver COPD "0 | 58.4 | 0 | 0 | 0 | 1 | 1 | 1 | 30 | 0 | 0 | 0 |
| MP | M | 79 | Welder COPD "0 | 53.2 | 0 | 0 | 0 | 0 | 0 | 1 | 32 | 3 | 4 | 3 |
| MS | M | 10 | Car/Bus driver COPD "0 | 36.3 | 0 | 0 | 0 | 1 | 1 | 0 | 18 | 3 | 3 | 3 |
| OI | M | 167 | Welder COPD "0 | 52.7 | 0 | 0 | n.d. | 1 | 0 | n.d. | 10 | 0 | 0 | n.d. |
| PC | M | 139 | Car/Bus driver COPD "0 | 61.8 | 0 | 2 | n.d. | 1 | 1 | n.d. | 30 | 0 | 0 | n.d. |
| PEM | M | 90 | Welder COPD "0 | 46.1 | 0 | 0 | 0 | 2 | 2 | 3 | 17 | 1 | 1 | 0 |
| PEM | M | 74 | Welder COPD "0 | 47.0 | 0 | 0 | 0 | -1 | -1 | 1 | 0 | -1 | -1 | -1 |
| PRM | M | 5 | Car/Bus driver COPD "0 | 57.2 | 0 | 0 | 0 | 1 | 1 | 1 | 60 | 6 | 6 | 5 |
| RM | M | 115 | Welder COPD "0 | 45.8 | 0 | 2 | 2 | 2 | 2 | 1 | 35 | 0 | 3 | 1 |
| RR | M | 36 | Car/Bus driver COPD "0 | 55.2 | 0 | 0 | 0 | 1 | 1 | 1 | 38 | 0 | 0 | 0 |
| RH | M | 91 | Welder COPD "0 | 61.1 | 0 | 0 | 0 | 1 | 1 | 0 | 85 | 5 | 3 | 3 |
| SB | F | 67 | Car/Bus driver COPD "0 | 49.3 | 0 | 0 | 0 | 0 | 0 | 0 | 15 | 2 | 2 | 2 |
| SW | M | 117 | Car/Bus driver COPD "0 | 52.2 | 0 | 0 | 0 | 0 | 0 | 1 | 40 | 0 | 2 | 2 |
| SIW | M | 118 | Welder COPD "0 | 49.7 | 0 | 0 | 0 | 0 | 0 | 2 | 27 | 3 | 3 | 2 |
| SR | M | 152 | Car/Bus driver COPD "0 | 38.6 | 0 | 0 | 0 | 0 | 0 | -1 | 10 | 0 | 0 | 0 |
| STJ | M | 21 | Car/Bus driver COPD "0 | 60.8 | 0 | 0 | 0 | 1 | 1 | 0 | 50 | 4 | 3 | 0 |
| STB | F | 56 | Car/Bus driver COPD "0 | 61.3 | 0 | 0 | n.d. | 0 | 0 | 0 | 25 | 0 | 0 | 0 |
| STS | M | 83 | Welder COPD "0 | 48.2 | 0 | 0 | 0 | 2 | 2 | 3 | 60 | 5 | 5 | 5 |
| STP | M | 156 | Welder COPD "0 | 47.0 | 0 | 0 | 0 | 0 | 0 | 0 | 15 | 0 | 0 | 0 |
| STA | M | 17 | Car/Bus driver COPD "0 | 45.4 | 0 | 0 | 0 | 0 | 0 | 2 | 20 | 4 | 4 | 4 |
| TJ | M | 19 | Car/Bus driver COPD "0 | 53.9 | 0 | 0 | 0 | 1 | 1 | 1 | 40 | 4 | 4 | 2 |
| TA | F | 46 | Car/Bus driver COPD "0 | 58.1 | 0 | 2 | 2 | 0 | 1 | -1 | 100 | 5 | 4 | 4 |
| WC | M | 172 | Welder COPD "0 | 42.9 | 0 | 0 | 0 | 0 | 2 | 0 | 36 | 4 | 4 | 3 |
| WW | M | 124 | Welder COPD "0 | 44.0 | 0 | 2 | 2 | 1 | 1 | 2 | 30 | 0 | 0 | 0 |
| WS | M | 65 | Welder COPD "0 | 30.5 | 0 | 0 | 1 | 0 | -1 | -1 | 10 | 0 | 0 | 0 |
| WR | M | 160 | Welder COPD "0 | 56.9 | 0 | 2 | 0 | 1 | 1 | 1 | 30 | 0 | 0 | 0 |
| WIR | M | 125 | Welder COPD "0 | 63.4 | 0 | 0 | 0 | 1 | 1 | 2 | 45 | 2 | 3 | 2 |
| ZAE | M | 93 | Welder COPD "0 | 51.7 | 0 | 0 | 0 | 2 | 2 | 2 | 10 | 1 | 1 | 0 |
| ZE | M | 6 | Car/Bus driver COPD "0 | 45.7 | 0 | 0 | 0 | 1 | 1 | 1 | 35 | 4 | 4 | 4 |
| n = 55 | | | Age (yrs, mean) 50.0 | | | | | | | PY (mean) | 32.2 | | | |

Fig. 3 (cont.)

C)

Manifest COPD at Visit 1

| Initials | Gender | ID | Clinical strata COPD (manifest) | Age | GOLD V1 | GOLD V2 | GOLD V3 | Intensity of Bronchitis V1 | Intensity of Bronchitis V2 | Intensity of Bronchitis V3 | Pack Years Total | Smoking habits V1 | Smoking habits V2 | Smoking habits V3 |
|---|---|---|---|---|---|---|---|---|---|---|---|---|---|---|
| CW | M | 45 | Driver COPD I-III | 59.0 | 1 | 0 | 0 | 1 | 0 | 1 | 10 | 0 | 0 | 0 |
| DJ | M | 85 | Driver COPD I-III | 41.6 | 1 | 0 | 0 | 1 | 1 | 1 | 8 | 1 | 2 | 2 |
| GW | M | 102 | Driver COPD I-III | 55.9 | 1 | 0 | 0 | -1 | -1 | -1 | 30 | 0 | 0 | 0 |
| HP | M | 98 | Driver COPD I-III | 70.2 | 1 | 1 | 2 | 1 | 1 | 1 | 20 | 0 | 0 | 0 |
| KA | M | 107 | Welder COPD I-III | 48.8 | 1 | 0 | 1 | 2 | 2 | 1 | 30 | 3 | 3 | 3 |
| KW | M | 55 | Driver COPD I-III | 54.1 | 1 | 0 | 0 | 1 | 1 | 1 | 50 | 2 | 2 | 2 |
| MM | F | 114 | Driver COPD I-III | 57.3 | 1 | 0 | 0 | 1 | 1 | 4 | 35 | 5 | 5 | 5 |
| RH | M | 116 | Driver COPD I-III | 71.6 | 1 | 1 | n.d. | 2 | 2 | n.d. | 45 | 0 | 0 | 0 |
| WH | M | 92 | Welder COPD I-III | 44.2 | 1 | 2 | 1 | 0 | 2 | 1 | 35 | 4 | 3 | 3 |
| DK | M | 87 | Welder COPD I-III | 50.8 | 2 | 2 | 2 | -1 | -1 | -1 | 5 | 1 | 1 | 1 |
| GG | M | 133 | Driver COPD I-III | 52.5 | 2 | 2 | n.d. | 0 | 0 | n.d. | 30 | 0 | 0 | 0 |
| AG | M | 71 | Welder COPD I-III | 56.5 | 2 | 2 | 2 | 1 | 1 | -1 | 20 | 0 | 0 | 0 |
| BD | M | 148 | Driver COPD I-III | 43.2 | 2 | 2 | 1 | 2 | 3 | 3 | 25 | 0 | 0 | 0 |
| CA | M | 37 | Driver COPD I-III | 65.8 | 2 | 3 | 4 | 1 | 1 | -1 | 40 | 5 | 2 | 5 |
| GG | M | 136 | Welder COPD I-III | 51.8 | 2 | 0 | 2 | 1 | 1 | 2 | 30 | 3 | 3 | 3 |
| HAH | M | 96 | Driver COPD I-III | 46.2 | 2 | 2 | 1 | 1 | 0 | 0 | 40 | 4 | 4 | 4 |
| HE | M | 99 | Driver COPD I-III | 48.9 | 2 | 3 | 2 | 1 | 1 | 2 | 25 | 0 | 0 | 0 |
| HF | M | 147 | Driver COPD I-III | 63.3 | 2 | 2 | 2 | 1 | 1 | 1 | 30 | 3 | 3 | 3 |
| HH | M | 151 | Driver COPD I-III | 56.2 | 2 | 2 | 2 | 3 | 3 | 2 | 30 | 3 | 3 | 3 |
| KT | M | 94 | Driver COPD I-III | 50.8 | 2 | 2 | 2 | -1 | 1 | 1 | 30 | 5 | 0 | 1 |
| LG | M | 109 | Driver COPD I-III | 60.0 | 2 | 2 | 2 | 1 | 1 | 2 | 40 | 4 | 3 | 1 |
| MB | F | 133 | Driver COPD I-III | 69.7 | 2 | 2 | 2 | 1 | 1 | 2 | 35 | 3 | 3 | 3 |
| MJ | M | 112 | Welder COPD I-III | 68.2 | 2 | 2 | 2 | 0 | 0 | 1 | 40 | 5 | 5 | 5 |
| MJ | M | 68 | Welder COPD I-III | 47.5 | 2 | 2 | 2 | 1 | 2 | 3 | 50 | 0 | 0 | 0 |
| MT | M | 171 | Welder COPD I-III | 48.8 | 2 | 1 | 2 | 1 | 2 | 2 | 35 | 2 | 3 | 3 |
| RJ | M | 75 | Driver COPD I-III | 49.8 | 2 | 2 | 2 | 1 | 1 | 1 | 40 | 3 | 3 | 3 |
| SCHR | M | 76 | Driver COPD I-III | 51.1 | 2 | 2 | 2 | 1 | 1 | 1 | 30 | 3 | 1 | 1 |
| SCHS | F | 130 | Driver COPD I-III | 53.0 | 2 | 2 | 3 | 1 | 2 | 2 | 30 | 4 | 4 | 3 |
| SE | F | 119 | Driver COPD I-III | 52.5 | 2 | 2 | 2 | 1 | 1 | 0 | 40 | 0 | 0 | 0 |
| SS | M | 104 | Welder COPD I-III | 39.9 | 2 | 0 | 0 | 2 | 2 | 2 | 15 | 2 | 2 | 2 |
| VA | M | 121 | Welder COPD I-III | 49.8 | 2 | 2 | 3 | 1 | 1 | 1 | 30 | 4 | 3 | 1 |
| WM | M | 9 | Driver COPD I-III | 48.2 | 2 | 2 | 2 | -1 | 0 | -1 | 25 | 3 | 3 | 3 |
| WT | M | 69 | Welder COPD I-III | 47.5 | 2 | 2 | 0 | 1 | 1 | 1 | 60 | 2 | 2 | 1 |
| ZJ | M | 78 | Welder COPD I-III | 60.2 | 2 | 2 | 2 | 1 | 1 | 2 | 35 | 0 | 0 | 2 |
| ZS | M | 127 | Driver COPD I-III | 27.4 | 2 | 2 | 0 | 2 | 4 | 4 | 9 | 3 | 5 | 4 |
| BH | M | 2 | Driver COPD I-III | 46.4 | 3 | 2 | 2 | 0 | 0 | -1 | 25 | 3 | 0 | 0 |
| CP | M | 100 | Welder COPD I-III | 70.8 | 3 | 3 | 3 | 0 | 1 | 0 | 70 | 0 | 0 | 0 |
| FW | M | 132 | Driver COPD I-III | 65.3 | 3 | 3 | 3 | 0 | 0 | 1 | 40 | 3 | 3 | 3 |
| BW | M | 38 | Driver COPD I-III | 68.5 | 3 | 3 | 3 | 1 | 1 | 1 | 60 | 4 | 4 | 3 |
| KE | M | 108 | Welder COPD I-III | 51.5 | 3 | 4 | 4 | 1 | 2 | 1 | 45 | 4 | 5 | 4 |
| KK | M | 73 | Welder COPD I-III | 55.5 | 3 | 3 | 3 | 1 | 1 | 3 | 25 | 1 | 1 | 1 |
| LH | M | 80 | Welder COPD I-III | 69.8 | 3 | 3 | n.d. | 1 | 1 | n.d. | 70 | 3 | 3 | 3 |
| MC | F | 111 | Driver COPD I-III | 62.2 | 3 | 3 | 4 | 0 | 0 | 0 | 40 | 0 | 0 | 0 |
| NP | M | 70 | Driver COPD I-III | 64.2 | 3 | 3 | 4 | 1 | 1 | 2 | 100 | 0 | 0 | 0 |
| SCHB | M | 146 | Driver COPD I-III | 57.8 | 3 | 3 | 3 | 2 | 2 | 2 | 60 | 3 | 4 | 3 |
| TG | M | 129 | Driver COPD I-III | 62.5 | 3 | 2 | 2 | 1 | 2 | 2 | 60 | 2 | 2 | 2 |
| WJ | M | 63 | Driver COPD I-III | 55.8 | 3 | 3 | 3 | 1 | 1 | 1 | 40 | 0 | 0 | 0 |
| HOH | M | 48 | Driver COPD I-III | 70.8 | 4 | 3 | 3 | -1 | 0 | 2 | 100 | 0 | 0 | 0 |
| JR | M | 110 | Driver COPD I-III | 55.3 | 4 | 3 | n.d. | 1 | 1 | n.d. | 40 | 4 | 1 | n.d. |
| | | n = 49 | Age (yrs, mean) 55.5 | | | | | | | | PY (mean) 38.7 | | | |

Fig. 3 (cont.)

D)

| No. of participants | | Healthy<br>16 | | GOLD at risk<br>55 | | GOLD I<br>9 | | | GOLD II<br>26 | | | GOLD III<br>12 | | | GOLD IV<br>2 | | | Total<br>120 | |
|---|---|---|---|---|---|---|---|---|---|---|---|---|---|---|---|---|---|---|---|
| Age | | 36 ± 12.2 | | 50 ± 9.5 | | 56 ± 10.4 | | p=0.083 | 52 ± 9.0 | | p=0.304 | 61 ± 7.6 | | p=0.0004 | 63 ± 11.0 | | p=0.054 | | |
| Packyears | | 0 | | 32 ± 26 | | 29 ± 15 | | p=0.729 | 33 ± 15 | | p=0.815 | 53 ± 21 | | p=0.004 | 70 ± 42 | | p=0.022 | | |
| Gender | F | 7 | (44%) | 8 | (15%) | 1 | (11%) | | 3 | (12%) | | 1 | (88%) | | 0 | | | 20 | (17%) |
| | M | 9 | (56%) | 47 | (85%) | 8 | (89%) | | 23 | (88%) | | 11 | (92%) | | 2 | (100%) | p=0.931 | 100 | (83%) |
| Occupation | Control (healthy) | 16 | | 0 | | 0 | | | 0 | | | 0 | | | 0 | | | 16 | (13%) |
| | Taxi/Bus driver | 0 | | 31 | (56%) | 7 | (78%) | | 16 | (62%) | | 8 | (67%) | | 2 | (100%) | p=0.594 | 64 | (53%) |
| | Welder | 0 | | 24 | (44%) | 2 | (22%) | | 10 | (38%) | | 4 | (33%) | | 0 | | | 40 | (33%) |
| Symptoms of chronic bronchitis (Cough & Phlegm) | No symptoms | 16 | (100%) | 0 | | 0 | | | 0 | | | 0 | | | 0 | | | 16 | (13%) |
| | frequently dry | 0 | | 24 | (44%) | 2 | (22%) | | 4 | (15%) | | 4 | (33%) | | 1 | (50%) | p=0.054 | 35 | (29%) |
| | productive | 0 | | 16 | (29%) | 5 | (56%) | | 18 | (69%) | | 7 | (58%) | | 1 | (50%) | | 47 | (39%) |
| | discolored | 0 | | 15 | (27%) | 2 | (22%) | | 4 | (15%) | | 1 | (8%) | | 0 | | | 22 | (18%) |
| Changes between baseline and visit 3 | | | | | | | | | | | | | | | | | | | |
| GOLD stage | deterioration | 0 | | 7 | (13%) | 1 | (11%) | | 3 | (12%) | | 3 | (25%) | | 0 | | | 14 | (12%) |
| | stable | 16 | (100%) | 48 | (87%) | 3 | (33%) | | 18 | (69%) | | 7 | (58%) | | 1 | (50%) | p=0.001 | 93 | (78%) |
| | improvement | 0 | | 0 | | 5 | (56%) | | 5 | (19%) | | 2 | (17%) | | 1 | (50%) | | 13 | (11%) |
| Cough & Phlegm | deterioration | 0 | | 11 | (20%) | 2 | (22%) | | 9 | (35%) | | 4 | (33%) | | 1 | (50%) | | 27 | (23%) |
| | stable | 16 | (100%) | 26 | (47%) | 5 | (56%) | | 12 | (46%) | | 7 | (58%) | | 0 | | p=0.058 | 66 | (55%) |
| | improvement | 0 | | 18 | (33%) | 2 | (22%) | | 5 | (19%) | | 1 | (8%) | | 1 | (50%) | | 27 | (23%) |
| Exacerbations (month 1-12) | yes | 0 | | 12 | (22%) | 3 | (33%) | | 4 | (15%) | | 5 | (42%) | | 1 | (50%) | p=0.308 | 25 | (21%) |
| | no | 16 | (100%) | 43 | (78%) | 6 | (67%) | | 22 | (85%) | | 7 | (58%) | | 1 | (50%) | | 95 | (79%) |
| Exacerbations (month 12-36) | yes | 0 | | 10 | (18%) | 3 | (33%) | | 14 | (54%) | | 5 | (42%) | | 0 | | p=0.008 | 32 | (27%) |
| | no | 16 | (100%) | 45 | (82%) | 6 | (67%) | | 12 | (46%) | | 7 | (58%) | | 2 | (100%) | | 88 | (73%) |

Figure 4:
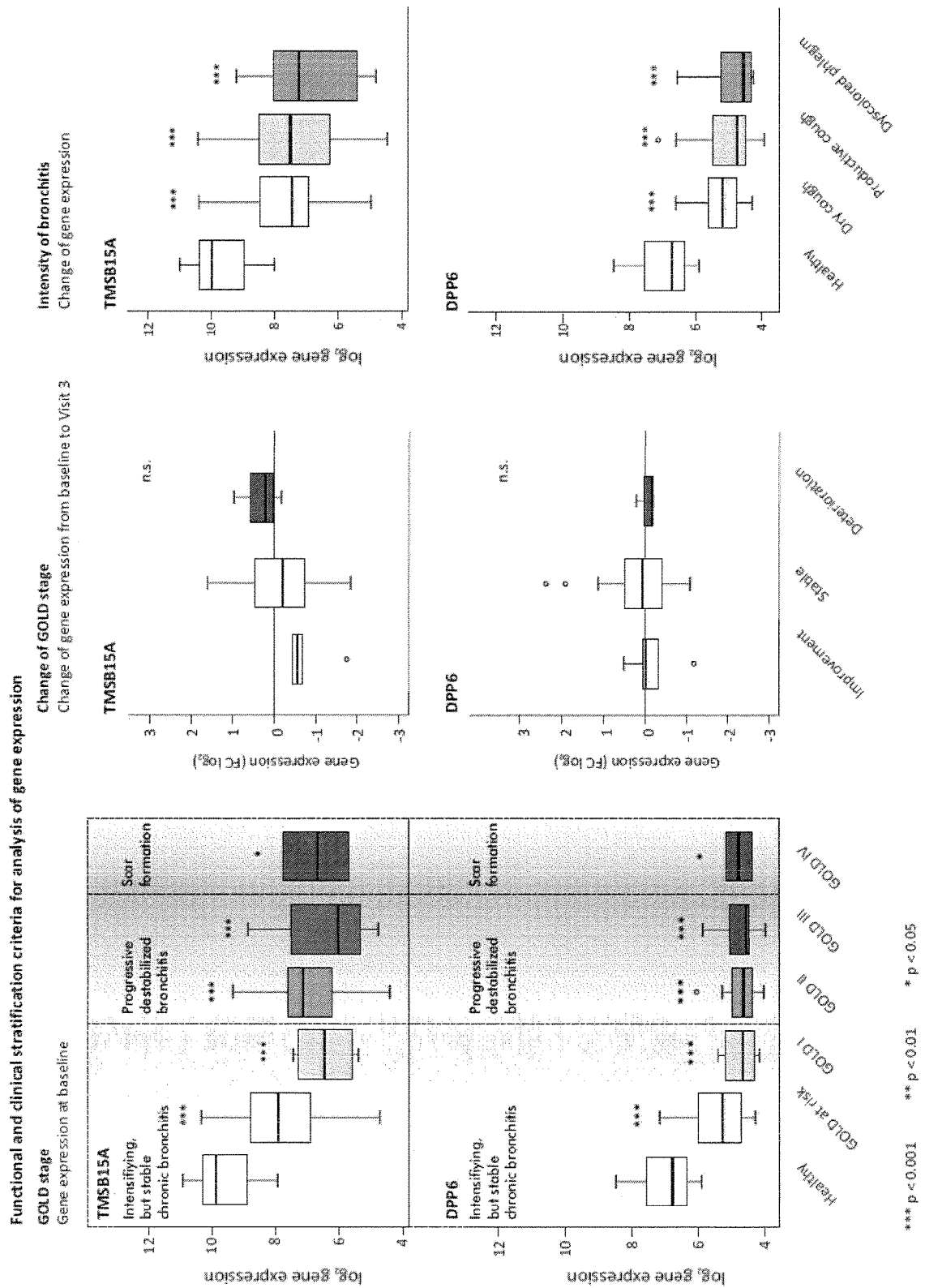
Figure 4:
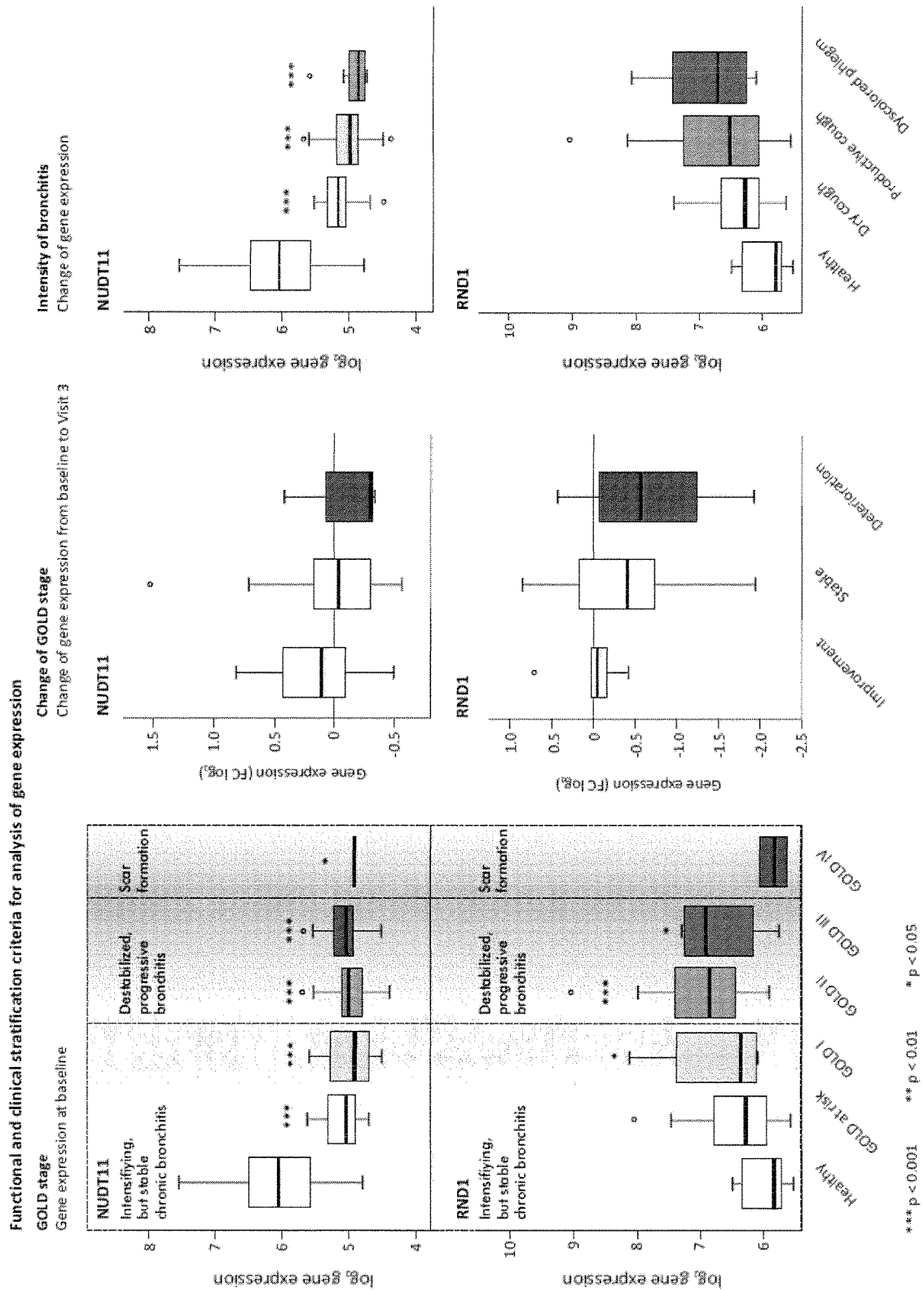
Figure 4:
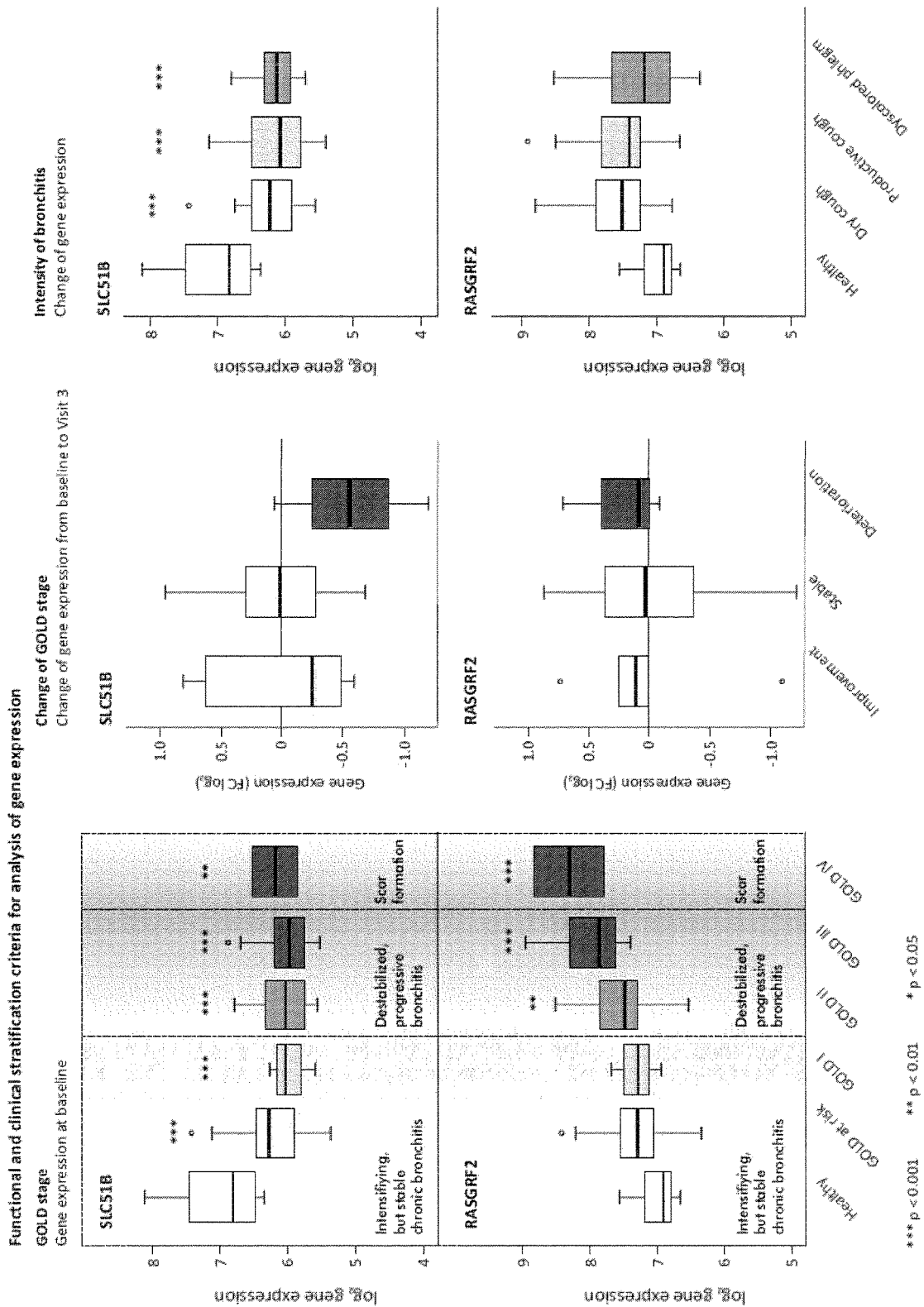

Fig. 4
A)
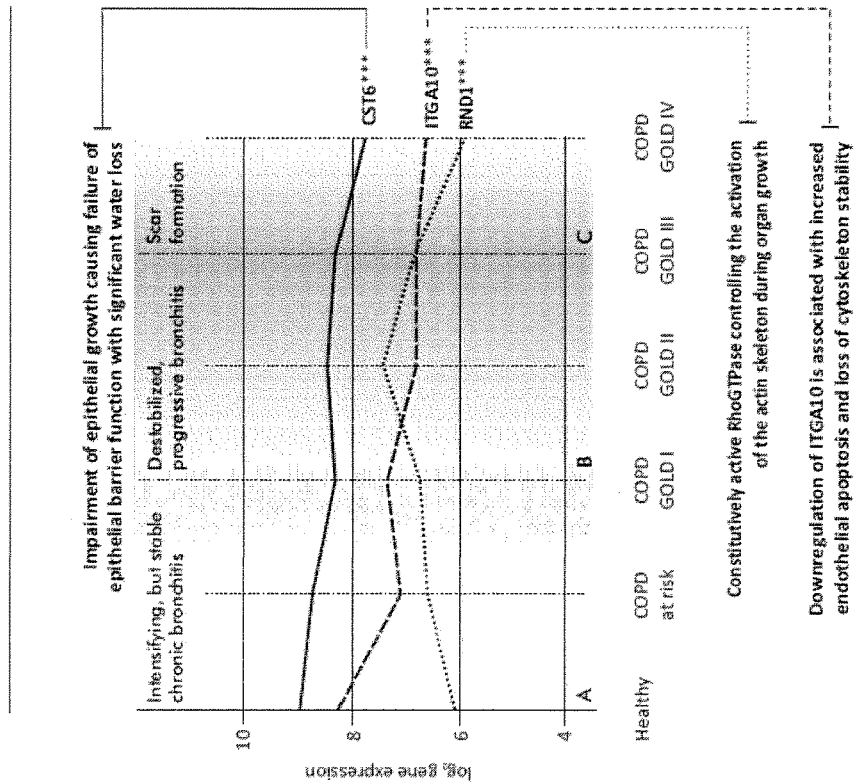
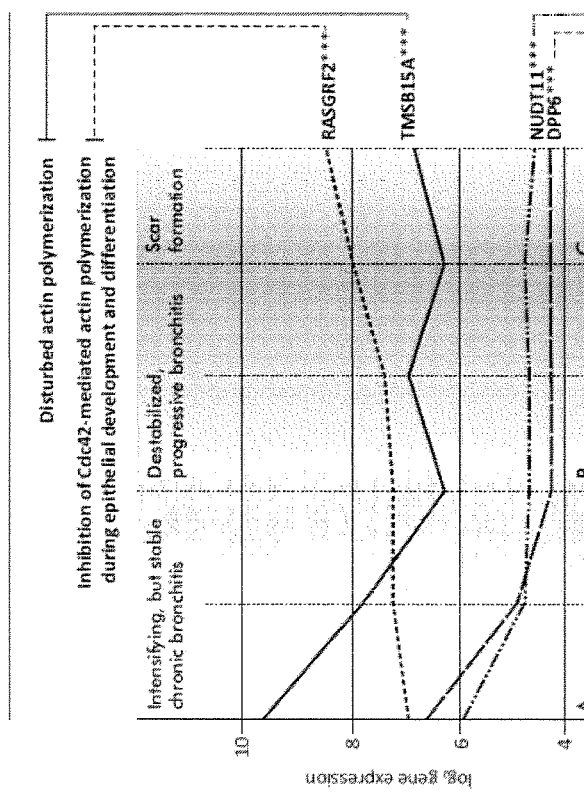
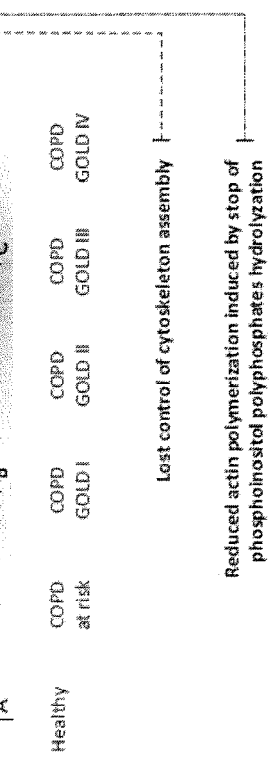

B)

c)

D)

A)

B)

C)

D)

E)

F)

G)

H)

Figure 6:
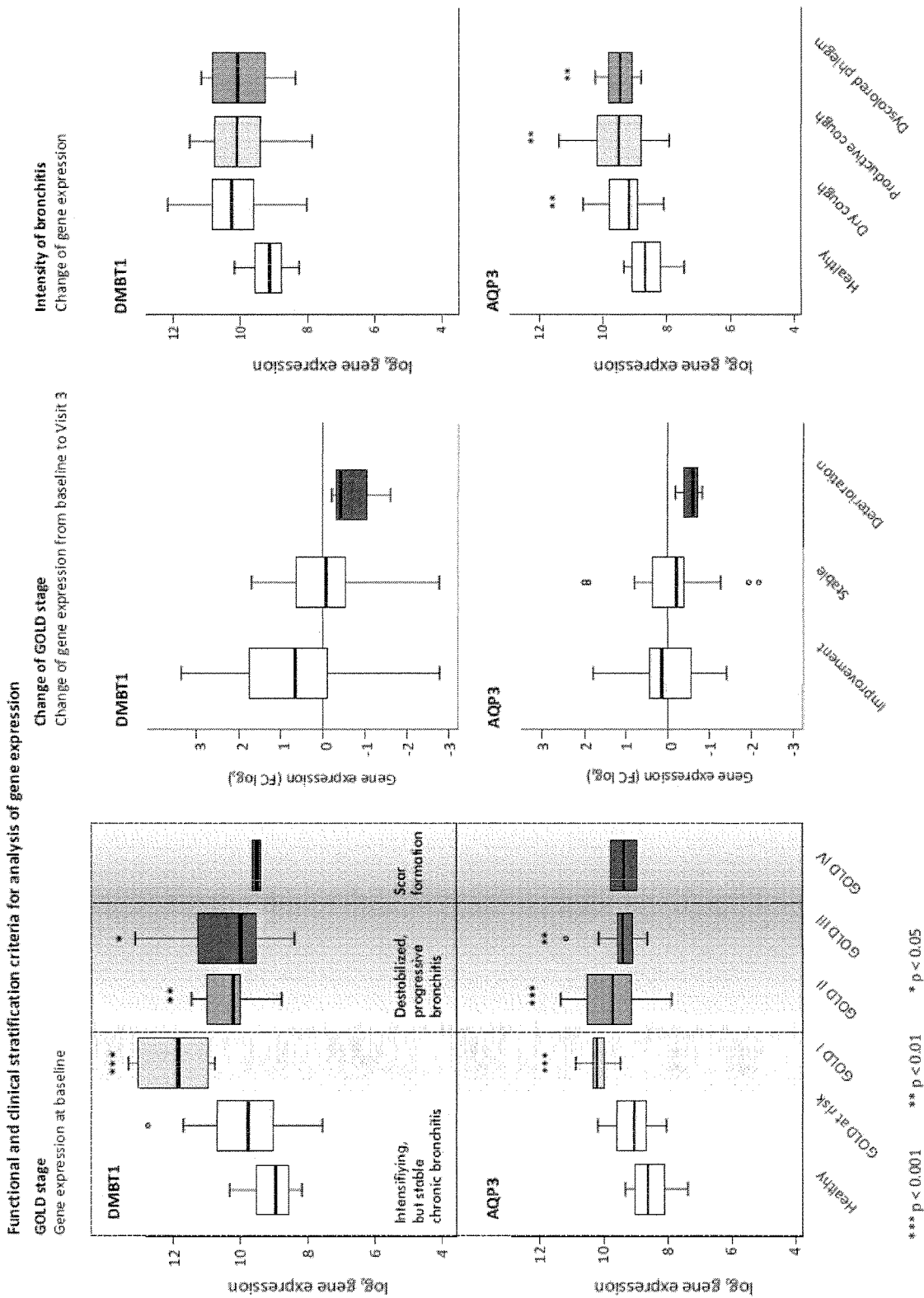
Figure 6:
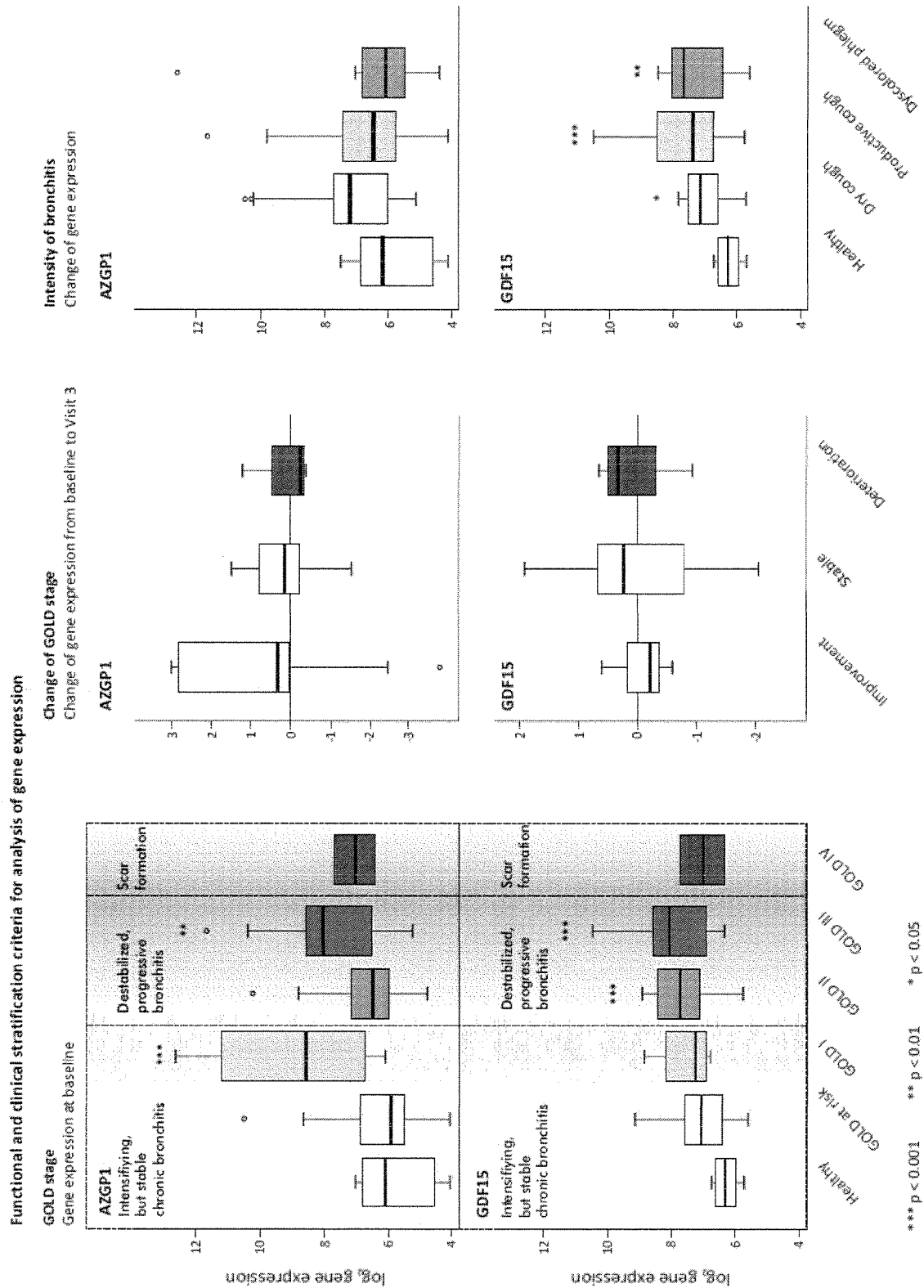
Figure 6:
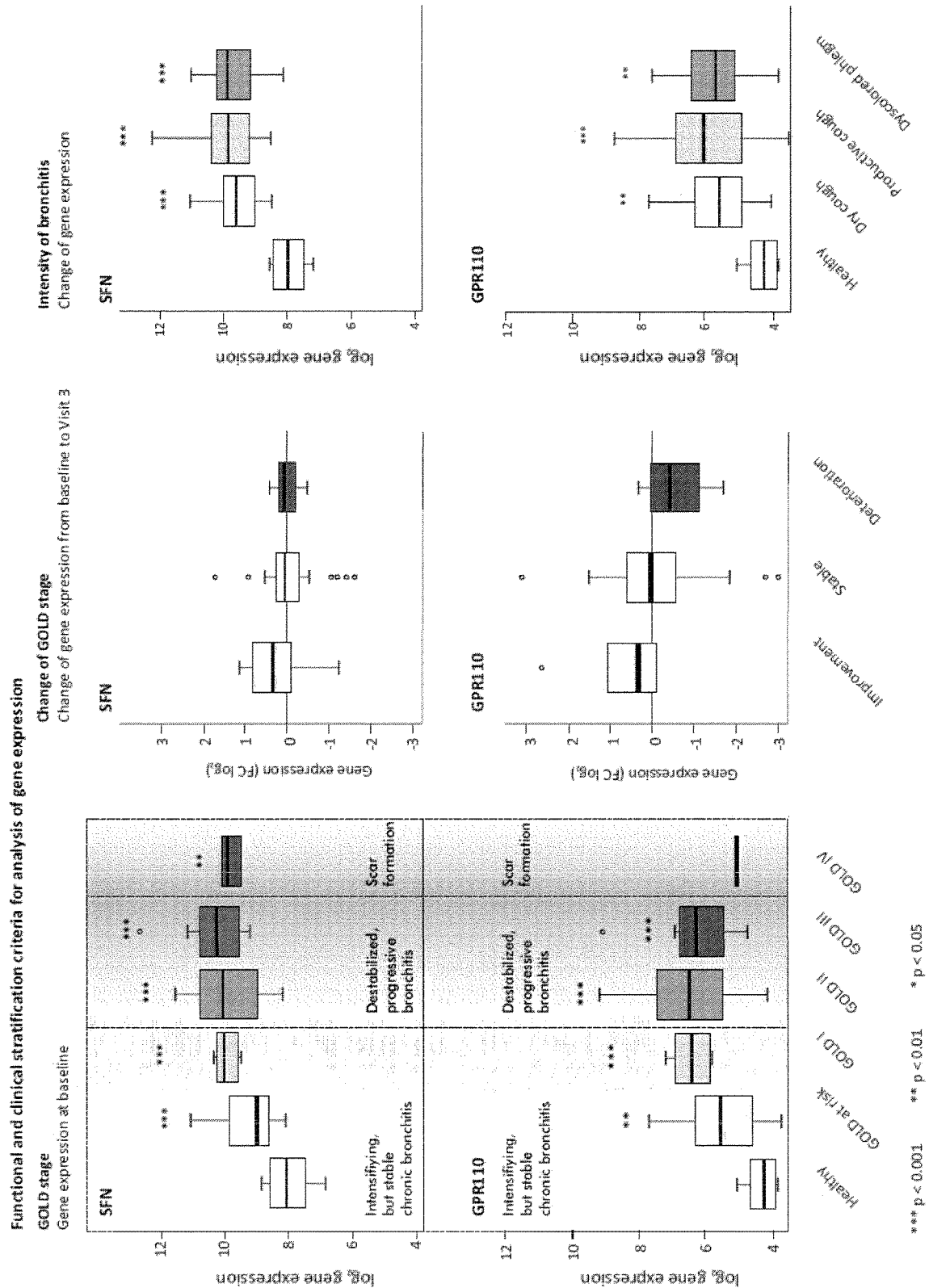
Figure 6:
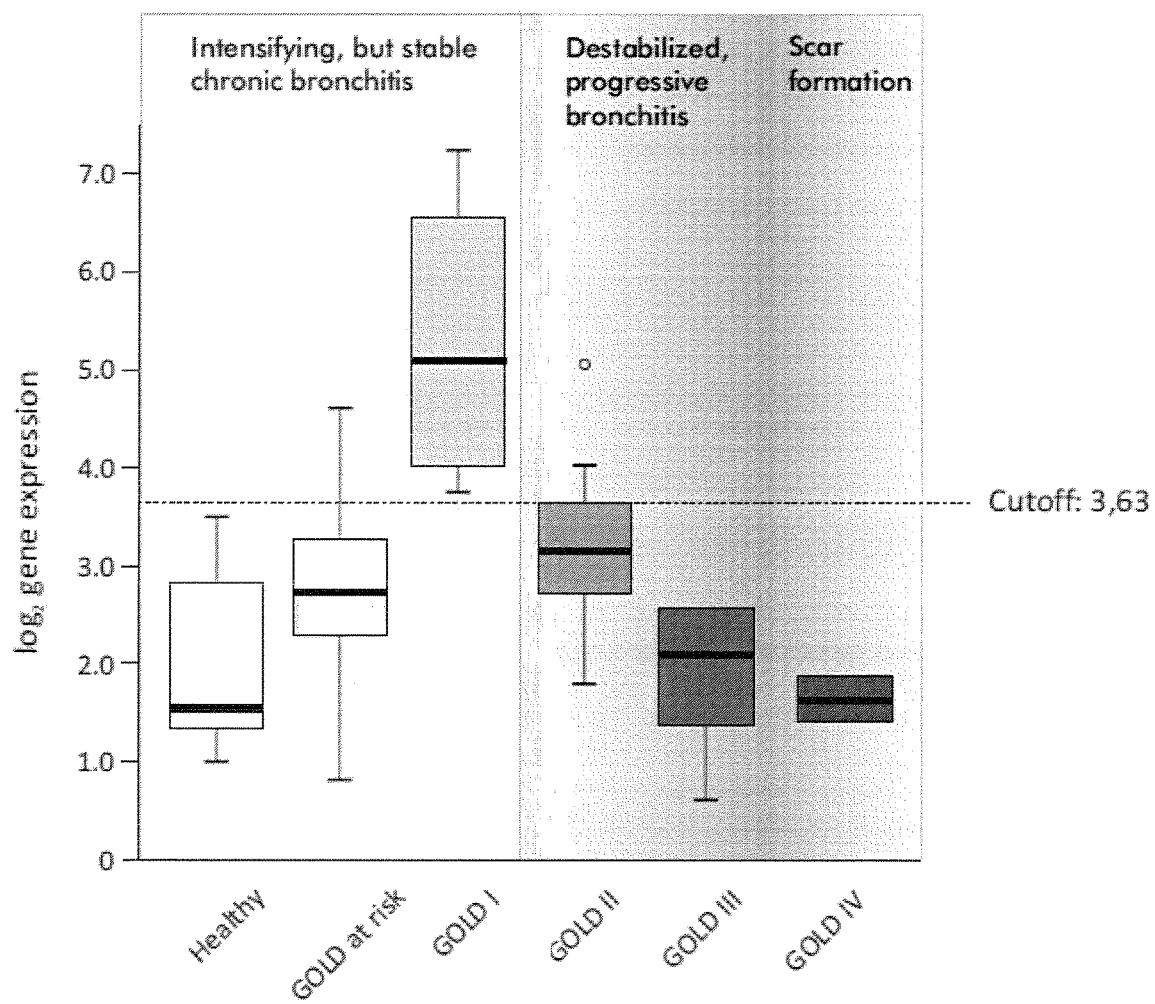

Fig. 6
A)
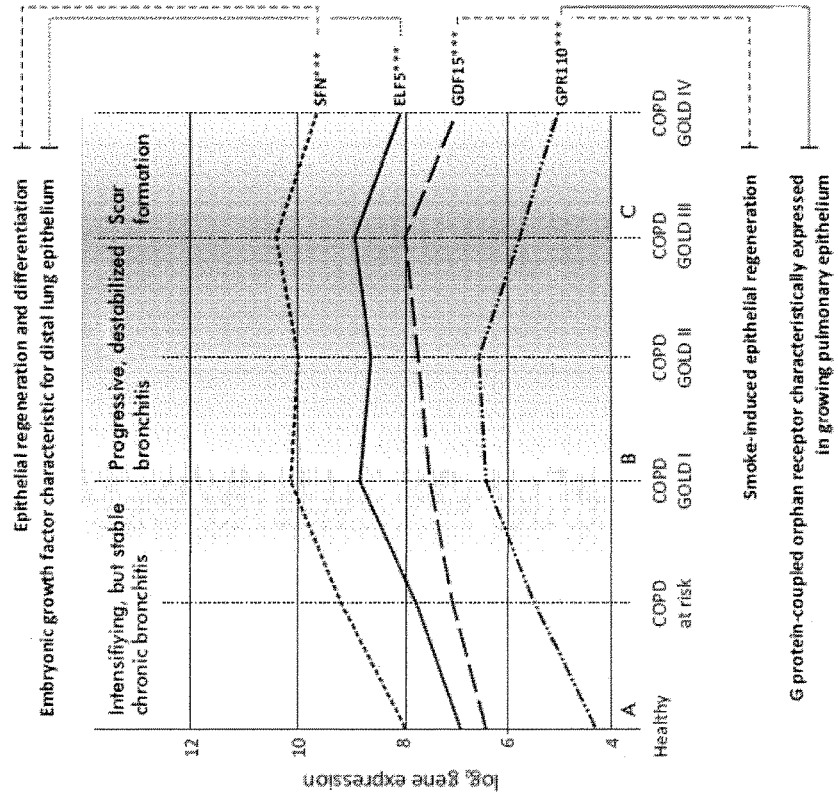
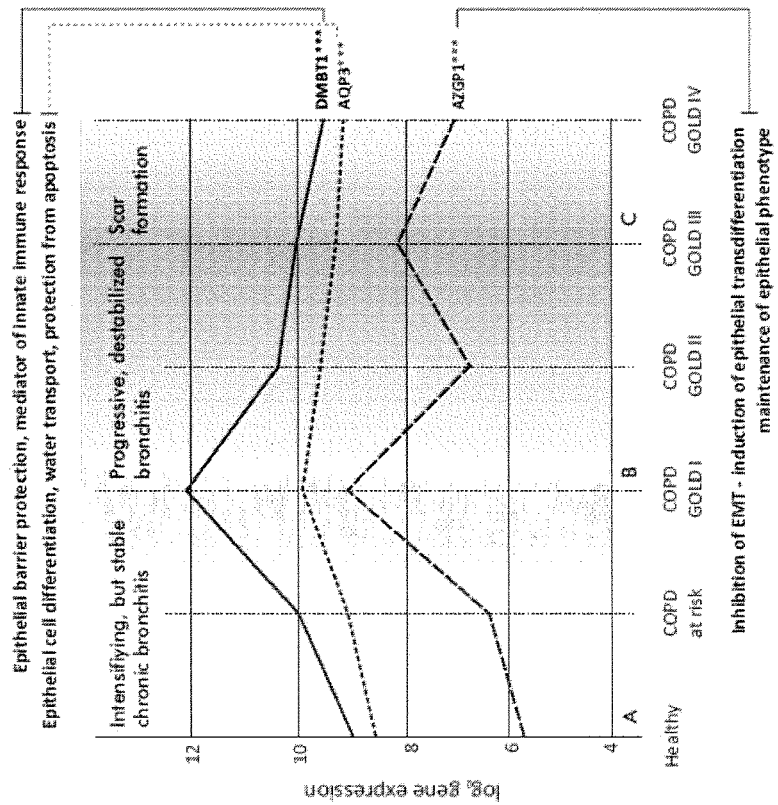

B)

c)

D)

E)

A)

B)

C)

D)

SEQUENCE LISTING

<160> NUMBER OF SEQ ID NOS: 59

<210> SEQ ID NO 1
<211> LENGTH: 2471
<212> TYPE: DNA
<213> ORGANISM: Homo sapiens

<400> SEQUENCE: 1

```
agaaagcgag cagccaccca gctccccgcc accgccatgg tccccgacac cgcctgcgtt      60
cttctgctca ccctggctgc cctcggcgcg tccggacagg gccagagccc gttgggctca     120
gacctgggcc cgcagatgct tcgggaactg caggaaacca acgcggcgct gcaggacgtg     180
cgggagctgc tgcggcagca ggtcaggag atcacgttcc tgaaaaacac ggtgatggag      240
tgtgacgcgt gcgggatgca gcagtcagta cgcaccggcc tacccagcgt gcggcccctg     300
ctccactgcg cgcccggctt ctgcttcccc ggcgtggcct gcatccagac ggagagcggc     360
gcgcgctgcg gcccctgccc cgcgggcttc acgggcaacg gctcgcactg caccgacgtc     420
aacgagtgca acgcccaccc ctgcttcccc cgagtccgct gtatcaacac cagcccgggg     480
ttccgctgcg aggcttgccc gccggggtac agcggcccca cccaccaggg cgtggggctg     540
gctttcgcca aggccaacaa gcaggtttgc acggacatca acgagtgtga gaccgggcaa     600
cataactgcg tccccaactc cgtgtgcatc aacacccggg gctccttcca gtgcggcccg     660
tgccagcccg gcttcgtggg cgaccaggcg tccggctgcc agcggcgcgc acagcgcttc     720
tgccccgacg gctcgcccag cgagtgccac gagcatgcag actgcgtcct agagcgcgat     780
ggctcgcggt cgtgcgtgtg tgccgttggc tgggccggca cgggatcct ctgtggtcgc     840
gacactgacc tagacggctt cccggacgag aagctgcgct gcccggagcg ccagtgccgt     900
aaggacaact gcgtgactgt gcccaactca gggcaggagg atgtggaccg cgatggcatc     960
ggagacgcct gcgatccgga tgccgacggg acgggggtcc ccaatgaaaa ggacaactgc    1020
ccgctggtgc ggaacccaga ccagcgcaac acggacgagg acaagtgggg cgatgcgtgc    1080
gacaactgcc ggtcccagaa gaacgacgac caaaaggaca cagaccagga cggccggggc    1140
gatgcgtgcg acgacgacat cgacggcgac cggatccgca accaggccga caactgccct    1200
agggtaccca actcagacca gaaggacagt gatggcgatg gtataggga tgcctgtgac    1260
aactgtcccc agaagagcaa cccggatcag gcggatgtgg accacgactt tgtgggagat    1320
gcttgtgaca cgatcaaga ccaggatgga gacggacatc aggactctcg ggacaactgt    1380
cccacggtgc ctaacagtgc ccaggaggac tcagaccacg atggcaggg tgatgcctgc    1440
gacgacgacg acgacaatga cggagtccct gacagtcggg acaactgccg cctggtgcct    1500
aaccccggcc aggaggacgc ggacagggac ggcgtgggcg acgtgtgcca ggacgacttt    1560
gatgcagaca aggtggtaga caagatcgac gtgtgtccgg agaacgctga agtcacgctc    1620
accgacttca gggccttcca gacagtcgtg ctggacccgg agggtgacgc gcagattgac    1680
cccaactggg tggtgctcaa ccagggaagg gagatcgtgc agacaatgaa cagcgaccca    1740
ggcctggctg tgggttacac tgccttcaat ggcgtggact cgagggcac gttccatgtg    1800
aacacggtca cggatgacga ctatgcgggc ttcatctttg gctaccagga cagctccagc    1860
ttctacgtgt tcatgtggaa gcagatggag caaacgtatt ggcaggcgaa ccccttccgt    1920
gctgtggccg agcctggcat ccaactcaag gctgtgaagt cttccacagg ccccggggaa    1980
cagctgcgga acgctctgtg gcatacagga gacacagagt cccaggtgcg gctgctgtgg    2040
aaggacccgc gaaacgtggg ttggaaggac aagaagtcct atcgttggtt cctgcagcac    2100
cggccccaag tgggctacat cagggtgcga ttctatgagg gccctgagct ggtggccgac    2160
agcaacgtgg tcttggacac aaccatgcgg ggtggccgcc tggggtctt ctgcttctcc    2220
caggagaaca tcatctgggc caacctgcgt taccgctgca atgacaccat cccagaggac    2280
```

```
tatgagaccc atcagctgcg gcaagcctag ggaccagggt gaggaccgc cggatgacag    2340 ccacctcac cgcggctgga tgggggctct gcacccagcc ccaagggtg gccgtcctga    2400 gggggaagtg agaagggctc agagaggaca aaataaagtg tgtgtgcagg gaaaaaaaaa    2460
aaaaaaaaaa a                                                        2471

<210> SEQ ID NO 2
<211> LENGTH: 5160
<212> TYPE: DNA
<213> ORGANISM: Homo sapiens

<400> SEQUENCE: 2
aaaacccgga ggagcgggat ggcgcgcttt gactctggag tgggagtggg agcgagcgct      60
tctgcgactc cagttgtgag agccgcaagg catgggaat tgacgccact caccgacccc     120
cagtctcaat ctcaacgctg tgaggaaacc tcgactttgc caggtcccca agggcagcgg    180
ggctcggcga gcgaggcacc cttctccgtc cccatcccaa tccaagcgct cctggcactg    240
acgacgccaa gagactcgag tgggagttaa agcttccagt gagggcagca ggtgtccagg    300
ccgggcctgc gggttcctgt tgacgtcttg ccctaggcaa aggtcccagt tccttctcgg    360
agccggctgt cccgcgccac tggaaaccgc acctccccgc agcatgggca ccagcctcag    420
cccgaacgac ccttggccgc taaacccgct gtccatccag cagaccacgc tcctgctact    480
cctgtcggtg ctggccactg tgcatgtggg ccagcggctg ctgaggcaac ggaggcggca    540
gctccggtcc gcgccccgg gcccgtttgc gtggccactg atcggaaacg cggcggcggt    600
gggccaggcg gctcacctct cgttcgctcg cctggcgcgg cgctacggcg acgttttcca    660
gatccgcctg ggcagctgcc ccatagtggt gctgaatggc gagcgcgcca tccaccaggc    720
cctggtgcag cagggctcgg ccttcgccga ccggccggcc ttcgcctcct tccgtgtggt    780
gtccggcggc cgcagcatgg cttttcggcca ctactcggag cactggaagg tgcagcggcg    840
cgcagcccac agcatgatgc gcaacttctt cacgcgccag ccgcgcagcc gccaagtcct    900
cgagggccac gtgctgagcg aggcgcgcga gctggtggcg ctgctggtgc gcggcagcgc    960
ggacggcgcc ttcctcgacc cgaggccgct gaccgtcgtg gccgtggcca acgtcatgag   1020
tgccgtgtgt ttcggctgcc gctacagcca cgacgacccc gagttccgtg agctgctcag   1080
ccacaacgaa gagttcgggc gcacggtggg cgcgggcagc ctggtggacg tgatgccctg   1140
gctgcagtac ttccccaacc cggtgcgcac cgttttccgc gaattcgagc agctcaaccg   1200
caacttcagc aacttcatcc tggacaagtt cttgaggcac tgcgaaagcc ttcggcccgg   1260
ggccgccccc cgcgacatga tggacgcctt tatcctctct gcggaaaaga aggcggccgg   1320
ggactcgcac ggtggtggcg cgcggctgga tttggagaac gtaccggcca ctatcactga   1380
catcttcggc gccagccagg acaccctgtc caccgcgctg cagtggctgc tcctcctctt   1440
caccaggtat cctgatgtgc agactcgagt gcaggcagaa ttggatcagg tcgtggggag   1500
ggaccgtctg ccttgtatgg gtgaccagcc caacctgccc tatgtcctgg ccttcctta    1560 tgaagccatg cgcttctcca gctttgtgcc tgtcactatt cctcatgcca ccactgccaa   1620
cacctctgtc ttgggctacc acattcccaa ggacactgtg gttttgtca accagtggtc    1680 tgtgaatcat gacccactga gtggcctaa cccggagaac tttgatccag ctcgattctt    1740
ggacaaggat ggcctcatca acaaggacct gaccagcaga gtgatgattt tttcagtggg   1800 caaaaggcg tgcattggcg aagaactttc taagatgcag ctttttctct tcatctccat    1860
cctggctcac cagtgcgatt tcagggccaa cccaaatgag cctgcgaaaa tgaatttcag   1920
```

```
ttatggtcta accattaaac ccaagtcatt taaagtcaat gtcactctca gagagtccat    1980
ggagctcctt gatagtgctg tccaaaattt acaagccaag gaaacttgcc aataagaagc    2040
aagaggcaag ctgaaatttt agaaatattc acatcttcgg agatgaggag taaaattcag    2100 ttttttcca  gttcctcttt tgtgctgctt ctcaattagc gtttaaggtg agcataaatc    2160
aactgtccat caggtgaggt gtgctccata cccagcggtt cttcatgagt agtgggctat    2220
gcaggagctt ctgggagatt tttttgagtc aaagacttaa agggcccaat gaattattat    2280
atacatactg catcttggtt atttctgaag gtagcattct ttggagttaa aatgcacata    2340
tagacacata cacccaaaca cttacaccaa actactgaat gaagcagtat tttggtaacc    2400
aggccatttt tggtgggaat ccaagattgg tctcccatat gcagaaatag acaaaaagta    2460
tattaaacaa agtttcagag tatattgttg aagagacaga gacaagtaat ttcagtgtaa    2520
agtgtgtgat tgaaggtgat aagggaaaag ataaagacca gaaattccct tttcacctttt   2580 tcaggaaaat aacttagact ctagtattta tgggtggatt tatccttttg ccttctggta    2640
tacttcctta cttttaagga taaatcataa agtcagttgc tcaaaagaa  atcaatagtt    2700 gaattagtga gtatagtggg gttccatgag ttatcatgaa ttttaaagta tgcattatta    2760
aattgtaaaa ctccaaggtg atgttgtacc tcttttgctt gccaaagtac agaatttgaa    2820
ttatcagcaa agaaaaaaaa aaaagccagc caagctttaa attatgtgac cataatgtac    2880
tgatttcagt aagtctcata ggttaaaaaa aaaagtcacc aaatagtgtg aaatatatta    2940
cttaactgtc cgtaagcagt atattagtat tatcttgttc aggaaaaggt tgaataatat    3000
atgccttgta taatattgaa aattgaaaag tacaactaac gcaaccaagt gtgctaaaaa    3060
tgagcttgat taaatcaacc acctattttt gacatggaaa tgaagcaggg tttctttttct   3120 tcactcaaat tttggcgaat ctcaaaatta gatcctaaga tgtgttctta tttttataac    3180
atctttattg aaattctatt tataatacag aatcttgttt tgaaaataac ctaattaata    3240
tattaaaatt ccaaattcat ggcatgctta aattttaact aaattttaaa gccattctga    3300
ttattgagtt ccagttgaag ttagtggaaa tctgaacatt ctcctgtgga aggcagagaa    3360
atctaagctg tgtctgccca atgaataatg gaaaatgcca tgaattacct ggatgttctt    3420
tttacgaggt gacaagagtt ggggacagaa ctcccattac aactgaccaa gtttctcttc    3480
tagatgattt tttgaaagtt aacattaatg cctgcttttt ggaaagtcag aatcagaaga    3540
tagtcttgga agctgtttgg aaaagacagt ggagatgagg tcagttgtgt ttttaagat    3600 ggcaattact ttggtagctg ggaaagcata aagctcaaat gaaatgtatg cattcacatt    3660
tagaaaagtg aattgaagtt tcaagtttta aagttcattg caattaaact tccaaagaaa    3720
gttctacagt gtcctaagtg ctaagtgctt attacatttt attaagcttt ttggaatctt    3780
tgtaccaaaa ttttaaaaaa gggagttttt gatagttgtg tgtatgtgtg tgtggggtgg    3840
ggggatggta agagaaaaga gagaaacact gaaaagaagg aaagatggtt aaacattttc    3900
ccactcattc tgaattaatt aatttggagc acaaaattca aagcatggac atttagaaga    3960
aagatgtttg gcgtagcaga gttaaatctc aaataggcta ttaaaaaagt ctacaacata    4020
gcagatctgt tttgtggttt ggaatattaa aaaacttcat gtaattttat tttaaaattt    4080
catagctgta cttcttgaat ataaaaaatc atgccagtat ttttaaaggc attagagtca    4140
actacacaaa gcaggcttgc ccagtacatt taaattttttt ggcacttgcc attccaaaat    4200
attatgcccc accaaggctg agacagtgaa tttgggctgc tgtagcctat ttttttagat    4260
```

| | |
|---|---|
| tgagaaatgt gtagctgcaa aaataatcat gaaccaatct ggatgcctca ttatgtcaac | 4320 |
| caggtccaga tgtgctataa tctgttttta cgtatgtagg cccagtcgtc atcagatgct | 4380 |
| tgcggcaaaa ggaaagctgt gtttatatgg aagaaagtaa ggtgcttgga gtttacctgg | 4440 |
| cttatttaat atgcttataa cctagttaaa gaaaggaaaa gaaaacaaaa aacgaatgaa | 4500 |
| aataactgaa tttggaggct ggagtaatca gattactgct ttaatcagaa accctcattg | 4560 |
| tgtttctacc ggagagagaa tgtatttgct gacaaccatt aaagtcagaa gttttactcc | 4620 |
| aggttattgc aataaagtat aatgtttatt aaatgcttca tttgtatgtc aaagctttga | 4680 |
| ctctataagc aaattgcttt tttccaaaac aaaaagatgt ctcaggtttg ttttgtgaat | 4740 |
| tttctaaaag ctttcatgtc ccagaactta gcctttacct gtgaagtgtt actacagcct | 4800 |
| taatattttc ctagtagatc tatattagat caaatagttg catagcagta tatgttaatt | 4860 |
| tgtgtgtttt tagctgtgac acaactgtgt gattaaaagg tatactttag tagacattta | 4920 |
| taactcaagg ataccttctt atttaatctt ttcttatttt tgtactttat catgaatgct | 4980 |
| tttagtgtgt gcataatagc tacagtgcat agttgtagac aaagtacatt ctggggaaac | 5040 |
| aacatttata tgtagccttt actgtttgat ataccaaatt aaaaaaaaat tgtatctcat | 5100 |
| tacttatact gggacaccat taccaaaata ataaaaatca ctttcataat cttgaaaaaa | 5160 |

<210> SEQ ID NO 3
<211> LENGTH: 2608
<212> TYPE: DNA
<213> ORGANISM: Homo sapiens

<400> SEQUENCE: 3

| | |
|---|---|
| ctcaccctga aggtgacagt tccttggaac cttccctgat ccttgtgatc ccaggctcca | 60 |
| agagtccacc cttcccagct cagctcagta cctcagccac ctccaagatc cctacactga | 120 |
| tcatgctttt cccaatctcc atgtcggcca cggagtttct tctggcctct gtcatcttct | 180 |
| gtctggtatt ctgggtaatc agggcctcaa gacctcaggt ccccaaaggc ctgaagaatc | 240 |
| caccagggcc atgggctgg cctctgattg gcacatgct gaccctggga agaacccgc | 300 |
| acctggcact gtcaaggatg agccagcagt atggggacgt gctgcagatc cgaattggct | 360 |
| ccacacccgt ggtggtgctg agcggcctgg acaccatccg gcaggccctg gtgcggcagg | 420 |
| gcgatgattt caagggccgg cccgacctct acaccttcac cctcatcagt aatggtcaga | 480 |
| gcatgtcctt cagcccagac tctggaccag tgtgggctgc ccgccggcgc ctggcccaga | 540 |
| atggcctgaa aagtttctcc attgcctctg acccagcctc ctcaacctcc tgctacctgg | 600 |
| aagagcatgt gagcaaggag gctgaggtcc tgataagcac gttgcaggag ctgatggcag | 660 |
| ggcctgggca ctttaacccc tacaggtatg tggtggtatc agtgaccaat gtcatctgtg | 720 |
| ccatttgctt tggccggcgc tatgaccaca ccaccaaga actgcttagc ctagtcaacc | 780 |
| tgaataataa tttcggggag gtggttggct ctggaaaccc agctgacttc atccctattc | 840 |
| ttcgctacct acccaaccct tccctgaatg ccttcaagga cctgaatgag aagttctaca | 900 |
| gcttcatgca gaagatggtc aaggagcact acaaaacctt tgagaagggc cacatccggg | 960 |
| acatcacaga cagcctgatt gagcactgtc aggagaagca gctggatgag aacgccaatg | 1020 |
| tccagctgtc agatgagaag atcattaaca tcgtcttgga cctctttgga gctgggtttg | 1080 |
| acacagtcac aactgctatc tcctggagcc tcatgtattt ggtgatgaac ccagggtac | 1140 |
| agagaaagat ccaagaggag ctagacacag tgattggcag gtcacggcgg ccccggctct | 1200 |
| ctgacagatc ccatctgccc tatatggagg ccttcatcct ggagaccttc cgacactctt | 1260 |

```
ccttcgtccc cttcaccatc ccccacagca caacaagaga cacaagtttg aaaggctttt     1320 acatcccca ggggcgttgt gtctttgtaa accagtggca gatcaaccat gaccagaagc     1380
tatgggtcaa cccatctgag ttcctacctg aacggtttct caccctgat ggtgctatcg     1440 acaaggtgtt aagtgagaag gtgattatct ttggcatggg caagcggaag tgtatcggtg     1500
agaccattgc ccgctgggag gtctttctct tcctggctat cctgctgcaa cgggtggaat     1560
tcagcgtgcc actgggcgtg aaggtggaca tgacccccat ctatgggcta accatgaagc     1620
atgcctgctg tgagcacttc caaatgcagc tgcgctctta ggtgcttgag agccctgagg     1680
cctagactct gtctacctgg tctggttggg cagccagacc agcaggctgg cctatgtggt     1740
ctaaggttca gcctgaaact catagacact gatctggctg cagttttgct atctgggctg     1800
tgggcaagcc taagggatcc tgcctgcccc taccctggac ttgcctctgc acccctcca     1860 gagacaacag gtaaaacagg gccacataga tgctgatgga gccttcccaa gttgtgcttg     1920
agccaggagg cctgctaggg ttaggaggtc cttaggcctc tgagaagctc tgaagaactc     1980
tctggaagcc cctgggccca gtacctagct ggctctgtga gggtgctgac tggcttcagc     2040
aagttagaac tagccaaacc aggaccctgt ccaatctttg acaattggga gctgccaaga     2100
gtgaagggaa gagacagccc aggatactgg cacagaggta gtctcactgc ttgaactagg     2160
ctgagcaatc tgaccctatg ggtctaggac acagttcctg gaacatcac attcctctgc     2220 ccttcctgca ggcaggaaca acagggctg ccttctggcc ttgtaagacc cttattgctg     2280
tcctggaggg gctggggact tgtgtctgcg gggatcagag cgcacaggga gtgcacatat     2340
ccaggcacca ggactagggc tggagtgagg gggggtatt tcaattacct tctattggtc     2400
tcccttctct acactcttgt aataaaatgt ctatttttaa tgtttgtaca caacaatcct     2460
tctattctag cctgcattga gcttgcatgc ttgcataaga gcttaagaac cattgattta     2520
atgtaatagg gaaaattcta acccaggtat ccaaaaatgt gtaagaacaa ctacctgagc     2580
taaataaaga tattgttcag aaatccta                                       2608
```

<210> SEQ ID NO 4
<211> LENGTH: 1665
<212> TYPE: DNA
<213> ORGANISM: Homo sapiens

<400> SEQUENCE: 4

```
cttctggtaa ggaggcccg tgatcagctc cagccatttg cagtcctggc tatcccagga       60
gcttacataa agggacaatt ggagcctgag aggtgacagt gctgacacta caaggctcgg      120
agctccgggc actcagacat catgagttgg tccttgcacc cccggaattt aattctctac      180
ttctatgctc ttttatttct ctcttcaaca tgtgtagcat atgttgctac cagagacaac      240
tgctgcatct tagatgaaag attcggtagt tattgtccaa ctacctgtgg cattgcagat      300
ttcctgtcta cttatcaaac caaagtagac aaggatctac agtctttgga agacatctta      360
catcaagttg aaaacaaaac atcagaagtc aaacagctga taaaagcaat ccaactcact      420
tataatcctg atgaatcatc aaaaccaaat atgatagacg ctgctacttt gaagtccagg      480
aaaatgttag aagaaattat gaaatatgaa gcatcgattt taacacatga ctcaagtatt      540
cgatatttgc aggaaatata taattcaaat aatcaaaaga ttgttaacct gaaagagaag      600
gtagcccagc ttgaagcaca gtgccaggaa ccttgcaaag acacggtgca aatccatgat      660
atcactggga aagattgtca agacattgcc aataagggag ctaaacagag cgggctttac      720
```

```
tttattaaac ctctgaaagc taaccagcaa ttcttagtct actgtgaaat cgatgggtct      780
ggaaatggat ggactgtgtt tcagaagaga cttgatggca gtgtagattt caagaaaaac      840
tggattcaat ataagaagg atttggacat ctgtctccta ctggcacaac agaattttgg       900
ctgggaaatg agaagattca tttgataagc acacagtctg ccatcccata tgcattaaga      960
gtggaactgg aagactggaa tggcagaacc agtactgcag actatgccat gttcaaggtg     1020
ggacctgaag ctgacaagta ccgcctaaca tatgcctact cgctggtgg ggatgctgga      1080
gatgcctttg atggctttga ttttggcgat gatcctagtg acaagttttt cacatcccat     1140
aatggcatgc agttcagtac ctgggacaat gacaatgata gtttgaagg caactgtgct      1200
gaacaggatg gatctggttg gtggatgaac aagtgtcacg ctggccatct caatggagtt     1260
tattaccaag gtggcactta ctcaaaagca tctactccta atggttatga taatggcatt     1320
atttgggcca cttggaaaac ccggtggtat tccatgaaga aaaccactat gaagataatc     1380
ccattcaaca gactcacaat ggagaagga cagcaacacc acctggggg agccaaacag       1440
gctggagacg tttaaaagac cgtttcaaaa gagatttact tttttaaagg actttatctg     1500
aacagagaga tataatattt ttcctattgg acaatggact tgcaaagctt cacttcattt     1560
taagagcaaa agaccccatg ttgaaaactc ataacagtt ttatgctgat gataatttat      1620
ctacatgcat ttcaataaac cttttgtttc ctaagactag aaaaa                     1665

<210> SEQ ID NO 5
<211> LENGTH: 840
<212> TYPE: DNA
<213> ORGANISM: Homo sapiens

<400> SEQUENCE: 5
agacccagag ccaatgcgtg gattagtccc tcctcctagt tgcagtctgg tagttgtcgc        60
tggccgtgtg acggctcgct gttgccctga aggcaggcga gccagctgcc caggaaaggt       120
ggaaagtggt agaagctgac ccctgagccc tgcaggtct ttaagtgcgt ttgtgcagcc        180
gatttcaagg ctaagagaga aagactgcct ctgatccctg aaggaagaaa aaaaaaaaa       240
aaacaggaaa aaaactcaac atggaaaatg tccccaagga aaacaaagtt gtggagaagg       300
ccccagtgca gaatgaagcc cccgctttag gaggtggtga ataccaggag cctggaggaa       360
atgttaaagg ggtttgggct ccacctgccc cgggttttgg agaggatgtg cccaataggc       420
ttgtcgataa cattgatatg atagatggag atggagatga tatggaacgg ttcatggagg      480
agatgagaga gctaaggagg aaaattaggg aacttcagtt gaggtacagt ctgcgcattc      540
ttataggga ccctcctcac catgatcatc atgatgagtt ttgccttatg ccttgaatct       600
tgaggttaat aatcataaaa tccctgcttt ctaaattcgc atttttcctg gtgtacctt       660
aatgtgaacc ttttggcatt cttctgcaat tttctgattg gagattgcat tttgacctag     720
tctgtaagtt tttctgtcag aagaggactt tcatcaactt tcatgaaag atgtttattg      780
catactgtaa agtaataaaa gcaatttaaa agcagtctaa aaaaaaaaaa aaaaaaaaa      840

<210> SEQ ID NO 6
<211> LENGTH: 8340
<212> TYPE: DNA
<213> ORGANISM: Homo sapiens

<400> SEQUENCE: 6
actaattttc tggagttcct gcccctgctc tgcgtcagcc ctcacgtcac ttcgccagca       60
gtagcagagg cggcggcggc ggctcccgga attgggttgg agcaggagcc tcgctggctg     120
```

```
cttcgctcgc gctctacgcg ctcagtcccc ggcggtagca ggagcctgga cccaggcgcc      180
gccggcgggc gtgaggcgcc ggagcccggc ctcgaggtgc ataccggacc cccattcgca      240
tctaacaagg aatctgcgcc ccagagagtc ccgggagcgc cgccggtcgg tgcccggcgc      300
gccgggccat gcagcgacgg ccgccgcgga gctccgagca gcggtagcgc cccctgtaa      360 agcggttcgc tatgccgggg ccactgtgaa ccctgccgcc tgccggaaca ctcttcgctc      420
cggaccagct cagcctctga taagctggac tcggcacgcc cgcaacaagc accgaggagt      480
taagagagcc gcaagcgcag ggaaggcctc cccgcacggg tggggaaag cggccggtgc       540 agcgcgggga caggcactcg ggctggcact ggctgctagg gatgtcgtcc tggataaggt      600
ggcatggacc cgccatggcg cggctctggg gcttctgctg gctggttgtg ggcttctgga      660
gggccgcttt cgcctgtccc acgtcctgca aatgcagtgc ctctcggatc tggtgcagcg      720
acccttctcc tggcatcgtg gcatttccga gattggagcc taacagtgta gatcctgaga      780
acatcaccga aattttcatc gcaaaccaga aaaggttaga aatcatcaac gaagatgatg      840
ttgaagctta tgtgggactg agaaatctga caattgtgga ttctggatta aaatttgtgg      900
ctcataaagc atttctgaaa aacagcaacc tgcagcacat caattttacc cgaaacaaac      960
tgacgagttt gtctaggaaa catttccgtc accttgactt gtctgaactg atcctggtgg     1020
gcaatccatt tacatgctcc tgtgacatta tgtggatcaa gactctccaa gaggctaaat     1080
ccagtccaga cactcaggat ttgtactgcc tgaatgaaag cagcaagaat attcccctgg     1140
caaacctgca gatacccaat tgtggtttgc catctgcaaa tctggccgca cctaacctca     1200
ctgtggagga aggaaagtct atcacattat cctgtagtgt ggcaggtgat ccggttccta     1260
atatgtattg ggatgttggt aacctggttt ccaaacatat gaatgaaaca agccacacac     1320
agggctcctt aaggataact aacatttcat ccgatgacag tgggaagcag atctcttgtg     1380
tggcggaaaa tcttgtagga gaagatcaag attctgtcaa cctcactgtg cattttgcac     1440
caactatcac atttctcgaa tctccaacct cagaccacca ctggtgcatt ccattcactg     1500
tgaaaggcaa ccccaaacca gcgcttcagt ggttctataa cggggcaata ttgaatgagt     1560
ccaaatacat ctgtactaaa atacatgtta ccaatcacac ggagtaccac ggctgcctcc     1620
agctggataa tcccactcac atgaacaatg gggactacac tctaatagcc aagaatgagt     1680
atgggaagga tgagaaacag atttctgctc acttcatggg ctggcctgga attgacgatg     1740
gtgcaaaccc aaattatcct gatgtaattt atgaagatta tggaactgca gcgaatgaca     1800
tcggggacac cacgaacaga agtaatgaaa tcccttccac agacgtcact gataaaaccg     1860
gtcgggaaca tctctcggtc tatgctgtgg tggtgattgc gtctgtggtg ggattttgcc     1920
ttttggtaat gctgtttctg cttaagttgg caagacactc caagtttggc atgaaagatt     1980
tctcatggtt tggatttggg aaagtaaaat caagacaagg tgttggccca gcctccgtta     2040
tcagcaatga tgatgactct gccagcccac tccatcacat ctccaatggg agtaacactc     2100
catcttcttc ggaaggtggc ccagatgctg tcattattgg aatgaccaag atccctgtca     2160
ttgaaaatcc ccagtacttt ggcatcacca acagtcagct caagccagac acatggccca     2220
gaggttcccc caagaccgcc tgataataat ttggtatttg gaggctcctg tgtcactgca     2280
ggaactaaag gaggctaaat ccatgcctga tgaggagaa gagttctatg ttatctgca      2340 aattctggcc agacaacatc ttgacgtcac tccttagctt ccataaccta gccaagcaag     2400
aagttgcctt tccaagacaa agcagtgtgc tctaatgact aacccctcaa agtactatgc     2460
```

```
cactttaact atagacccat ctcctcgatc aatcaggatg gcaagatgga gctgaggagc   2520
tcagcaacat caagtctgga gttggtcttt aactcaacta gctcgtttag acgtgtctga   2580
acaccacatc acctgacagc acggggtggt ttcccagtaa aatttacaaa ctcagctcaa   2640
gggcagctgt gttgctttcc tttccttgac tgctgagaaa cttttttgaca gggaacaatg   2700 gaaacacacc ttctgagctg aaacaaacaa acagaaacaa aacatactaa ccagcaaaat   2760 ccccaaaatca tcaatcttgg gttctcttga agggcaggag tgtgttttat cttctcccgt   2820
cggagcaaac actatagatg tcctccctaa aattctgtct tccctagagc agccttgtaa   2880
attagctagg gtcctagggt tgaggcctaa atcaacttaa aattgtctct aaatatgtac   2940
ctggatgtgt ttgtacttgc agagcatgcc ctcttcatgt gcctagggct agtaactccc   3000
tgtggcagag gcatgtaaag tattctgact tttttttttt caacttaatt ccatttccaa   3060
tgaaatggat ttttaaaaat tttctccaga gtgtgccata cttctccagc tattatagtt   3120
aatgtgtgtg tatccttgtg tatatgtgtg tttgtgtgtg catatgtgtt ttcctagtgg   3180
ttacatgctt actaggcaat tatgtaaata agcacagatt cataggccag ctaggcctga   3240
ggaaagaaga cattataaag ggagggagta ttttaacatt agctaaagct atcacacaag   3300
gcacccattc tgctcccctc aacagccaca gcccacttcg tccttgtctt accaataagg   3360
ggaaaggctg gaggtgatat ttttcacaga accgcagagg ttttgaacat atttgcaaca   3420
ttactttgag tacacatgag caaaaattct gaattcatc caggacccca gaagctcatt   3480
agatcaaaga gtgcggggcc cctcagagtt accagagatt atctgcagac ttcagtgcaa   3540
tcgaatgacc atggtccatt tgatggtca gaggtaggac tgaaaaacgg gtagaaacaa   3600
ttgctttagc gcttccttct gtactttgcc tattaatgtt ttgtctttca aaaatatatt   3660
ttctcctaat tgtttaattg gccaaataat ggctgctttg ggagttgttt gtatgccttg   3720
gaaggccatg gcctgcactt taaaaataag ctaagtccat tctgcccagc acgagcatta   3780
ggacagagaa tgcacttatt ttaggatcct taaaaattgc ttcttttatg gcacactggg   3840
ttgacgactc atctcgtggg agccttcatg gcacattgct gctgttctgc aggtcccaat   3900
acaattcctt cccctctca gtgccacggc cccccattg ctagctacaa caatttgata   3960
tcatattccc ttttcaactc caaaggagat gataagaagc tatcaaataa tgcttttaaaa   4020 aagcaacttg agtttcttaa aagaaaggaa atgaatacat gctgcataat tacatttaaa   4080
atgtaagcca tgttattata agccgcactg agatgaagat ttgttagcaa accagtttca   4140
agcacactca cagtgaagta aaatcatgtt tttagcatct gaccattggg taatattatt   4200
ctttgttatc aaaagagaaa tatcacccaa gtatagtata cttagacctc ctagaggaaa   4260
cactccagtc ctaagcttgg tgtctgaaaa gaaaaacaaa aataaagatt atggatttag   4320
gtcagggaga cagagtgata ttctgaagac tgtgtttact ccctcatcat cggccaacca   4380
agatggagtt ctgcatcctg cacatatcag acatttcagt ccaatttcac caaagcatca   4440
gtgatgttct agaagcatcc cagcagatgg aggatcctaa tgtatttgtt ctgggtattt   4500
cccaaggccc agcctgactg gagtgtgtgt accaacagga tgaatccaat caagctacgc   4560 ccccatttg gtttcggatt ggccactctt gcatgtgcta gtagattgtg gaccaggacc   4620
agctgagcaa acacagttgc agagtagcct cctatgttgc taagaagctc ctgctaccca   4680
ggtgctttga acaattgagt gctccctctg gttaagtaga gatggcacca ccggagtttt   4740
tcttggatgt gaggctcaat cctttacggc agctattata acaaagtgaa ggttttctcc   4800
ctgggaaatg cagcttttct ctgtctttac taattctgcc agcctgtgag agtaaccacc   4860
```

```
gtagctgggc ttcttctcag attaattgtc atgccaggtc tccttcctgg ggagctgtga    4920
tgctgctctg aggttgattg ctgaggttgt agtgggtttt tgtttgtttt tgtttagttt    4980
ttcttgattg ttcttctttc tcttgaatgg caagagaaga aacactttct ctaacccacg    5040
gccaggaagg aaatggggag agagctactt cttagttcaa cctggttgcc acataaagga    5100
atctctctcc ttggactcag cccctaactg gaagcaagag ccactgccct ctgagactga    5160
gagagcagcc cgaggaggag atgaatccat tctgcccttt gtttgggttt gcttcctgtc    5220
agtgagagaa tgctgaggca gttcctgtta tgtgaaactt tcattttaa aaccaggaca     5280 gtcctaaaca gactggaatg agttggtcaa tcccagttgg tataggccca atgattttg      5340 ctagtaagat aggattgtct tcctcaccca aaatgccttc aagtgcccta aatgggtat      5400 tttaaaataa gaataaataa tgtagattta gtagaaaacc tggaaaacat aagaaacaaa    5460
gatgaaacga aaagtcccat gtaattccac cagttagagt taaccactga tatcgtttgg   5520
atatatggct ttctagtctt gtggatatcc ttttaatctc ttgtaatata aagtctgacc    5580
atatgtgtcc ttgcatttgt ttgtactgga ctctgttaat atttctatag taatggctca    5640
ctttggggag attgtgctgc acagtgtgta ggaagcacat tgggtgtatt attcccagtt    5700
ttgtattttg tatttccttg gagatgtgca ggggttaaga gcggggtct ggccatagct      5760 ggccacgtca gactctcata tggtaagtat cacagagcac atgaggcctg tgttatgcgc    5820
tggaaagact caggaaatga gaggctctct tgttctgaca aggcaggctg agagctctca    5880
tttagggtca tcactccaga taactccaaa tgcagtttat tgctcaactg aagcagatga    5940
tcactttttg cctccaagtt cttcaccta gctagctcct ttcaaagagc cgagtatgct     6000
ggatcttaaa gggccaaact agttacatct catacatttc ctgatgttta gggatgcctt    6060
cacttccatc aaggatacct tggctgtgca aggacctctg atagctggag tctccttttg    6120
gtcactccca gctttgctta aacttgatgg agtttgctgt ccagtgatcc ccggatcttt    6180
catcatgaaa gccttccttc ctctcctgat gtctcaggcc tctagaccta gactggggtt    6240
ctggcaagga ggcctctatc aatagtatga catccaataa tatgttagtg ttgatatttt    6300
gcacagtaat attaagttta agagattata aaatgagtt caaatgaata agttcctgtg     6360
atgtaagaga ttagatatgt gtgatttcag aaccaaaggc agggggaat cccagaaaga     6420 aaacaataat ataatcctag tttctatata ttatttttat tcattactgt atatgggtag    6480
agatcaatat tctttcttat gctgttacta ttaattaaca catttttaa ccatgccatt     6540 gaacttttgg gtgcattaaa gtggaaccca agctcctcat tagataataa tggcatttgg    6600
actgagtgcc atattcctaa atttccaata aagtggttga tatagagagg acaggataaa    6660
gccctatagt gtgcagttat atcaaaacag ctagtctcca ctttagggaa tgcctttact    6720
agagattaca tgaaatgtct gcttataaaa taagcagaga tggcaccact aagcagccac    6780
ctgaattgtt ttcctacagg aatgattact tttcagatcc atttatgttt tcatgctcaa    6840
tacttactcc ccttccctgc aacacccaaa gagtttactt ttgcaagtca tttggtcttc    6900
agtctactac tgaggaatag agaggcacta actgctttac ccaggatcag aactcatgtt    6960
cttaccttct attaatagag tacttgagcc agatggacta actggtctca cattttctct    7020
atcttggttt tacttccata aacatcaata tctttaccca catgattttt ccatcctccc    7080
atttttttcc atatgtatta gggttcagga actatgatgc taatgatcac atttcttcct    7140
agttcctaat ttcattagtg ccatttcctg atatctacag aaacaattat caatacatgt    7200
```

| | |
|---|---|
| agctgcttga gccttattta gaaggctagc cttttctttttc caagtgctgt cagaatgtat | 7260 |
| acatttagtc tgtctttttc ccttttagga gtctttgttc tgggttgatg gcaaaattcc | 7320 |
| tcttttttaca tgtgagattt ttgatttcac tgaattctac ctagattttt atggacattg | 7380 |
| gattttaaag aggaaaacac tcattttctt agtaagatat tggtgataca tagctatgcc | 7440 |
| attgatttcc atactcctga gctttgggga gggagacagt ggccaagtag caggcagaat | 7500 |
| aagatcatca ctcatgtcct gaatcaatca cactttcctt ctcggattgt gtatatgctc | 7560 |
| tgccacttcc tacatattac atcctgagtt tttaagtaaa gtggatctta gccagatttg | 7620 |
| agtctaatgg ctgattcatc ggcatagttc ttggcgttaa catctcagtg tcctctttag | 7680 |
| ttctctttga ggattcatgt cattgagggc ctttgtgcct ccacttgtct cagtatgagg | 7740 |
| aagaactttg gtgtgagggc ggagctatgt gaagggttgc tgggttgggg gattagttca | 7800 |
| tatggtcccc atgccatcta tttacttttg gagagagggg actttgagtg ggtgggtatg | 7860 |
| gatagatgtt cctcaaggaa accctgctgg ctaatgggca ctacatctgt gtattactgt | 7920 |
| gattctctct gtaagctccc catgtggcca aggaccccc tcctaccagg gcacttcctg | 7980 |
| ccacctcatt gcactggtct caaccattca gcctgctgct gctgcaccat gttgggctgc | 8040 |
| ggtaggatag ggaaggggtt ctgttgattg ctaaatgttg cctaacttta tttccctctc | 8100 |
| ccacatttca tgcaagggag cggacctaac acatgacttg cattctcttc ctatgttcag | 8160 |
| aaactccagg gcttgcccac gtgtatgtat gagtgaccaa tggagcttgg aattcttttat | 8220 |
| ctatatgatc tgtccgaaaa tgagatcttt tgtactggaa tttgtgatgt agttgatcat | 8280 |
| tcagagccaa acgcatatac caataaagac aagactgtca tataaaaaaa aaaaaaaaaa | 8340 |

<210> SEQ ID NO 7
<211> LENGTH: 8292
<212> TYPE: DNA
<213> ORGANISM: Homo sapiens

<400> SEQUENCE: 7

| | |
|---|---|
| actaattttc tggagtttct gccccctgctc tgcgtcagcc ctcacgtcac ttcgccagca | 60 |
| gtagcagagg cggcggcggc ggctcccgga attgggttgg agcaggagcc tcgctggctg | 120 |
| cttcgctcgc gctctacgcg ctcagtcccc ggcggtagca ggagcctgga cccaggcgcc | 180 |
| gccggcgggc gtgaggcgcc ggagcccggc ctcgaggtgc ataccggacc cccattcgca | 240 |
| tctaacaagg aatctgcgcc ccagagagtc ccgggagcgc cgccggtcgg tgcccggcgc | 300 |
| gccgggccat gcagcgacgg ccgccgcgga gctccgagca gcgtagcgc cccctgtaa | 360 |
| agcggttcgc tatgccgggg ccactgtgaa ccctgccgcc tgccggaaca ctcttcgctc | 420 |
| cggaccagct cagcctctga taagctggac tcggcacgcc cgcaacaagc accgaggagt | 480 |
| taagagagcc gcaagcgcag ggaaggcctc cccgcacggg tgggggaaag cggccggtgc | 540 |
| agcgcgggga caggcactcg ggctggcact ggctgctagg gatgtcgtcc tggataaggt | 600 |
| ggcatggacc cgccatggcg cggctctggg gcttctgctg gctggttgtg ggcttctgga | 660 |
| gggccgcttt cgcctgtccc acgtcctgca aatgcagtgc ctctcggatc tggtgcagcg | 720 |
| acccttctcc tggcatcgtg gcatttccga gattggagcc taacagtgta gatcctgaga | 780 |
| acatcaccga aattttcatc gcaaaccaga aaaggttaga aatcatcaac gaagatgatg | 840 |
| ttgaagctta tgtgggactg agaaatctga caattgtgga ttctggatta aaatttgtgg | 900 |
| ctcataaagc atttctgaaa aacagcaacc tgcagcacat caattttacc cgaaacaaac | 960 |
| tgacgagttt gtctaggaaa catttccgtc accttgactt gtctgaactg atcctggtgg | 1020 |

```
gcaatccatt tacatgctcc tgtgacatta tgtggatcaa gactctccaa gaggctaaat    1080
ccagtccaga cactcaggat ttgtactgcc tgaatgaaag cagcaagaat attccctgg    1140 caaacctgca gatacccaat tgtggtttgc catctgcaaa tctggccgca cctaacctca    1200
ctgtggagga aggaaagtct atcacattat cctgtagtgt ggcaggtgat ccggttccta    1260
atatgtattg ggatgttggt aacctggttt ccaaacatat gaatgaaaca agccacacac    1320
agggctcctt aaggataact aacatttcat ccgatgacag tgggaagcag atctcttgtg    1380
tggcggaaaa tcttgtagga gaagatcaag attctgtcaa cctcactgtg cattttgcac    1440
caactatcac atttctcgaa tctccaacct cagaccacca ctggtgcatt ccattcactg    1500
tgaaaggcaa ccccaaacca gcgcttcagt ggttctataa cggggcaata ttgaatgagt    1560
ccaaatacat ctgtactaaa atacatgtta ccaatcacac ggagtaccac ggctgcctcc    1620
agctggataa tcccactcac atgaacaatg gggactacac tctaatagcc aagaatgagt    1680
atgggaagga tgagaaacag atttctgctc acttcatggg ctggcctgga attgacgatg    1740
gtgcaaaccc aaattatcct gatgtaattt atgaagatta tggaactgca gcgaatgaca    1800
tcggggacac cacgaacaga agtaatgaaa tcccttccac agacgtcact gataaaaccg    1860
gtcgggaaca tctctcggtc tatgctgtgg tggtgattgc gtctgtggtg ggattttgcc    1920
ttttggtaat gctgtttctg cttaagttgg caagacactc caagtttggc atgaaaggcc    1980
cagcctccgt tatcagcaat gatgatgact ctgccagccc actccatcac atctccaatg    2040
ggagtaacac tccatcttct tcggaaggtg gcccagatgc tgtcattatt ggaatgacca    2100
agatccctgt cattgaaaat ccccagtact ttggcatcac aacagtcag ctcaagccag    2160 acacatggcc cagaggttcc cccaagaccg cctgataata atttggtatt tggaggctcc    2220
tgtgtcactg caggaactaa aggaggctaa atccatgcct gatggaggag aagagttcta    2280
tggttatctg caaattctgg ccagacaaca tcttgacgtc actccttagc ttccataacc    2340
tagccaagca agaagttgcc tttccaagac aaagcagtgt gctctaatga ctaaccctc    2400 aaagtactat gccactttaa ctatagaccc atctcctcga tcaatcagga tggcaagatg    2460
gagctgagga gctcagcaac atcaagtctg gagttggtct ttaactcaac tagctcgttt    2520
agacgtgtct gaacaccaca tcacctgaca gcacggggtg gtttcccagt aaaatttaca    2580
aactcagctc aagggcagct gtgttgcttt cctttccttg actgctgaga aacttttga    2640 cagggaacaa tggaaacaca ccttctgagc tgaaacaaac aaacagaaac aaaacatact    2700
aaccagcaaa atccccaaat catcaatctt gggttctctt gaagggcagg agtgtgtttt    2760
atcttctccc gtcggagcaa acactataga tgtcctccct aaaattctgt cttccctaga    2820
gcagccttgt aaattagcta gggtcctagg gttgaggcct aaatcaactt aaaattgtct    2880
ctaaatatgt acctggatgt gtttgtactt gcagagcatg ccctcttcat gtgcctaggg    2940
ctagtaactc cctgtggcag aggcatgtaa agtattctga ctttttttt ttcaacttaa    3000 ttccatttcc aatgaaatgg attttttaaaa attttctcca gagtgtgcca tacttctcca    3060
gctattatag ttaatgtgtg tgtatccttg tgtatatgtg tgtttgtgtg tgcatatgtg    3120
ttttcctagt ggttacatgc ttactaggca attatgtaaa taagcacaga ttcataggcc    3180
agctaggcct gaggaaagaa gacattataa agggagggag tattttaaca ttagctaaag    3240
ctatcacaca aggcacccat tctgctcccc tcaacagcca cagcccactt cgtccttgtc    3300
ttaccaataa ggggaaaggc tggaggtgat atttttcaca gaaccgcaga ggttttgaac    3360
```

```
atatttgcaa cattactttg agtacacatg agcaaaaatt ctgaattaca tccaggaccc    3420
cagaagctca ttagatcaaa gagtgcgggg cccctcagag ttaccagaga ttatctgcag    3480
acttcagtgc aatcgaatga ccatggtcca ttttgatggt cagaggtagg actgaaaaac    3540
gggtagaaac aattgcttta gcgcttcctt ctgtactttg cctattaatg ttttgtcttt    3600
caaaaatata ttttctccta attgtttaat tggccaaata atggctgctt tgggagttgt    3660
ttgtatgcct tggaaggcca tggcctgcac tttaaaaata agctaagtcc attctgccca    3720
gcacgagcat taggacagag aatgcactta ttttaggatc cttaaaaatt gcttctttta    3780
tggcacactg ggttgacgac tcatctcgtg ggagccttca tggcacattg ctgctgttct    3840
gcaggtccca atacaattcc ttcccctct cagtgccacg gccccccat tgctagctac      3900
aacaatttga tatcatattc ccttttcaac tccaaaggag atgataagaa gctatcaaat    3960
aatgctttaa aaagcaact tgagtttctt aaaagaaagg aaatgaatac atgctgcata    4020
attacattta aaatgtaagc catgttatta taagccgcac tgagatgaag atttgttagc    4080
aaaccagttt caagcacact cacagtgaag taaaatcatg ttttagcat ctgaccattg    4140
ggtaatatta ttctttgtta tcaaaagaga aatatcaccc aagtatagta tacttagacc    4200
tcctagagga aacactccag tcctaagctt ggtgtctgaa aagaaaaaca aaataaaga    4260
ttatggattt aggtcaggga gacagagtga tattctgaag actgtgttta ctccctcatc    4320
atcggccaac caagatggag ttctgcatcc tgcacatatc agacatttca gtccaatttc    4380
accaaagcat cagtgatgtt ctagaagcat cccagcagat ggaggatcct aatgtatttg    4440
ttctgggtat ttcccaaggc ccagcctgac tggagtgtgt gtaccaacag gatgaatcca    4500
atcaagctac gccccccattt tggtttcgga ttggccactc ttgcatgtgc tagtagattg    4560
tggaccagga ccagctgagc aaacacagtt gcagagtagc ctcctatgtt gctaagaagc    4620
tcctgctacc caggtgcttt gaacaattga gtgctccctc tggttaagta gagatggcac    4680
caccggagtt tttcttggat gtgaggctca atcctttacg gcagctatta taacaaagtg    4740
aaggttttct ccctgggaaa tgcagctttt ctctgtcttt actaattctg ccagcctgtg    4800
agagtaacca ccgtagctgg gcttcttctc agattaattg tcatgccagg tctccttcct    4860
ggggagctgt gatgctgctc tgaggttgat tgctgaggtt gtagtgggtt tttgtttgtt    4920
tttgtttagt ttttcttgat tgttcttctt tctcttgaat ggcaagagaa gaaacacttt    4980
ctctaaccca cggccaggaa ggaaatgggg agagagctac ttcttagttc aacctggttg    5040
ccacataaag gaatctctct ccttggactc agccctaac tggaagcaag agccactgcc     5100
ctctgagact gagagagcag cccgaggagg agatgaatcc attctgccct tgtttgggt     5160
ttgcttcctg tcagtgagag aatgctgagg cagttcctgt tatgtgaaac tttcattttt    5220
aaaaccagga cagtcctaaa cagactggaa tgagttggtc aatcccagtt ggtataggcc    5280
caatgatttt tgctagtaag ataggattgt cttcctcacc caaaatgcct tcaagtgccc    5340
taaaatgggt attttaaaat aagaataaat aatgtagatt tagtagaaaa cctggaaaac    5400
ataagaaaca aagatgaaac gaaaagtccc atgtaattcc accagttaga gttaaccact    5460
gatatcgttt ggatatatgg cttctagtc ttgtggatat ccttttaatc tcttgtaata     5520
taaagtctga ccatatgtgt ccttgcattt gtttgtactg gactctgtta atatttctat    5580
agtaatggct cactttgggg agattgtgct gcacagtgtg taggaagcac attgggtgta    5640
ttattcccag ttttgtattt tgtatttcct tggagatgtg caggggttaa gagcgggggt    5700
ctggccatag ctggccacgt cagactctca tatggtaagt atcacagagc acatgaggcc    5760
```

```
tgtgttatgc gctggaaaga ctcaggaaat gagaggctct cttgttctga caaggcaggc   5820
tgagagctct catttagggt catcactcca gataactcca aatgcagttt attgctcaac   5880
tgaagcagat gatcactttt tgcctccaag ttcttcaccc tagctagctc ctttcaaaga   5940
gccgagtatg ctggatctta aagggccaaa ctagttacat ctcatacatt tcctgatgtt   6000
tagggatgcc ttcacttcca tcaaggatac cttggctgtg caaggacctc tgatagctgg   6060
agtctccttt tggtcactcc cagctttgct taaacttgat ggagtttgct gtccagtgat   6120
ccccggatct ttcatcatga aagccttcct tcctctcctg atgtctcagg cctctagacc   6180
tagactgggg ttctggcaag gaggcctcta tcaatagtat gacatccaat aatatgttag   6240
tgttgatatt ttgcacagta atattaagtt taagagatta taaaaatgag ttcaaatgaa   6300
taagttcctg tgatgtaaga gattagatat gtgtgatttc agaaccaaag caggggggga   6360
atcccagaaa gaaaacaata atataatcct agtttctata tattattttt attcattact   6420
gtatatgggt agagatcaat attctttctt atgctgttac tattaattaa cacatttttt   6480
aaccatgcca ttgaactttt gggtgcatta aagtggaacc caagctcctc attagataat   6540
aatggcattt ggactgagtg ccatattcct aaatttccaa taaagtggtt gatatagaga   6600
ggacaggata aagccctata gtgtgcagtt atatcaaaac agctagtctc cactttaggg   6660
aatgccttta ctagagatta catgaaatgt ctgcttataa aataagcaga gatggcacca   6720
ctaagcagcc acctgaattg ttttcctaca ggaatgatta cttttcagat ccatttatgt   6780
tttcatgctc aatacttact ccccttccct gcaacaccca aagagtttac ttttgcaagt   6840
catttggtct tcagtctact actgaggaat agagaggcac taactgcttt acccaggatc   6900
agaactcatg ttcttacctt ctattaatag agtacttgag ccagatggac taactggtct   6960 cacatttttct ctatcttggt tttacttcca taaacatcaa tatctttacc cacatgattt   7020
ttccatcctc ccatttttttt ccatatgtat tagggttcag gaactatgat gctaatgatc   7080
acatttcttc ctagttccta atttcattag tgccatttcc tgatatctac agaaacaatt   7140
atcaatacat gtagctgctt gagccttatt tagaaggcta gcctttcttt tccaagtgct   7200
gtcagaatgt atacatttag tctgtctttt tcccttttag gagtctttgt tctgggttga   7260
tggcaaaatt cctctttttta catgtgagat ttttgatttc actgaattct acctagattt   7320
ttatggacat tggattttaa agaggaaaac actcatttttc ttagtaagat attggtgata   7380
catagctatg ccattgattt ccatactcct gagctttggg gagggagaca gtggccaagt   7440
agcaggcaga ataagatcat cactcatgtc ctgaatcaat cacactttcc ttctcggatt   7500
gtgtatatgc tctgccactt cctacatatt acatcctgag ttttttaagta aagtggatct   7560 tagccagatt tgagtctaat ggctgattca tcggcatagt tcttggcgtt aacatctcag   7620
tgtcctcttt agttctcttt gaggattcat gtcattgagg gcctttgtgc ctccacttgt   7680
ctcagtatga ggaagaactt tggtgtgagg gcggagctat gtgaagggtt gctgggttgg   7740
gggattagtt catatggtcc ccatgccatc tatttacttt tggagagagg ggactttgag   7800
tgggtgggta tggatagatg ttcctcaagg aaaccctgct ggctaatggg cactacatct   7860
gtgtattact gtgattctct ctgtaagctc cccatgtggc caaggacccc cctcctacca   7920
gggcacttcc tgccacctca ttgcactggt ctcaaccatt cagcctgctg ctgctgcacc   7980
atgttgggct gcgtaggat agggaagggg ttctgttgat tgctaaatgt tgcctaactt   8040 tatttcccctc tcccacattt catgcaaggg agcggaccta acacatgact tgcattctct   8100
```

```
tcctatgttc agaaactcca gggcttgccc acgtgtatgt atgagtgacc aatggagctt    8160
ggaattcttt atctatatga tctgtccgaa aatgagatct tttgtactgg aatttgtgat    8220
gtagttgatc attcagagcc aaacgcatat accaataaag acaagactgt catataaaaa    8280
aaaaaaaaaa aa                                                       8292

<210> SEQ ID NO 8
<211> LENGTH: 549
<212> TYPE: DNA
<213> ORGANISM: Homo sapiens

<400> SEQUENCE: 8
acctccgcca ggaactgcag gcccacctgt ctgcaaccca gctgaggcca tgccctcccc      60
agggaccgtc tgcagcctcc tgctcctcgg catgctctgg ctggacttgg ccatggcagg     120
ctccagcttc ctgagccctg aacaccagag agtccagaga aaggagtcga agaagccacc     180
agccaagctg cagcccccgag ctctagcagg ctggctccgc ccggaagatg gaggtcaagc    240
agaaggggca gaggatgaac tggaagtccg gttcaacgcc ccctttgatg ttggaatcaa     300
gctgtcaggg gttcagtacc agcagcacag ccaggccctg ggaagtttc ttcaggacat      360 cctctgggaa gaggccaaag aggccccagc cgacaagtga tcgcccacaa gccttactca    420
cctctctcta gtttagaag cgctcatctg gcttttcgct tgcttctgca gcaactccca     480
cgactgttgt acaagctcag gaggcgaata atgttcaaa ctgtaaaaaa aaaaaaaaaa    540
aaaaaaaaa                                                          549

<210> SEQ ID NO 9
<211> LENGTH: 501
<212> TYPE: DNA
<213> ORGANISM: Homo sapiens

<400> SEQUENCE: 9
agttccccaa agataacaca gctttgcaca gtggatgttt acttgctggt ggtcttatct      60
aagatcaaca ttggcagctg tgcccggaga ggcctccagg gtccagcaga gaaaggagtc    120
gaagaagcca ccagccaagc tgcagccccg agctctagca ggctggctcc gcccggaaga   180
tggaggtcaa gcagaagggg cagaggatga actggaagtc cggttcaacg ccccctttga   240
tgttggaatc aagctgtcag gggttcagta ccagcagcac agccaggccc tggggaagtt   300
tcttcaggac atcctctggg aagaggccaa agaggcccca gccgacaagt gatcgcccac   360
aagccttact cacctctctc taagtttaga agcgctcatc tggcttttcg cttgcttctg   420
cagcaactcc cacgactgtt gtacaagctc aggaggcgaa taaatgttca aactgtaaaa   480
aaaaaaaaaa aaaaaaaaa a                                              501

<210> SEQ ID NO 10
<211> LENGTH: 498
<212> TYPE: DNA
<213> ORGANISM: Homo sapiens

<400> SEQUENCE: 10
agttccccaa agataacaca gctttgcaca gtggatgttt acttgctggt ggtcttatct      60
aagatcaaca ttggcagctg tgcccggaga ggcctccagg gtccagagaa aggagtcgaa    120
gaagccacca gccaagctgc agcccccgagc tctagcaggc tggctccgcc cggaagatgg   180
aggtcaagca gaaggggcag aggatgaact ggaagtccgg ttcaacgccc cctttgatgt   240
tggaatcaag ctgtcagggg ttcagtacca gcagcacagc caggccctgg ggaagtttct   300
```

```
tcaggacatc ctctgggaag aggccaaaga ggccccagcc gacaagtgat cgcccacaag    360
ccttactcac ctctctctaa gtttagaagc gctcatctgg cttttcgctt gcttctgcag    420
caactcccac gactgttgta caagctcagg aggcgaataa atgttcaaac tgtaaaaaaa    480
aaaaaaaaaa aaaaaaaa                                                  498

<210> SEQ ID NO 11
<211> LENGTH: 384
<212> TYPE: DNA
<213> ORGANISM: Homo sapiens

<400> SEQUENCE: 11
agttccccaa agataacaca gctttgcaca gtggatgttt acttgctggt ggtcttatct     60
aagatcaaca ttggcagctg tgcccggaga ggcctccagg gtccagttca acgccccctt    120
tgatgttgga atcaagctgt caggggttca gtaccagcag cacagccagg ccctggggaa    180
gtttcttcag gacatcctct gggaagaggc caaagaggcc ccagccgaca gtgatcgcc     240 cacaagcctt actcacctct ctctaagttt agaagcgctc atctggcttt tcgcttgctt    300
ctgcagcaac tcccacgact gttgtacaag ctcaggaggc gaataaatgt tcaaactgta    360
aaaaaaaaaa aaaaaaaaaa aaaa                                           384

<210> SEQ ID NO 12
<211> LENGTH: 1939
<212> TYPE: DNA
<213> ORGANISM: Homo sapiens

<400> SEQUENCE: 12
agtttggacg gctgcttccc accagcaaag accacgactg gagagccgag ccggaggcag     60
ctgggaaaca tgaagagcgt cttgctgctg accacgctcc tcgtgcctgc acacctggtg    120
gccgcctgga gcaataatta tgcggtggac tgccctcaac actgtgacag cagtgagtgc    180
aaaagcagcc cgcgctgcaa gaggacagtg ctcgacgact gtggctgctg ccgagtgtgc    240
gctgcagggc ggggagaaac ttgctaccgc acagtctcag gcatggatgg catgaagtgt    300
ggcccggggc tgaggtgtca gccttctaat ggggaggatc cttttggtga agagtttggt    360
atctgcaaag agcatgacat ggcatctgga gatggcaata ttgtgagaga agaagttgtg    420
aaagagaatg ctgccgggtc tcccgtaatg aggaaatggt taaatccacg ctgatcccgg    480
ctgtgatttc tgagagaagg ctctattttc gtgattgttc aacacacagc caacatttta    540
ggaactttct agattatagc ataaggacat gtaattttg aagaccaaat gtgatgcatg     600
gtggatccag aaaacaaaaa gtaggatact tacaatccat aacatccata tgactgaaca    660
cttgtatgtg tttgttaaat attcgaatgc atgtagattt gttaaatgtg tgtgtatagt    720
aacactgaag aactaaaaat gcaatttagg taatcttacg tggagacagg tcaaccaaag    780
agggagctag gcaaagctga agaccgcagt gagtcaaatt agttctttga ctttgatgta    840
cattaatgtt gggatatgga atgaagactt aagagcagga gaagatgggg agggggtggg    900
agtgggaaat aaaatattta gcccttcctt ggtaggtagc ttctctagaa tttaattgtg    960
cttttttttt tttttttggc tttgggaaaa gtcaaaataa acaaccaga aaaccccctga   1020 aggaagtaag atgtttgaag cttatggaaa tttgagtaac aaacagcttt gaactgagag   1080
caatttcaaa aggctgctga tgtagttccc gggttacctg tatctgaagg acggttctgg   1140
ggcataggaa acacatacac ttccataaat agctttaacg tatgccacct cagagataaa   1200
```

```
tctaagaagt attttaccca ctggtggttt gtgtgtgtat gaaggtaaat atttatatat    1260 tttataaat aaatgtgtta gtgcaagtca tcttccctac ccatatttat catcctcttg     1320
aggaaagaaa tctagtatta tttgttgaaa atggttagaa taaaactatg actctataag    1380
gttttcaaac atctgaggca tgataaattt attatccata attatagtaa taataacctt    1440
aataagcata agaaaaacag agtcactctg gatttcaaaa atgtcaaaaa atgagcaaca    1500
gagggtcctt atttaaacat aagtgctgtg acttaggtga atttttcaatt taaggtagaa   1560 aataagtttt taggaggttt gtaaaagaag aatcaatttt cagcagaaaa catgtcaact    1620
ttaaaatata gtttatttttc atatttttttt cttttaaact tggttgataa gtggaattag   1680
gagtatattt gaaagaatct tagcacaaac aggactgttg tactagatgt tcttaggaaa    1740
tatctcagaa gtattttatt tgaagtgaag aacttattta agaattattt cagtatttac    1800
ctgtatttta ttcttgaagt tggccaacag agttgtgaat gtgtgtggga aggcctttga    1860
atgtaaagct gcataagctg ttaggttttg ttttaaaagg acatgtttat tattgttcaa    1920
taaaaaagaa caagataca                                                  1939

<210> SEQ ID NO 13
<211> LENGTH: 882
<212> TYPE: DNA
<213> ORGANISM: Homo sapiens

<400> SEQUENCE: 13 cacccttttcc agatacacac ccgtttagtg cgagaaatgg agcggttggg gagaggatct    60
cccgaggggg ctggattgag aatgggtacc atttgagatc tcctaggagg ccggccatcg   120
ggcaatgtct gatggagtcc agccggtgga ggagactgaa aggaaacagc ctgcttcctg    180
caggtccgcg ggagggaggt ctttaagtgc gtttgtgcag ccgatttcaa ggctaagaga    240
gaaagactgc ctctgatccc tgaaggaaga aaaaaaaaaa aaaacagga aaaaaactca    300 acatggaaaa tgtccccaag gaaaacaaag ttgtggagaa ggccccagtg cagaatgaag    360
cccccgcttt aggaggtggt gaataccagg agcctggagg aaatgttaaa ggggtttggg    420
ctccacctgc cccgggtttt ggagaggatg tgcccaatag gcttgtcgat aacattgata    480
tgatagatgg agatggagat gatatggaac ggttcatgga ggagatgaga gagctaagga    540
ggaaaattag ggaacttcag ttgaggtaca gtctgcgcat tcttataggg gacccctcctc   600 accatgatca tcatgatgag ttttgcctta tgccttgaat cttgaggtta ataatcataa    660
aatccctgct ttctaaaattc gcattttttcc tggtgtacct ttaatgtgaa ccttttggca    720
ttcttctgca atttttctgat tggagattgc attttgacct agtctgtaag tttttctgtc    780
agaagaggac tttcatcaac tttcatggaa agatgtttat tgcatactgt aaagttaata    840
agcaatttta aaagcagtct aaaaaaaaaa aaaaaaaaa aa                         882

<210> SEQ ID NO 14
<211> LENGTH: 1278
<212> TYPE: DNA
<213> ORGANISM: Homo sapiens

<400> SEQUENCE: 14
ccattggcct gtagattcac ctcccctggg cagggcccca ggacccagga taatatctgt    60
gcctcctgcc cagaaccctc caagcagaca caatggtaag aatggtgcct gtcctgctgt   120
ctctgctgct gcttctgggt cctgctgtcc cccaggagaa ccaagatggt cgttactctc    180
tgacctatat ctacactggg ctgtccaagc atgttgaaga cgtccccgcg tttcaggccc    240
```

```
ttggctcact caatgacctc cagttctttta gatacaacag taaagacagg aagtctcagc    300
ccatgggact ctggagacag gtggaaggaa tggaggattg aagcaggac agccaacttc      360 agaaggccag ggaggacatc tttatggaga ccctgaaaga catcgtggag tattacaacg     420
acagtaacgg gtctcacgta ttgcaggaa ggtttggttg tgagatcgag aataacagaa       480
gcagcggagc attctggaaa tattactatg atggaaagga ctacattgaa ttcaacaaag    540
aaatcccagc ctgggtcccc ttcgacccag cagcccagat aaccaagcag aagtgggagg    600
cagaaccagt ctacgtgcag cgggccaagg cttacctgga ggaggagtgc cctgcgactc    660
tgcggaaata cctgaaatac agcaaaaata tcctggaccg gcaagatcct ccctctgtgg    720
tggtcaccag ccaccaggcc ccaggagaaa agaagaaact gaagtgcctg gcctacgact    780
tctacccagg gaaaattgat gtgcactgga ctcgggccgg cgaggtgcag gagcctgagt    840
tacggggaga tgttcttcac aatggaaatg gcacttacca gtcctgggtg gtggtggcag    900
tgcccccgca ggacacagcc cctactcct gccacgtgca gcacagcagc ctggcccagc      960
ccctcgtggt gccctgggag gccagctagg aagcaagggt tggaggcaat gtgggatctc    1020
agacccagta gctgcccttc ctgcctgatg tgggagctga accacagaaa tcacagtcaa    1080
tggatccaca aggcctgagg agcagtgtgg ggggacagac aggaggtgga tttggagacc    1140
gaagactggg atgcctgtct tgagtagact tggacccaaa aaatcatctc accttgagcc    1200 caccccacc ccattgtcta atctgtagaa gctaataaat aatcatccct ccttgcctag      1260
cataaaaaaa aaaaaaaa                                                    1278

<210> SEQ ID NO 15
<211> LENGTH: 1801
<212> TYPE: DNA
<213> ORGANISM: Homo sapiens

<400> SEQUENCE: 15
gggttatatg atctctttgg ctttagggaa ttactccata ccagctctga gatttccagc      60
tcagcgatgc ccccaggtcc ctgggagagc tgcttctggg tggggggcct cattttgtgg    120
ctcagcgttg gaagttcagg ggatgcacct cctaccccac agccaaagtg cgctgacttc    180
cagagcgcca accttttga aggcaccgat ctcaaagtcc agtttctcct ctttgtccct      240
tcgaatccta gctgtgggca gctagtagaa ggaagcagtg acctccaaaa ctctgggttc     300
aatgccactc tgggaaccaa actaattatc catggattca gggtttttagg aacaaagcct    360 tcctggattg acacatttat tagaacccctt ctgcgtgcaa cgaatgctaa tgtgattgcc    420
gtggactgga tttatgggtc tacaggagtc tacttctcag ctgtgaaaaa tgtgctgggt    480
gtgtcggaat cctcaatcca catcattggt gttagcctgg ggcccacgt tgggggcatg     540 gtgggacagc tcttcggagg ccagctggga cagatcacag gcctggaccc cgctggacct    600
gagtacacca gggccagtgt ggaagagcgc ttggatgctg gagatgccct cttcgtggaa    660
gccatccaca cagacaccga caatttgggt attcggattc ccgttggaca tgtggactac    720
ttcgtcaacg gaggccaaga ccaacctggc tgccccacct tctttttacgc aggttatagt    780 tatctgatct gtgatcacat gagggctgtg cacctctaca tcagcgccct ggagaattcc    840
tgtccactga tggcctttcc ctgtgccagc tacaaggcct tccttgctgg acgctgtctg    900
gattgcttta acccttttct gctttcctgc ccaaggatag gactggtgga acaaggtggt    960
gtcaagatag agccgctccc caaggaagtg aaagtctacc tcctgactac ttccagtgct   1020
```

```
ccgtactgca tgcatcacag cctcgtggag tttcacttga aggaactgag aaacaaggac    1080
accaacatcg aggttacctt ccttagcagt aacatcacct cttcatctaa gatcaccata    1140
cctaagcagc aacgctatgg gaaaggaatc atagcccatg ccaccccaca atgccagata    1200
aaccaagtga aattcaagtt tcagtcttcc aaccgagttt ggaaaaaaga ccggactacc    1260
attattggga agttctgcac tgcccttttg cctgtcaatg acagagaaaa gatggtctgc    1320
ttacctgaac cagtgaactt acaagcaagt gtgactgttt cctgtgacct gaagatagcc    1380
tgtgtgtagt ttaacctggg caggacacat ctccctgcat ttttttttt ttttgagag     1440 agaggtgtga tgagggatgt gtgtgtgcag cttattgtag accattacta ctaaggagaa    1500
aagcaaagct ctttcttatt ttcctcataa tcagctaccc tggaggggag ggagaactca    1560
ttttacagaa cttggtttcc tttgccgatc ttatgtacat acccatttta gctttcccat    1620
gcatacttaa ctgcacttgc tttatctcct tgggcattcg tacttaggat tcaatagaaa    1680
catgtacagg gtaaacaatt ttttaaaaat aaaacttcat ggagtatctg aaaaaaaaaa    1740
aaaaaaaaaa aaaaaaaaa  aaaaaaaaaa aaaaaaaaaa aaaaaaaaaa aaaaaaaaaa    1800
a                                                                    1801

<210> SEQ ID NO 16
<211> LENGTH: 1647
<212> TYPE: DNA
<213> ORGANISM: Homo sapiens

<400> SEQUENCE: 16
gggttatatg atctctttgg ctttagggaa ttactccata ccagctctga gatttccagc      60
tcagcgatgc ccccaggtcc ctgggagagc tgcttctggg tgggggggcct cattttgtgg    120 ctcagcgttg gaagttcagg gttttaggaa caaagccttc ctggattgac acatttatta    180
gaacccttct gcgtgcaacg aatgctaatg tgattgccgt ggactggatt tatgggtcta    240
caggagtcta cttctcagct gtgaaaaatg tgattaagtt gagcctcgag atctcccttt    300
tcctcaataa actcctggtg ctgggtgtgt cggaatcctc aatccacatc attggtgtta    360
gcctgggggc ccacgttggg ggcatggtgg gacagctctt cggaggccag ctgggacaga    420
tcacaggcct ggaccccgct ggacctgagt acaccagggc cagtgtggaa gagcgcttgg    480
atgctggaga tgccctcttc gtggaagcca tccacacaga caccgacaat ttgggtattc    540
ggattcccgt tggacatgtg gactacttcg tcaacggagg ccaagaccaa cctggctgcc    600
ccaccttctt ttacgcaggt tatagttatc tgatctgtga tcacatgagg gctgtgcacc    660
tctacatcag cgccctggag aattcctgtc cactgatggc ctttccctgt gccagctaca    720
aggccttcct gctggacgc  tgtctggatt gctttaaccc ttttctgctt tcctgcccaa    780
ggataggact ggtggaacaa ggtggtgtca agatagagcc gctccccaag gaagtgaaag    840
tctacctcct gactacttcc agtgctccgt actgcatgca tcacagcctc gtggagtttc    900
acttgaagga actgagaaac aaggacacca acatcgaggt taccttcctt agcagtaaca    960
tcacctcttc atctaagatc accataccta agcagcaacg ctatgggaaa ggaatcatag    1020
cccatgccac cccacaatgc cagataaacc aagtgaaatt caagtttcag tcttccaacc    1080
gagtttggaa aaaagaccgg actaccatta ttgggaagtt ctgcactgcc ttttgcctg    1140 tcaatgacag agaaagatg gtctgcttac ctgaaccagt gaacttacaa gcaagtgtga    1200
ctgtttcctg tgacctgaag atagcctgtg tgtagtttaa cctgggcagg acacatctcc    1260
ctgcattttt tttttttttt tgagagagag gtgtgatgag ggatgtgtgt gtgcagctta    1320
```

| | |
|---|---|
| ttgtagacca ttactactaa ggagaaaagc aaagctcttt cttattttcc tcataatcag | 1380 |
| ctaccctgga ggggagggag aactcatttt acagaacttg gtttcctttg ccgatcttat | 1440 |
| gtacataccc attttagctt tcccatgcat acttaactgc acttgcttta tctccttggg | 1500 |
| cattcgtact taggattcaa tagaaacatg tacagggtaa acaattttt aaaaataaaa | 1560 |
| cttcatggag tatctgaaaa aaaaaaaaaa aaaaaaaaa aaaaaaaaaa aaaaaaaaaa | 1620 |
| aaaaaaaaaa aaaaaaaaaa aaaaaaa | 1647 |

<210> SEQ ID NO 17
<211> LENGTH: 5622
<212> TYPE: DNA
<213> ORGANISM: Homo sapiens

<400> SEQUENCE: 17

| | |
|---|---|
| ggcacgtgga ctcccttta tccagtgact gtcaggtcga tcatatgccg aggacgatga | 60 |
| tcccgccggg ggagtgcacg tacgcggccc ggaagcggag gaggccctg cagaaacaga | 120 |
| ggcccgccgt gggggcagag aagtccaacc cctccaagcg acaccgggac cgcctcaacg | 180 |
| ccgagttgga ccacctggcc agcctgctgc cgttcccgcc tgacatcatc tccaagctgg | 240 |
| acaagctttc tgtcctgcgc ctcagtgtca gttacctccg ggtgaagagc ttcttccaag | 300 |
| tcgtgcagga gcagagctca cggcagcctg cggccggcgc ccctcgccc ggagacagct | 360 |
| gtcctcttgc agggtctgcc gtgctggagg aaggctgct gttggagtct cttaatggct | 420 |
| ttgctctggt cgtgagtgca gaagggacga tattttatgc atcagcaacg atcgtggact | 480 |
| atctgggctt ccatcagacg gatgtaatgc accagaacat ttatgactac atccacgtgg | 540 |
| acgaccgcca ggacttctgc cggcagctcc actgggccat ggaccctccc caggtggtgt | 600 |
| tgggcagcc ccgcccttg gagacaggag atgatgctat cctggggagg ctgctcaggg | 660 |
| cccaggagtg gggcacaggc acgcccaccg agtactcggc cttcctgacc cgctgcttca | 720 |
| tctgccgtgt gcgctgcctg ctggacagca cctcgggctt cctgacgatg cagttttcaag | 780 |
| gaaaactaaa attcctgttt ggacagaaga agaaggcgcc gtcaggagcc atgctcccgc | 840 |
| cgcggctgtc gctgttctgc attgcggcac ccgttctcct cccctccgca gcggagatga | 900 |
| aaatgaggag cgcgctcctg agggcaaaac ccagagcaga caccgcagcc accgcggatg | 960 |
| caaaagtaaa agccaccacc agtctgtgcg aatcggaact gcatggaaaa cccaattact | 1020 |
| cagcaggaag gagcagcaga gagagcggcg ttttggtgct cagggaacag actgacgctg | 1080 |
| gccgatgggc acaggttccc gccagggccc catgcctgtg cctccggggt ggccctgacc | 1140 |
| ttgtccttga ccccaagggg ggctcagggg acagggagga ggagcagcac aggatgctga | 1200 |
| gcagggcctc tggagtgaca gggcggaggg agactccagg acccacaaag cccctgccct | 1260 |
| ggacagcggg aaagcacagt gaggatggtg ccaggccgag gctgcagccc agcaagaatg | 1320 |
| acccgccctc cctgcgcccc atgccccgcg gctcctgcct gccctgcccg tgtgtccagg | 1380 |
| gcactttcag gaactcgccc atctctcacc cgccgagccc gtccccagt gcctactcca | 1440 |
| gccggaccag cagacccatg cgggatgtcg gtgaggacca ggtgcaccct cccctctgcc | 1500 |
| actttcccca gaggagcctg cagcaccagc tccctcagcc tggagctcag cgttttgcca | 1560 |
| cgaggggcta tcccatggag gacatgaagc tgcaaggtgt accgatgcct ccggggggacc | 1620 |
| tgtgtggtcc gacgctgctg ctagatgtgt ccatcaagat ggagaaggac tctgggtgtg | 1680 |
| agggtgctgc agacggctgt gtgcccagcc aggtgtggct gggggccagt gacaggagcc | 1740 |

```
acccagccac cttccctacc aggatgcacc tgaaaacaga gccagactct cggcaacagg    1800
tgtacatctc gcacctgggg cacggcgtgc gggggggctca gccccatggg agggccactg   1860
ctgggcgcag cagggagctg accccttttcc accctgcaca ctgtgcctgc ctggagccca   1920
cagacggcct tccccagtcg gagcctcccc accagctctg tgcacggggc cgaggtgaac    1980
agtcctgcac ctgcagagct gctgaggccg cccctgtggt caagcgggag cccttggact    2040
caccccagtg ggctactcac agccagggaa tggtgcccgg gatgttgccc aaaagtgcct    2100
tggccacgct ggtcccgccc caagcttcgg ggtgcacatt cctgccatag cgcagtgacc    2160
accatccaag ctcagatctg tgtgtctacg ctcagatgcg tcggtggctg ggctgccctg    2220
ctcctggtca ggccggagcc cgtcctaaga cacacgcttt gcagagctgt gcatgcgcag    2280
tctgctagtg tgtgtgtgca gcatacgcag gagcctatcc tgaattttgt aaaatatccc    2340
aacagttctt aaatgaaaac tggccttaag tctattcaag catgacagca tttctctttg    2400
aggaattaaa atctttagga aagtgatcat ggctggacag cttcatgccc cagaggcagc    2460
gagcacccgt cccatggctg ccaagtccac agtcggggat gaagcagtcg ggtgatgctc    2520
ccaagtccgc agtcggggat gaagcggtcg ggtgatgctc ccaagtccgc agtcggggat    2580
gaagcggtcg ggtgacacac ctagctcagc cctcccaggc cacctgcagc tcccagcctg    2640
tgctgtgcag gcagggtcag cccatcgcca cagtgcactg tagaggccag cacacggcaa    2700
attagaaata caacacgcgg agaaagggggt ccgtgagccc actcatagag gaatctagaa    2760
cgttccaggc agcagaggct ggcagcgtgg gtcccacact gccccacacc gtgcggcagg    2820
tgctccatgg cgccatgaca gagtctgagg ccagacctgg actggaattg acagcataac    2880
ccctgttcct tctggacatc tcccgagttc tcagtgggtc tctgcggacg gttcttccta    2940
atctgcctct tggtacatca cgtaatacag agttcacaga ctccgggttt ggaagtacag    3000
agaaacacac aacgtagaga aagacacag gaaactgcgc tgcctgtggg ggtttctctc    3060
tggctggctg tacagttcac tcaaatgagg gttcccattg ccatcctagg agaataatta    3120
gggacaagac agacaagtat taatagcatt aaaacagttg taaaggcgat attttctgag    3180
agtaggaaat ttggatacaa aagcataagt cagaaagtga aggtcaccaa tccaccaacc    3240
cgagaaccta cagctgatgg tgcatttcag gcttcttcca cggtctggcc tggaaccccca    3300 cccggctggt gcaggcatca gatcaggtg tagaagtcac cccaagcaag aggaagccag    3360
gcagtgaggc cctggggtgt ggctgcagct gggcccacct gtgcgggggt gggaaggccc    3420
catcctcagg gagagggcat cggcgccctg acgtcagctc cactgggagt ggcaggagct    3480
gtgggagccc atgggtgagg gacccaccac cccgctgcac tgtgcattgt gcctcccgtg    3540
tggacgccct ctctgttgtt ggcccgcggg tgagggaccc accacccta gggacccacc    3600 accccgccgc actgtgcatt ctgcctcctg tgtggacgcc ctctctgttg tcagtggctt    3660
tgaggtgtca gtgcttactt agatgctggt ttaatgctgg acccatttgt taaacgcacc    3720
ttcactttgt caaacccag gtttggttgg caggactggg tcttctgccc aatgccaggt    3780
gcctgcgcct tcagtggcc tggttcttgg acagtttgcc cccatgtggc agggatagggg    3840 ataaggatct cctctcagta ctggaagaga acagccaacc atctgagccc agagtcacag    3900
atccatcgtg gcccctatg accccaagc cctaccgagg gggcactcac tctctgctta    3960
gccagggggc gtcttcaaaa aggtgacctc catgctgtgc tgtcgtgggt gtgagacgtg    4020
ctcatggcct tccactgcca tctctccctt atctgatgcc taaagtcacg atggggacag    4080
agctacccag gggccagcca tggggtgacc agccacctga gggtcagtca cctgtggaga    4140
```

```
gcaggcacct gtgaagacca ggcacctgag gactggcgcc tacttcccac tttggcccta    4200
cactggcaca gagcccctct ttattcattt ctcatgctga gcatggcaca cttctggcct    4260
ctgggcattt atggatttaa gaccaggatg gtatttcaga agcttccac ttccttccta     4320 ttctaaccga gtgcccagct cctttgctga tcatggaaag acccttaata attaggcctg    4380
caggccaggc gcagtggctc atgcctataa tcccagcact ttaggaggtc aaggtaggag    4440
gatcgcttaa gcccaggagt tcaagaccag cctgggcaac acaggaagaa tgtgtctcta    4500
caaaaaataa ttaaaaatca gatctgctgt atccctgaaa aagtctcaat caacatgcat    4560
gttccactct tggagttccc tgttctgagg gccagccacg tcctgtgtcc tggagcttag    4620
ccctcagcag ctcccttcag cctgggcgcc gcctgggtcc caaacgtggc agctgctctt    4680
ccagtctcgg ggccgaggag ggcagggagc tcagtgactg agagtcttgt gtatcacatg    4740
tcttgagtgt cctggagcca acggctgtca ctgggaaaaa caccaggccc caaagatcga    4800
atcagagacg tggctgcgtg tttgcgattg tagccaggcc cttcagtgtc atcaaaggag    4860
cactggggcc tccttaagca cagacggcag cccctgccca ggaggcttct tcaccacgtc    4920 ctgcccctgca gcctcccaga cctttagatg cgccccctgcc caaggccctc ctggtgacag    4980
gtgccagatt gagtggtggg ttgctgccag gcaggccacg ctgtgttgac gctgcactca    5040
gcacgtgggt gttggctctg ccggttttgt ggtgtgggga ccctacagga ggctgcggcc    5100
ctgagagcct gggatcagcg aggtgtccga catcccttcc tcaacggcaa caaaaactcc    5160
ccaagtcagc actttggtta ttttatagcc acaaccctct tggaaaacag tggggaagac    5220
tatggaacat agaaagtgtg gatgtatcac ttctctctaa aatgtcattg ttagcactaa    5280
ttacaggttc atgttttttct gtgtatgtag cttttcccta tatagctgaa aaagtattaa    5340
agtcaaatat aaggtgggaa tgggatggaa gggaggagat caatacaact tatatttttg    5400
cagtttctac tggaagaaaa aagttttcaa tacctagacc aacttgttga attttttaaa    5460
cttatgcact ataaatgcaa ctttctctac tgctttctca gtgcctttag gaagctttca    5520
aatttttttg tactgtggtt tgtattaaat ttgcaatatt gatgtaaaat acatgacatg    5580
ctagtacatg tttaacaaaa atttaaaaaa aaaaaaaaa aa                         5622
```

<210> SEQ ID NO 18
<211> LENGTH: 2039
<212> TYPE: DNA
<213> ORGANISM: Homo sapiens

<400> SEQUENCE: 18

```
gtaggtgtca cttatatcac aaggctacag gtgtctttat ttccactgca cgctggtgct      60
gggagcgcct gccttctctt gccttgaaag cctcctcttt ggacctagcc accgctgccc     120
tcacggtaat gttggactcg gtgacacaca gcaccttcct gcctaatgca tccttctgcg     180 atccctgat gtcgtggact gatctgttca gcaatgaaga gtactaccct gccttttgagc    240 atcagacaga tgctgattcc aactgcttga aaacaagtgg catcaaaagt caagactgtc     300
acagtcatag tagaacaagc ctccaaagtt ctcatctatg ggaatttgta cgagacctgc     360
ttctatctcc tgaagaaaac tgtggcattc tggaatggga agatagggaa caaggaattt     420
ttcgggtggt aaatcggaa gccctggcaa agatgtgggg acaaaggaag aaaaatgaca     480
gaatgacata tgaaaagttg agcagagccc tgagatacta ctataaaaca ggaatttttgg    540 agcgggttga ccgaaggtta gtgtacaaat ttggaaaaaa tgcacacggg tggcaggaag     600
```

| | |
|---|---|
| acaagctatg atctgctcca ggcatcaagc tcattttatg gatttctgtc ttttaaaaca | 660 |
| atcagattgc aatagacatt cgaaaggctt cattttcttc tcttttttt taacctgcaa | 720 |
| acatgctgat aaaatttctc cacatctcag cttacatttg gattcagagt tgttgtctac | 780 |
| ggagggtgag agcagaaact cttaagaaat cctttcttct ccctaagggg atgaggggat | 840 |
| gatcttttgt ggtgtcttga tcaaacttta ttttcctaga gttgtggaat gacaacagcc | 900 |
| catgccattg atgctgatca gagaaaaact attcaattct gccattagag acacatccaa | 960 |
| tgctcccatc ccaaaggttc aaaagttttc aaataactgt ggcagctcac caaaggtggg | 1020 |
| ggaaagcatg attagtttgc aggttatggt aggagagggt gagatataag acatacatac | 1080 |
| tttagatttt aaattattaa agtcaaaaat ccatagaaaa gtatccctt ttttttttt | 1140 |
| gagacgggtt ctcactatgt tgcccagggc tggtcttgaa ctcctatgct caagtgatcc | 1200 |
| tcccacctcg gcctcccaaa gtactgtgat tacaagcgtg agccacggca cctgggcaga | 1260 |
| aaagtatctt aattaatgaa agagctaagc catcaagctg ggacttaatt ggatttaaca | 1320 |
| taggttcaca gaaagtttcc taaccagagc atctttttga ccactcagca aaacttccac | 1380 |
| agacatcctt ctggacttaa acacttaaca ttaaccacat tattaattgt tgctgagttt | 1440 |
| attccccctt ctaactgatg gctggcatct gatatgcaga gttagtcaac agacactggc | 1500 |
| atcaattaca aaatcactgc tgtttctgtg attcaagctg tcaacacaat aaaatcgaaa | 1560 |
| ttcattgatt ccatctctgg tccagatgtt aaacgtttat aaaaccggaa atgtcctaac | 1620 |
| aactctgtaa tggcaaatta aattgtgtgt cttttttgtt ttgtctttct acctgatgtg | 1680 |
| tattcaagcg ctataacacg tatttccttg acaaaaatag tgacagtgaa ttcacactaa | 1740 |
| taaatgttca taggttaaag tctgcactga cattttctca tcaatcactg gtatgtaagt | 1800 |
| tatcagtgac tgacagctag gtggactgcc cctaggactt ctgtttcacc agagcaggaa | 1860 |
| tcaagtggtg aggcactgaa tcgctgtaca ggctgaagac ctccttatta gagttgaact | 1920 |
| tcaaagtaac ttgttttaaa aaatgtgaat tactgtaaaa taatctatt tggattcatg | 1980 |
| tgttttccag gtggatatag tttgtaaaca atgtgaataa agtatttaac atgtaaaaa | 2039 |

<210> SEQ ID NO 19
<211> LENGTH: 2222
<212> TYPE: DNA
<213> ORGANISM: Homo sapiens

<400> SEQUENCE: 19

| | |
|---|---|
| ggctgagtgg tttgctcctt cccctctctc tgggaggctg agcaggggtg ccgggttgct | 60 |
| caggccatgg gagccacacc tgttattgct gcctctgatt tgtgtgacac tgagaagccc | 120 |
| acaggcctgt ccctccaact cggtggaccc tctctgtgtg catttggtgt gtgagccagc | 180 |
| tctgagaagg gttcagaagc cactggaggc atctgggac ctcagcttcc atgccatctc | 240 |
| tgcctcactc ccacagggta atgttggact cggtgacaca cagcaccttc ctgcctaatg | 300 |
| catccttctg cgatccccctg atgtcgtgga ctgatctgtt cagcaatgaa gagtactacc | 360 |
| ctgcctttga gcatcagaca ggttactcct ttttaatga cgctgaagaa agcaaggcca | 420 |
| ccatcaaaga ctatgctgat tccaactgct tgaaaacaag tggcatcaaa agtcaagact | 480 |
| gtcacagtca tagtagaaca agcctccaaa gttctcatct atgggaattt gtacgagacc | 540 |
| tgcttctatc tcctgaagaa aactgtggca ttctggaatg ggaagatagg gaacaaggaa | 600 |
| ttttttcgggt ggttaaatcg gaagccctgg caaagatgtg gggacaaagg aagaaaaatg | 660 |
| acagaatgac atatgaaaag ttgagcagag ccctgagata ctactataaa acaggaattt | 720 |

| | |
|---|---:|
| tggagcgggt tgaccgaagg ttagtgtaca aatttggaaa aaatgcacac gggtggcagg | 780 |
| aagacaagct atgatctgct ccaggcatca agctcatttt atggatttct gtcttttaaa | 840 |
| acaatcagat tgcaatagac attcgaaagg cttcattttc ttctcttttt ttttaacctg | 900 |
| caaacatgct gataaaattt ctccacatct cagcttacat ttggattcag agttgttgtc | 960 |
| tacggagggt gagagcagaa actcttaaga aatcctttct tctccctaag gggatgaggg | 1020 |
| gatgatcttt tgtggtgtct tgatcaaact ttatttcct agagttgtgg aatgacaaca | 1080 |
| gcccatgcca ttgatgctga tcagagaaaa actattcaat tctgccatta gagacacatc | 1140 |
| caatgctccc atcccaaagg ttcaaaagtt ttcaaataac tgtggcagct caccaaaggt | 1200 |
| gggggaaagc atgattagtt tgcaggttat ggtaggagag ggtgagatat aagacataca | 1260 |
| tactttagat tttaaattat taaagtcaaa atccataga aaagtatccc ttttttttt | 1320 |
| tttgagacgg ttctcacta tgttgcccag gctggtctt gaactcctat gctcaagtga | 1380 |
| tcctcccacc tcggcctccc aaagtactgt gattacaagc gtgagccacg gcacctgggc | 1440 |
| agaaaagtat cttaattaat gaaagagcta agccatcaag ctgggactta attggattta | 1500 |
| acataggttc acagaaagtt tcctaaccag agcatctttt tgaccactca gcaaaacttc | 1560 |
| cacagacatc cttctggact taaacactta acattaacca cattattaat tgttgctgag | 1620 |
| tttattcccc cttctaactg atggctggca tctgatatgc agagttagtc aacagacact | 1680 |
| ggcatcaatt acaaaatcac tgctgtttct gtgattcaag ctgtcaacac aataaaatcg | 1740 |
| aaattcattg attccatctc tggtccagat gttaaacgtt tataaaaccg gaaatgtcct | 1800 |
| aacaactctg taatggcaaa ttaaattgtg tgtcttttt gttttgtctt tctacctgat | 1860 |
| gtgtattcaa gcgctataac acgtatttcc ttgacaaaaa tagtgacagt gaattcacac | 1920 |
| taataaatgt tcataggtta aagtctgcac tgacattttc tcatcaatca ctggtatgta | 1980 |
| agttatcagt gactgacagc taggtggact gcccctagga cttctgtttc accagagcag | 2040 |
| gaatcaagtg gtgaggcact gaatcgctgt acaggctgaa gacctcctta ttagagttga | 2100 |
| acttcaaagt aacttgtttt aaaaaatgtg aattactgta aaataatcta ttttggattc | 2160 |
| atgtgttttc caggtggata tagtttgtaa acaatgtgaa taaagtattt aacatgtaaa | 2220 |
| aa | 2222 |

<210> SEQ ID NO 20
<211> LENGTH: 1214
<212> TYPE: DNA
<213> ORGANISM: Homo sapiens

<400> SEQUENCE: 20

| | |
|---|---:|
| agaaggttta aggccggaaa gggaaatgaa ggggcccggc gctaaccctc taaggacctg | 60 |
| ttttgcttct gtttaaacca aatgggcagt ctgtcattac acacaccctg ggtcttcata | 120 |
| tgtggccgcc aggtaggagc atcacagtca agctacggga gaaacagtt tccaggaaac | 180 |
| tggaaatgaa cggcccgagt gctttccagg ggctcatctg tgggaagtat aatggaatgt | 240 |
| gcttacaagg gccagcagga gtgcctggtc gagacgggag ccctgggcc aatggcattc | 300 |
| cgggtacacc tgggatccca ggtcgggatg gattcaaagg agaaaagggg gaatgtctga | 360 |
| gggaaagctt tgaggagtcc tggacaccca actacaagca gtgttcatgg agttcattga | 420 |
| attatggcat agatcttggg aaaattgcgg agtgtacatt tacaaagatg cgttcaaata | 480 |
| gtgctctaag agttttgttc agtggctcac ttcggctaaa atgcagaaat gcatgctgtc | 540 |

| | |
|---|---|
| agcgttggta tttcacattc aatggagctg aatgttcagg acctcttccc attgaagcta | 600 |
| taatttattt ggaccaagga agccctgaaa tgaattcaac aattaatatt catcgcactt | 660 |
| cttctgtgga aggactttgt gaaggaattg gtgctggatt agtggatgtt gctatctggg | 720 |
| ttggtacttg ttcagattac ccaaaaggag atgcttctac tggatggaat tcagtttctc | 780 |
| gcatcattat tgaagaacta ccaaaataaa tgctttaatt ttcatttgct acctcttttt | 840 |
| ttattatgcc ttggaatggt tcacttaaat gacattttaa ataagtttat gtatacatct | 900 |
| gaatgaaaag caaagctaaa tatgtttaca gaccaaagtg tgatttcaca ctgtttttaa | 960 |
| atctagcatt attcattttg cttcaatcaa aagtggtttc atattttttt ttagttggtt | 1020 |
| agaatacttt cttcatagtc acattctctc aacctataat ttggaatatt gttgtggtct | 1080 |
| tttgtttttt ctcttagtat agcatttta aaaaaatata aaagctacca atctttgtac | 1140 |
| aatttgtaaa tgttaagaat ttttttata tctgttaaat aaaaattatt tccaacaacc | 1200 |
| ttaatatctt taaa | 1214 |

<210> SEQ ID NO 21
<211> LENGTH: 618
<212> TYPE: DNA
<213> ORGANISM: Homo sapiens

<400> SEQUENCE: 21

| | |
|---|---|
| gcggccgcaa gctcggcact cacggctctg agggctccga cggcactgac ggccatggcg | 60 |
| cgttcgaacc tcccgctggc gctgggcctg gccctggtcg cattctgcct cctggcgctg | 120 |
| ccacgcgacg cccgggcccg gccgcaggag cgcatggtcg gagaactccg ggacctgtcg | 180 |
| cccgacgacc cgcaggtgca gaaggcggcg caggcggccg tggccagcta caacatgggc | 240 |
| agcaacagca tctactactt ccgagacacg cacatcatca aggcgcagag ccagctggtg | 300 |
| gccggcatca gtacttcct gacgatggag atggggagca cagactgccg caagaccagg | 360 |
| gtcactggag accacgtcga cctcaccact tgcccctgg cagcagggc gcagcaggag | 420 |
| aagctgcgct gtgactttga ggtccttgtg gttccctggc agaactcctc tcagctccta | 480 |
| aagcacaact gtgtgcagat gtgataagtc cccgagggcg aaggccattg gtttggggc | 540 |
| catggtggag ggcacttcag gtccgtgggc cgtatctgtc acaataaatg gccagtgctg | 600 |
| cttcttgcaa aaaaaaaa | 618 |

<210> SEQ ID NO 22
<211> LENGTH: 2324
<212> TYPE: DNA
<213> ORGANISM: Homo sapiens

<400> SEQUENCE: 22

| | |
|---|---|
| gtaggtgtca cttatatcac aaggctacag gtgtctttat ttccactgca cgctggtgct | 60 |
| gggagcgcct gccttctctt gccttgaaag cctcctcttt ggacctagcc accgctgccc | 120 |
| tcacggtaat gttggactcg gtgacacaca gcaccttcct gcctaatgca tccttctgcg | 180 |
| atcccctgat gtcgtggact gatctgttca gcaatgaaga gtactaccct gcctttgagc | 240 |
| atcagacagc ctgtgactca tactggacat cagtccaccc tgaatactgg actaagcgcc | 300 |
| atgtgtggga gtggctccag ttctgctgcg accagtacaa gttggacacc aattgcatct | 360 |
| ccttctgcaa cttcaacatc agtggcctgc agctgtgcag catgacacag gaggagttcg | 420 |
| tcgaggcagc tggcctctgc ggcgagtacc tgtacttcat cctccagaac atccgcacac | 480 |
| aaggttactc cttttttaat gacgctgaag aaagcaaggc caccatcaaa gactatgctg | 540 |

```
attccaactg cttgaaaaca agtggcatca aaagtcaaga ctgtcacagt catagtagaa    600
caagcctcca aagttctcat ctatgggaat ttgtacgaga cctgcttcta tctcctgaag    660
aaaactgtgg cattctggaa tgggaagata gggaacaagg aattttttcgg gtggttaaat   720 cggaagccct ggcaaagatg tggggacaaa ggaagaaaaa tgacagaatg acatatgaaa    780
agttgagcag agccctgaga tactactata aaacaggaat tttggagcgg gttgaccgaa    840
ggttagtgta caaatttgga aaaaatgcac acgggtggca ggaagacaag ctatgatctg    900
ctccaggcat caagctcatt ttatggattt ctgtctttta aaacaatcag attgcaatag    960
acattcgaaa ggcttcattt tcttctcttt tttttaacc tgcaaacatg ctgataaaat    1020
ttctccacat ctcagcttac atttggattc agagttgttg tctacggagg gtgagagcag   1080
aaactcttaa gaaatccttt cttctcccta aggggatgag gggatgatct tttgtggtgt    1140
cttgatcaaa ctttattttc ctagagttgt ggaatgacaa cagcccatgc cattgatgct    1200
gatcagagaa aaactattca attctgccat tagagacaca tccaatgctc ccatcccaaa    1260
ggttcaaaag ttttcaaata actgtggcag ctcaccaaag gtgggggaaa gcatgattag    1320
tttgcaggtt atggtaggag agggtgagat ataagacata catactttag atttttaaatt   1380 attaaagtca aaaatccata gaaaagtatc cctttttttt tttttgagac gggttctcac    1440
tatgttgccc agggctggtc ttgaactcct atgctcaagt gatcctccca cctcggcctc    1500
ccaaagtact gtgattacaa gcgtgagcca cggcacctgg gcagaaaagt atcttaatta    1560
atgaaagagc taagccatca agctgggact taattggatt taacataggt tcacagaaag    1620
tttcctaacc agagcatctt tttgaccact cagcaaaact tccacagaca tccttctgga    1680
cttaaacact taacattaac cacattatta attgttgctg agtttattcc cccttctaac    1740
tgatggctgg catctgatat gcagagttag tcaacagaca ctggcatcaa ttacaaaatc    1800
actgctgttt ctgtgattca agctgtcaac acaataaaat cgaaattcat tgattccatc    1860
tctggtccag atgttaaacg tttataaaac cggaaatgtc ctaacaactc tgtaatggca    1920
aattaaattg tgtgtctttt ttgttttgtc tttctacctg atgtgtattc aagcgctata    1980
acacgtattt ccttgacaaa aatagtgaca gtgaattcac actaataaat gttcataggt    2040
taaagtctgc actgacattt tctcatcaat cactggtatg taagttatca gtgactgaca    2100
gctaggtgga ctgcccctag gacttctgtt tcaccagagc aggaatcaag tggtgaggca    2160
ctgaatcgct gtacaggctg aagacctcct tattagagtt gaacttcaaa gtaacttgtt    2220
ttaaaaaatg tgaattactg taaaataatc tattttggat tcatgtgttt tccaggtgga    2280 tatagttttgt aaacaatgtg aataaagtat ttaacatgta aaaa                    2324
```

<210> SEQ ID NO 23
<211> LENGTH: 1166
<212> TYPE: DNA
<213> ORGANISM: Homo sapiens

<400> SEQUENCE: 23

```
gctccgggaa tttcccctggc ccggccgctc cgggctttcc agtctcaacc atgcataaaa     60
agggttcgcc gatcttgggg agccacacag cccgggtcgc aggcacctcc ccgccagctc    120
tcccgcttct cgcacagctt cccgacgcgt ctgctgagcc ccatggccca cgccacgctc    180
tccgccgccc ccagcaatcc ccggctcctg cgggtggcgc tgctgctcct gctcctggtg    240
gccgccagcc ggcgcgcagc aggagcgtcc gtggtcactg aactgcgctg ccagtgcttg    300
```

```
cagacactgc agggaattca cctcaagaac atccaaagtg tgaatgtaag gtcccccgga     360
ccccactgcg cccaaaccga agtcatagcc acactcaaga atgggaagaa agcttgtctc     420
aaccccgcat cccccatggt tcagaaaatc atcgaaaaga tactgaacaa ggggagcacc     480
aactgacagg agagaagtaa gaagcttatc agcgtatcat tgacacttcc tgcagggtgg     540
tccctgccct taccagagct gaaaatgaaa agagaacag cagctttcta gggacagctg      600
gaaaggactt aatgtgtttg actatttctt acgagggttc tacttattta tgtatttatt     660
tttgaaagct tgtattttaa tattttacat gctgttattt aaagatgtga gtgtgtttca     720
tcaaacatag ctcagtcctg attatttaat tggaatatga tgggttttaa atgtgtcatt     780
aaactaatat ttagtgggag accataatgt gtcagccacc ttgataaatg acagggtggg     840
gaactggagg gtgggggggat tgaaatgcaa gcaattagtg gatcactgtt agggtaaggg    900
aatgtatgta cacatctatt ttttatactt tttttttaaa aaagaatgt cagttgttat     960 ttattcaaat tatctcacat tatgtgttca acattttat gctgaagttt cccttagaca     1020 tttatgtct tgcttgtagg gcataatgcc ttgtttaatg tccattctgc agcgtttctc      1080
tttcccttgg aaaagagaat ttatcattac tgttacattt gtacaaatga catgataata     1140
aaagttttat gaaaaaaaaa aaaaaa                                          1166

<210> SEQ ID NO 24
<211> LENGTH: 5189
<212> TYPE: DNA
<213> ORGANISM: Homo sapiens

<400> SEQUENCE: 24
gggaaagtga agaaaacaga aaaggagagg gacagaggcc agaggacttc tcatactgga     60
cagaaaccga tcaggcatgg aactccccctt cgtcactcac ctgttcttgc ccctggtgtt    120
cctgacaggt ctctgctccc cctttaacct ggatgaacat cacccacgcc tattcccagg    180
gccaccagaa gctgaatttg gatacagtgt cttacaacat gttggggtg gacagcgatg      240 gatgctggtg ggcgccccct gggatgggcc ttcaggcgac cggaggggggg acgtttatcg    300 ctgcccgtgta gggggggccc acaatgcccc atgtgccaag ggccacttag gtgactacca    360
actgggaaat tcatctcatc ctgctgtgaa tatgcacctg gggatgtctc tgttagagac     420
agatggtgat gggggattca tggcctgtgc ccctctctgg tctcgtgctt gtggcagctc    480
tgtcttcagt tctgggatat gtgcccgtgt ggatgcttca ttccagcctc agggaagcct   540
ggcacccact gcccaacgct gcccaacata catggatgtt gtcattgtct tggatggctc    600
caacagcatc taccctggt ctgaagttca gaccttccta cgaagactgg tagggaaact    660
gtttattgac ccagaacaga tacaggtggg actggtacag tatggggaga gccctgtaca    720
tgagtggtcc ctgggagatt tccgaacgaa ggaagaagtg gtgagagcag caaagaacct    780
cagtcggcgg gagggacgag aaacaaagac tgcccaagca ataatggtgg cctgcacaga    840
agggttcagt cagtcccatg ggggccgacc cgaggctgcc aggctactgg tggttgtcac    900
tgatggagag tcccatgatg gagaggagct tcctgcagca ctaaaggcct gtgaggctgg    960
aagagtgaca cgctatggga ttgcagtcct tggtcactac ctccggcggc agcgagatcc    1020
cagctctttc ctgagagaaa ttagaactat tgccagtgat ccagatgagc gattcttctt    1080
caatgtcaca gatgaggctg ctctgactga cattgtggat gcactaggag atcggatttt    1140
tggccttgaa gggtcccatg cagaaaacga aagctccttt gggctggaaa tgtctcagat    1200
tggtttctcc actcatcggc taaaggatgg gattctttt gggatggtgg gggcctatga     1260
```

```
ctggggaggc tctgtgctat ggcttgaagg aggccaccgc cttttccccc cacgaatggc    1320
actggaagac gagttccccc ctgcactgca gaaccatgca gcctacctgg gttactctgt    1380
ttcttccatg cttttgcggg gtggacgccg cctgtttctc tctggggctc ctcgatttag    1440
acatcgagga aaagtcatcg ccttccagct taagaaagat ggggctgtga gggttgccca    1500
gagcctccag ggggagcaga ttggttcata ctttggcagt gagctctgcc cattggatac    1560
agatagggat ggaacaactg atgtcttact tgtggctgcc cccatgttcc tgggaccccca   1620 gaacaaggaa acaggacgtg tttatgtgta tctggtaggc cagcagtcct tgctgaccct    1680
ccaaggaaca cttcagccag aaccccccca ggatgctcgg tttggctttg ccatgggagc    1740
tcttcctgat ctgaaccaag atggttttgc tgatgtggct gtggggcgc ctctggaaga     1800 tgggcaccag ggagcactgt acctgtacca tggaacccag agtggagtca ggccccatcc    1860
tgcccagagg attgctgctg cctccatgcc acatgccctc agctactttg gccgaagtgt    1920
ggatggtcgg ctagatctgg atggagatga tctggtcgat gtggctgtgg gtgcccaggg    1980
ggcagccatc ctgctcagct cccggcccat tgtccatctg accccatcac tggaggtgac    2040
cccacaggcc atcagtgtgg ttcagaggga ctgtaggcgg cgaggccaag aggcagtctg    2100
tctgactgca gcccttcgct tccaagtgac ctcccgtact cctggtcgct gggatcacca    2160
attctacatg aggttcaccg catcactgga tgaatggact gctggggcac gtgcagcatt    2220
tgatggctct ggccagaggt tgtcccctcg gaggctccgg ctcagtgtgg ggaatgtcac    2280
ttgtgagcag ctacttccc atgtgctgga tacatcagat tacctccggc cagtggcctt     2340
gactgtgacc tttgccttgg acaatactac aaagccaggg cctgtgctga atgagggctc    2400
acccacctct atacaaaagc tggtcccctt ctcaaaggat tgtggccctg acaatgaatg    2460
tgtcacagac ctggtgcttc aagtgaatat ggacatcaga ggctcaggaa aggccccatt    2520
tgtggttcga ggtggccggc ggaaagtgct ggtatctaca actctggaga acagaaagga    2580
aaatgcttac aatacgagcc tgagtctcat cttctctaga aacctccacc tggccagtct    2640
cactcctcag agagagagcc caataaaggt ggaatgtgcc gcccccttctg ctcatgcccg   2700 gctctgcagt gtggggcatc ctgtcttcca gactggagcc aaggtgacct ttctgctaga    2760
gtttgagttt agctgctcct ctctcctgag ccaggtcttc gtgaagctga ctgccagcag    2820
tgacagcctg gagagaaatg ggaccttca agataacaca gccagacct cagcctacat      2880 ccaatatgag ccccacctcc tgttctctag tgagtctacc ctgcaccgct atgaggttca    2940
cccatatggg accctcccag tgggtcctgg cccagaattc aaaaccactc tcagggttca    3000
gaacctaggc tgctatgtgg tcagtggcct catcatctca gccctccttc agctgtggc     3060 ccatgggggc aattacttcc tatcactgtc tcaagtcatc actaacaatg caagctgcat    3120
agtgcagaac ctgactgaac ccccaggccc acctgtgcat ccagaggagc ttcaacacac    3180
aaacagactg aatgggagca atactcagtg tcaggtggtg aggtgccacc ttgggcagct    3240
ggcaaagggg actgaggtct ctgttggact attgaggctg gttcacaatg aatttttccg    3300
aagagccaag ttcaagtccc tgacggtggt cagcaccttt gagctgggaa ccgaagaggg    3360
cagtgtccta cagctgactg aagcctcccg ttggagtgag agcctcttgg aggtggttca    3420
gacccggcct atcctcatct ccctgtggat cctcataggc agtgtcctgg agggttgct    3480 cctgcttgct ctccttgtct tctgcctgtg gaagcttggc ttctttgccc ataagaaaat    3540
ccctgaggaa gaaaaagag aagagaagtt ggagcaatga atgtagaata agggtctaga    3600
```

```
aagtcctccc tggcagcttc ttcaagagac ttgcataaaa gcagaggttt gggggctcag    3660
atgggacaag aagccgcctc tggactatct ccccagacca gcagcctgac ttgactttg     3720 agtcctaggg atgctgctgg ctagagatga ggctttacct cagacaagaa gagctggcac    3780
caaaactagc catgctccca ccctctgctt ccctcctcct cgtgatcctg gttccatagc    3840
caacactggg gcttttgttt ggggtccttt tatccccagg aatcaataat ttttttgcct    3900
aggtgcctga ctcctttcag attccctctt tatcttccct cacagtttgg aaaggatgag    3960
ggttatcttc ctcgattctt ccaccctctc actttcctgc ctgttcccca ctccacagga    4020
gggagctgac gttggcttga aaggagtaaa gtcaacatct gctgctttcc tgtggactct    4080
ggtgattcat agagccggat ggggagagtc aacaggaaaa aaggagggag gaggaaaagc    4140
cacaagagac attctgtaca attccaagga acagagaagc ctttagacag gcaactgcca    4200 tccccctga aacctgagac ctgtagtgca ctcgaccgcc ctcaggtgtt ggtgaaacag     4260
agctgccccc aggctcgctg gcataggct tcctgattcc aagcctttc tgggagcaaa      4320 gccagggcct ggtgcctgat tttctgaagc caggagccct caggtggctg gagctggaat    4380
agcagggagg actgggtgta cctaggcagt attttctcta cttctctcaa gtcttatact    4440
cactcttgag ccctccttgg ggcctgctta gaaagcagac aggagagaga gtactgctac    4500
ttgatgatgg gaaatgcttt cactttacca gctttgggaa gcagcagccc catgggatct    4560
aaaagtgtgg agtctgcatt aagaaaccta catgggtggc atgggctct ggggagcaag     4620 cccttacttg ctcagcactg gttatgtagc acaaatagct cctaggaaaa tgtttctggg    4680
gcaaccctag aaccctggtc atattttgca gggtttctct ggtggaatca gtttgccagc    4740
ccttgcttga tgcttactgg aaatctccag gttaatttct atctctgatc cctccccaac    4800
ccactccata tttgggtcat ggacagtaaa ggcagttgga ttctcataga caactgggta    4860
acttatattt ctttgtaatc aagacttgag atatcgaagt cagttattgg tctccagagt    4920
gcagctctgg gagccttttg aagaatcagc actcattaag agctgagaag agagaagacc    4980
tgattgggtg gttgactagc agtcacagaa cctgtcctcc caggctgttc ctgaggcctg    5040
accacagtat ttattttggc atgtctctgg ccttctgcag aggcccaccc tcatgggcat    5100
tgtctctgtt tcccagtggg gtggacagta tatcagatgg tcagaacaaa taaagttcag    5160
tgtcaaatga aaaaaaaaaa aaaaaaaa                                      5189
```

<210> SEQ ID NO 25
<211> LENGTH: 2005
<212> TYPE: DNA
<213> ORGANISM: Homo sapiens

<400> SEQUENCE: 25

```
tttcctctca gggggcagca ggaagtgagg agaaagggct gggatgggag gcgggagcgg     60
atgggaggga atgggggttta tcaagtcctc ggcgagctgc ccaacgggca gcagctggcg   120
caagtagcct agctggagag gctcacccca ggaaggaggg aggccaccga cctactgggc    180
cgacggactc ccacacagtt cctgagctgg tgccaggcag gtgacacctc ctgcagcccc    240
cagcatgcgg gcaggcccag gccccaccgt tacattggcc ctggtgctgg cggtgtcatg    300
ggccatggag ctcaagccca cagcaccacc catcttcact ggccggccct tgtggtagc     360 gtgggacgtg cccacacagg actgtggccc acgcctcaag gtgccactgg acctgaatgc    420
ctttgatgtg caggcctcac ctaatgaggg ttttgtgaac cagaatatta ccatcttcta    480
ccgcgaccgt ctaggcctgt atccacgctt cgattctgcc ggaaggtctg tgcatggtgg    540
```

```
tgtgccacag aatgtcagcc tttgggcaca ccggaagatg ctgcagaaac gtgtggagca      600
ctacattcgg acacaggagt ctgcggggct ggcggtcatc gactgggagg actggcgacc      660
tgtgtgggtg cgcaactggc aggacaaaga tgtgtatcgc cggttatcac gccagctagt      720
ggccagtcgt caccctgact ggcctccaga ccgcatagtc aaacaggcac aatatgagtt      780
tgagttcgca gcacagcagt tcatgctgga gacactgcgt tatgtcaagg cagtgcggcc      840
ccggcacctc tggggcttct acctctttcc tgactgctac aatcatgatt atgtgcagaa      900
ctgggagagc tacacaggcc gctgccctga tgttgaggtg gcccgcaatg accagctggc      960
ctggctgtgg gctgagagca cggccctctt cccgtctgtc tacctggacg agacacttgc     1020
ttcctcccgc catggccgca actttgtgag cttccgtgtt caggaggccc ttcgtgtggc     1080
tcgcacccac catgccaacc atgcactccc agtctacgtc ttcacacgac ccacctacag     1140
ccgcaggctc acgggcttac gtgagatgga cctcatctct accattggcg agagtgcggc     1200
cctgggcgca gctggtgtca tcctctgggg tgacgcgggg tacaccacaa gcacggagac     1260
ctgccagtac ctcaaagatt acctgacacg gctgctggtc ccctacgtgg tcaatgtgtc     1320
ctgggccacc caatattgca gccgggccca gtgccatggc catgggcgct gtgtgcgccg     1380
caacccagt gccagtacct tcctgcatct cagcaccaac agtttccgcc tagtgcctgg      1440
ccatgcacct ggtgaacccc agctgcgacc tgtgggggag ctcagttggg ccgacattga     1500
ccacctgcag acacacttcc gctgccagtg ctacttgggc tggagtggtg agcaatgcca     1560
gtgggaccat aggcaggcag ctggaggtgc cagcgaggcc tgggctgggt cccacctcac     1620
cagtctgctg gctctggcag ccctggcctt tacctggacc ttgtaggggt ctcctgccta     1680
gctgcctagc aagctggcct ctaccacaag ggctctctta ggcatgtagg accctgcagg     1740
gggtggacaa actggagtct ggagtgggca gagccccag gaagcccagg agggcatcca      1800
taccagctcg caccccctg ttctaagggg gaggggaagt ccctgggagg cccttctct       1860
ccctgccaga ggggaaggag ggtacagctg ggctggggag gacctgaccc tactcccttg     1920
ccctagatag tttattatta ttattatttt ggggtctctt ttgtaaatta aacataaaac     1980
aattgcttct ctgcttggat tttgt                                           2005
```

<210> SEQ ID NO 26
<211> LENGTH: 5802
<212> TYPE: DNA
<213> ORGANISM: Homo sapiens

<400> SEQUENCE: 26

```
tttatagcag cagtagaaat ataccaccct agaggacaca cctccttta gctaggtacc       60
tataaatgtc caggattttc tattcaattg agaagaaccc agcaaaatgg ggatctccac      120
agtcatcctt gaaatgtgtc ttttatgggg acaagttcta tctacaggtg ggtggatccc      180
aaggactaca gactacgctt cactgattcc ctcggaggtg cccttggatc caactgtagc      240
agaaggttct ccatttccct cggagtcgac cctggagtca actgtagcag aaggttctcc      300
gatttccttg gagtcaaccc tggagtcaac cgtagcagaa ggttctctga ttccctcaga      360
gtcaaccctg gagtcaactg tagcagaagg atctgattct ggtttggccc tgaggctggt      420
gaatggagat ggcaggtgtc agggccgagt ggagatccta taccgaggct cctggggcac      480
cgtgtgtgat gacagctggg acaccaatga tgccaacgtg gtctgtaggc agctgggttg      540
tggctgggcc atgtcagctc caggaaatgc ctggtttggc cagggctcag gacccattgc      600
```

```
cctgatgat gtgcgctgct caggacacga atcctacctg tggagctgcc cccacaatgg      660
ctggctctcc cataactgtg gccatggtga agatgctggt gttatctgct cagctgccca     720
gcctcagtca acactcaggc cagaaagttg gcctgtcagg atatcaccac ctgtacccac     780
agaaggatct gaatccagtt tggccctgag gctggtgaat ggaggcgaca ggtgtcgagg     840
ccgagtggag gtcctatacc gaggctcctg gggcaccgtg tgtgatgact actgggacac     900
caatgatgcc aatgtggtct gcaggcagct gggctgtggc tgggccatgt cagccccagg     960
aaatgcccag tttggccagg gctcaggacc cattgtcctg gatgatgtgc gctgctcagg    1020
acatgagtcc tacctgtgga gctgccccca caatggctgg ctcacccaca actgtggcca    1080
tagtgaagac gctggtgtca tctgctcagc tccccagtcc cggccgacac ccagcccaga    1140
tacttggccg acctcacatg catcaacagc aggacctgaa tccagtttgg ccctgaggct    1200
ggtgaatgga ggtgacaggt gtcagggccg agtggaggtc ctataccgag gctcctgggg    1260
caccgtgtgt gatgatagct gggacaccag tgacgccaat gtggtctgcc ggcagctggg    1320
ctgtggctgg gccacgtcag ccccaggaaa tgcccggttt ggccagggtt caggacccat    1380
tgtcctggat gacgtgcgct ctcaggcta tgagtcctac ctgtggagct gcccccacaa    1440
tggctggctc tcccataact gtcagcacag tgaagacgct ggtgtcatct gctcagctgc    1500
ccactcctgg tcgacgccca gtccagacac attgccgacc atcaccttgc ctgcatcgac    1560
agtaggatct gaatccagtt tggccctgag gctggtgaat ggaggtgaca ggtgtcaggg    1620
ccgagtggag gtcctatacc aaggctcctg gggcaccgtg tgcgatgaca gctgggacac    1680
caatgatgcc aatgtcgtct gcaggcaact gggctgtggc tgggccatgt cagccccagg    1740
aaatgcccgg tttggtcagg gctcaggacc cattgtcctg gatgatgtgc gctgctcagg    1800
acacgagtct acctgtgga gctgcccccca caatggctgg ctctcccaca actgtggcca    1860
tagtgaagac gctggtgtca tctgctcagc ttcccagtcc cggccaacac ctagtccaga    1920
cacttggcca acctcacatg catcaacagc aggatctgaa tccagtttgg ccctgaggct    1980
ggtgaatgga ggtgacaggt gtcagggccg agtggaggtc ctataccgag gctcctgggg    2040
caccgtgtgt gatgactact gggacaccaa tgatgccaat gtggtttgca ggcagctggg    2100
ctgtggctgg gccatgtcag ccccaggaaa tgcccggttt ggccagggtt caggacccat    2160
tgtcctggat gatgtgcgct gctcaggaca tgagtcctat ctgtggagct gcccccacaa    2220
tggctggctc tcccacaact gtggccatca tgaagacgct ggtgtcatct gctcagcttc    2280
ccagtcccag ccgacaccca gcccagacac ttggccaacc tcacatgcat caacagcagg    2340
atctgaatcc agtttggccc tgaggctggt gaatggaggt gacaggtgtc agggccgagt    2400
ggaggtccta taccgaggct cctggggcac cgtgtgtgat gactactggg acaccaatga    2460
tgccaatgtg gtttgcaggc agctgggctg tggctgggcc acgtcagccc caggaaatgc    2520
ccggtttggc cagggttcag gacccattgt cctggatgat gtgcgctgct caggacatga    2580
gtcctatctg tggagctgcc cccacaatgg ctggctctcc cacaactgtg gccatcatga    2640
agacgctggt gtcatctgct cagcttccca gtcccagccg acacccagcc agacacttg    2700 gccaacctct cgtgcatcaa cagcaggatc tgaatccact ttggccctga ctggtgaa    2760 tggaggtgac aggtgtcgag gccgagtgga ggtcctatac caaggctcct ggggcaccgt    2820
gtgtgatgac tactgggaca ccaatgatgc caacgtggtc tgcaggcagc tgggctgtgg    2880
ctgggccatg tcagccccag gaaatgccca gtttggccag ggctcaggac ccattgtcct    2940
ggatgatgtg cgctgctcag gacacgagtc ttacctgtgg agctgccccc acaatggctg    3000
```

```
gctctcccac aactgtggcc atcatgaaga tgctggtgtc atctgctcag ctgctcagtc   3060
ccagtcaacg cccaggccag atacttggct gaccaccaac ttaccggcat tgacagtagg   3120
atctgaatcc agtttggctc tgaggctggt gaatggaggt gacaggtgtc gaggccgagt   3180
ggaggtcctg tatcgaggct cctggggaac cgtgtgtgat gacagctggg acaccaatga   3240
tgccaatgtg gtctgcaggc agctgggctg tggctgggcc atgtcggccc aggaaatgc    3300 ccggtttggc cagggctcag gacccattgt cctggatgat gtgcgctgct cagggaatga   3360
gtcctacctg tggagctgcc cccacaaagg ctggctcacc cacaactgtg gccatcacga   3420
agacgctggt gtcatctgct cagccaccca aataaattct actacgacag attggtggca   3480
tccaacaact acaaccactg caagaccctc ttcaaattgt ggtggcttct tattctatgc   3540
cagtgggaca ttctccagcc catcctaccc tgcatactac cccaacaatg ctaagtgtgt   3600
ttgggaaata gaagtgaatt ctggttatcg cataaacctg gcttcagta atctgaaatt    3660 ggaggcacac cataactgca gttttgatta tgttgaaatc tttgatggat cattgaatag   3720
cagtctcctg ctggggaaaa tctgtaatga taccaggcaa atatttacat cttcttacaa   3780
ccgaatgacc attcactttc gaagtgacat cagtttccaa aacactggct ttttggcttg   3840
gtataactcc ttcccaagcg atgccacctt gaggttggtc aatttaaatt catcctatgg   3900
tctatgtgcc gggcgtgtag aaatttacca tggtggcacc tggggacag tttgtgatga    3960 ctcctggacc attcaggaag ctgaggtggt ctgcagacag ctagggtgtg gacgtgcagt   4020
ttcagccctt ggaaatgcat attttggctc tggctctggc cccatcaccc tggacgatgt   4080
agagtgctca gggacggaat ccactctctg gcagtgccgg aaccgaggct ggttctccca   4140
caactgtaat catcgtgaag atgctggtgt catctgctca ggaaaccatc tatcgacacc   4200
tgctcctttt ctcaacatca cccgtccaaa cacagattat tcctgcggag gcttcctatc   4260
ccaaccatca ggggactttt ccagcccatt ctatcccggg aactatccaa acaatgccaa   4320
gtgtgtgtgg gacattgagg tgcaaaacaa ctaccgtgtg actgtgatct tcagagatgt   4380
ccagcttgaa ggtggctgca actatgatta tattgaagtt ttcgatggcc cctaccgcag   4440
ttcccctctc attgctcgag tttgtgatgg ggccagaggc tccttcactt cttcctccaa   4500
cttcatgtcc attcgcttca tcagtgacca cagcatcaca aggagagggt tccgggctga   4560
gtactactcc agtccctcca atgacagcac caacctgctc tgtctgccaa atcacatgca   4620
agccagtgtg agcaggagct atctccaatc cttgggcttt tctgccagtg accttgtcat   4680
ttccacctgg aatggatact acgagtgtcg gccccagata acgccgaacc tggtgatatt   4740
cacaattccc tactcaggct gcggcacctt caagcaggca gacaatgaca ccatcgacta   4800
ttccaacttc ctcacagcag ctgtctcagg tggcatcatc aagaggagga cagacctccg   4860
tattcacgtc agctgcagaa tgcttcagaa cacctgggtc gacaccatgt acattgctaa   4920
tgacaccatc cacgttgcta ataacaccat ccaggtcgag gaagtccagt atggcaattt   4980
tgacgtgaac atttcctttt atacttcctc atctttcttg tatcctgtga ccagccgccc   5040
ttactacgtg gacctgaacc aggacttgta cgttcaggct gaaatcctcc attctgatgc   5100
tgtactgacc ttgtttgtgg acacctgcgt ggcatcacca tactccaatg acttcacgtc   5160
tttgacttat gatctaatcc ggagtggatg cgtgagggat gacacctacg accctactc    5220 ctcgccatct cttcgcattg cccgcttccg gttcagggcc ttccacttcc tgaaccgctt   5280
cccctccgtg tacctgcgtt gtaaaatggt ggtgtgcaga gcgtatgacc cctcttcccg   5340
```

| | |
|---|---|
| ctgctaccga ggctgtgtgt tgaggtcgaa gagggatgtg ggctcctacc aggaaaaggt | 5400 |
| ggacgtcgtc ctgggtccca tccagctgca gaccccccca cgccgagaag aggagcctcg | 5460 |
| gtaggtggtc gctctcagac cccactgtcc accggggcgc agacccctga ctcggggact | 5520 |
| tgggatgttc ctcttggtgt catattccaa ctcagattga gccctacatt gtgctgcacc | 5580 |
| tggtcatacg gagttgaatc agacctggtt cccgcctccc ccaaggctca tggtccttgg | 5640 |
| aggacccgtt gcagggtgag gtcaagagag ttctgacctg gatggcccat agacctgacg | 5700 |
| tcccagaatc catgcttctc atctgcaaaa tgaaaatgtc aatacttact tcttagcact | 5760 |
| gttgagaggg ttacttacat aaaggaattt tggtgaaact gc | 5802 |

<210> SEQ ID NO 27
<211> LENGTH: 1220
<212> TYPE: DNA
<213> ORGANISM: Homo sapiens

<400> SEQUENCE: 27

| | |
|---|---|
| agtcccagct cagagccgca acctgcacag ccatgcccgg gcaagaactc aggacggtga | 60 |
| atggctctca gatgctcctg gtgttgctgg tgctctcgtg gctgccgcat gggggcgccc | 120 |
| tgtctctggc cgaggcgagc cgcgcaagtt cccgggacc ctcagagttg cactccgaag | 180 |
| actccagatt ccgagagttg cggaaacgct acgaggacct gctaaccagg ctgcgggcca | 240 |
| accagagctg gaagattcg aacaccgacc tcgtcccggc cctgcagtc cggatactca | 300 |
| cgccagaagt gcggctggga tccggcggcc acctgcacct gcgtatctct cgggccgccc | 360 |
| ttcccgaggg gctccccgag gcctcccgcc ttcaccgggc tctgttccgg ctgtccccga | 420 |
| cggcgtcaag gtcgtgggac gtgacacgac cgctgcggcg tcagctcagc cttgcaagac | 480 |
| cccaggcgcc cgcgctgcac ctgcgactgt cgccgccgcc gtcgcagtcg gaccaactgc | 540 |
| tggcagaatc ttcgtccgca cggccccagc tggagttgca cttgcggccg caagccgcca | 600 |
| gggggcgccg cagagcgcgt gcgcgcaacg gggaccactg tccgctcggg cccgggcgtt | 660 |
| gctgccgtct gcacacggtc cgcgcgtcgc tggaagacct gggctgggcc gattgggtgc | 720 |
| tgtcgccacg ggaggtgcaa gtgaccatgt gcatcggcgc gtgcccgagc cagttccggg | 780 |
| cggcaaacat gcacgcgcag atcaagacga gcctgcaccg cctgaagccc gacacggtgc | 840 |
| cagcgccctg ctgcgtgccc gccagctaca atcccatggt gctcattcaa aagaccgaca | 900 |
| ccggggtgtc gctccagacc tatgatgact tgttagccaa agactgccac tgcatatgag | 960 |
| cagtcctggt ccttccactg tgcacctgcg cggaggacgc gacctcagtt gtcctgccct | 1020 |
| gtggaatggg ctcaaggttc ctgagacacc cgattcctgc ccaaacagct gtatttatat | 1080 |
| aagtctgtta tttattatta atttattggg gtgaccttct tggggactcg gggctggtc | 1140 |
| tgatggaact gtgtatttat ttaaaactct ggtgataaaa ataaagctgt ctgaactgtt | 1200 |
| aaaaaaaaaa aaaaaaaaaa | 1220 |

<210> SEQ ID NO 28
<211> LENGTH: 1882
<212> TYPE: DNA
<213> ORGANISM: Homo sapiens

<400> SEQUENCE: 28

| | |
|---|---|
| agcgctccta taaagggagc caccagcgct ggaggccgct gctcgctgcg ccaccgcctc | 60 |
| ccgccacccc tgcccgcccg acagcgccgc cgcctgcccc gccatgggtc gacagaagga | 120 |
| gctggtgtcc cgctgcgggg agatgctcca catccgctac cggctgctcc gacaggcgct | 180 |

```
ggccgagtgc ctggggaccc tcatcctggt gatgtttggc tgtggctccg tggcccaggt      240
tgtgctcagc cggggcaccc acggtggttt cctcaccatc aacctggcct ttggctttgc      300
tgtcactctg ggcatcctca tcgctggcca ggtctctggg cccacctga accctgccgt       360 gacctttgcc atgtgcttcc tggctcgtga gccctggatc aagctgccca tctacaccct      420
ggcacagacg ctgggagcct tcttgggtgc tggaatagtt tttgggctgt attatgatgc      480
aatctggcac ttcgccgaca accagctttt gtttcgggc cccaatggca cagccggcat       540
ctttgctacc taccctctg acacttggaa tatgatcaat ggcttctttg accagttcat       600
aggcacagcc tccttatcg tgtgtgtgct ggccattgtt gacccctaca caacccgt        660 cccccgaggc ctggaggcct tcaccgtggg cctggtggtc ctggtcattg cacctccat      720 gggcttcaac tccggctatg ccgtcaaccc tgcccgggac tttggccccc gccttttac      780 agcccttgcg ggctggggct ctgcagtctt cacgaccggc cagcattggt ggtgggtgcc      840
catcgtgtcc ccactcctgg gctccattgc gggtgtcttc gtgtaccagc tgatgatcgg      900
ctgccacctg gagcagcccc caccctccaa cgaggaagag aatgtgaagc tggcccatgt      960
gaagcacaag gagcagatct gagtgggcag gggccatctc cccactccgc tgccctggcc    1020
ttgagcatcc actgactgtc caagggccac tcccaagaag ccccttcac gatccaccct     1080 ttcaggctaa ggagctccct atctaccctc accccacgag acagccctt caggatttcc      1140 actggacctt gcccaaatag caccttaggc cactgcccct aagctggggt ggaaccggaa     1200
tttgggtcaa tacatccttt tgtctcccaa gggaagagaa tgggcagcag gtatgtgtgt     1260
gtgtgcatgt gtgtgcatgt gtgtgcatgt gtgtgcaggg gtgtgtgtgt gtggggggg     1320 ttcccagata ttcagggcaa gggaccagtc ggaagggatt ctggctattg ggggagccca     1380
gagacagggg aaggcagcct gtccatctgt gcataaggag aggaaagttc cagggtgtgt     1440
atgtttcagg ggcttcacat ggaggagctg cagatagata tgtgtttctg tgtatgtgta     1500
tgtctgcctt tttttctaag tgggggcttc tacaggcttc tgggaagtag ggtggatgtg    1560
ggtagggctg ggaggagggg gccacagctt aggtttggag ctctggatgt acatacataa    1620
gtaggagcag tgggacgtgt ttctgtcata atgcaggcat gaagggtgga gtgaagtcag    1680
gtcataagtt tcatgtttgc ttttgttttg ttttgttttt aatgtatgta gcagatgtta    1740
cagtcttagg gatccgggat gggagacccc actttagaaa gggtcgtcac tcctttaatc    1800
ctctactcaa caatgtactc ttttactttt atattaaaaa aataaaaata aatatgtgcc    1860
taaaacctcc aaaaaaaaaa aa                                             1882

<210> SEQ ID NO 29
<211> LENGTH: 1336
<212> TYPE: DNA
<213> ORGANISM: Homo sapiens

<400> SEQUENCE: 29
gagagacaca gagtccggca ttggtcccag gcagcagtta gcccgccgcc cgcctgtgtg       60
tccccagagc catggagaga gccagtctga tccagaaggc caagctggca gagcaggccg      120
aacgctatga ggacatggca gccttcatga aaggcgccgt ggagaagggc gaggagctct      180
cctgcgaaga gcgaaacctg ctctcagtag cctataagaa cgtggtgggc ggccagaggg      240
ctgcctggag ggtgctgtcc agtattgagc agaaaagcaa cgaggagggc tcggaggaga      300
aggggcccga ggtgcgtgag taccgggaga aggtggagac tgagctccag ggcgtgtgcg      360
```

```
acaccgtgct gggcctgctg gacagccacc tcatcaagga ggccgggac gccgagagcc      420
gggtcttcta cctgaagatg aagggtgact actaccgcta cctggccgag gtggccaccg      480
gtgacgacaa gaagcgcatc attgactcag cccggtcagc ctaccaggag gccatggaca      540
tcagcaagaa ggagatgccg cccaccaacc ccatccgcct gggcctggcc ctgaactttt      600
ccgtcttcca ctacgagatc gccaacagcc ccgaggaggc catctctctg gccaagacca      660
ctttcgacga ggccatggct gatctgcaca ccctcagcga ggactcctac aaagacagca      720
ccctcatcat gcagctgctg cgagacaacc tgacactgtg gacggccgac aacgccgggg      780
aagaggggg cgaggctccc caggagcccc agagctgagt gttgcccgcc accgccccgc      840
cctgccccct ccagtccccc accctgccga gaggactagt atggggtggg aggccccacc      900
cttctcccct aggcgctgtt cttgctccaa agggctccgt ggagagggac tggcagagct      960
gaggccacct ggggctgggg atcccactct tcttgcagct gttgagcgca cctaaccact     1020
ggtcatgccc ccaccctgc tctccgcacc cgcttcctcc cgaccccagg accaggctac     1080
ttctcccctc ctcttgcctc cctcctgccc ctgctgcctc tgatcgtagg aattgaggag     1140
tgtcccgcct tgtggctgag aactggacag tggcagggc tggagatggg tgtgtgtgtg     1200
tgtgtgtgtg tgtgtgtgtg tgtgcgcgcg cgccagtgca agaccgagat tgagggaaag     1260
catgtctgct gggtgtgacc atgtttcctc tcaataaagt tccctgtga cactcaaaaa     1320
aaaaaaaaa aaaaaa                                                     1336

<210> SEQ ID NO 30
<211> LENGTH: 8171
<212> TYPE: DNA
<213> ORGANISM: Homo sapiens

<400> SEQUENCE: 30
gaggcagggg tgagaccggc ggccaccgt gagccctccg caccgcacc atgcagaaga       60
gcgtgcgcta caacgagggg cacgcccgt acctggcctt tctggcgcgc aaggagggca      120
ccaagcgcgg cttcctgagt aagaagacgg ccgaggcgag ccgctggcac gagaagtggt      180
tcgccctcta ccagaatgtg ctcttctact tcgagggcga gcagagctgc cgcccggcgg      240
gcatgtacct cctggagggc tgcagctgcg aacgaacgcc cgcgccaccc agggccggcg      300
ccgggcaggg aggcgtccga gacgcgctgg acaagcagta ttactttact gttcttttg      360
gccatgaagg tcagaagcca ctggagctgc gctgtgagga ggagcaggat ggtaaagagt      420
ggatggaggc cattcaccaa gccagttatg cagacatttt gattgagagg gaagtattaa      480
tgcagaagta cattcatcta gttcagatcg tagagacaga aaaaattgca gctaaccaac      540
tccgacatca acttgaagat caagacacag aaatcgaaag gcttaaatca gagattattg      600
ctcttaataa aaccaaagaa cgaatgcgac cttaccaaag caaccaagaa gacgaagatc      660
cagacatcaa gaagattaaa aaggttcaga gcttcatgcg aggatggttg tgcagaagga      720
aatggaagac catcgtgcag gattacattt gttctcctca tgctgaaagt atgaggaaga      780
gaaaccagat tgtgttcacc atggtggagg cagagtcaga gtacgttcac cagctctaca      840
tcctggtcaa tggctttctc cggccctgc gtatggccgc cagctccaag aagcccccca      900
tcagccacga cgacgtcagc agtatttttc ttaacagtga acaatcatg tttcttcatg      960
aaatatttca tcaaggacta aaggcaagga tagcaaactg gcccacttta atttttagctg    1020
atctgtttga tattttgctc cccatgctga acatttatca agaatttgtg cgtaatcacc    1080
agtacagcct gcaagttctc gccaattgta agcaaaacag agattttgac aaactcttaa    1140
```

```
aacagtatga agccaatcca gcctgtgagg ggaggatgct ggagacattc ttgacctatc    1200
ccatgtttca gatccccaga tatatcatca cactccatga gctccttgct cacacacccc    1260
atgagcatgt ggaaaggaaa agcctggagt ttgccaaatc aaagctagag gaactatcca    1320
gagtaatgca cgatgaagtc agcgacactg aaaacataag gaaaaacctt gccatcgaaa    1380
gaatgatcgt ggagggctgt gacatcttgc tggacaccag ccaaacgttc atccgccaag    1440
gttctcttat tcaagtacct tccgttgaga ggggaaaact tagtaaagtt cgcctgggtt    1500
cgttgtcttt gaaaaaggaa ggagagagac aatgcttctt atttacaaaa cacttttta    1560 tatgtacaag aagttcagga gggaagcttc atctgctcaa gacaggtggg gttctgtctc    1620
taatagactg cacattgatt gaggagccag atgcaagcga tgatgactct aaaggttctg    1680
ggcaagtgtt tgggcacctg gattttaaaa tagtggtgga gcctcctgac gctgccgcct    1740
tcactgttgt cttgttagca ccctcacgcc aggagaaagc tgcctggatg agtgacatca    1800
gtcagtgtgt ggacaatata cgatgtaatg gtttaatgac tatagtgttt gaagagaatt    1860
ccaaagtcac tgtgccacat atgattaagt ctgatgcccg tcttcataaa gacgacactg    1920
acatttgctt cagtaaaaca ctcaactcct gcaaagtgcc ccagatccgt tatgccagcg    1980
tggagcgcct cttggaacga ctgacagact tgcggtttct tagtattgat ttcctcaaca    2040
cctttctgca cacctatcgt attttcacta ctgccgctgt ggtgctgggg aaactctccg    2100
acatatacaa gaggcctttc acctccatcc ctgtcaggtc attggaattg ttttttgcta    2160
ccagccagaa caacagaggt gaacatttgg tggatggcaa atccccacgt ctgtgtcgca    2220
aattctcttc cccgccacca ctggctgtgt ccagaacatc ttccccagtg agggccagaa    2280
agctgtcttt gacttctccc ttgaactcaa agataggagc attggacctg acaacttcca    2340
gcagtcccac caccaccacc cagagtcccg ctgcgtctcc accaccacac actggtcaga    2400
taccactgga tctcagcaga ggcctctctt ctccagagca aagcccggga acggtagaag    2460
agaatgtcga taacccacgc gtggatctgt gtaacaagct aaaacgaagt attcaaaaag    2520
cagtcctaga gtctgcacca gcggaccgag caggagtgga aagctcccct gcagcggaca    2580
ccacagaact ttcaccttgc agatccccct caactcctcg gcacctccgc tatcgacagc    2640
ctggaggaca gacggcggac aatgccacct gctctgtttc accggcttct gcttttgcaa    2700
tagccacagc tgcagcagga catggagtc accaggctt aacaacacc gagagaacat    2760 gtgataaaga gtttattata cggagaacgg ctaccaatcg agttctgaac gtcctccgtc    2820
actgggtctc aaagcacgca caggatttcg aactcaacaa tgaactaaag atgaatgtcc    2880
taaatttgct agaagaagtt ttgcgagacc cagaccttct tccccaagaa aggaaagccg    2940
ccgcgaatat cctcagggcc ctttcacaag atgaccaaga tgcatccac ctaaaattag    3000 aggatataat tcaaatgact gactgcatga aggccgaatg ctttgagtcc ttgtcggcca    3060
tggagctggc agaacagatc accctcctgg accatgtcat tttcagaagc attccctacg    3120
aggagtttct tgggcagggg tggatgaagc tggataaaaa cgaaagaact ccttacatta    3180
tgaaaaccag ccaacacttc aatgacatga gtaacctggt ggcctcccag ataatgaact    3240
atgctgatgt cagctcccgt gccaacgcca tcgagaaatg ggtggcagtg gcggacatct    3300
gccgatgcct gcacaactac aacggcgtgc tggagatcac ctcggcctta aacagaagtg    3360
ccatctacag gctgaagaaa acctgggcaa aggtctctaa gcagacaaaa gctctaatgg    3420
acaaacttca aaagactgtt tcctctgaag gaagatttaa aaatcttaga gaaacccttaa   3480
```

```
aaaattgtaa ccctcctgca gttccttatc ttgggatgta cttgacagac ctggcattta    3540
ttgaagaagg aacaccaaac tttactgagg aaggccttgt caatttctcc aaaatgagaa    3600
tgatatcaca catcatcaga gagatacgcc agttccagca gacttcctac agaatagatc    3660
atcagccaaa ggtcgcacag tacttgcttg acaaagacct tatcatagat gaagatacgc    3720
tatatgagct gtcactaaaa attgaacctc gactccctgc ttgaagatct ggccttgccc    3780
ctgagtccac gggatgttca tggaaagcag gacagacaga attgtgtatg ccttgcctat    3840
cacggtacag cacgaagcca ggctcctttc tccaccaaag aagatggaac cagactggaa    3900
ttctgtctcc agagagaaac ccagctgttt gggtcaaaga cagatgcttc agacttgggt    3960
gggaaggtga agatggcta tttagaaagc tggtggcacg ttttacataa gggaatgtca    4020
gatgggagat gctagttgcc attttaacaa agcaggtaaa tcggtaaatt ttaaactctg    4080
tccatgttct gttagaactc agggacaagg atccatgaaa aagacctgtg atgtttctct    4140
ggcgctttac tggcctgggc acacctacca atcttctagg atttgactgg ttccattaca    4200
tttccttttg gtataagctt cacagaaaag ctgacacttc ctctacagag atggaccaaa    4260
acataagcaa tttcagtcta cagcatgtgc atggttgtca gtgcattcta aatatttcta    4320
tgtgaggaat ggtaccttct gaaactgcct ttccagtctt taggcaatgg gataggaaag    4380
aaagaatgaa acacaaatgg atttgtatgt aacatttcct taattaaatg cagtaggctg    4440
tgccccagag gattccagac agtggctggc tgaggtgggt ggggagcttt ccttgagac    4500 tgttggtcct aagaagccag ccctttttgga gaggcagctg caaaaaggtg cacgcccatc    4560
tcaccgacaa aactgtggaa cagaaggcca ccaagtgctg tggggaatca tgggtttcag    4620
tgctgagtga aaatctatac ctaaaaatca tctctgcacc ttgctttgtt tgttttcttt    4680
ccccactcat agtactgcag gaatctattc tcatttacac agacctttt ttaggcttac     4740 tatgaacatt ggctgtattt ttttttaaaca gtttagtgaa attttctttt caaacccac    4800 acttccatat gctgttcgta gatctctttc tttaaaaact gatgttgaga gatctctgag    4860
aatattataa gtgcatggga aatgggccca accaccgaac agctcttaca ttacaaaacc    4920
aaatgcaagg gttagtcctg ctacctgagg ctggggaagt gaccttcctt ttcccaagat    4980
tgtcagttgt tgaagaaata gggctatctc attgtttacc tccctcttct cttctcaggg    5040
agactgctgc tttaaaagaa ggaagagaaa aaatatagtt ctatttccct gaacctgttg    5100
cacctgacat tttctcttag cagcatgaaa cttattgatg ctgacaatga aaaatggatc    5160
tgtctggctg ctttccctct ttccttgcac tttaattatg ttgctagagc taacagacta    5220
ataaattcca cctgctggct cttaagactc agtgaaagag ctagcattgg taatgcacca    5280
tagaggtaga gaatgtacac tttctgcacg gtaagtgcca tctctgtatg taactatata    5340
gtgaaatatc aactaagtaa aagaaaatat aatatttgaa gaccattccc aaaatatttt    5400
caatagttca tattagccaa cagtgtagca ctcaacccaa ggagggttcc ttatggatgc    5460
tttctttttc ttttttaaag ttgcttgttt gttctcttta gtttcaaata agaggttgac    5520
gcatcttgat gcatgatgag aagcatgggc tgtttggatc ctaacaacgc ataacttgtg    5580
atttatttct cagtgctcca gaaactgagg gtttgaaata atatgtatca gttgcaccaa    5640
acacctcaag gtcttgcaga agaaaagtaa aggttagctt tcatggctca aaagcatagt    5700
cctgaagggt gaactaaaac cgggacaaat ctgtgagagg accacacaca tactagtttc    5760
gggccaaaca acacgtggaa aggtgcatgc attctactct gccttggagt tgccagagtc    5820
cttcagaggg aaagggatgg ttctgtgtgc acttttttctg gaagttcgga ctcatttctt    5880
```

```
tgacccaaat gttccagaga cactgcagcc attcttatta acaaaaaata agacaggagt      5940
ttccaaatgc tccttcccct ttggatcgca gcttttcttc aactagtgac aaagcttttg      6000
cgcctatttc ctgcaggatg ttggaactgc cccgcactgg tcatattagg cactgtcaat      6060
tgctatgctg acttttaggg ggttttttgtt tgtttgaaaa acagggtctc accatgttgc      6120
ccaggctggt ctcgaactcc tggactcaag caatcttcct gcctcagcct ctcaagcagc      6180
tgggactgca ggggtgtgcc actcactagc cttttcgcatt tttgtttgag aattacacca     6240
ctttctggag tctgcagcct tcctggagct gcaagagggc aagagagaga gctccacctc      6300
tgagggagtg tctgttgatg acctgcacta ttcgtgtgcc agctgggaga ggaatgcaca      6360
ttttaaaatc ccttcaattt ggtcaaatta aaatcccca agagcaattt gcagtgtttt       6420
ttctggtcgt taaagtaccc atcctcttct gcctacacac aaagcatgca ttcccagctg      6480
catctgcctc tagtccatta tggagaccca tttctaagag gagatgggag gtcaacctct      6540
aacagccaag tagcgaacat gtatactgta aaattaacct agaaaatcag aagaaaaatc     6600
caatttcatg ctttcgaatg aatgcccaca ttttgtactg tcaacgaaat tatcttggag     6660
cttttagggg atgccttttc gttattaact gagacatcta gttttgctac agggacaaat     6720
ctcttaccta atccaatata ttatttgaca gattcaggca tgaagtaaaa cgtcgtcact     6780
tttccttagt gcttttctga aggaatttaa agacggaatt ttaaacggcc attgcaatat     6840
tttcaagtgg ctctcatacc aagtcccatt actgtttgtt aaatttcagt acgtcttaaa    6900
gtactactta taaacaaatg aaactcagag aaactgaatc acctggaaga gaaaaatcca    6960
ttatggtccc atgtggagtg aataatgatg gatcagcacc ctttctctca tgttattgta    7020
taagacgaga cttttgggcc agcagcgatt gggcagcttt taaattctta actgaaaaga    7080
gtaatgcaat acagggatta ttcccaataa aattaacttt tatttaaaag caagagattt     7140
tacttagctt tttttttttca agtttgatt ttatcccctt gaaaaaaaat ctcttcactt      7200
taaagtataa aggttttttaa aaatccaatt gcaaaatgta ttattttac aactatcgaa      7260 aaggcataaa agagaacata ctatttatgg ctgaagggta tagccaggct aatgtgcaca     7320
gagggaatca ataaataaaa ctcttttcaa tttcagtaag aaatcagatt gtaagtttaa    7380
tggctccatt atagatacca ccgtgtaata gaagacttaa gtcaatgaaa tctaatcagt    7440
gtgtcatttc tcagcggcca ttggtgactt aaaattaaga tgaggcagag ccaaaatgga    7500
aaacagtcat tttgttgtag gtataaacac atgaacgatt cagaaaatta ttcatctcag    7560
ctgccatgca gcatgacatt aacattagga ttgatagcac tagtctgatc tgctcaagga    7620
aaataatagt tctattatac ttaatgatgt tggttttttac acagctcatt tcattttttca    7680 ctagaaagcc agttatgaaa gagagctggc ctaggcatcc cggccctgag tcctaggccc      7740
agtctccaac tggaaaacct taggctggtg tttacacatc cctgagcctc agtttcctca     7800
tctgcaaaac ggtgtgaata gtaatccctg tgctgcttat ctcacagggc tattgtgagg     7860
accaaatgga ttagactgta aactgcaaag tgctgtccgc acatgaggtc atctgattac     7920
tgtcctcaga tctcttttgt agaggatttc aatgtatttc tttatcattt gagtgtgtgt     7980
gtgatggacg aatatgtgtg tgagtttgag aagcatatcg ttcgtgtcca gttactttgc     8040
aaatttgtgg acatttgtga ttggacagag gggtttgtgc tgtggcctaa cacttgccaa      8100
gtgaggtgta ggttatgcct atatgcaaat taaacttcac cttcttgaa tattcaaaaa      8160 aaaaaaaaaa a                                                          8171
```

<210> SEQ ID NO 31
<211> LENGTH: 2089
<212> TYPE: DNA
<213> ORGANISM: Homo sapiens

<400> SEQUENCE: 31

| | | | | | |
|---|---|---|---|---|---|
| agtttggacg | gctgcttccc | accagcaaag | accacgactg | gagagccgag | ccggaggcag | 60 |
| ctgggaaaca | tgaagagcgt | cttgctgctg | accacgctcc | tcgtgcctgc | acacctggtg | 120 |
| gccgcctgga | gcaataatta | tgcggtggac | tgccctcaac | actgtgacag | cagtgagtgc | 180 |
| aaaagcagcc | cgcgctgcaa | gaggacagtg | ctcgacgact | gtggctgctg | ccgagtgtgc | 240 |
| gctgcagggc | ggggagaaac | ttgctaccgc | acagtctcag | gcatggatgg | catgaagtgt | 300 |
| ggcccggggc | tgaggtgtca | gccttctaat | ggggaggatc | cttttggtga | agagtttggt | 360 |
| atctgcaaag | actgtcccta | cggcaccttc | gggatggatt | gcagagagac | ctgcaactgc | 420 |
| cagtcaggca | tctgtgacag | ggggacggga | aaatgcctga | aattcccctt | cttccaatat | 480 |
| tcagtaacca | agtcttccaa | cagatttgtt | tctctcacgg | agcatgacat | ggcatctgga | 540 |
| gatggcaata | ttgtgagaga | agaagttgtg | aaagagaatg | ctgccgggtc | tcccgtaatg | 600 |
| aggaaatggt | taaatccacg | ctgatcccgg | ctgtgatttc | tgagagaagg | ctctattttc | 660 |
| gtgattgttc | aacacacagc | caacatttta | ggaactttct | agattatagc | ataaggacat | 720 |
| gtaattttttg | aagaccaaat | gtgatgcatg | gtggatccag | aaaacaaaaa | gtaggatact | 780 |
| tacaatccat | aacatccata | tgactgaaca | cttgtatgtg | tttgttaaat | attcgaatgc | 840 |
| atgtagattt | gttaaatgtg | tgtgtatagt | aacactgaag | aactaaaaat | gcaatttagg | 900 |
| taatcttacg | tggagacagg | tcaaccaaag | agggagctag | gcaaagctga | agaccgcagt | 960 |
| gagtcaaatt | agttctttga | ctttgatgta | cattaatgtt | gggatatgga | atgaagactt | 1020 |
| aagagcagga | gaagatgggg | aggggtggg | agtgggaaat | aaaatattta | gcccttcctt | 1080 |
| ggtaggtagc | ttctctagaa | tttaattgtg | ctttttttttt | tttttttggc | tttgggaaaa | 1140 |
| gtcaaaataa | acaaccaga | aaacccctga | aggaagtaag | atgtttgaag | cttatggaaa | 1200 |
| tttgagtaac | aaacagcttt | gaactgagag | caatttcaaa | aggctgctga | tgtagttccc | 1260 |
| gggttacctg | tatctgaagg | acggttctgg | ggcataggaa | acacatacac | ttccataaat | 1320 |
| agctttaacg | tatgccacct | cagagataaa | tctaagaagt | attttaccca | ctggtggttt | 1380 |
| gtgtgtgtat | gaaggtaaat | atttatatat | ttttataaat | aaatgtgtta | gtgcaagtca | 1440 |
| tcttccctac | ccatatttat | catcctcttg | aggaaagaaa | tctagtatta | tttgttgaaa | 1500 |
| atggttagaa | taaaactatg | actctataag | gttttcaaac | atctgaggca | tgataaattt | 1560 |
| attatccata | attatagtaa | taataacctt | aataagcata | agaaaaacag | agtcactctg | 1620 |
| gatttcaaaa | atgtcaaaaa | atgagcaaca | gagggtcctt | atttaaacat | aagtgctgtg | 1680 |
| acttaggtga | atttttcaatt | taaggtagaa | aataagtttt | taggaggttt | gtaaaagaag | 1740 |
| aatcaatttt | cagcagaaaa | catgtcaact | ttaaaatata | gtttattttc | atattttttt | 1800 |
| cttttaaact | tggttgataa | gtggaattag | gagtatattt | gaaagaatct | tagcacaaac | 1860 |
| aggactgttg | tactagatgt | tcttaggaaa | tatctcagaa | gtattttatt | tgaagtgaag | 1920 |
| aacttattta | agaattattt | cagtatttac | ctgtatttta | ttcttgaagt | tggccaacag | 1980 |
| agttgtgaat | gtgtgtggga | aggccttga | atgtaaagct | gcataagctg | ttaggttttg | 2040 |
| ttttaaaagg | acatgtttat | tattgttcaa | taaaaaagaa | caagataca | | 2089 |

<210> SEQ ID NO 32
<211> LENGTH: 7686
<212> TYPE: DNA
<213> ORGANISM: Homo sapiens

<400> SEQUENCE: 32

| | | | | | |
|---|---|---|---|---|---|
| tttatagcag | cagtagaaat | ataccaccct | agaggacaca | cctccttta | gctaggtacc | 60 |
| tataaatgtc | caggattttc | tattcaattg | agaagaaccc | agcaaaatgg | ggatctccac | 120 |
| agtcatcctt | gaaatgtgtc | ttttatgggg | acaagttcta | tctacaggtg | ggtggatccc | 180 |
| aaggactaca | gactacgctt | cactgattcc | ctcggaggtg | cccttggatc | caactgtagc | 240 |
| agaaggttct | ccatttccct | cggagtcgac | cctggagtca | actgtagcag | aaggttctcc | 300 |
| gatttccttg | gagtcaaccc | tggagtcaac | cgtagcagaa | ggttctctga | ttccctcaga | 360 |
| gtcaaccctg | gagtcaactg | tagcagaagg | atctgattct | ggtttggccc | tgaggctggt | 420 |
| gaatggagat | ggcaggtgtc | agggccgagt | ggagatccta | taccgaggct | cctggggcac | 480 |
| cgtgtgtgat | gacagctggg | acaccaatga | tgccaacgtg | gtctgtaggc | agctgggttg | 540 |
| tggctgggcc | atgtcagctc | aggaaatgc | ctggtttggc | cagggctcag | gacccattgc | 600 |
| cctggatgat | gtgcgctgct | caggacacga | atcctacctg | tggagctgcc | ccacaatgg | 660 |
| ctggctctcc | cataactgtg | gccatggtga | agatgctggt | gttatctgct | cagctgccca | 720 |
| gcctcagtca | acactcaggc | cagaaagttg | gcctgtcagg | atatcaccac | ctgtacccac | 780 |
| agaaggatct | gaatccagtt | tggccctgag | gctggtgaat | ggaggcgaca | ggtgtcgagg | 840 |
| ccgagtggag | gtcctatacc | gaggctcctg | gggcaccgtg | tgtgatgact | actgggacac | 900 |
| caatgatgcc | aatgtggtct | gcaggcagct | gggctgtggc | tgggccatgt | cagccccagg | 960 |
| aaatgcccag | tttggccagg | gctcaggacc | cattgtcctg | gatgatgtgc | gctgctcagg | 1020 |
| acatgagtcc | tacctgtgga | gctgccccca | caatggctgg | ctcacccaca | actgtggcca | 1080 |
| tagtgaagac | gctggtgtca | tctgctcagc | tccccagtcc | cggccgacac | ccagcccaga | 1140 |
| tacttggccg | acctcacatg | catcaacagc | aggacctgaa | tccagtttgg | ccctgaggct | 1200 |
| ggtgaatgga | ggtgacaggt | gtcagggccg | agtggaggtc | ctataccgag | ctcctggggg | 1260 |
| caccgtgtgt | gatgatagct | gggacaccag | tgacgccaat | gtggtctgcc | ggcagctggg | 1320 |
| ctgtggctgg | gccacgtcag | ccccaggaaa | tgcccggttt | ggccagggtt | caggacccat | 1380 |
| tgtcctggat | gacgtgcgct | gctcaggcta | tgagtcctac | ctgtggagct | gccccacaa | 1440 |
| tggctggctc | tcccataact | gtcagcacag | tgaagacgct | ggtgtcatct | gctcagctgc | 1500 |
| ccactcctgg | tcgacgccca | gtccagacac | gttgccgacc | atcaccttac | ctgcatcgac | 1560 |
| agtaggatct | gaatccagtt | tggccctgag | gctggtgaat | ggaggtgaca | ggtgtcaggg | 1620 |
| ccgagtggag | gtcctatacc | gaggctcctg | ggcaccgtg | tgtgatgaca | gctgggacac | 1680 |
| caatgatgcc | aatgtggtct | gcaggcagct | gggctgtggc | tgggccatgt | tggccccagg | 1740 |
| aaatgcccgg | tttggtcagg | gctcaggacc | cattgtcctg | gatgacgtgc | gctgctcagg | 1800 |
| gaatgagtcc | tacttgtgga | gctgcccccca | caatggctgg | ctctcccata | actgtggcca | 1860 |
| tagtgaagac | gctggtgtca | tctgctcagg | acctgaatcc | agtttggccc | tgaggctggt | 1920 |
| gaatggaggt | gacaggtgtc | agggccgagt | ggaggtccta | taccgaggct | cttggggcac | 1980 |
| cgtgtgtgat | gacagctggg | acaccaatga | tgccaatgtg | gtctgcaggc | agctgggctg | 2040 |
| tggctgggcc | acgtcagccc | caggaaatgc | ccggtttggt | cagggctcag | gacccattgt | 2100 |
| cctggatgat | gtgcgctgct | caggacatga | gtcctacctg | tggagctgcc | ccaacaatgg | 2160 |

| | |
|---|---|
| ctggctctcc cacaactgtg gccatcatga agatgctggt gtcatctgct cagctgccca | 2220 |
| gtcccggtcg acgcccaggc cagacacgtt gtcgaccatc acgttacctc catcgacagt | 2280 |
| aggatctgaa tccagtttga ccctgaggct ggtgaatgga agtgacaggt gtcagggccg | 2340 |
| agtagaggtc ctataccgag gctcctgggg caccgtgtgt gatgacagct gggataccaa | 2400 |
| tgatgccaat gtggtctgca ggcagctggg ctgtggctgg gccacgtcgg ccccaggaaa | 2460 |
| tgcccggttt ggccagggct caggacccat tgttctggat gatgtgcgct gctcaggaca | 2520 |
| cgagtcctac ctgtggagct gcccccacaa tggctggctc tcccacaact gtggccatca | 2580 |
| tgaagatgct ggtgtcatct gctcagtttc ccagtcccgg ccgacaccca gtccagatac | 2640 |
| ttggccgacc tcacatgcat caacagcagg acctgaatcc agtttggccc tgaggctggt | 2700 |
| gaatggaggt gacaggtgtc agggccgagt ggaggtccta taccgaggct cctgggcac | 2760 |
| cgtgtgtgat gatagctggg acaccagtga cgccaatgtg gtctgccggc agctgggctg | 2820 |
| tggctgggcc acgtcagccc caggaaatgc ccggtttggc cagggttcag gacccattgt | 2880 |
| cctggatgac gtgcgctgct caggctatga gtcctacctg tggagctgcc ccacaatgg | 2940 |
| ctggctctcc cataactgtc agcacagtga agacgctggt gtcatctgct cagctgccca | 3000 |
| ctcctggtcg acgcccagtc cagacacatt gccgaccatc accttgcctg catcgacagt | 3060 |
| aggatctgaa tccagtttgg ccctgaggct ggtgaatgga ggtgacaggt gtcagggccg | 3120 |
| agtggaggtc ctataccaag gctcctgggg caccgtgtgc gatgacagct gggacaccaa | 3180 |
| tgatgccaat gtcgtctgca ggcaactggg ctgtggctgg gccatgtcag ccccaggaaa | 3240 |
| tgcccggttt ggtcagggct caggacccat tgtcctggat gatgtgcgct gctcaggaca | 3300 |
| cgagtcttac ctgtggagct gcccccacaa tggctggctc tcccacaact gtggccatag | 3360 |
| tgaagacgct ggtgtcatct gctcagcttc ccagtcccgg ccaacaccta gtccagacac | 3420 |
| ttggccaacc tcacatgcat caacagcagg atctgaatcc agtttggccc tgaggctggt | 3480 |
| gaatggaggt gacaggtgtc agggccgagt ggaggtccta taccgaggct cctgggcac | 3540 |
| cgtgtgtgat gactactggg acaccaatga tgccaatgtg gtttgcaggc agctgggctg | 3600 |
| tggctgggcc atgtcagccc caggaaatgc ccggtttggc cagggttcag gacccattgt | 3660 |
| cctggatgat gtgcgctgct caggacatga gtcctatctg tggagctgcc ccacaatgg | 3720 |
| ctggctctcc cacaactgtg gccatcatga agacgctggt gtcatctgct cagcttccca | 3780 |
| gtcccagccg acacccagcc cagacacttg gccaacctca catgcatcaa cagcaggatc | 3840 |
| tgaatccagt ttggccctga ggctggtgaa tggaggtgac aggtgtcagg ccgagtgga | 3900 |
| ggtcctatac cgaggctcct ggggcaccgt gtgtgatgac tactgggaca ccaatgatgc | 3960 |
| caatgtggtt tgcaggcagc tgggctgtgg ctgggccacg tcagcccag gaaatgcccg | 4020 |
| gtttggccag ggttcaggac ccattgtcct ggatgatgtg cgctgctcag acatgagtc | 4080 |
| ctatctgtgg agctgccccc acaatggctg gctctcccac aactgtgcc atcatgaaga | 4140 |
| cgctggtgtc atctgctcag cttcccagtc ccagccgaca cccagcccag acacttggcc | 4200 |
| aacctcacat gcatcaacag caggatctga atccagtttg ccctgaggc tggtgaatgg | 4260 |
| aggtgacagg tgtcagggcc gagtggaggt cctataccga ggctcctggg gcaccgtgtg | 4320 |
| tgatgactac tgggacacca atgatgccaa tgtggtttgc aggcagctgg gctgtggctg | 4380 |
| ggccacgtca gccccaggaa atgcccggtt tggccagggt tcaggaccca ttgtcctgga | 4440 |
| tgatgtgcgc tgctcaggac atgagtccta tctgtggagc tgcccccaca atggctggct | 4500 |
| ctcccacaac tgtggccatc atgaagacgc tggtgtcatc tgctcagctt cccagtccca | 4560 |

```
gccgacaccc agcccagaca cttggccaac ctctcgtgca tcaacagcag gatctgaatc    4620
cactttggcc ctgagactgg tgaatggagg tgacaggtgt cgaggccgag tggaggtcct    4680
ataccaaggc tcctggggca ccgtgtgtga tgactactgg gacaccaatg atgccaacgt    4740
ggtctgcagg cagctgggct gtggctgggc catgtcagcc ccaggaaatg cccagtttgg    4800
ccagggctca ggacccattg tcctggatga tgtgcgctgc tcaggacacg agtcttacct    4860
gtggagctgc cccacacaatg gctggctctc ccacaactgt ggccatcatg aagatgctgg    4920
tgtcatctgc tcagctgctc agtcccagtc aacgcccagg ccagatactt ggctgaccac    4980
caacttaccg gcattgacag taggatctga atccagtttg gctctgaggc tggtgaatgg    5040
aggtgacagg tgtcgaggcc gagtggaggt cctgtatcga ggctcctggg aaccgtgtg    5100 tgatgacagc tgggacacca atgatgccaa tgtggtctgc aggcagctgg gctgtggctg    5160
ggccatgtcg gccccaggaa atgcccggtt tggccagggc tcaggaccca ttgtcctgga    5220
tgatgtgcgc tgctcaggga atgagtccta cctgtggagc tgcccccaca aaggctggct    5280
cacccacaac tgtggccatc acgaagacgc tggtgtcatc tgctcagcca cccaaataaa    5340
ttctactacg acagattggt ggcatccaac aactacaacc actgcaagac cctcttcaaa    5400
ttgtggtggc ttcttattct atgccagtgg gacattctcc agcccatcct accctgcata    5460
ctaccccaac aatgctaagt gtgtttggga aatagaagtg aattctggtt atcgcataaa    5520
cctgggcttc agtaatctga aattggaggc acaccataac tgcagttttg attatgttga    5580
aatctttgat ggatcattga atagcagtct cctgctgggg aaaatctgta atgataccag    5640
gcaaatattt acatcttctt acaaccgaat gaccattcac tttcgaagtg acatcagttt    5700
ccaaaacact ggcttttttgg cttggtataa ctccttccca agcgatgcca ccttgaggtt    5760
ggtcaattta aattcatcct atggtctatg tgccggcgt gtagaaattt accatggtgg    5820 cacctgggggg acagtttgtg atgactcctg gaccattcag gaagctgagg tggtctgcag    5880
acagctaggg tgtggacgtg cagtttcagc ccttggaaat gcatattttg gctctggctc    5940
tggccccatc accctggacg atgtagagtg ctcaggacg gaatccactc tctggcagtg    6000
ccggaaccga ggctggttct cccacaactg taatcatcgt gaagatgctg gtgtcatctg    6060
ctcaggaaac catctatcga cacctgctcc ttttctcaac atcacccgtc caaacacaga    6120
ttattcctgc ggaggcttcc tatcccaacc atcagggacg ttttccagcc cattctatcc    6180
cgggaactat ccaaacaatg ccaagtgtgt gtgggacatt gaggtgcaaa acaactaccg    6240
tgtgactgtg atcttcagag atgtccagct tgaaggtggc tgcaactatg attatattga    6300
agttttcgat ggcccctacc gcagttcccc tctcattgct cgagtttgtg atggggccag    6360
aggctccttc acttcttcct ccaacttcat gtccattcgc ttcatcagtg accacagcat    6420
cacaaggaga gggttccggg ctgagtacta ctccagtccc tccaatgaca gcaccaacct    6480
gctctgtctg ccaaatcaca tgcaagccag tgtgagcagg agctatctcc aatccttggg    6540 ctttttctgcc agtgaccttg tcatttccac ctggaatgga tactacgagt gtcggcccca    6600
gataacgccg aacctggtga tattcacaat tccctactca ggctgcggca ccttcaagca    6660
ggcagacaat gacaccatcg actattccaa cttcctcaca gcagctgtct caggtggcat    6720
catcaagagg aggacagacc tccgtattca cgtcagctgc agaatgcttc agaacacctg    6780
ggtcgacacc atgtacattg ctaatgacac catccacgtt gctaataaca ccatccaggt    6840
cgaggaagtc cagtatggca attttgacgt gaacatttcc ttttatactt cctcatcttt    6900
```

| | |
|---|---|
| cttgtatcct gtgaccagcc gcccttacta cgtggacctg aaccaggact tgtacgttca | 6960 |
| ggctgaaatc ctccattctg atgctgtact gaccttgttt gtggacacct gcgtggcatc | 7020 |
| accatactcc aatgacttca cgtctttgac ttatgatcta atccggagtg gatgcgtgag | 7080 |
| ggatgacacc tacggaccct actcctcgcc atctcttcgc attgcccgct tccggttcag | 7140 |
| ggccttccac ttcctgaacc gcttcccctc cgtgtacctg cgttgtaaaa tggtggtgtg | 7200 |
| cagagcgtat gacccctctt cccgctgcta ccgaggctgt gtgttgaggt cgaagaggga | 7260 |
| tgtgggctcc taccaggaaa aggtggacgt cgtcctgggt cccatccagc tgcagacccc | 7320 |
| cccacgccga agaggagc ctcggtaggt ggtcgctctc agaccccact gtccaccggg | 7380 |
| gcgcagaccc ctgactcggg gacttgggat gttcctcttg gtgtcatatt ccaactcaga | 7440 |
| ttgagcccta cattgtgctg cacctggtca tacggagttg aatcagacct ggttcccgcc | 7500 |
| tcccccaagg ctcatggtcc ttggaggacc cgttgcaggg tgaggtcaag agagttctga | 7560 |
| cctggatggc ccatagacct gacgtccag aatccatgct tctcatctgc aaaatgaaaa | 7620 |
| tgtcaatact tacttcttag cactgttgag agggttactt acataaagga attttggtga | 7680 |
| aactgc | 7686 |

<210> SEQ ID NO 33
<211> LENGTH: 1665
<212> TYPE: DNA
<213> ORGANISM: Homo sapiens

<400> SEQUENCE: 33

| | |
|---|---|
| agttggaggg aggcagggaa tctggcttga ttggcgtgct gagacgcacc tggcgcaacc | 60 |
| ctcccttctg aatcgaagtt caagtcccgc ggacactgca accatgaagg agagacgggc | 120 |
| cccccagcca gtcgtggcca gatgtaagct cgttctggtc ggggacgtgc agtgtgggaa | 180 |
| gaccgcgatg ttgcaagtgt tagcgaagga ttgctatcca gagacctatg tgcccaccgt | 240 |
| gttcgaaaat tacacagcct gttttggaga cagaggaacag agggtggagc ttagtctctg | 300 |
| ggatacctca ggatctcccct actacgataa tgtccgtcca ctctgctaca gcgactcgga | 360 |
| tgcagtatta ctatgttttg acatcagccg tccagagaca gtggacagcg cactcaagaa | 420 |
| gtggaggaca gaaatcctag attattgtcc cagcacccgc gttttgctca ttggctgcaa | 480 |
| gacagacctg cgaacagacc tgagtactct gatggagctg tcccaccaga agcaggcgcc | 540 |
| catctcctat gagcagggtt gtgcaatagc aaagcagctg ggtgcagaaa tctacctgga | 600 |
| aggctcagct ttcacctcag aaaagagcat ccacagcatc tttcggacgg catccatgct | 660 |
| gtgtctgaac aagcctagcc cactgcccca aagagccct gtccgaagcc tctccaaacg | 720 |
| actgctccac ctccccagtc gctctgaact catctcttct accttcaaga aggaaaaggc | 780 |
| caaaagctgt tccattatgt gaagtggaaa ttgaggggg gagacaaccc cctacttcct | 840 |
| cccttgggt gcagaggcac ggggagaggg aggatgagac aatttaggac actggacatg | 900 |
| agttttcag atggccacgg tgagggcttg aaggagaca ggaatggggc gaggaaggag | 960 |
| ccaggcccgg catgaggacc tgacgctgag agaaccat cataccccaa gccaggcact | 1020 |
| agattttgga gggggcgact accccagtgc cccccccgct ccagaggaag gaaagctgtg | 1080 |
| ggggacgggg ggcatgctgg cctcatgggc ttggggggcct acagcagcct caccttcagc | 1140 |
| ttcatgcctc ttccacacag cgtttccatg caggtcaggg gatgggaggg gtccctgagc | 1200 |
| ccttcccttc ccctctaagg aggcagcaac ggagagtggg gaagtggagc ggcagctccc | 1260 |
| ttgggggctt agcccaggtg cttcgtaact gcaatcggaa gtgcaggagc tggtcagagc | 1320 |

```
caatgagaag gaaacctcat ctttgcatag cccatgcctc atggagaggt gacatcatac   1380
attcacatgc ttctcaccta agtccccagg gtccaaggga gaagcccag accccccttct   1440 cttgcagagt gtgggggtgg tggtgctgca ggggcagggc tgggtggggg tcaccagact   1500
ttttctgccc ttagggtagt acagctggca tttgttttat agactcttgt ctttggaatt   1560 gggggggaggg ggggagtgtt tcaatctgtt atatgttctg tgtttaatga agaaaaccta   1620
tttattaatg aaaaatataa tacatataaa gaatttggct ccgta                  1665

<210> SEQ ID NO 34
<211> LENGTH: 1849
<212> TYPE: DNA
<213> ORGANISM: Homo sapiens

<400> SEQUENCE: 34
gggttatatg atctctttgg ctttagggaa ttactccata ccagctctga gatttccagc     60
tcagcgatgc ccccaggtcc ctgggagagc tgcttctggg tgggggggcct cattttgtgg   120 ctcagcgttg gaagttcagg ggatgcacct cctacccccac agccaaagtg cgctgacttc   180
cagagcgcca accttttttga aggcaccgat ctcaaagtcc agtttctcct ctttgtccct   240
tcgaatccta gctgtgggca gctagtagaa ggaagcagtg acctccaaaa ctctgggttc   300
aatgccactc tgggaaccaa actaattatc catggattca gggttttagg aacaaagcct   360
tcctggattg acacatttat tagaacccctt ctgcgtgcaa cgaatgctaa tgtgattgcc   420
gtggactgga tttatgggtc tacaggagtc tacttctcag ctgtgaaaaa tgtgattaag   480
ttgagcctcg agatctcccct tttcctcaat aaactcctgg tgctgggtgt gtcggaatcc   540
tcaatccaca tcattggtgt tagcctgggg gcccacgttg ggggcatggt gggacagctc   600
ttcggaggcc agctgggaca gatcacaggc ctggaccccg ctggacctga gtacaccagg   660
gccagtgtgg aagagcgctt ggatgctgga gatgccctct tcgtggaagc catccacaca   720
gacaccgaca atttgggtat tcggattccc gttggacatg tggactactt cgtcaacgga   780
ggccaagacc aacctggctg ccccaccttc ttttacgcag gttatagtta tctgatctgt   840
gatcacatga gggctgtgca cctctacatc agcgccctgg agaattcctg tccactgatg   900 gccttttccct gtgccagcta caaggccttc cttgctggac gctgtctgga ttgctttaac   960
ccttttctgc tttcctgccc aaggatagga ctggtggaac aaggtggtgt caagatagag  1020 ccgctccca aggaagtgaa agtctacctc ctgactactt ccagtgctcc gtactgcatg  1080
catcacagcc tcgtggagtt tcacttgaag gaactgagaa acaaggacac caacatcgag  1140
gttaccttcc ttagcagtaa catcacctct tcatctaaga tcaccatacc taagcagcaa  1200
cgctatggga aaggaatcat agcccatgcc acccccacaat gccagataaa ccaagtgaaa  1260
ttcaagtttc agtcttccaa ccgagtttgg aaaaaagacc ggactaccat tattgggaag  1320
ttctgcactg ccctttttgcc tgtcaatgac agagaaaaga tggtctgctt acctgaacca  1380
gtgaacttac aagcaagtgt gactgtttcc tgtgacctga atagccctg tgtgtagttt  1440 aacctgggca ggacacatct ccctgcattt ttttttttt tttgagagag aggtgtgatg  1500
agggatgtgt gtgtgcagct tattgtagac cattactact aaggagaaaa gcaaagctct  1560 ttccttatttt cctcataatc agctaccctg gaggggaggg agaactcatt ttacagaact  1620
tggtttcctt tgccgatctt atgtacatac ccatttttagc tttcccatgc atacttaact  1680
gcacttgctt tatctccttg ggcattcgta cttaggattc aatagaaaca tgtacagggt  1740
```

```
aaacaatttt ttaaaaataa aacttcatgg agtatctgaa aaaaaaaaaa aaaaaaaaaa    1800
aaaaaaaaaa aaaaaaaaaa aaaaaaaaaa aaaaaaaaaa aaaaaaaaa                1849

<210> SEQ ID NO 35
<211> LENGTH: 7656
<212> TYPE: DNA
<213> ORGANISM: Homo sapiens

<400> SEQUENCE: 35
tttatagcag cagtagaaat ataccaccct agaggacaca cctccttta gctaggtacc      60 tataaatgtc caggattttc tattcaattg agaagaaccc agcaaaatgg ggatctccac    120
agtcatcctt gaaatgtgtc ttttatgggg acaagttcta tctacaggtg ggtggatccc    180
aaggactaca gactacgctt cactgattcc ctcggaggtg cccttggatc caactgtagc    240
agaaggttct ccatttccct cggagtcgac cctggagtca actgtagcag aaggttctcc    300
gatttccttg gagtcaaccc tggagtcaac cgtagcagaa ggttctctga ttccctcaga    360
gtcaaccctg gagtcaactg tagcagaagg atctgattct ggtttggccc tgaggctggt    420
gaatggagat ggcaggtgtc agggccgagt ggagatccta taccgaggct cctggggcac    480
cgtgtgtgat gacagctggg acaccaatga tgccaacgtg gtctgtaggc agctgggttg    540
tggctgggcc atgtcagctc caggaaatgc ctggtttggc cagggctcag gacccattgc    600
cctggatgat gtgcgctgct caggacacga atcctacctg tggagctgcc ccacaatgg     660 ctggctctcc cataactgtg gccatggtga agatgctggt gttatctgct cagctgccca    720
gcctcagtca acactcaggc cagaaagttg gcctgtcagg atatcaccac ctgtacccac    780
agaaggatct gaatccagtt tggccctgag gctggtgaat ggaggcgaca ggtgtcgagg    840
ccgagtggag gtcctatacc gaggctcctg ggcaccgtg tgtgatgact actgggacac     900
caatgatgcc aatgtggtct gcaggcagct gggctgtggc tgggccatgt cagccccagg    960
aaatgcccag tttggccagg gctcaggacc cattgtcctg gatgatgtgc gctgctcagg    1020
acatgagtcc tacctgtgga gctgccccca caatggctgg ctcacccaca actgtggcca    1080
tagtgaagac gctggtgtca tctgctcagc tccccagtcc cggccgacac ccagcccaga    1140
tacttggccg acctcacatg catcaacagc aggacctgaa tccagtttgg ccctgaggct    1200
ggtgaatgga ggtgacaggt gtcagggccg agtggaggtc ctataccgag ctcctgggg    1260 caccgtgtgt gatgatagct gggacaccag tgacgccaat gtggtctgcc ggcagctggg    1320
ctgtggctgg gccacgtcag ccccaggaaa tgcccggttt ggccagggtt caggacccat    1380
tgtcctggat gacgtgcgct gctcaggcta tgagtcctac ctgtggagct gccccacaa     1440 tggctggctc tcccataact gtcagcacag tgaagacgct ggtgtcatct gctcagacac    1500
gttgccgacc atcaccttac ctgcatcgac agtaggatct gaatccagtt tggccctgag    1560
gctggtgaat ggaggtgaca ggtgtcaggg ccgagtggag gtcctatacc gaggctcctg    1620
gggcaccgtg tgtgatgaca gctgggacac caatgatgcc aatgtggtct gcaggcagct    1680
gggctgtggc tgggccatgt tggccccagg aaatgcccgg tttggtcagg gctcaggacc    1740
cattgtcctg gatgacgtgc gctgctcagg aatgagtcc tacttgtgga gctgccccca     1800
caatggctgg ctctcccata actgtggcca tagtgaagac gctggtgtca tctgctcagg    1860
acctgaatcc agtttggccc tgaggctggt gaatggaggt gacaggtgtc agggccgagt    1920
ggaggtccta taccgaggct cttggggcac cgtgtgtgat gacagctggg acaccaatga    1980
tgccaatgtg gtctgcaggc agctgggctg tggctgggcc acgtcagccc caggaaatgc    2040
```

```
ccggtttggt cagggctcag gacccattgt cctggatgat gtgcgctgct caggacatga   2100
gtcctacctg tggagctgcc ccaacaatgg ctggctctcc cacaactgtg gccatcatga   2160
agatgctggt gtcatctgct cagctgccca gtcccggtcg acgcccaggc cagacacgtt   2220
gtcgaccatc acgttacctc catcgacagt aggatctgaa tccagtttga ccctgaggct   2280
ggtgaatgga agtgacaggt gtcagggccg agtagaggtc ctataccgag gctcctgggg   2340
caccgtgtgt gatgacagct gggataccaa tgatgccaat gtggtctgca ggcagctggg   2400
ctgtggctgg gccacgtcgg ccccaggaaa tgcccggttt ggccagggct caggacccat   2460
tgttctggat gatgtgcgct gctcaggaca cgagtcctac ctgtggagct gcccccacaa   2520
tggctggctc tcccacaact gtggccatca tgaagatgct ggtgtcatct gctcagtttc   2580
ccagtcccgg ccgacaccca gtccagatac ttggccgacc tcacatgcat caacagcagg   2640
acctgaatcc agtttggccc tgaggctggt gaatggaggt gacaggtgtc agggccgagt   2700
ggaggtccta taccgaggct cctggggcac cgtgtgtgat gatagctggg acaccagtga   2760
cgccaatgtg gtctgccggc agctgggctg tggctgggcc acgtcagccc aggaaatgc    2820
ccggtttggc cagggttcag gacccattgt cctggatgac gtgcgctgct caggctatga   2880
gtcctacctg tggagctgcc cccacaatgg ctggctctcc cataactgtc agcacagtga   2940
agacgctggt gtcatctgct cagctgccca ctcctggtcg acgcccagtc cagacacatt   3000
gccgaccatc accttgcctg catcgacagt aggatctgaa tccagtttgg ccctgaggct   3060
ggtgaatgga ggtgacaggt gtcagggccg agtggaggtc ctataccaag gctcctgggg   3120
caccgtgtgc gatgacagct gggacaccaa tgatgccaat gtcgtctgca ggcaactggg   3180
ctgtggctgg gccatgtcag ccccaggaaa tgcccggttt ggtcagggct caggacccat   3240
tgtcctggat gatgtgcgct gctcaggaca cgagtcttac ctgtggagct gcccccacaa   3300
tggctggctc tcccacaact gtggccatag tgaagacgct ggtgtcatct gctcagcttc   3360
ccagtcccgg ccaacaccta gtccagacac ttggccaacc tcacatgcat caacagcagg   3420
atctgaatcc agtttggccc tgaggctggt gaatggaggt gacaggtgtc agggccgagt   3480
ggaggtccta taccgaggct cctggggcac cgtgtgtgat gactactggg acaccaatga   3540
tgccaatgtg gtttgcaggc agctgggctg tggctgggcc atgtcagccc aggaaatgc    3600
ccggtttggc cagggttcag gacccattgt cctggatgat gtgcgctgct caggacatga   3660
gtcctatctg tggagctgcc ccacaatgg ctggctctcc cacaactgtg gccatcatga    3720
agacgctggt gtcatctgct cagcttccca gtcccagccg acaccagcc cagacacttg     3780
gccaacctca catgcatcaa cagcaggatc tgaatccagt ttggccctga ggctggtgaa   3840
tggaggtgac aggtgtcagg gccgagtgga ggtcctatac cgaggctcct ggggcaccgt   3900
gtgtgatgac tactgggaca ccaatgatgc caatgtggtt tgcaggcagc tgggctgtgg   3960
ctgggccacg tcagcccag gaaatgcccg gtttggccag ggttcaggac ccattgtcct    4020
ggatgatgtg cgctgctcag gacatgagtc ctatctgtgg agctgccccc acaatggctg   4080
gctctcccac aactgtggcc atcatgaaga cgctggtgtc atctgctcag cttcccagtc   4140
ccagccgaca cccagcccag acacttggcc aacctcacat gcatcaacag caggatctga   4200
atccagtttg ccctgaggc tggtgaatgg aggtgacagg tgtcagggcc gagtggaggt     4260
cctataccga ggctcctggg gcaccgtgtg tgatgactac tgggacacca atgatgccaa   4320
tgtggtttgc aggcagctgg gctgtggctg ggccacgtca gccccaggaa atgcccggtt   4380
```

```
tggccagggt tcaggaccca ttgtcctgga tgatgtgcgc tgctcaggac atgagtccta    4440
tctgtggagc tgcccccaca atggctggct ctcccacaac tgtggccatc atgaagacgc    4500
tggtgtcatc tgctcagctt cccagtccca gccgacaccc agcccagaca cttggccaac    4560
ctctcgtgca tcaacagcag gatctgaatc cactttggcc ctgagactgg tgaatggagg    4620
tgacaggtgt cgaggccgag tggaggtcct ataccaaggc tcctgggca ccgtgtgtga     4680
tgactactgg gacaccaatg atgccaacgt ggtctgcagg cagctgggct gtggctgggc    4740
catgtcagcc ccaggaaatg cccagtttgg ccagggctca ggacccattg tcctggatga    4800
tgtgcgctgc tcaggacacg agtcttacct gtggagctgc ccccacaatg gctggctctc    4860
ccacaactgt ggccatcatg aagatgctgg tgtcatctgc tcagctgctc agtcccagtc    4920
aacgcccagg ccagatactt ggctgaccac caacttaccg gcattgacag taggatctga    4980
atccagtttg gctctgaggc tggtgaatgg aggtgacagg tgtcgaggcc gagtggaggt    5040
cctgtatcga ggctcctggg gaaccgtgtg tgatgacagc tgggacacca atgatgccaa    5100
tgtggtctgc aggcagctgg gctgtggctg gccatgtcg gccccaggaa atgcccggtt     5160
tggccagggc tcaggaccca ttgtcctgga tgatgtgcgc tgctcaggga atgagtccta    5220
cctgtggagc tgcccccaca aaggctggct cacccacaac tgtggccatc acgaagacgc    5280
tggtgtcatc tgctcagcca cccaaataaa ttctactacg acagattggt ggcatccaac    5340
aactacaacc actgcaagac cctcttcaaa ttgtggtggc ttcttattct atgccagtgg    5400
gacattctcc agcccatcct accctgcata ctaccccaac aatgctaagt gtgtttggga    5460
aatagaagtg aattctggtt atcgcataaa cctgggcttc agtaatctga aattggaggc    5520
acaccataac tgcagttttg attatgttga aatctttgat ggatcattga atagcagtct    5580
cctgctgggg aaaatctgta atgataccag gcaaatattt acatcttctt acaaccgaat    5640
gaccattcac tttcgaagtg acatcagttt ccaaaacact ggcttttttgg cttggtataa    5700
ctccttccca agcgatgcca ccttgaggtt ggtcaattta aattcatcct atggtctatg    5760
tgccgggcgt gtagaaattt accatggtgg cacctggggg acagtttgtg atgactcctg    5820
gaccattcag gaagctgagg tggtctgcag acagctaggg tgtggacgtg cagtttcagc    5880
ccttggaaat gcatattttg gctctggctc tggccccatc accctggacg atgtagagtg    5940
ctcagggacg gaatccactc tctggcagtg ccggaaccga ggctggttct cccacaactg    6000
taatcatcgt gaagatgctg gtgtcatctg ctcaggaaac catctatcga cacctgctcc    6060
tttttctcaac atcacccgtc caaacacaga ttattcctgc ggaggcttcc tatcccaacc    6120
atcaggggac ttttccagcc cattctatcc cgggaactat ccaaacaatg ccaagtgtgt    6180
gtgggacatt gaggtgcaaa acaactaccg tgtgactgtg atcttcagag atgtccagct    6240
tgaaggtggc tgcaactatg attatattga agttttcgat ggcccctacc gcagttcccc    6300
tctcattgct cgagttttgtg atggggccag aggctccttc acttcttcct ccaacttcat    6360
gtccattcgc ttcatcagtg accacagcat cacaaggaga gggttccggg ctgagtacta    6420
ctccagtccc tccaatgaca gcaccaacct gctctgtctg ccaaatcaca tgcaagccag    6480
tgtgagcagg agctatctcc aatccttggg cttttctgcc agtgacccttg tcatttccac    6540
ctggaatgga tactacgagt gtcggcccca gataacgccg aacctggtga tattcacaat    6600
tccctactca ggctgcggca ccttcaagca ggcagacaat gacaccatcg actattccaa    6660
cttcctcaca gcagctgtct caggtggcat catcaagagg aggacagacc tccgtattca    6720
cgtcagctgc agaatgcttc agaacacctg ggtcgacacc atgtacattg ctaatgacac    6780
```

-continued

| | |
|---|---|
| catccacgtt gctaataaca ccatccaggt cgaggaagtc cagtatggca attttgacgt | 6840 |
| gaacatttcc ttttatactt cctcatcttt cttgtatcct gtgaccagcc gcccttacta | 6900 |
| cgtggacctg aaccaggact tgtacgttca ggctgaaatc ctccattctg atgctgtact | 6960 |
| gaccttgttt gtggacacct gcgtggcatc accatactcc aatgacttca cgtctttgac | 7020 |
| ttatgatcta atccggagtg gatgcgtgag ggatgacacc tacggaccct actcctcgcc | 7080 |
| atctcttcgc attgcccgct tccggttcag ggccttccac ttcctgaacc gcttcccctc | 7140 |
| cgtgtacctg cgttgtaaaa tggtggtgtg cagagcgtat gaccctctt cccgctgcta | 7200 |
| ccgaggctgt gtgttgaggt cgaagaggga tgtgggctcc taccaggaaa aggtggacgt | 7260 |
| cgtcctgggt cccatccagc tgcagacccc ccacgccga aagaggagc ctcggtaggt | 7320 |
| ggtcgctctc agaccccact gtccaccggg gcgcagaccc ctgactcggg gacttgggat | 7380 |
| gttcctcttg gtgtcatatt ccaactcaga ttgagcccta cattgtgctg cacctggtca | 7440 |
| tacggagttg aatcagacct ggttcccgcc tcccccaagg ctcatggtcc ttggaggacc | 7500 |
| cgttgcaggg tgaggtcaag agagttctga cctggatggc ccatagacct gacgtcccag | 7560 |
| aatccatgct tctcatctgc aaaatgaaaa tgtcaatact tacttcttag cactgttgag | 7620 |
| agggttactt acataaagga attttggtga aactgc | 7656 |

<210> SEQ ID NO 36
<211> LENGTH: 2413
<212> TYPE: DNA
<213> ORGANISM: Homo sapiens

<400> SEQUENCE: 36

| | |
|---|---|
| cccgggctcg cgggcagacg gaggcgcctc tctttcccg cccctcgcct cggccctttc | 60 |
| tcttcccagc acctcggctg ttccccggcg gcggcagcgg cagcggcggc ccacacagca | 120 |
| gcgagaggcg agaggaggct gcctcgagga ggctgcctcg aggatgaagt gcaaacccaa | 180 |
| ccagacgcgg acctacgacc ccgaggggtt caagaagcgg gcggcgtgcc tgtgcttccg | 240 |
| gagcgaacgc gaggacgagg tcctgttagt gagtagcagc cggtacccgg accgctggat | 300 |
| cgtgccgggc gggggcatgg agcccgagga ggagccgggc ggtgcggcgg tccgagaggt | 360 |
| gtacgaagaa gcgggagtca aggggaagtt aggccggctc ctgggcgtct tcgaacagaa | 420 |
| ccaggatcgc aagcacagaa cgtacgtgta tgtactgact gtcacggagc tgctggagga | 480 |
| ttgggaagat tcggttagca ttgggaggaa gcgagagtgg ttcaaagtcg aagatgccat | 540 |
| caaggttctc cagtgccaca agcccgtgca cgccgaatat ctgagagaaac taaagctggg | 600 |
| cggttcccca accaatggaa actccatggc cccatcctcg ccagatagcg atccctaatg | 660 |
| aacagcaaag atgttcagta ttgtgctgaa agaaacattg atgtgaaccc agtgatcagt | 720 |
| ggaattgtca agtacaggtg agcacttctg tgttcccaag aagacagctc atctggtttc | 780 |
| ttcctgcatc ttgggacact ccttccctgt ctataccact gactcttgct ctggttgttg | 840 |
| tactcttata cgtgaataga ctcttaattc agcacctata gccttttgtt gtgctttttt | 900 |
| gatgtgtctg ccttcattag actatgatgt ctttgagagc aaagactatt tttccttact | 960 |
| cttttgcatat tctgcatctg agacactact tgaaatatgt ttggcatcac tgaaggttct | 1020 |
| ttgattcaat taatattttg taatcaccgt gtggcaaaac attcccttc caatctggtg | 1080 |
| ctagtagagt atatgctatc taggcaccat gtgtgtggct tttgtgtatc aggtgtttca | 1140 |
| gaaatatttc aagacagttg taagatgttt gaggacaaga attattactc ctatttctat | 1200 |

| | | | | | |
|---|---|---|---|---|---|
| gtcataccac | acagtagctg | cacagtttta | agattatgcc | atcacctagg | gtaatgtttt | 1260 |
| gtagaatcag | tccttcgtgt | aacaactcta | gtgtttttgt | actgttgatg | atttgcttaa | 1320 |
| attttattca | aaaactatca | cttgctataa | aggtaattgt | aaaaataaat | acagtggacg | 1380 |
| caaaataatg | ttgtgagttt | ttataaaaat | aaattttaaa | atgatatata | agacattttt | 1440 |
| ttgcaatgcc | tgccctaacc | acttcttaca | tgtcatctta | acatctcttt | gaggaaacac | 1500 |
| tgtttcctca | ttttacagat | ttaacatact | gtattatttg | atgccagagc | caacaggcta | 1560 |
| tatcataggc | agtttccaaa | cttaattatg | ccatttagtt | tgtctagatt | tcttttgcct | 1620 |
| ctctcactga | tccatttggc | tgtagttttc | atccctttc | cagtacacac | agctagctcc | 1680 |
| tcatcctacc | tggtttctgc | atatgagaat | gcagagggct | gagagagggc | aaaattgttg | 1740 |
| tcatttagaa | aaggcattta | ggaaagaggc | tgctattaga | ggggaacaca | agtgaaggt | 1800 |
| ttttttaaaa | aagaggactt | gcatcagctg | cctccagaac | aattttaaga | aaataacaaa | 1860 |
| gatgtttaga | agaaatctta | cggagtttgc | catgggatgt | gtgatatcag | cagtcttcag | 1920 |
| ctccttacaa | attaccaaaa | gtggttctaa | tatgctagtt | tgtttgattt | tttcttttat | 1980 |
| attataaagc | aattgcatcg | ataaaagctt | ggactccatt | ttagtgtgac | actcttcctc | 2040 |
| atgataccag | tgaaatgtat | tgattgtgtc | cccagttgtt | acataatttg | aaataaaaat | 2100 |
| ataacttctt | gatttattgt | tttttaagat | gtgatatggt | actgtggtta | tgttgtttta | 2160 |
| aaaaatgatt | atcttttaga | gaagtatact | gaaaaatgta | caggtgaaat | gatatgttac | 2220 |
| tggtattcgc | ttcaaaatca | tctgagtgtg | gggtaattga | gtacatagat | gaaacaagat | 2280 |
| tggccataaa | ttggtaattg | ctgaagctgt | gtgatggatg | tttgagagtt | cattatacta | 2340 |
| ttctctatac | ttttgtatat | gtttgaaatt | ttccataata | aaaattgaaa | aaagtaaaaa | 2400 |
| aaaaaaaaaa | aaa | | | | | 2413 |

<210> SEQ ID NO 37
<211> LENGTH: 862
<212> TYPE: DNA
<213> ORGANISM: Homo sapiens

<400> SEQUENCE: 37

| | | | | | |
|---|---|---|---|---|---|
| cttggcggtg | acgcacggcc | ctcacgtgac | cgggagctgc | agagctacgc | agccttcggt | 60 |
| gcagtcgtca | ctcgtgtctc | gctaccagct | ccccgctgcc | ctgcgctcgg | cgggctggca | 120 |
| tccggcccgg | gggaaagcgg | accagccctt | ctgcaggtct | gcggggccaa | gtgtcccggc | 180 |
| ggcgcacctc | gtggcgagaa | tcgggagaag | gaggagacta | caaggatagg | cccaggagta | 240 |
| atggagtcca | aagagaaacg | agcagtaaac | agtctcagca | tggaaaatgc | caaccaagaa | 300 |
| aatgaagaaa | aggagcaagt | tgctaataaa | ggggagccct | tggccctccc | tttggatgct | 360 |
| ggtgaatact | gtgtgcctag | aggaaatcgt | aggcggttcc | gcgttaggca | gcccatcctg | 420 |
| cagtatagat | gggatatgat | gcataggctt | ggagaaccac | aggcaaggat | gagagaagag | 480 |
| aatatggaaa | ggattgggga | ggaggtgaga | cagctgatgg | aaaagctgag | ggaaaagcag | 540 |
| ttgagtcata | gtctgcgggc | agtcagcact | gacccccctc | accatgacca | tcatgatgag | 600 |
| ttttgcctta | tgccctgaat | cctgatggtt | tccctaaagt | tattacggaa | acagacccct | 660 |
| gctttcgaat | ttacatgttc | atgatgtgcc | cttgttgtaa | acctttacct | gtcacttgtt | 720 |
| tacgtgggtc | tcctattacc | agcttctaat | tgaatattgt | gttttgaac | cagtctgtaa | 780 |
| gattttgtt | agcagaagaa | ttttacctat | tgcatggaaa | gatgctcatt | atagtgaagt | 840 |
| taataaagca | cctttaaaaa | gc | | | | 862 |

<210> SEQ ID NO 38
<211> LENGTH: 7080
<212> TYPE: DNA
<213> ORGANISM: Homo sapiens

<400> SEQUENCE: 38

| | | | | | |
|---|---|---|---|---|---|
| gagctagcgc | tcaagcagag | cccagcgcgg | tgctatcgga | cagagcctgg | cgagcgcaag | 60 |
| cggcgcgggg | agccagcggg | gctgagcgcg | gccagggtct | gaacccagat | ttcccagact | 120 |
| agctaccact | ccgcttgccc | acgccccggg | agctcgcggc | gcctggcggt | cagcgaccag | 180 |
| acgtccgggg | ccgctgcgct | cctggcccgc | gaggcgtgac | actgtctcgg | ctacagaccc | 240 |
| agagggagca | cactgccagg | atgggagctg | ctggaggca | ggacttcctc | ttcaaggcca | 300 |
| tgctgaccat | cagctggctc | actctgacct | gcttccctgg | ggccacatcc | acagtggctg | 360 |
| ctgggtgccc | tgaccagagc | cctgagttgc | aaccctggaa | ccctggccat | gaccaagacc | 420 |
| accatgtgca | tatcggccag | ggcaagacac | tgctgctcac | ctcttctgcc | acggtctatt | 480 |
| ccatccacat | ctcagaggga | ggcaagctgg | tcattaaaga | ccacgacgag | ccgattgttt | 540 |
| tgcgaacccg | gcacatcctg | attgacaacg | gaggagagct | gcatgctggg | agtgccctct | 600 |
| gcccttttcca | gggcaatttc | accatcattt | tgtatggaag | ggctgatgaa | ggtattcagc | 660 |
| cggatcctta | ctatggtctg | aagtacattg | ggttggtaa | aggaggcgct | cttgagttgc | 720 |
| atggacagaa | aaagctctcc | tggacatttc | tgaacaagac | ccttcaccca | ggtggcatgg | 780 |
| cagaaggagg | cttatttttt | gaaaggagct | ggggccaccg | tggagttatt | gttcatgtca | 840 |
| tcgaccccaa | atcaggcaca | gtcatccatt | ctgaccggtt | tgacacctat | agatccaaga | 900 |
| aagagagtga | acgtctggtc | cagtatttga | acgcggtgcc | cgatggcagg | atcctttctg | 960 |
| ttgcagtgaa | tgatgaaggt | tctcgaaatc | tggatgacat | ggccaggaag | gcgatgacca | 1020 |
| aattgggaag | caaacacttc | ctgcaccttg | gatttagaca | cccttggagt | tttctaactg | 1080 |
| tgaaaggaaa | tccatcatct | tcagtggaag | accatattga | atatcatgga | catcgaggct | 1140 |
| ctgctgctgc | ccgggtattc | aaattgttca | agacagagca | tggcgaatat | ttcaatgttt | 1200 |
| ctttgtccag | tgagtgggtt | caagacgtgg | agtggacgga | gtggttcgat | catgataaag | 1260 |
| tatctcagac | taaaggtggg | gagaaaattt | cagacctctg | gaaagctcac | ccaggaaaaa | 1320 |
| tatgcaatcg | tcccattgat | atacaggcca | ctacaatgga | tggagttaac | ctcagcaccg | 1380 |
| aggttgtcta | caaaaaggc | caggattata | ggtttgcttg | ctacgaccgg | ggcagagcct | 1440 |
| gccgagcta | ccgtgtacgg | ttcctctgtg | ggaagcctgt | gaggcccaaa | ctcacagtca | 1500 |
| ccattgacac | caatgtgaac | agcaccattc | tgaacttgga | ggataatgta | cagtcatgga | 1560 |
| aacctggaga | tacctggtc | attgccagta | ctgattactc | catgtaccag | gcagaagagt | 1620 |
| tccaggtgct | tccctgcaga | tcctgcgccc | ccaaccaggt | caaagtggca | gggaaaccaa | 1680 |
| tgtacctgca | catcggggag | gagatagacg | gcgtggacat | gcgggcggag | gttgggcttc | 1740 |
| tgagccggaa | catcatagtg | atgggggaga | tggaggacaa | atgctacccc | tacagaaacc | 1800 |
| acatctgcaa | tttctttgac | ttcgataccct | tgggggcca | catcaagttt | gctctgggat | 1860 |
| ttaaggcagc | acacttggag | ggcacggagc | tgaagcatat | gggacagcag | ctggtgggtc | 1920 |
| agtacccgat | tcacttccac | ctggccggtg | atgtagacga | aagggaggt | tatgacccac | 1980 |
| ccacatacat | cagggacctc | tccatccatc | atacattctc | tcgctgcgtc | acagtccatg | 2040 |
| gctccaatgg | cttgttgatc | aaggacgttg | tgggctataa | ctctttgggc | cactgcttct | 2100 |

-continued

```
tcacggaaga tgggccggag gaacgcaaca cttttgacca ctgtcttggc ctccttgtca    2160
agtctggaac cctcctcccc tcggaccgtg acagcaagat gtgcaagatg atcacagagg    2220
actcctaccc ggggtacatc cccaagccca ggcaagactg caatgctgtg tccaccttct    2280
ggatggccaa tcccaacaac aacctcatca actgtgccgc tgcaggatct gaggaaactg    2340
gattttggtt tattttttcac cacgtaccaa cgggcccctc cgtgggaatg tactccccag    2400
gttattcaga gcacattcca ctgggaaaat tctataacaa ccgagcacat tccaactacc    2460
gggctggcat gatcatagac aacggagtca aaaccaccga ggcctctgcc aaggacaagc    2520
ggccgttcct ctcaatcatc tctgccagat acagccctca ccaggacgcc gacccgctga    2580
agccccggga gccggccatc atcagacact tcattgccta caagaaccag gaccacgggg    2640
cctggctgcg cggcgggat gtgtggctgg acagctgccg gtttgctgac aatggcattg    2700
gcctgaccct ggccagtggt ggaaccttcc cgtatgacga cggctccaag caagagataa    2760
agaacagctt gtttgttggc gagagtggca acgtggggac ggaaatgatg gacaatagga    2820
tctgggcccc tggcggcttg gaccatagcg gaaggaccct ccctataggc cagaattttc    2880
caattagagg aattcagtta tatgatggcc ccatcaacat ccaaaactgc actttccgaa    2940
agtttgtggc cctggagggc cggcacacca gcgccctggc cttccgcctg aataatgcct    3000
ggcagagctg cccccataac aacgtgaccg gcattgcctt tgaggacgtt ccgattactt    3060
ccagagtgtt cttcggagag cctgggccct ggttcaacca gctggacatg gatgggata    3120
agacatctgt gttccatgac gtcgacggct ccgtgtccga gtaccctggc tcctacctca    3180
cgaagaatga caactggctg gtccggcacc cagactgcat caatgttccc gactggagag    3240
ggccatttg cagtgggtgc tatgcacaga tgtacattca agcctacaag accagtaacc    3300
tgcgaatgaa gatcatcaag aatgacttcc ccagccaccc tctttacctg gaggggcgc    3360
tcaccaggag cacccattac cagcaatacc aaccggttgt caccctgcag aagggctaca    3420
ccatccactg ggaccagacg gccccgccg aactcgccat ctggctcatc aacttcaaca    3480
agggcgactg gatccgagtg gggctctgct acccgcgagg caccacattc tccatcctct    3540
cggatgttca caatcgcctg ctgaagcaaa cgtccaagac gggcgtcttc gtgaggacct    3600
tgcagatgga caaagtggag cagagctacc ctggcaggag ccactactac tgggacgagg    3660
actcaggggct gttgttcctg aagctgaaag ctcagaacga gagagagaag tttgctttct    3720
gctccatgaa aggctgtgag aggataaaga ttaaagctct gattccaaag aacgcaggcg    3780
tcagtgactg cacagccaca gcttacccca agttcaccga gagggctgtc gtagacgtgc    3840
cgatgcccaa gaagctcttt ggttctcagc tgaaaacaaa ggaccatttc ttggaggtga    3900
agatggagag ttccaagcag cacttcttcc acctctggaa cgacttcgct acattgaag    3960
tggatgggaa gaagtacccc agttcggagg atggcatcca ggtggtggtg attgacggga    4020
accaagggcg cgtggtgagc cacacgagct tcaggaactc cattctgcaa ggcataccat    4080
ggcagctttt caactatgtg gcgaccatcc ctgacaattc catagtgctt atggcatcaa    4140
agggaagata cgtctccaga ggcccatgga ccagagtgct ggaaaagctt ggggcagaca    4200
ggggtctcaa gttgaaagag caaatggcat tcgttggctt caaaggcagc ttccggccca    4260
tctgggtgac actggacact gaggatcaca agccaaaat cttccaagtt gtgcccatcc    4320
ctgtggtgaa gaagaagaag ttgtgaggac agctgccgcc cggtgccacc tcgtggtaga    4380
ctatgacggt gactcttggc agcagaccag tgggggatgg ctgggtcccc cagcccctgc    4440
cagcagctgc ctgggaaggc cgtgtttcag ccctgatggg ccaagggaag gctatcagag    4500
```

```
accctggtgc tgccacctgc ccctactcaa gtgtctacct ggagcccctg gggcggtgct    4560
ggccaatgct ggaaacattc actttcctgc agcctcttgg gtgcttctct cctatctgtg    4620
cctcttcagt gggggtttgg ggaccatatc aggagacctg ggttgtgctg acagcaaaga    4680
tccactttgg caggagccct gacccagcta ggaggtagtc tggagggctg gtcattcaca    4740
gatccccatg gtcttcagca gacaagtgag ggtggtaaat gtaggagaaa gagccttggc    4800
cttaaggaaa tctttactcc tgtaagcaag agccaacctc acaggattag gagctggggt    4860
agaactggct atccttgggg aagaggcaag ccctgcctct ggccgtgtcc acctttcagg    4920
agactttgag tggcaggttt ggacttggac tagatgactc tcaaaggccc ttttagttct    4980
gagattccag aaatctgctg catttcacat ggtacctgga acccaacagt tcatggatat    5040
ccactgatat ccatgatgct gggtgcccca gcgcacacgg gatggagagg tgagaactaa    5100
tgcctagctt gaggggtctg cagtccagta gggcaggcag tcaggtccat gtgcactgca    5160
atgccaggtg gagaaatcac agagaggtaa aatggaggcc agtgccattt cagaggggag    5220
gctcaggaag gcttcttgct tacaggaatg aaggctgggg gcattttgct gggggagat     5280 gaggcagcct ctggaatggc tcagggattc agccctccct gccgctgcct gctgaagctg    5340
gtgactacgg ggtcgccctt tgctcacgtc tctctggccc actcatgatg gagaagtgtg    5400
gtcagagggg agcaatgggc tttgctgctt atgagcacag aggaattcag tccccaggca    5460
gccctgcctc tgactccaag agggtgaagt ccacagaagt gagctcctgc cttagggcct    5520
catttgctct tcatccaggg aactgagcac aggggcctc caggagaccc tagatgtgct     5580
cgtactccct cggcctggga tttcagagct ggaaatatag aaaatatcta gcccaaagcc    5640 ttcatttaa cagatgggga aagtgagccc ccaagatggg aaagaaccac acagctaagg     5700
gagggcctgg ggagccccac cctagccctt gctgccacac cacattgcct caacaaccgg    5760
ccccagagtg cccaggcact cctgaggtag cttctggaaa tggggacaag tcccctcgaa    5820
ggaaaggaaa tgactagagt agaatgacag ctagcagatc tcttccctcc tgctcccagc    5880
gcacacaaac ccgccctccc cttggtgttg gcggtccctg tggccttcac tttgttcact    5940
acctgtcagc ccagcctggg tgcacagtag ctgcaactcc ccattggtgc tacctggctc    6000
tcctgtctct gcagctctac aggtgaggcc cagcagaggg agtagggctc gccatgtttc    6060
tggtgagcca atttggctga tcttgggtgt ctgaacagct attgggtcca ccccagtccc    6120
tttcagctgc tgcttaatgc cctgctctct ccctggccca ccttatagag agcccaaaga    6180
gctcctgtaa gagggagaac tctatctgtg gtttataatc ttgcacgagg caccagagtc    6240
tccctgggtc ttgtgatgaa ctacatttat ccccttttcct gccccaacca caaactcttt   6300
ccttcaaaga gggcctgcct ggctccctcc acccaactgc acccatgaga ctcggtccaa    6360
gagtccattc cccaggtggg agccaactgt cagggaggtc tttcccacca aacatctttc    6420
agctgctggg aggtgaccat agggctctgc ttttaaagat atggctgctt caaaggccag    6480
agtcacagga aggacttctt ccagggagat tagtggtgat ggagaggaga gttaaaatga    6540
cctcatgtcc ttcttgtcca cggttttgtt gagttttcac tcttctaatg caagggtctc    6600
acactgtgaa ccacttagga tgtgatcact ttcaggtggc caggaatgtt gaatgtcttt    6660
ggctcagttc atttaaaaaa gatatctatt tgaaagttct cagagttgta catatgtttc    6720
acagtacagg atctgtacat aaaagttttct ttcctaaacc attcaccaag agccaatatc   6780
taggcatttt cttggtagca caaatttttct tattgcttag aaaattgtcc tccttgttat   6840
```

-continued

```
ttctgtttgt aagacttaag tgagttaggt ctttaaggaa agcaacgctc ctctgaaatg    6900
cttgtctttt ttctgttgcc gaaatagctg gtccttttc gggagttaga tgtatagagt    6960
gtttgtatgt aaacatttct tgtaggcatc accatgaaca agatatatt ttctatttat    7020 ttattatatg tgcacttcaa gaagtcactg tcagagaaat aaagaattgt cttaaatgtc    7080
```

<210> SEQ ID NO 39
<211> LENGTH: 5676
<212> TYPE: DNA
<213> ORGANISM: Homo sapiens

<400> SEQUENCE: 39

```
ggcacgtgga ctcccttta ccagtgact gtcaggtcga tcatatgccg aggacgatga      60
tcccgccggg ggagtgcacg tacgcgggcc ggaagcggag gaggcccctg cagaaacaga    120
ggcccgccgt gggggcagag aagtccaacc cctccaagcg acaccgggac cgcctcaacg    180
ccgagttgga ccacctggcc agcctgctgc cgttcccgcc tgacatcatc tccaagctgg    240
acaagctttc tgtcctgcgc ctcagtgtca gttacctccg ggtgaagagc ttcttccaag    300
tcgtgcagga gcagagctca cggcagcctg cggccggcgc ccctcgcccc ggagacagct    360
gtcctcttgc agggtctgcc gtgctggagg gaaggctgct gttggagtct cttaatggct    420
ttgctctggt cgtgagtgca gaagggacga tattttatgc atcagcaacg atcgtggact    480
atctgggctt ccatcagacg gatgtaatgc accagaacat ttatgactac atccacgtgg    540
acgaccgcca ggacttctgc cggcagctcc actgggccat ggaccctccc caggtggtgt    600 tgggcagcc ccgccccttg gagacaggag atgatgctat cctggggagg ctgctcaggg    660
cccaggagtg gggcacaggc acgcccaccg agtactcggc cttcctgacc cgctgcttca    720
tctgccgtgt gcgctgcctg ctggacagca cctcgggctt cctggcccgg gggtcacagg    780
cttggcagct gcggctctgc tgtcccgagc cactcatgac gatgcagttt caaggaaaac    840
taaaattcct gtttggacag aagaagaagg cgccgtcagg agccatgctc ccgccgcggc    900
tgtcgctgtt ctgcattgcg gcacccgttc tcctcccctc cgcagcggag atgaaaatga    960
ggagcgcgct cctgagggca aaaccccgag cagacaccgc agccaccgcg gatgcaaaag    1020
taaaagccac caccagtctg tgcgaatcgg aactgcatgg aaaacccaat tactcagcag    1080
gaaggagcag cagagagagc ggcgttttgg tgctcaggga acagactgac gctgccgat    1140 gggcacaggt tcccgccagg gccccatgcc tgtgcctccg gggtggccct gaccttgtcc    1200
ttgaccccaa gggggctca ggggacaggg aggaggagca gcacaggatg ctgagcaggg    1260
cctctggagt gacagggcgg agggagactc caggacccac aaagcccctg ccctggacag    1320
cgggaaagca cagtgaggat ggtgccaggc cgaggctgca gcccagcaag aatgacccgc    1380 cctcctgcg ccccatgccc cgcggctcct gcctgccctg cccgtgtgtc cagggcactt    1440
tcaggaactc gccccatctct cacccgccga gccgtcccc cagtgcctac tccagccgga    1500
ccagcagacc catgcgggat gtcggtgagg accaggtgca ccctcccctc tgccactttc    1560
cccagaggag cctgcagcac cagctccctc agcctggagc tcagcgtttt gccacgaggg    1620
gctatcccat ggaggacatg aagctgcaag gtgtaccgat gcctccgggg gacctgtgtg    1680
gtccgacgct gctgctagat gtgtccatca agatggagaa ggactctggg tgtgagggtg    1740
ctgcagacgg ctgtgtgccc agccaggtgt ggctgggggc cagtgacagg agccaccccag    1800 ccaccttccc taccaggatg cacctgaaaa cagagccaga ctctcggcaa caggtgtaca    1860
tctcgcacct ggggcacggc gtgcgggggg ctcagcccca tgggagggcc actgctgggc    1920
```

```
gcagcaggga gctgacccct ttccaccctg cacactgtgc ctgcctggag cccacagacg   1980
gccttcccca gtcggagcct ccccaccagc tctgtgcacg gggccgaggt gaacagtcct   2040
gcacctgcag agctgctgag gccgcccctg tggtcaagcg ggagcccttg gactcacccc   2100
agtgggctac tcacagccag ggaatggtgc ccgggatgtt gcccaaaagt gccttggcca   2160
cgctggtccc gccccaagct tcggggtgca cattcctgcc atagcgcagt gaccaccatc   2220
caagctcaga tctgtgtgtc tacgctcaga tgcgtcggtg gctgggctgc cctgctcctg   2280
gtcaggccgg agcccgtcct aagacacacg ctttgcagag ctgtgcatgc gcagtctgct   2340
agtgtgtgtg tgcagcatac gcaggagcct atcctgaatt ttgtaaaata tcccaacagt   2400
tcttaaatga aaactggcct taagtctatt caagcatgac agcatttctc tttgaggaat   2460
taaaatcttt aggaaagtga tcatggctgg acagcttcat gccccagagg cagcgagcac   2520
ccgtcccatg gctgccaagt ccacagtcgg ggatgaagca gtcgggtgat gctcccaagt   2580
ccgcagtcgg ggatgaagcg gtcgggtgat gctcccaagt ccgcagtcgg ggatgaagcg   2640
gtcgggtgac acacctagct cagccctccc aggccacctg cagctcccag cctgtgctgt   2700
gcaggcaggg tcagcccatc gccacagtgc actgtagagg ccagcacacg gcaaattaga   2760
aatacaacac gcggagaaag gggtccgtga gcccactcat agaggaatct agaacgttcc   2820
aggcagcaga ggctggcagc gtgggtccca cactgcccca ccgtgcgg caggtgctcc   2880 atggcgccat gacagagtct gaggccagac ctggactgga attgacagca taaccctgt   2940 tccttctgga catctcccga gttctcagtg ggtctctgcg gacggttctt cctaatctgc   3000
ctcttggtac atcacgtaat acagagttca cagactccgg gtttggaagt acagagaaac   3060
acacaacgta gagagaagac acaggaaact gcgctgcctg tgggggtttc tctctggctg   3120
gctgtacagt tcactcaaat gagggttccc attgccatcc taggagaata attagggaca   3180
agacagacaa gtattaatag cattaaaaca gttgtaaagg cgatattttc tgagagtagg   3240
aaatttggat acaaaagcat aagtcagaaa gtgaaggtca ccaatccacc aacccgagaa   3300
cctacagctg atggtgcatt tcaggcttct tccacggtct ggcctggaac cccacccggc   3360
tggtgcaggc atcagatcag ggtgtagaag tcaccccaag caagaggaag ccaggcagtg   3420
aggccctggg gtgtggctgc agctgggccc acctgtgcgg gggtgggaag gccccatcct   3480
cagggagagg gcatcggcgc cctgacgtca gctccactgg gagtggcagg agctgtggga   3540
gcccatgggt gagggaccca ccaccccgct gcactgtgca ttgtgcctcc cgtgtggacg   3600
ccctctctgt tgttggcccg cgggtgaggg acccaccacc cctagggacc caccaccccg   3660
ccgcactgtg cattctgcct cctgtgtgga cgccctctct gttgtcagtg gctttgaggt   3720
gtcagtgctt acttagatgc tggtttaatg ctggacccat tgttaaacg caccttcact   3780 ttgtcaaaac ccaggtttgg ttggcaggac tgggtcttct gcccaatgcc aggtgcctgc   3840
gcctctcagt ggcctggttc ttggacagtt gccccatg tggcagggat agggataagg   3900
atctcctctc agtactggaa gagaacagcc aaccatctga gcccagagtc acagatccat   3960
cgtggccccc tatgaccccc aagccctacc gaggggcac tcactctctg cttagccagg   4020
gggcgtcttt caaaaggtga cctccatgct gtgctgtcgt gggtgtgaga cgtgctcatg   4080
gccttccact gccatctctc ccttatctga tgcctaaagt cacgatgggg acagagctac   4140
ccaggggcca gccatgggt gaccagccac ctgagggtca gtcacctgtg gagagcaggc   4200
acctgtgaag accaggcacc tgaggactgg cgcctacttc ccactttggc cctacactgg   4260
```

```
cacagagccc ctctttattc atttctcatg ctgagcatgg cacacttctg gcctctgggc    4320
atttatggat ttaagaccag gatggtattt cagaagcttc ccacttcctt cctattctaa    4380
ccgagtgccc agctcctttg ctgatcatgg aaagacccctt aataattagg cctgcaggcc    4440
aggcgcagtg gctcatgcct ataatcccag cactttagga ggtcaaggta ggaggatcgc    4500
ttaagcccag gagttcaaga ccagcctggg caacacagga agaatgtgtc tctacaaaaa    4560
ataattaaaa atcagatctg ctgtatccct gaaaaagtct caatcaacat gcatgttcca    4620
ctcttggagt tccctgttct gagggccagc cacgtcctgt gtcctggagc ttagccctca    4680
gcagctccct tcagcctggg cgccgcctgg gtcccaaacg tggcagctgc tcttccagtc    4740
tcggggccga ggagggcagg gagctcagtg actgagagtc ttgtgtatca catgtcttga    4800
gtgtcctgga gccaacggct gtcactggga aaaacaccag gccccaaaga tcgaatcaga    4860
gacgtggctg cgtgtttgcg attgtagcca ggcccttcag tgtcatcaaa ggagcactgg    4920
ggcctcctta agcacagacg gcagcccctg cccaggaggc ttcttcacca cgtcctgccc    4980
tgcagcctcc cagaccttta gatgcgcccc tgcccaaggc cctcctggtg acaggtgcca    5040
gattgagtgg tgggttgctg ccaggcaggc cacgctgtgt tgacgctgca ctcagcacgt    5100
gggtgttggc tctgccggtt ttgtggtgtg gggaccctac aggaggctgc ggccctgaga    5160
gcctgggatc agcgaggtgt ccgacatccc ttcctcaacg gcaacaaaaa ctccccaagt    5220
cagcactttg gttatttttat agccacaacc ctcttggaaa acagtgggga agactatgga    5280
acatagaaag tgtggatgta tcacttctct ctaaaatgtc attgttagca ctaattacag    5340
gttcatgttt ttctgtgtat gtagcttttc cctatatagc tgaaaagta ttaaagtcaa    5400 atataaggtg ggaatgggat ggaagggagg agatcaatac aacttatatt tttgcagttt    5460
ctactggaag aaaaaagttt tcaataccta gaccaacttg ttgaattttt aaaacttatg    5520
cactataaat gcaactttct ctactgcttt ctcagtgcct ttaggaagct ttcaaatttt    5580
tttgtactgt ggtttgtatt aaatttgcaa tattgatgta aaatacatga catgctagta    5640
catgtttaac aaaaatttaa aaaaaaaaa aaaaaa                               5676
```

<210> SEQ ID NO 40
<211> LENGTH: 1763
<212> TYPE: DNA
<213> ORGANISM: Homo sapiens

<400> SEQUENCE: 40

```
cttctggtaa ggaggcccccg tgatcagctc cagccatttg cagtcctggc tatcccagga     60
gcttacataa agggacaatt ggagcctgag aggtgacagt gctgacacta caaggctcgg    120
agctccgggc actcagacat catgagttgg tccttgcacc cccggaattt aattctctac    180
ttctatgctc ttttatttct ctcttcaaca tgtgtagcat atgttgctac cagagacaac    240
tgctgcatct tagatgaaag attcggtagt tattgtccaa ctacctgtgg cattgcagat    300
ttcctgtcta cttatcaaac caaagtagac aaggatctac agtctttgga agacatctta    360
catcaagttg aaaacaaaac atcagaagtc aaacagctga taaaagcaat ccaactcact    420
tataatcctg atgaatcatc aaaaccaaat atgatagacg ctgctacttt gaagtccagg    480
aaaatgttag aagaaattat gaaatatgaa gcatcgattt taacacatga ctcaagtatt    540
cgatatttgc aggaaatata taattcaaat aatcaaaaga ttgttaacct gaaagagaag    600
gtagcccagc ttgaagcaca gtgccaggaa ccttgcaaag acacggtgca aatccatgat    660
atcactggga aagattgtca agacattgcc aataagggag ctaaacagag cgggctttac    720
```

```
tttattaaac ctctgaaagc taaccagcaa ttcttagtct actgtgaaat cgatgggtct      780
ggaaatggat ggactgtgtt tcagaagaga cttgatggca gtgtagattt caagaaaaac      840
tggattcaat ataaagaagg atttggacat ctgtctccta ctggcacaac agaattttgg      900
ctgggaaatg agaagattca tttgataagc acacagtctg ccatcccata tgcattaaga      960
gtggaactgg aagactggaa tggcagaacc agtactgcag actatgccat gttcaaggtg     1020
ggacctgaag ctgacaagta ccgcctaaca tatgcctact cgctggtgg ggatgctgga      1080 gatgcctttg atggctttga ttttggcgat gatcctagtg acaagttttt cacatcccat     1140
aatggcatgc agttcagtac ctgggacaat gacaatgata gtttgaagg caactgtgct       1200 gaacaggatg gatctggttg gtggatgaac aagtgtcacg ctggccatct caatggagtt     1260
tattaccaag gtggcactta ctcaaaagca tctactccta atggttatga taatggcatt     1320
atttgggcca cttggaaaac ccggtggtat tccatgaaga aaaccactat gaagataatc     1380
ccattcaaca gactcacaat ggagaagga cagcaacacc acctgggggg agccaaacag       1440
gtcagaccag agcaccctgc ggaaacagaa tatgactcac tttaccctga ggatgatttg     1500
tagaaaatta actgctaact tctattgacc cacaaagttt cagaaattct ctgaaagttt     1560
cttccttttt tctcttacta tatttattga tttcaagtct tctattaagg acatttagcc     1620
ttcaatggaa attaaaactc atttaggact gtatttccaa attactgata tcagagttat     1680
ttaaaaattg tttatttgag gagataacat ttcaactttg ttcctaaata tataataata     1740
aaatgattga ctttatttgc aaa                                             1763

<210> SEQ ID NO 41
<211> LENGTH: 666
<212> TYPE: DNA
<213> ORGANISM: Homo sapiens

<400> SEQUENCE: 41
gggtggctta gcactgcagg gctctgcgcg ggaacgctaa cctggtccgg agcgagtctg       60
ggtctcagcc ccgcgaacag cctttcacga gtcttcaagc tttcaggcta tcttctagtc      120
aagatgagtg ataagccaga cttgtcggaa gtggagaagt ttgacaggtc aaaactgaag      180
aaaactaata ctgaagaaaa aaatactctt ccctcaaagg aaactatcca gcaagagaaa      240
gagtgtgttc aaacatcata aaatggggat cgcctcccaa cagcagattt cgacattacc      300
tgagagtctt gattttaggc ttgttttttg taaacccatg tgtttgtaga gattttaggc      360
gtcttcggat atcttctcac ctatgttccc tggctaagaa gtcagaggta gccaatgttt      420
ccttaaattc attttttaaac ttaccattgg tgcatatgtt ccagatggca gatgctgtca     480
ataatctcac cattgatgac ctttgtgtat gtagttcttg catcctatac tggataagcc      540
tgttttaacc tgctatgatg ggtgcttcca ttgcttcata atcttcatga agttgcatgc      600
ttttgcagct tttcacagtt tatttgcatt tctaatgtag taataaagta accaatataa      660
tcatta                                                                 666

<210> SEQ ID NO 42
<211> LENGTH: 1437
<212> TYPE: DNA
<213> ORGANISM: Homo sapiens

<400> SEQUENCE: 42
attgctgatg gatcagtgag cctgtgttca tgccagtgag ctgctgtggc tcagatactg       60
```

| | |
|---|---|
| atactttctt tccaaacagc ataagaagtg attgagccac aagtatactg aaggaagggc | 120 |
| tccctcgagt tctggtgtga agagataaat caccagtcac agactatgca cccgactgct | 180 |
| gctgttcagt ccagggaaaa tgaaagttgg agtgctgtgg ctcatttctt tcttcacctt | 240 |
| cactgacggc cacggtggct tcctggggaa aaatgatggc atcaaaacaa aaaagaact | 300 |
| cattgtgaat aagaaaaaac atctaggccc agtcgaagaa tatcagctgc tgcttcaggt | 360 |
| gacctataga gattccaagg agaaaagaga tttgagaaat tttctgaagc tcttgaagcc | 420 |
| tccattatta tggtcacatg gctaattag aattatcaga gcaaaggcta ccacagactg | 480 |
| caacagcctg aatggagtcc tgcagtgtac ctgtgaagac agctacacct ggtttcctcc | 540 |
| ctcatgcctt gatccccaga actgctacct tcacacggct ggagcactcc caagctgtga | 600 |
| atgtcatctc aacaacctca gccagagtgt caatttctgt gagagaacaa agatttgggg | 660 |
| cactttcaaa attaatgaaa ggtttacaaa tgaccttttg aattcatctt ctgctatata | 720 |
| ctccaaatat gcaaatggaa ttgaaattca acttaaaaaa gcatatgaaa gaattcaagg | 780 |
| ttttgagtcg gttcaggtca cccaatttcg aatgtcactc ttgtcgccca agttggagtg | 840 |
| caatggcaca atctaggctc actgcaaccc tgcaacctct gcctaccggg ttcaagagat | 900 |
| tccctgcct cagcctccca gtagctgga attacaggca cctgccacca catccagcta | 960 |
| acttttttg tatttttact agagacaggg tttcaccatg ttggccacac tggtctcaaa | 1020 |
| ctcctgacct caggtgatcc gcctgcctcg gccccaaag tgctgggatt acaggcatga | 1080 |
| gccaccacat ctggcctagg accttaaata ttggaaagca tcctcaaaac tgtgggtcag | 1140 |
| tgagtagaac tacaaaacaa tagcagtagg gcagaaactt gaaagaaggc aggagatcat | 1200 |
| ggtgacagtg gatgggaaaa agtgagggtt ggggataagg gttgcgggtt gtcgaagggt | 1260 |
| ggatttctc cttcagcaac tacaggagat atgatgcctc ataattcgga gccagaagtg | 1320 |
| gggctttggg tgagatatct ttgcacagat aacatgtata catcatagtt caaaacccag | 1380 |
| tagtcattgt ttacagcaaa taagaaata tttagtaaat taaaaaaaaa aaaaaaa | 1437 |

<210> SEQ ID NO 43
<211> LENGTH: 2413
<212> TYPE: DNA
<213> ORGANISM: Homo sapiens

<400> SEQUENCE: 43

| | |
|---|---|
| tttcctctca gggggcagca ggaagtgagg agaaagggct gggatgggag gcgggagcgg | 60 |
| atgggaggga atggggttta tcaagtcctc ggcgagctgc ccaacgggca gcagctggcg | 120 |
| caagtagcct agctggagag gctcaccca ggaaggaggg aggccaccga cctactgggc | 180 |
| cgacggactc ccacacaggg ctggcggcgc cgcggagctg ggaggactga accaccggcc | 240 |
| tcgggctgca ggggaaacat ttcaggctga ctggcgctcg tggctgagac tcccatagaa | 300 |
| agcccggctc agaggggcat tagggtccta aatgggcggc cacgtccctc tgcagaggac | 360 |
| ctggggctct tcgagcccga aacgaggcac cggcaccgag aaaggtggac cacaccttcc | 420 |
| cgccccgtcc gcaagtccaa tcccgggccc acctccgcac tggagtctta aagggccagc | 480 |
| gtgcctgggg gcgagccag cagaggcgct gagccgggcc gcgcctgggc gaacggccgg | 540 |
| agcgggctgg gctgggcccg ggatggcggt ggccctggcg ccggtcccgg tggcgccccg | 600 |
| cgcgagttcc tgagctggtg ccaggcaggt gacacctcct gcagccccca gcatgcgggc | 660 |
| aggcccaggc cccaccgtta cattggccct ggtgctggcg gtgtcatggg ccatggagct | 720 |
| caagcccaca gcaccacca tcttcactgg ccggcccttt gtggtagcgt gggacgtgcc | 780 |

```
cacacaggac tgtggcccac gcctcaaggt gccactggac ctgaatgcct ttgatgtgca    840
ggcctcacct aatgagggtt ttgtgaacca gaatattacc atcttctacc gcgaccgtct    900
aggcctgtat ccacgcttcg attctgccgg aaggtctgtg catggtggtg tgccacagaa    960
tgtcagcctt tgggcacacc ggaagatgct gcagaaacgt gtggagcact acattcggac   1020
acaggagtct gcggggctgg cggtcatcga ctgggaggac tggcgacctg tgtgggtgcg   1080
caactggcag gacaaagatg tgtatcgccg gttatcacgc cagctagtgg ccagtcgtca   1140
ccctgactgg cctccagacc gcatagtcaa acaggcacaa tatgagtttg agttcgcagc   1200
acagcagttc atgctggaga cactgcgtta tgtcaaggca gtgcggcccc ggcacctctg   1260
gggcttctac ctctttcctg actgctacaa tcatgattat gtgcagaact gggagagcta   1320
cacaggccgc tgccctgatg ttgaggtggc ccgcaatgac cagctggcct ggctgtgggc   1380
tgagagcacg gccctcttcc cgtctgtcta cctggacgag acacttgctt cctcccgcca   1440
tggccgcaac tttgtgagct tccgtgttca ggaggccctt cgtgtggctc gcacccacca   1500
tgccaaccat gcactcccag tctacgtctt cacacgaccc acctacagcc gcaggctcac   1560
ggggcttagt gagatggacc tcatctctac cattggcgag agtgcggccc tgggcgcagc   1620
tggtgtcatc ctctggggtg acgcggggta caccacaagc acggagacct gccagtacct   1680
caaagattac ctgacacggc tgctggtccc ctacgtggtc aatgtgtcct gggccaccca   1740
atattgcagc cgggcccagt gccatggcca tgggcgctgt gtgcgccgca accccagtgc   1800
cagtaccttc ctgcatctca gcaccaacag tttccgccta gtgcctggcc atgcacctgg   1860
tgaaccccag ctgcgacctg tgggggagct cagttgggcc gacattgacc acctgcagac   1920
acacttccgc tgccagtgct acttgggctg gagtggtgag caatgccagt gggaccatag   1980
gcaggcagct ggaggtgcca gcgaggcctg ggctgggtcc cacctcacca gtctgctggc   2040
tctggcagcc ctggccttta cctggaccct gtagggtgtct cctgcctagc tgcctagcaa   2100
gctggcctct accacaaggg ctctcttagg catgtaggac cctgcagggg gtggacaaac   2160
tggagtctgg agtgggcaga gcccccagga agcccaggag ggcatccata ccagctcgca   2220 ccccccctgtt ctaaggggga ggggaagtcc ctgggaggcc ccttctctcc ctgccagagg   2280
ggaaggaggg tacagctggg ctggggagga cctgacccta ctcccttgcc ctagatagtt   2340
tattattatt attattttgg ggtctctttt gtaaattaaa cataaaacaa ttgcttctct   2400
gcttggattt tgt                                                      2413
```

<210> SEQ ID NO 44
<211> LENGTH: 1279
<212> TYPE: DNA
<213> ORGANISM: Homo sapiens

<400> SEQUENCE: 44

```
gggagggaga gaggcgcgcg ggtgaaaggc gcattgatgc agcctgcggc ggcctcggag     60
cgcggcggag ccagacgctg accacgttcc tctcctcggt ctcctccgcc tccagctccg    120
cgctgcccgg cagccgggag ccatgcgacc ccagggcccc gccgcctccc cgcagcggct    180
ccgcggcctc ctgctgctcc tgctgctgca gctgcccgcg ccgtcgagcg cctctgagat    240
ccccaagggg aagcaaaagg cgcagctccg gcagagggag gtggtggacc tgtataatgg    300
aatgtgctta caagggccag caggagtgcc tggtcgagac gggagccctg gggccaatgg    360
cattccgggt acacctggga tcccaggtcg ggatggattc aaaggagaaa aggggggaatg    420
```

```
tctgagggaa agctttgagg agtcctggac acccaactac aagcagtgtt catggagttc      480
attgaattat ggcatagatc ttgggaaaat tgcggagtgt acatttacaa agatgcgttc      540
aaatagtgct ctaagagttt tgttcagtgg ctcacttcgg ctaaaatgca gaaatgcatg      600
ctgtcagcgt tggtatttca cattcaatgg agctgaatgt tcaggacctc ttcccattga      660
agctataatt tatttggacc aaggaagccc tgaaatgaat tcaacaatta atattcatcg      720
cacttcttct gtggaaggac tttgtgaagg aattggtgct ggattagtgg atgttgctat      780
ctgggttggt acttgttcag attacccaaa aggagatgct tctactggat ggaattcagt      840
ttctcgcatc attattgaag aactaccaaa ataaatgctt taattttcat ttgctacctc      900
tttttttatt atgccttgga atggttcact taaatgacat tttaaataag tttatgtata      960
catctgaatg aaaagcaaag ctaaatatgt ttacagacca aagtgtgatt tcacactgtt     1020
tttaaatcta gcattattca ttttgcttca atcaaaagtg gtttcaatat ttttttttagt     1080 tggttagaat actttcttca tagtcacatt ctctcaacct ataatttgga atattgttgt     1140
ggtcttttgt ttttctctt agtatagcat ttttaaaaaa atataaaagc taccaatctt     1200
tgtacaattt gtaaatgtta agaattttt ttatatctgt taaataaaaa ttatttccaa     1260
caaccttaat atctttaaa                                                  1279

<210> SEQ ID NO 45
<211> LENGTH: 4571
<212> TYPE: DNA
<213> ORGANISM: Homo sapiens

<400> SEQUENCE: 45
gcagtcagag ctgcctctcg ccctcgctag ctgggctcgc agcctcttcc tccctccctg       60
gctcctggct ttttgtttaa agcaacaccc accctccatc caggcttttt ttctttcttt      120
ctttattggt agcggccaaa aagagttgat tgctattggg atccgctgag taaagacacg      180
ggcaggggtg cgcggaggtg agaaaactga agacctggaa gatttttttt tccttcaaaa      240
acccgtttcc atccagtctt cagccagtcc agtctacttt aatcctcacc aggacaatgg      300
attaagtttc tcttccctgg accagaagtc gggttcggac ttggggcaaa atgaaggaaa      360
aggccatgat caagaccgct aagatgcagg ggaacgtgat ggagctggtg gggagtaacc      420
ctccgcagag gaattggaaa ggaatagcaa ttgcactgct tgtcattctg gtcatctgct      480
ccttgatcgt cacctcggtc atacttctga caccagcgga agataatagt ctgtctcaaa      540
agaagaaggt cactgtagaa gatctcttca gtgaagactt caaaattcat gaccccgagg      600
ctaagtggat aagtgataca gaattcatct acagagaaca gaaaggaaca gtgagactgt      660
ggaatgttga aacaaatact tctactgtct taatagaagg caaaaaaatt gaatcattaa      720
gagccatcag atatgaaata tctccagata gagagtatgc acttttttca tacaatgtgg      780
aacccatata tcaacactcg tatactggat attacgtcct gagcaaaatt cctcatgggg      840
atcctcaaag tctggaccca ccagaagtca gcaatgcaaa acttcagtat gcaggatggg      900
gccctaaagg ccaacagctg atatttattt ttgaaaacaa tatctactac tgtgcacatg      960
tcgggaaaca ggccatccgt gtggtctcca ctggcaagga aggtgtgatt tacaatggcc     1020
tcagtgactg gctgtatgaa gaggagattt tgaagacaca catcgcacac tggtggtctc     1080 cggatgcac gagactcgcc tacgccgcca tcaatgattc ccgtgtcccc atcatggagc     1140
tcccaactta caccggctcc atctacccca ccgtgaagcc ctaccactat cccaaggctg     1200
gaagtgagaa ccccagcatt tccctacacg ttattggctt aaatggaccc acccatgatc     1260
```

```
tggagatgat gccgcctgat gatccacgga tgagggagta ctacatcacc atggtgaagt    1320
gggccaccag caccaaggtc gccgtgacct ggctgaaccg ggcgcagaac gtgtccatcc    1380
tcaccctctg cgacgccacc acggggtct gcacgaagaa acacgaggat gaaagtgagg     1440
cctggctcca cagacagaat gaagaacctg tgttctccaa ggatggccga aagttttct     1500
tcatcagagc catcccccag ggaggacgag ggaaattcta tcacatcacg gtgtcctcgt    1560
cccagcccaa cagcagcaac gacaacatcc agtccatcac ctccggggac tgggacgtga    1620
ccaagatcct agcctacgat gagaagggga ataagatcta cttcctgagc acggaggacc    1680
tgcctcggag acgacaactc tacagtgcca acacggtggg caacttcaac aggcagtgcc    1740
tctcctgtga cctggttgag aactgcacct acttcagcgc ttccttcagc catagcatgg    1800
acttcttcct gctcaagtgc gaaggtcctg gtgttcctat ggtgacggtg cacaacacaa    1860
cagataagaa aaaaatgttt gacctagaaa caaatgaaca tgtcaagaag gccataaatg    1920
accgacagat gcctaaagtg gaatacaggg acattgagat tgatgattac aacctgccca    1980
tgcagatact gaagccagca accttcaccg acaccaccca ctaccctctg ctcctggtgg    2040
tggatggcac cccaggcagc cagagtgtgg ctgagaagtt cgaggtgagc tgggagacgg    2100
tgatggtgag cagccacggc gcggtggtgg taaagtgtga cggccgtggc agcggcttcc    2160
aagggaccaa gctcctgcac gaagtgaggc ggcggctggg cttgctggag gagaaggacc    2220
agatggaggc cgtgcggacg atgctgaagg agcagtacat tgacaggacg cgcgtggccg    2280
tgtttgggaa ggattacggt ggctacctga gcacctacat cctcccagca aagggagaaa    2340
atcaaggcca gacattcacc tgcggctctg ctctctctcc aataacagac ttcaaactct    2400
atgcctctgc gttttccgag aggtacttgg gcctccatgg acttgacaac agagcatacg    2460
agatgaccaa ggtagcccat cgagtctccg cgctggaaga acagcagttc ctgatcattc    2520
atccccactgc cgatgaaaaa attcatttcc agcacacagc agaactcatt acacaactaa    2580
ttaggggaaa ggctaattac agcttacaga tttacccgga cgaaagccat tactttacca    2640
gctccagcct caaacagcat ctgtaccggt ccatcatcaa cttcttcgtg gaatgcttca    2700
ggatccagga caaactgctg acagtcacag cgaaagagga cgaggaggag gactaagctc    2760
aggtcgctct aagcacaaac gtggctcttt ctacaaccag atgcaaccga gggatttccc    2820
tgccctccct cttccctcgg aggggcgggg cgggcgggg ccgggtgttc catagcatgt     2880
gtgtctcgga tgcggaaggc agttttgctt gggaaacaag ctccttcccc ggggtcatca    2940
ctcacggcct ccatggcacc agggacaacg ctgtccccgc agcagcgcct cctcccggcg    3000
cccgagagac cggcacgcca cggcccctcc cccaaggaac agagcaaagg atggtggccg    3060
caggccccac gcgagcccac aggacaccgg cccctagatt ccagccacca agcggaagca    3120
tgagacccgc ccacactagc ctctgtgttc ccgttaggga catcacaccc tgtctcacgt    3180
cgcagtgcca tggacgcagc agttacagca ccattgtttt agcagtgcgt gttcatatat    3240
gggcttgcta cttcctgtaa tgaggacgtt caacatggtg aggggctaca agaaaacgct    3300
tttctgtaca gagtcttact gtagctacgc taatggttaa cctgatagaa ttaactcgta    3360
tttttctatg gttttaacct gatgctccac tgtctccgtc atggggttgt tttgctgttt    3420
ggggttgggc cttgtttccc tttcctttct ccagtccacg tgtagacttt gcgcttgatg    3480
aagaagcaga tcgaagtaa ctgctccctc tcaaggttg tcttcagacg tcttggggac      3540
gttcctaaac actgaggggg aagacagcca atagcaccca ttaaaagaaa tacctaaata   3600
```

| | |
|---|---|
| aaacctctct cccactcagc tatgctaggg cttggctgta ggtgtgcact gtctatttac | 3660 |
| atccgtcctt acaaccatcc ttgtcctcct tggtaccgta tcaagctctt tcccatgaca | 3720 |
| tttggtttaa aaaaaaaaaa aaaaaaaaaa aaaaacaga aaaagacaa agcgtcaact | 3780 |
| ccacccacag gcccgctgtg tgtgctcggg ccacgggagt cctgagggtt ctgtgggcct | 3840 |
| gcgcgcatcc ctctcccatc gtgggggtgg ctccgtgacc ttcctgccac gagcaggagg | 3900 |
| ttgatgatgt gctacgttag ccttgtaaga tacaccccca ccaaatgtgc agccggtgtt | 3960 |
| cccagtgtat atttcattct cttgtatata aaggaagcaa tgtgtgtcag gcctctgtgc | 4020 |
| agtcaaccca gcctcctccc gccagtgcta acccgtgtt gagcctgcat gctgacactg | 4080 |
| tggccgatct ggactctaga agtgctagtt tgaaatatat ccattactgt catttccttt | 4140 |
| tgagcttgtg acaagctga atgtcaggac tgacttcgcc agctcccagc cctgcggggg | 4200 |
| tgtccttggc atcccatcag cagaggagat gcgtccctgt tgcattttgg cgtttgggggc | 4260 |
| tttgggttta tccacatgag ctctgaacgt ccgttatagt tagggtgatt ggaaggtctc | 4320 |
| catcactggg tgttttaaag gtgattcacc accatttgtg aaaggaccaa cgtgctgata | 4380 |
| aacaggaccg atccgagtgc tacatgactg tgcgtttgct atttcaatgg gcctgaacga | 4440 |
| ctacaaagcc agctaggtct ggaaggggaa gccagctctg gccacgacat ctggtcggag | 4500 |
| ggaagtgggg atgtggcatg gtagcgtctg ttcatccatg gaataaaaca ttatttacc | 4560 |
| aaaaaaaaaa a | 4571 |

<210> SEQ ID NO 46
<211> LENGTH: 4460
<212> TYPE: DNA
<213> ORGANISM: Homo sapiens

<400> SEQUENCE: 46

| | |
|---|---|
| actaagcagc ggcagcttcc tgcttcggat cctctctctg ctgcttgcat ttaaagagca | 60 |
| aactcgtctt gtctacccac cctccctccc ccatcctccc caaaatagcc ttgtgatttc | 120 |
| ggaagtatgg actaaaatca cactcctcct taccttaccg cttggactct ggtggctccc | 180 |
| aactcgccgt cagaccccac ctgccccggt ggtgggaagc gcctggacag accatgacca | 240 |
| cagccaagga gccaagcgct tcggggaaat ccgtgcagca gcaggaacag gagctggtgg | 300 |
| ggagtaaccc tccgcagagg aattggaaag gaatagcaat tgcactgctt gtcattctgg | 360 |
| tcatctgctc cttgatcgtc acctcggtca tacttctgac accagcggaa gataatagtc | 420 |
| tgtctcaaaa gaagaaggtc actgtagaag atctcttcag tgaagacttc aaaattcatg | 480 |
| accccgaggc taagtggata agtgatacag aattcatcta cagagaacag aaaggaacag | 540 |
| tgagactgtg gaatgttgaa acaaatactt ctactgtctt aatagaaggc aaaaaaattg | 600 |
| aatcattaag agccatcaga tatgaaatat ctccagatag agagtatgca ctttttttcat | 660 |
| acaatgtgga acccatatat caacactcgt atactggata ttacgtcctg agcaaaattc | 720 |
| ctcatgggga tcctcaaagt ctggacccac cagaagtcag caatgcaaaa cttcagtatg | 780 |
| caggatgggg ccctaaaggc caacagctga tatttatttt tgaaaacaat atctactact | 840 |
| gtgcacatgt cggaaacag gccatccgt tggtctccac tggcaaggaa ggtgtgattt | 900 |
| acaatggcct cagtgactgg ctgtatgaag aggagatttt gaagacacac atcgcacact | 960 |
| ggtggtctcc ggatggcacg agactcgcct acgccgccat caatgattcc cgtgtcccca | 1020 |
| tcatggagct cccaacttac accggctcca tctacccccac cgtgaagccc taccactatc | 1080 |
| ccaaggctgg aagtgagaac cccagcattt ccctacacgt tattggctta aatggaccca | 1140 |

```
cccatgatct ggagatgatg ccgcctgatg atccacggat gagggagtac tacatcacca   1200
tggtgaagtg ggccaccagc accaaggtcg ccgtgacctg gctgaaccgg gcgcagaacg   1260
tgtccatcct caccctctgc gacgccacca cggggggtctg cacgaagaaa cacgaggatg   1320
aaagtgaggc ctggctccac agacagaatg aagaacctgt gttctccaag gatggccgaa   1380 agttttctt catcagagcc atccccagg gaggacgagg gaaattctat cacatcacgg   1440
tgtcctcgtc ccagcccaac agcagcaacg acaacatcca gtccatcacc tccggggact   1500
gggacgtgac caagatccta gcctacgatg agaaggggaa taagatctac ttcctgagca   1560
cggaggacct gcctcggaga cgacaactct acagtgccaa cacggtgggc aacttcaaca   1620
ggcagtgcct ctcctgtgac ctggttgaga actgcaccta cttcagcgct tccttcagcc   1680
atagcatgga cttcttcctg ctcaagtgcg aaggtcctgg tgttcctatg gtgacggtgc   1740
acaacacaac agataagaaa aaaatgtttg acctagaaac aaatgaacat gtcaagaagg   1800
ccataaatga ccgacagatg cctaaagtgg aatacaggga cattgagatt gatgattaca   1860
acctgcccat gcagatactg aagccagcaa ccttcaccga caccacccac taccctctgc   1920
tcctggtggt ggatggcacc ccaggcagcc agagtgtggc tgagaagttc gaggtgagct   1980
gggagacggt gatggtgagc agccacggcg cggtggtggt aaagtgtgac ggccgtggca   2040
gcggcttcca agggaccaag ctcctgcacg aagtgaggcg gcggctgggc ttgctggagg   2100
agaaggacca gatggaggcc gtgcggacga tgctgaagga gcagtacatt gacaggacgc   2160
gcgtggccgt gtttgggaag gattacggtg gctacctgag cacctacatc ctcccagcaa   2220
agggagaaaa tcaaggccag acattcacct gcggctctgc tctctctcca ataacagact   2280
tcaaactcta tgcctctgcg ttttccgaga ggtacttggg cctccatgga cttgacaaca   2340
gagcatacga tgatgaccaag gtagcccatc gagtctccgc gctggaagaa cagcagttcc   2400
tgatcattca tcccactgcc gatgaaaaaa ttcatttcca gcacacagca gaactcatta   2460
cacaactaat taggggaaag gctaattaca gcttacagat ttacccggac gaaagccatt   2520
actttaccag ctccagcctc aaacagcatc tgtaccggtc catcatcaac ttcttcgtgg   2580
aatgcttcag gatccaggac aaactgctga cagtcacagc gaaagaggac gaggaggagg   2640
actaagctca ggtcgctcta agcacaaacg tggctctttc tacaaccaga tgcaaccgag   2700
ggatttccct gccctccctc ttccctcgga ggggcggggc ggggcggggc cggtgttcc   2760 atagcatgtg tgtctcggat gcggaaggca gttttgcttg ggaaacaagc tccttccccg   2820
gggtcatcac tcacggcctc catggcacca gggacaacgc tgtccccgca gcagcgcctc   2880
ctcccggcgc ccgagagacc ggcacgccac ggcccctccc ccaaggaaca gagcaaagga   2940
tggtggccgc aggccccacg cgagcccaca ggacaccggc ccctagattc cagccaccaa   3000
gcggaagcat gagacccgcc cacactagcc tctgtgttcc cgttagggac atcacaccct   3060
gtctcacgtc gcagtgccat ggacgcagca gttacagcac cattgtttta gcagtgcgtg   3120
ttcatatatg ggcttgctac ttcctgtaat gaggacgttc aacatggtga ggggctacaa   3180
gaaaacgctt ttctgtacag agtcttactg tagctacgct aatggttaac ctgatagaat   3240
taactcgtat ttttctatgg ttttaacctg atgctccact gtctccgtca tggggttgtt   3300
ttgctgtttg gggttgggcc ttgtttccct ttccttctc cagtccacgt gtagactttg   3360
cgcttgatga agaagcagat cggaagtaac tgctccctcc tcaaggttgt cttcagacgt   3420
cttggggacg ttcctaaaca ctgagggga agacagccaa tagcacccat taaaagaaat   3480
```

```
acctaaataa aacctctctc ccactcagct atgctagggc ttggctgtag gtgtgcactg    3540
tctatttaca tccgtcctta caaccatcct tgtcctcctt ggtaccgtat caagctcttt    3600
cccatgacat ttggtttaaa aaaaaaaaaa aaaaaaaaaa aaaacagaa aaaagacaaa     3660
gcgtcaactc cacccacagg cccgctgtgt gtgctcgggc cacggagtc ctgagggttc     3720
tgtgggcctg cgcgcatccc tctcccatcg tgggggtggc tccgtgacct tcctgccacg    3780
agcaggaggt tgatgatgtg ctacgttagc cttgtaagat acaccccac caaatgtgca     3840
gccggtgttc ccagtgtata tttcattctc ttgtatataa aggaagcaat gtgtgtcagg    3900
cctctgtgca gtcaacccag cctcctcccg ccagtgctaa ccccgtgttg agcctgcatg    3960
ctgacactgt ggccgatctg gactctagaa gtgctagttt gaaatatatc cattactgtc    4020
atttcctttt gagcttgtgg acaagctgaa tgtcaggact gacttcgcca gctcccagcc    4080
ctgcggggt gtccttggca tcccatcagc agaggagatg cgtccctgtt gcattttggc     4140
gtttgggct ttgggtttat ccacatgagc tctgaacgtc cgttatagtt agggtgattg     4200
gaaggtctcc atcactgggt gttttaaagg tgattcacca ccatttgtga aaggaccaac    4260
gtgctgataa acaggaccga tccgagtgct acatgactgt gcgtttgcta tttcaatggg    4320
cctgaacgac tacaaagcca gctaggtctg aaggggaag ccagctctgg ccacgacatc     4380
tggtcggagg gaagtgggga tgtggcatgg tagcgtctgt tcatccatgg aataaaacat    4440
tattttacca aaaaaaaaa                                                 4460

<210> SEQ ID NO 47
<211> LENGTH: 4542
<212> TYPE: DNA
<213> ORGANISM: Homo sapiens
<400> SEQUENCE: 47
gctgctgctg ctgctgcctc cccaccgcct ttttttttt ttaatctgga gcggggtggg     60
gagtgggaac cggagagaaa gcaaaatatt aaaaagcccc aaagacagcc agcaggagcg    120
cggtgcccga tggcttcgct gtaccagagg ttcactggca agatcaacac ctcgaggtcc    180
ttccccgcgc ccccggaggc gagtcacctc ctgggcggcc aggggcccga ggaggacggc    240
ggcgcaggag ccaagcccct cggcccgcgg gcgcaggcgg cggcgccccg ggagcgcggc    300
ggcggcggcg gcggcgcggg tggccggccc cggttccagt accaggcgcg gagcgatggt    360
gacgaggagg acgagctggt ggggagtaac cctccgcaga ggaattggaa aggaatagca    420
attgcactgc ttgtcattct ggtcatctgc tccttgatcg tcacctcggt catacttctg    480
acaccagcgg aagataatag tctgtctcaa aagaagaagg tcactgtaga agatctcttc    540
agtgaagact tcaaaattca tgaccccgag gctaagtgga taagtgatac agaattcatc    600
tacagagaac agaaaggaac agtgagactg tggaatgttg aaacaaatac ttctactgtc    660
ttaatagaag gcaaaaaaat tgaatcatta agagccatca gatatgaaat atctccagat    720
agagagtatg cactttttc atacaatgtg gaacccatat atcaacactc gtatactgga    780
tattacgtcc tgagcaaaat tcctcatggg gatcctcaaa gtctggaccc accagaagtc    840
agcaatgcaa aacttcagta tgcaggatgg ggccctaaag ccaacagct gatatttat     900
tttgaaaaca atatctacta ctgtgcacat gtcgggaaac aggccatccg tgtggtctcc    960
actggcaagg aaggtgtgat ttacaatggc ctcagtgact ggctgtatga agaggagatt    1020
ttgaagacac acatcgcaca ctggtggtct ccggatggca cgagactcgc ctacgccgcc    1080
atcaatgatt cccgtgtccc catcatggag ctcccaactt acaccggctc catctacccc    1140
```

```
accgtgaagc cctaccacta tcccaaggct ggaagtgaga accccagcat ttccctacac   1200
gttattggct taaatggacc cacccatgat ctggagatga tgccgcctga tgatccacgg   1260
atgagggagt actacatcac catggtgaag tgggccacca gcaccaaggt cgccgtgacc   1320
tggctgaacc gggcgcagaa cgtgtccatc ctcaccctct gcgacgccac cacggggggtc  1380
tgcacgaaga acacgagga tgaaagtgag gcctggctcc acagacagaa tgaagaacct   1440
gtgttctcca aggatggccg aaagtttttc ttcatcagag ccatccccca gggaggacga   1500
gggaaattct atcacatcac ggtgtcctcg tcccagccca acagcagcaa cgacaacatc   1560
cagtccatca cctccgggga ctgggacgtg accaagatcc tagcctacga tgagaagggg   1620
aataagatct acttcctgag cacggaggac ctgcctcgga gacgacaact ctacagtgcc   1680
aacacggtgg gcaacttcaa caggcagtgc ctctcctgtg acctggttga gaactgcacc   1740
tacttcagcg cttccttcag ccatagcatg gacttcttcc tgctcaagtg cgaaggtcct   1800
ggtgttccta tggtgacggt gcacaacaca acagataaga aaaaaatgtt tgacctagaa   1860
acaaatgaac atgtcaagaa ggccataaat gaccgacaga tgcctaaagt ggaatacagg   1920
gacattgaga ttgatgatta caacctgccc atgcagatac tgaagccagc aaccttcacc   1980
gacaccaccc actaccctct gctcctggtg gtggatggca ccccaggcag ccagagtgtg   2040
gctgagaagt cgaggtgag ctgggagacg gtgatggtga gcagccacgg cgcggtggtg   2100
gtaaagtgtg acggccgtgg cagcggcttc caagggacca agctcctgca cgaagtgagg   2160
cggcggctgg gcttgctgga ggagaaggac cagatggagg ccgtgcggac gatgctgaag   2220
gagcagtaca ttgacaggac gcgcgtggcc gtgtttggga aggattacgg tggctacctg   2280
agcacctaca tcctcccagc aaagggagaa aatcaaggcc agacattcac ctgcggctct   2340
gctctctctc caataacaga cttcaaactc tatgcctctg cgttttccga gaggtacttg   2400
ggcctccatg gacttgacaa cagagcatac gagatgacca aggtagccca tcgagtctcc   2460
gcgctggaag aacagcagtt cctgatcatt catcccactg ccgatgaaaa aattcatttc   2520
cagcacacag cagaactcat tacacaacta attaggggaa aggctaatta cagcttacag   2580
atttacccgg acgaaagcca ttactttacc agctccagcc tcaaacagca tctgtaccgg   2640
tccatcatca acttcttcgt ggaatgcttc aggatccagg acaaactgct gacagtcaca   2700
gcgaaagagg acgaggagga ggactaagct caggtcgctc taagcacaaa cgtggctctt   2760
tctacaacca gatgcaaccg agggatttcc ctgccctccc tcttccctcg gaggggcggg   2820
gcggggcggg gccgggtgtt ccatagcatg tgtgtctcgg atgcggaagg cagttttgct   2880
tgggaaacaa gctccttccc cggggtcatc actcacggcc tccatggcac cagggacaac   2940
gctgtccccg cagcagcgcc tcctcccggc gcccgagaga ccggcacgcc acggcccctc   3000
ccccaaggaa cagagcaaag gatggtggcc gcaggcccca gcgagccca caggacaccg   3060
gcccctagat tccagccacc aagcggaagc atgagacccg cccacactag cctctgtgtt   3120
cccgttaggg acatcacacc ctgtctcacg tcgcagtgcc atggacgcag cagttacagc   3180
accattgttt tagcagtgcg tgttcatata tgggcttgct acttcctgta atgaggacgt   3240
tcaacatggt gaggggctac aagaaaaacgc ttttctgtac agagtcttac tgtagctacg   3300
ctaatggtta acctgataga attaactcgt attttttctat ggttttaacc tgatgctcca   3360
ctgtctccgt catggggttg ttttgctgtt tggggttggg ccttgtttcc ctttcctttc   3420
tccagtccac gtgtagactt tgcgcttgat gaagaagcag atcggaagta actgctccct   3480
```

```
cctcaaggtt gtcttcagac gtcttgggga cgttcctaaa cactgagggg gaagacagcc   3540
aatagcaccc attaaaagaa atacctaaat aaaacctctc tcccactcag ctatgctagg   3600
gcttggctgt aggtgtgcac tgtctatttta catccgtcct acaaccatc cttgtcctcc    3660 ttggtaccgt atcaagctct ttcccatgac atttggttta aaaaaaaaaa aaaaaaaaa     3720 aaaaaaacag aaaaaagaca aagcgtcaac tccacccaca ggcccgctgt gtgtgctcgg   3780
gccacgggag tcctgagggt tctgtgggcc tgcgcgcatc cctctcccat cgtgggggtg   3840
gctccgtgac cttcctgcca cgagcaggag gttgatgatg tgctacgtta gccttgtaag   3900
atacaccccc accaaatgtg cagccggtgt tcccagtgta tatttcattc tcttgtatat   3960
aaaggaagca atgtgtgtca ggcctctgtg cagtcaaccc agcctcctcc cgccagtgct   4020
aaccccgtgt tgagcctgca tgctgacact gtggccgatc tggactctag aagtgctagt   4080
ttgaaatata tccattactg tcatttcctt ttgagcttgt ggacaagctg aatgtcagga   4140
ctgacttcgc cagctcccag ccctgcgggg gtgtccttgg catcccatca gcagaggaga   4200
tgcgtccctg ttgcattttg gcgtttgggg ctttgggttt atccacatga gctctgaacg   4260
tccgttatag ttagggtgat tggaaggtct ccatcactgg gtgttttaaa ggtgattcac   4320
caccatttgt gaaaggacca acgtgctgat aaacaggacc gatccgagtg ctacatgact   4380
gtgcgtttgc tatttcaatg ggcctgaacg actacaaagc cagctaggtc tggaagggga   4440
agccagctct ggccacgaca tctggtcgga gggaagtggg gatgtggcat ggtagcgtct   4500
gttcatccat ggaataaaac attattttac caaaaaaaa aa                       4542

<210> SEQ ID NO 48
<211> LENGTH: 940
<212> TYPE: DNA
<213> ORGANISM: Homo sapiens

<400> SEQUENCE: 48
cctgggcgtg tgctaaggcc agagctacca gatgggtcca gctgccgcag gctctccagg     60
cactgtcccc taagtgacag ctgttactgc ctgggagagc tcaagtgcaa agactatcct    120
gttctcccat aaagaggagg aaaaggaaga tacagaaatc ggtgctgctc caacagcag    180 atcaaggcag tcgtcaggaa ctcaggatcc gggggtctt cacggcttct ctgcccaggg    240
gccagaaccg aggaggccag gagggctgct ggggctaagg ggtctaagga cctcgttgca    300
cacgctacca ggagcagggg catggagcac agtgaggggg ctcccggaga cccagccggt    360
actgtggtac cccaggagct gctggaagag atgctttggt ttttttcgtgt ggaagatgca    420 tctccctgga atcattccat ccttgccctg gcagctgtgg tggtcattat aagcatggtc    480
ctcctgggaa gaagcatcca ggcaagcaga aagaaaaga tgcagccacc agaaaaagaa    540
actccagaag tcctgcattt ggatgaggcc aaggatcaca acagcctaaa caacctaaga    600
gaaactttgc tctcagaaaa gccaaacttg gcccaggtgg aacttgagtt aaaagagaga    660
gatgtgctgt cagtttttcct tccggatgta ccagaaactg agagctagtg agggttcaga    720
gaagccccat cctaagccag acacatgatg tgggctcagc tcagtggcct gaaacctctc    780
aggttttaga gtctctccca agaagccgct ttttcttttt tctttcttttc tttttttttt    840 tcttagcaga tacaatgaat gaactgcaag caaactaaaa ttctgttatt aaaaaaatc    900 ttttattaaa atgctcctgg aagggagcag gtggtattgc                          940

<210> SEQ ID NO 49
<211> LENGTH: 5018
```

<212> TYPE: DNA
<213> ORGANISM: Homo sapiens

<400> SEQUENCE: 49

```
gcccgggact atcccttcgc ggtgtagcgg cagccggaga cctggctgag gaggcaaccg      60
cgtagacacc tccctgctta gaaaacaaac actgaaccag accgatccca gttggagggt     120
tcgaaaatgt tccagacagc ctgtcgggag gggttgttgt tgctgttgga ctaaatagct     180
attcctgatt ggtcatgtat agggtttttt aaggcgggtg gggggaggag ggggtagagg     240
aaaggctcca aacacctgca ggttgggggc ggaaagctgt ttgcgattcc ctggactggt     300
tggtcgggga caggaggtaa ttcccagcca ttgaccccca tttctctctc tccctccctc     360
ttgccctgcc tctttctctc caccccatc tttcctggaa actcgctttg ggcgcggcag      420
atcgcccagg accacaccgc agcgtaactg caggcctctc agcgaaaaag ggggaaagca     480
aagacccggg tgtgcatcct cttcctcggc ttccgcccct ttccggcgga gtggagatcc     540
tattcagagg ggccggtctc tctaaatatg ccccaggatg accgagcggc cgccgagcga     600
ggcggctcgc agtgaccccc agctagaggg acgggacgcg gccgaggcca gcatggcccc     660
cccgcacctg gtcctgctga acggcgtcgc caaggagacg agccgcgcgg ccgcagcgga     720
gcccccagtc atcgaactgg gcgcgcgcgg aggcccgggg ggcggccctg ccggtggggg     780
cggcgccgcg agagacttaa agggccgcga cgcggcgacg gccgaagcgc gccatcgggt     840
gcccaccacc gagctgtgca gacctcccgg gcccgcccg gccccgcgc cgcctcggt       900
tacagcggag ctgcccggcg acggccgcat ggtgcagctg agtcctcccg cgctggctgc     960
ccccgccgcc cccggccgcg cgctgctcta cagcctcagc cagccgctgg cctctctcgg    1020
cagcgggttc tttggggagc cggatgcctt ccctatgttc accaccaaca atcgagtgaa    1080
gaggagacct tcccctatg agatggagat tactgatggt ccccacacca aagttgtgcg    1140
gcgtatcttc accaacagcc gggagcgatg gcggcagcag aatgtgaacg ggcctttgc     1200
cgagctccgc aagctgatcc ccacacatcc cccggacaag aagctcagca agaatgagat    1260
cctccgcctg gccatgaagt atatcaactt cttggccaag ctgctcaatg accaggagga    1320
ggagggcacc cagcgggcca agactggcaa ggaccctgtg gtggggctg gtggggtgg     1380
aggtggggga gggggcggcg cgccccaga tgacctcctg caagacgtgc tttccccaa     1440
ctccagctgc ggcagctccc tggatggggc agccagcccg gacagctaca cggaggagcc    1500
cgcgcccaaa cacacggccc gcagcctcca tcctgccatg ctgcctgccg ccgatggagc    1560
cggccctcgg tgatgggtct gggccaccag gatcagccag gagggcgttc ttaggctgct    1620
gggatggtgg gcttcagggc aggtggggtg agaattgggc ggctctgaag caaggcggtg    1680
gacttgaact ttcctggatg tctgaacttt gggaagcctt tactgaccct ggggctggct    1740
tttctgtttc ctgtaccagt aggagatcag aaaaatggag caaagtggta ggtactttt     1800
gtgaagacgg cacggtcttc cctcttccct cagtcccaaa tccttcccaa gtaagaggct    1860
ggagttgtca ctgcttttgg cctggagttt gggatccctg tctttcctaa gacctggggt    1920
tgtcagctct catctgaggc atccagcagt ctctgccttg cctttagccc ctcccaagct    1980
ggctggggtg gcctgtgtgg ccacttctgt ccatatttat aggtacccaa tagctgccca    2040
tttcgtgagc cccatcttca cccaggccta tgttgatcca tccagcttgc cagatgctgc    2100
agagtcacaa gcctcgaggt gccttcttca gggcctggtt gaagaagatg atcagtggac    2160
agtctgctct agatgagctg ggccggaggg tcaggaaacc cagtcgccct tacttcttgc    2220
```

```
cctggggatc aaagttctgc tttctcccca atgagacttg ccttcctaag cctgtggctg    2280
tggagacaat gtctgcagcc ctgagaaagc cctgtcgggc tttgtgtgaa ggcagagaaa    2340
gggacaatga tagtagagtg atatggagca agagatattt tgggcatgtg ggcttcaact    2400
cctcgacatc actgttcatg ctggcgagtg aatgccagtg tgctgatggg cgtacgctgg    2460
tgctgagtag atgcgcagcc ccatctgtgc attctcctgg atgcttagag ggatttcttt    2520
gctgtaagat gtctgtttgc tgatggtctg gtctatgttc cgaattgagc acaaaacctg    2580
tcctatgaat gctttgcatt tggaattttt gcttgacttc agttattggt ggaatcttta    2640
gcgctcaata ggaccaggat ccagcctcac ttctagggta tgggaaatcc aatcagagac    2700
caggccctgg ctaagaccca acatatgca cattcactta gcagaacctt aaacaccct     2760 cagttgtgca gcttttggtc atcaagggtg cgtctgggag gttggtttaa tgcaatagaa    2820
gtgctcccct ctgaaagttg tacatgaaat ttttgtaaat cacatcctta tccttcatct    2880
tttaaagaaa taaccactgc aagtcctttt gtaaagtgaa gaatcctttt gtagaatgaa    2940
ccactgcccc ttcattgatt tcctgtgtca atccagatgg tgggatgtgg ttttcttaag    3000
gtgaggcctg tctgtgacct gcatctaagc ccatgggaca aattgcacag aagtcctgta    3060
tgtctgtcat tgtacccctta agtcacccta gccctctccc tctaggctct gccttcgagg    3120
tcagaggaga gatagcctgt ggccctgtcc tgccatgcaa gaactcatca ctgtggctgt    3180
ctggaaagcc ccccttata gtttgggctt cagcctagtg gcttgtcctc accatgatgg    3240
ggccctaatt cagccatgta cagacagaga atatgtctgc tcctttcccc ttccttttaa    3300
gtaaggtcca attctcgagc ttggggcaac attgttcacc tttgtagcac tcaggctctc    3360
cattcaattt caggctcccc agatcatgtt ttggtgaaaa ttagggttgg ttccttttcca   3420 acgtttggaa gatcctgtga ggagccccat ctgtctaaag atagagtcat tgctgtagga    3480
tctaaggctg tttgcttcac cgtggattcg cttgagttag gaatgagaag tagccacagt    3540
atggatgggt ggatgggttt tatgagatgg atcacatatt ttattaagaa ctcaaacttc    3600
tggctccctc ttctttcaga cttgccatgt gactctggct tggcctatct cctagggcta    3660
tggtgtggac tgaatgggat catgaaagta gacagttttg agaacgtaaa gaactttttc    3720 tttttccctca atctcaatcc tgcagtgggg tttcgcagcc tgagtccacg acctaggcag    3780
taggccggtg tgcctgactg cccagcattt gggtaattta gattgtaaac cgctttggcc    3840
tgagttattg agattgtcct catttctcca gattatctat ttgtgtgtgt gtgtgtgtgt    3900
gtgtgagaga cggtgtcttg ttctgtcact caggctggag tacagtggtg ccatcattgc    3960
tgtctgcagc cttgaactct gggctcaagc aatcctctca cctcagcctc ccgagtaggg    4020
aggaccacag gtgtgagcca ccacacctgg ctaatttta ctttttttt tttttggtag     4080 agatggagtc ttgctatatt gcccaggctg gtcttgaagt cctggcttca ggcaattctc    4140
ctgcctttgc ctccagaagc actgggatca caggtgtcag ccattgcacc cagcccagat    4200
tgtcttaatt tctatcttgt tccaaggcca gggacagtaa taagaatgga aaagagatat    4260
gggaacactg gcagactgtg taaaatgtaa tgcaactacc caaaacaagc ctggtaggaa    4320
agggcaagtc tttaggtctt tgtaagaact aaagaagatc tgtaattttt attttcacccc   4380 tctgtacccc atgaccttat ccttcctctc cttccttgtt acccatgaaa aactggcaac    4440
attccaagaa tagcatctgt acaaggggga agaacataa aggtaaaaca aaacaaaaca    4500
acattttgag aacaaagatg accataacca ctgaaggaa tcacatcttt taagacaaat    4560
tcatattctt ttatttgtta tggcagatga caagatggta caacctttat tcttttccaa    4620
```

| | |
|---|---:|
| aataaaacaa agggcacagc atctgtagtc agccgacaac tatttcggcc ttttggggt | 4680 |
| gggtctggcc gtacttgtga tttcgatggt acgtgaccct ctgctgaaga cttgcccccct | 4740 |
| gcccgtgtac atagtgcatt gtttctgtgg gcgggcccag cactttccgt caacgttgta | 4800 |
| ctgtatgtga tgaattgcgt tggtctctgc attttctgc agaagaggag taaccgctcc | 4860 |
| aggtaccttg acctttgtac agcccagagg ccaacactgt gggtgtgtga ctctttagca | 4920 |
| aaaaaaccc atgtggtgat gatgtgtata tatatgtgag gatgtatcgg gaagatttct | 4980 |
| aaataaaagt tttacaaagg ggaaaaaaaa aaaaaaa | 5018 |

<210> SEQ ID NO 50
<211> LENGTH: 3024
<212> TYPE: DNA
<213> ORGANISM: Homo sapiens

<400> SEQUENCE: 50

| | |
|---|---:|
| aggatatctt tagccaaagg aaaagctccg cattcccacc cagtccagaa attgaaatac | 60 |
| tatcagggg caagagcctt tctctccagc tacacactcc atctcccggg agcaagggga | 120 |
| aactccgaga ggagggcaac agagccagca tcttgccagg gccccggagg aggggttccc | 180 |
| cgctacgcct gtgccggagg agttccagtc accgagcgag gggcgcaagg gtgggtgcat | 240 |
| cctgcgctgc ggcgggcgcg ctacccgac gctggtgtgc agagccacat gaagcctgct | 300 |
| ggggactggg ggccagggag cagcaagcca gctgggactg aggcggacgc tgtctcaggg | 360 |
| agacgctgac tcgcaaagac actcccttcc ttgtgcctgg gtaaaaagtc tcctcctggg | 420 |
| gtccctggcc atcctgaata tccagaatgg tgtttctgaa gttcttctgc atgagtttct | 480 |
| tctgccacct gtgtcaaggc tacttcgatg gcccctcta cccagagatg tccaatggga | 540 |
| ctctgcacca ctacttcgtg cccgatgggg actatgagga gaacgatgac cccgagaagt | 600 |
| gccagctgct cttcagggtg agtgaccaca ggcgctgctc caggggag gggagccagg | 660 |
| ttggcagcct gctgagcctc accctgcggg aggagttcac cgtgctgggc cgccaggtgg | 720 |
| aggatgctgg gcgcgtgctg gagggcatca gcaaaagcat ctcctacgac ctagacgggg | 780 |
| aagagagcta tggcaagtac ctgcggcggg agtcccacca gatcggggat gcctactcca | 840 |
| actcggacaa atccctcact gagctggaga gcaagttcaa gcagggccag gaacaggaca | 900 |
| gccggcagga gagcaggctc aacgaggact ttctgggaat gctggtccac accaggtccc | 960 |
| tgctgaagga gacactggac atctctgtgg ggctcaggga caaatacgag ctgctggccc | 1020 |
| tcaccattag gagccatggg acccgactag gtcggctgaa aaatgattat cttaaagtat | 1080 |
| aggtggaagg atacaaatgc tagaaagagg gaatcaaatc agcccgtttt ggagggtgg | 1140 |
| gggacagaag atgggctac atttccccca tacctactat tttttttatat cccgatttgc | 1200 |
| actttgagaa tacatctaag gtcatctttc aaaagagaaa aattggacac ttgagtgact | 1260 |
| ttgtttttag ttttgtttt gtacattatt tatgtgattg ttatgaatt gtcacctgga | 1320 |
| aagaacaatt ttaagcaatg tcatttctag atgggtttct aattctgcag agacacccgt | 1380 |
| ttcagccaca tctaaaagag cacagtttat gtggtgcgga attaaacttc cccatcctgc | 1440 |
| agattatgtg gaaataccca aagataatag tgcatagctc ctttcagcct ctagccttca | 1500 |
| ctcctgggct ccaaaagcta tcccagttgc ctgttttca aatgaggttc aaggtgctgc | 1560 |
| tttgcatgcc tgccaaccca tggaagttgt ttcttacttc ttttctctct tatttattaa | 1620 |
| ccatggtctg agagttgttt ttgttctatg taacagtatt gccacaaaac tataggcaaa | 1680 |

| | |
|---|---|
| tcgtgtttgc agggagattt ctgatgcctc tgtgggtgtg tgtaagttaa agtggccaca | 1740 |
| tttaagaagg ccaagctttg tagtggttgc acagtcacac tgatatgctg atttgctctt | 1800 |
| tctcattgta tgtctatgct ttgtcatcag tgctatagta aattacaaag aaataggtag | 1860 |
| attgtatgaa catacccaca aatgcctatg atttaggtta ccaatgtatt ctttctcatt | 1920 |
| tggggttttg cttctgtctg tctgtttatt ggaaacttgt acttcaagta gggggaatcc | 1980 |
| taattctaat aactccttag ctaagtttta ttattcaggc aataaacatg ttttcatgta | 2040 |
| atactggctt actttgtaat ttacatctgt aactttcata tttctaaaag gggccaatgc | 2100 |
| aaaaggagag agaaggactg gatttaagcc agtttactta gagtatatga taaagaaggc | 2160 |
| agaggaatag ctacatattt ggcaattctc ctctctgtag tcaccctgac atcctcacaa | 2220 |
| gaaaacaaat ctagccattg cccaaacttt aaatttgatc tctataggtc tgcttaaaga | 2280 |
| ctcaaatttt ctccagtttc tctcataaat tcaattgcaa aagtttctga caaggctcat | 2340 |
| accctgtacc cttatgcaga gcaagcattc catcctaagt tataaactac agtgatgttt | 2400 |
| aattttgaag ccaggtctac attatttaat taatggcttc aaaaggtgga gatgcacttt | 2460 |
| atttaatgtc tttccctagc taattcttac tctcaccatta aatatgcttt cttgttgcat | 2520 |
| atatgcacag atacacacac acacacacac gaaaataaat aaatgttcat attcttctgt | 2580 |
| tcaacagaca tttattttct cctctccctt gaataagaaa ataagttttc cattcctatg | 2640 |
| aactgtctaa tatctttcta ttacagaagg ggaaactgag gctgggaaag gctaaatgac | 2700 |
| ttatcctcca tcagttataa cagcccctgg tcttcttaaa tttaaacacg ggacttcccg | 2760 |
| aactaatttt tttaaggata ctgaaaaatg agagagagtg gtcgaatgcc tgaaattttg | 2820 |
| cttaacttac tgtacttaaa atcaattata acttcttttt gttactcagg gccccacttt | 2880 |
| ttgttgcttt ctagacttgt gtgtagaaag aagattaatg atcacttaaa gtagtttcct | 2940 |
| tctttattct gaaaaaatga ggaaaaaata acaacagtgg caaataaaat catatttggt | 3000 |
| actaaaaaaa aaaaaaaaaa aaaa | 3024 |

<210> SEQ ID NO 51
<211> LENGTH: 7111
<212> TYPE: DNA
<213> ORGANISM: Homo sapiens

<400> SEQUENCE: 51

| | |
|---|---|
| gcgtcagccc tcacgtcact tcgccagcag tagcagaggc ggcggcggcg gctcccggaa | 60 |
| ttgggttgga gcaggagcct cgctggctgc ttcgctcgcg ctctacgcgc tcagtccccg | 120 |
| gcggtagcag gagcctggac ccaggcgccg ccggcgggcg tgaggcgccg gagcccggcc | 180 |
| tcgaggtgca taccgacccc ccattcgcat ctaacaagga atctgcgccc cagagagtcc | 240 |
| cgggagcgcc gccggtcggt gcccggcgcg ccgggccatg cagcgacggc cgccgcggag | 300 |
| ctccgagcag cggtagcgcc ccctgtaaa gcggttcgct atgccggggc cactgtgaac | 360 |
| cctgccgcct gccggaacac tcttcgctcc ggaccagctc agcctctgat aagctggact | 420 |
| cggcacgccc gcaacaagca ccgaggagtt aagagagccg caagcgcagg gaaggcctcc | 480 |
| ccgcacgggt gggggaaagc ggccggtgca gcgcggggac aggcactcgg gctggcactg | 540 |
| gctgctaggg atgtcgtcct ggataaggtg gcatggaccc gccatggcgc ggctctgggg | 600 |
| cttctgctgg ctggttgtgg gcttctggag ggccgctttc gcctgtccca cgtcctgcaa | 660 |
| atgcagtgcc tctcggatct ggtgcagcga cccttctcct ggcatcgtgg catttccgag | 720 |
| attggagcct aacagtgtag atcctgagaa catcaccgaa attttcatcg caaaccagaa | 780 |

```
aaggttagaa atcatcaacg aagatgatgt tgaagcttat gtgggactga gaaatctgac    840
aattgtggat tctggattaa aatttgtggc tcataaagca tttctgaaaa acagcaacct    900
gcagcacatc aattttaccc gaaacaaact gacgagtttg tctaggaaac atttccgtca    960
ccttgacttg tctgaactga tcctggtggg caatccattt acatgctcct gtgacattat   1020
gtggatcaag actctccaag aggctaaatc cagtccagac actcaggatt tgtactgcct   1080
gaatgaaagc agcaagaata ttccctggc aaacctgcag atacccaatt gtggtttgcc    1140
atctgcaaat ctggccgcac ctaacctcac tgtggaggaa ggaaagtcta tcacattatc   1200
ctgtagtgtg gcaggtgatc cggttcctaa tatgtattgg gatgttggta acctggtttc   1260
caaacatatg aatgaaacaa gccacacaca gggctcctta aggataacta acatttcatc   1320
cgatgacagt gggaagcaga tctcttgtgt ggcggaaaat cttgtaggag aagatcaaga   1380
ttctgtcaac ctcactgtgc attttgcacc aactatcaca tttctcgaat ctccaacctc   1440
agaccaccac tggtgcattc cattcactgt gaaaggcaac cccaaaccag cgcttcagtg   1500
gttctataac ggggcaatat tgaatgagtc caaatacatc tgtactaaaa tacatgttac   1560
caatcacacg gagtaccacg gctgcctcca gctggataat cccactcaca tgaacaatgg   1620
ggactacact ctaatagcca agaatgagta tgggaaggat gagaaacaga tttctgctca   1680
cttcatgggc tggcctggaa ttgacgatgg tgcaaaccca aattatcctg atgtaattta   1740
tgaagattat ggaactgcag cgaatgacat cggggacacc acgaacagaa gtaatgaaat   1800
cccttccaca gacgtcactg ataaaaccgg tcgggaacat ctctcggtct atgctgtggt   1860
ggtgattgcg tctgtggtgg gattttgcct tttggtaatg ctgtttctgc ttaagttggc   1920 aagcacactcc aagtttggca tgaaaggttt tgttttgttt cataagatcc cactggatgg   1980
gtagctgaaa taaggaaaa gacagagaaa ggggctgtgg tgcttgttgg ttgatgctgc    2040
catgtaagct ggactcctgg gactgctgtt ggcttatccc gggaagtgct gcttatctgg   2100
ggttttctgg tagatgtggg cggtgtttgg aggctgtact atatgaagcc tgcatatact   2160
gtgagctgtg attggggaac accaatgcag aggtaactct caggcagcta agcagcacct   2220
caagaaaaca tgttaaatta atgcttctct tcttacagta gttcaaatac aaaactgaaa   2280
tgaaatccca ttggattgta cttctcttct gaaaagtgtg cttttgacc ctactggaca    2340 tttattgact taattgcttc tgtttattaa aattgacctg caaagttaaa aaaaaattaa   2400
agttgagaac aggtataagt gcacactgaa tagtctaatc tacatgtaac acatatttta   2460
gtgtgatttt ctatactcta atcagcactg aattcagagg gtttgacttt ttcatctata   2520
acacagtgac taaagagtt aagggtatat ataccatcac tttgggactt ggtagtatta    2580
ttaaaaggtt atttccttca ctgtcaataa aagtccaaat gtttagctta ggtctgagag   2640
tcaaacaatg ttaaggattg tcttaaagtt ccttagccag caaaacaaaa caaaacaaaa   2700
caaacaaatg aaaacgtttt aaaaagaaga agaagaaaaa aacaagaac aagcagcaac    2760 agctgttttg ttgggctat agatttaagt taggcatagt caatttcaga ataactaaga    2820
gtggaatata tgcatatggt gaaattataa ccttgcccctt ttttatttgc cctctgcgat   2880
ccacctgctt tttagaagtc tgccgagtga gaaggccaca gtatctcatg ctgtttgcat   2940
tacagaactg cagcttttct actctgaaaa ggcctgggag cagaatggct ggcctgctgt   3000
gagcaggaga ggagattcta agaaggatag tcccccctac aacatactgt catactgctg   3060
ggttttcatg ggtaggaaag cttgtcctga ccccagcagc aaagaggtgg caggtcgcta   3120
```

```
atgaatatat gctttataat gtccttcttc attgctgaga gggcagcctt agagctgtgg    3180
atttctgcat ccccccctgag tctgacccat ggacacctgt ttcattcact ttagcatcac    3240 agtgacctt  gtatgctctg ttcagtctgt gtcaggcagt atgcttgtcc tgaagagagg    3300
tttggctatc cccaccccac cccacccac  cctgttcctt ttttatcagg aggacttcag    3360
agccaggcct gcagcatttt gtttgaaaac acaatcagct ctgacagtta gacatgcaca    3420
cagacgccat agctggattg gaaacattga tgttttaaaa atttatttt  tttggaaata    3480 gttgcacaaa tgctgcaatt tagctttaag gttctataga ttttaacta  gtccaacaca    3540 gtcagaaaca ttgttttgaa tcctctgtaa accaaggcat taatcttaat aaaccaggat    3600
ccatttaggt accacttgat ataaaaagga tatccataat gaatatttta tactgcatcc    3660
tttacattag ccactaaata cgttattgct tgatgaagac ctttcacaga atcctatgga    3720
ttgcagcatt tcacttggct acttcatacc catgccttaa agaggggcag tttctcaaaa    3780
gcagaaacat gccgccagtt ctcaagtttt cctcctaact ccatttgaat gtaagggcag    3840
ctggccccca atgtggggag gtccgaacat tttctgaatt cccatttct  tgttcgcggc    3900 taaatgacag tttctgtcat tacttagatt ccgatctttc ccaaaggtgt tgatttacaa    3960
agaggccagc taatagcaga aatcatgacc ctgaaagaga gatgaaattc aagctgtgag    4020 ccagcagga  gctcagtatg gcaaaggttc ttgagaatca gccatttggt acaaaaaaga    4080
tttttaaagc ttttatgtta taccatggag ccatagaaag gctatggatt gtttaagaac    4140
tattttaaag tgttccagac ccaaaaagga aaaataaaaa aaaggaata  tttgtaccca    4200 acagctagaa ggattgcaag gtagattttt gttttaaaat ggagagaagt ggacagataa    4260
ggccatttaa tatatcaaag atcagttgac atctcctagg gaatgatgaa acagcaggc    4320 tattagaaaa ttatttcata tagttctcgt gttcttttct ttttttaat  ccctgaaggg    4380 atgatcagta acatagcttc tcttttctgt actctagacc ccccttttc  atcatttgtc    4440 ttttatgtc  tcccataaga aatgtgcttt ttagagcttc ctaatgcatg tgttgcatta    4500
ttgcagcatt agaaaggag  aggtagcatt tttgctgaaa tcgggcctgt cactctccaa    4560
taaaggttct ggcacttcaa tgccaggcag gtctcctaaa tgaacagaat gatctgtgtg    4620
agccgatgcc tgcccttcca gagggggccac tgtccccagc cgcagccaac tgtgtcccac    4680
aggaatggga gcctaggttt ccaaatcttg tgattcttta ggagaaacat gaaacctgga    4740
tttcgtgtga aatgtcccga ttgttaaaaa gttggctcaa ttattttaa  aacatttgt    4800 aagccaacaa aagtctgtgg gctgccagtt tattacttt  gtcttaaaac atgatcattg    4860
ttctctcacg gtatccttct gtcttcccgt tgcaaattca cttttctttc ttcctgacat    4920
tgccattgag ggctttgtta ccacaagcta agaaactgag tttaacagcc cagttatctg    4980
caacatgtca attcccttg  ctcctctcct gtgattccca ccatgctgtg accctcagct    5040 gtctccctt  gctgggaatt ctgcaccaat gtctcccctc aacccattcc ctggttggtc    5100
ctactcccgt gtggccagag acatcctagc aaatccttcc tcctattata tctgacacta    5160 atttctttc  aacagcgctc atgtctcttg gcccagtcag gtgctgccag gtttagatag    5220
gaaagtacat gtcccatttt catgggtgcc cttaatgtgg tccacgtcct atatcttatt    5280
atatttactc atggctcaat ggggcctcc  agagaccctc tcaggctgct gagctagact    5340
aaggaatgca tccaccgtca tcacatgaga cactgactct gtgacgacaa aagtacaaac    5400
agtctgaggc taagaaaggt tcatctcaca acaggaaaaa caaatctcaa cacacattag    5460
agataattga ttcagggggtt ttctctccca gtctcccagc agggactgat ttcatttctg    5520
```

```
acccactagg ttttctttcc agaaataggt agcaaggaca agaactaaac aatcccagcc    5580
ccacccagca acacagaaca caggagtttg cttttggctt ctcactctcc aagtaaccct    5640
gaattaggcc cagaatggct gaggcttgga gcatctcctc agacagagca gaggcgacac    5700
ctcttcaggg gtgtgtggag taaatagctc gaagagctga agacagaaaa ccagtttcac    5760
gccaggtgcg agagagagca taatggaggg aagcccgctt tctctctcct cttcttttct    5820
ctttatttct ttagagcact tgacttttt ttctctctct ctctagtatt ctaaactgac    5880
cccatgacca actgagaatt tattttgtt tcattggttg tttcacagaa ttagaacaca    5940
cacgactttt tattcctcca ttgcaaaatg gaatcaagat actacacaag acctgtgctt    6000
tcttcctttg catgatttac acctccgcct gttttggtgc tagctgtcta gaacttctct    6060
cttggtttga atctgattcc ttcacactac actagaagtt tatttcatct tgttttgtct    6120
agactccaga tacagaggga cagctggact gaggacaagc aattccatct agcatagggt    6180
ctctcagggt tggtgcatcc agccacatgg gcagggccag tcacatctag tctatgtccc    6240
cagagccctt ggagttgcgc agcttagctg acttgactcc aaggaaatta gtacagaagt    6300
aaccactcta ttaagtgtgt tctgctatgt tcacatgcct gtagtacctg caaaccatgc    6360
caggttcatc taaagacata ggggaagatt aaggactctt ttggacagac catgaattga    6420
atttgctgcc aggtgctgcc agactgaatt tggctgacag aactcccagc ccaggaaagt    6480
tccatgacaa tgactgtcgc agaaggaaat ttcccactaa agtcagtcca ttttcaagtt    6540
ttggtcttca gagacaaaag aacgtccag ccacctgatt ttgatggtga ggtaactcta    6600
agttgaattc aggctagtgt tgcagtatag ctttggcatg ttcatgagtg agcacccaga    6660
atgtgttgaa ccaaccccca cccctaacta ctgactatga ctgcagtggg ttttatggg    6720 gaaaaaagt gtgaaaagca aaagaaagg aacagagatt ttttatcacc tttattgtaa    6780
gacagtccat ttatgaattg agtataaaca catacaaagt aacaagagat tcctaagaaa    6840
cgcaaatcct tgagtttcac gcacttcatg ttcaaccatt tgctgtaatc cagaggcagc    6900
ctgtgaatca ttctcatgcc ctgttttttt ttttttttc ctataatgtt ctgggtttaa    6960
aagccatctt ttccacattt tctgtaaata atggataatc atttaaaaa tttttatttt    7020 tagtgctgtt ttaacaatgt agatagatca taaatgtact tgctgaattc aatcatttt    7080 aacaagccaa taaagtttga taattcatct c                                 7111
```

<210> SEQ ID NO 52
<211> LENGTH: 5560
<212> TYPE: DNA
<213> ORGANISM: Homo sapiens

<400> SEQUENCE: 52

```
aagacggatt ctcagacaag gcttgcaaat gccccgcagc catcatttaa ctgcacccgc      60
agaatagtta cggtttgtca cccgaccctc ccggatcgcc taatttgtcc ctagtgagac     120
cccgaggctc tgcccgcgcc tggcttcttc gtagctggat gcatatcgtg ctccgggcag     180
cgcgggcgca gggcacgcgt tcgcgcacac cctagcacac atgaacacgc gcaagagctg     240
aaccaagcac ggtttccatt tcaaaaaggg agacagcctc taccgcgatt gtagaagaga     300
ctgtggtgtg aattagggac cgggaggcgt cgaacggagg aacggttcat cttagagact     360
aattttctgg agtttctgcc cctgctctgc gtcagccctc acgtcacttc gccagcagta     420
gcagaggcgg cggcggcggc tcccggaatt gggttggagc aggagcctcg ctggctgctt     480
```

```
cgctcgcgct ctacgcgctc agtccccggc ggtagcagga gcctggaccc aggcgccgcc      540
ggcgggcgtg aggcgccgga gcccggcctc gaggtgcata ccggaccccc attcgcatct      600
aacaaggaat ctgcgcccca gagagtcccg ggagcgccgc cggtcggtgc ccggcgcgcc      660
gggccatgca gcgacggccg ccgcggagct ccgagcagcg gtagcgcccc cctgtaaagc      720
ggttcgctat gccggggcca ctgtgaaccc tgccgcctgc cggaacactc ttcgctccgg      780
accagctcag cctctgataa gctggactcg gcacgcccgc aacaagcacc gaggagttaa      840
gagagccgca agcgcaggga aggcctcccc gcacgggtgg gggaaagcgg ccggtgcagc      900
gcggggacag gcactcgggc tggcactggc tgctagggat gtcgtcctgg ataaggtggc      960
atggacccgc catggcgcgg ctctggggct tctgctggct ggttgtgggc ttctggaggg     1020
ccgctttcgc ctgtcccacg tcctgcaaat gcagtgcctc tcggatctgg tgcagcgacc     1080
cttctcctgg catcgtggca tttccgagat tggagcctaa cagtgtagat cctgagaaca     1140
tcaccgaaat tttcatcgca aaccagaaaa ggttagaaat catcaacgaa gatgatgttg     1200
aagcttatgt gggactgaga aatctgacaa ttgtggattc tggattaaaa tttgtggctc     1260
ataaagcatt tctgaaaaac agcaacctgc agcacatcaa ttttacccga aacaaactga     1320
cgagtttgtc taggaaacat ttccgtcacc ttgacttgtc tgaactgatc ctggtgggca     1380
atccatttac atgctcctgt gacattatgt ggatcaagac tctccaagag gctaaatcca     1440
gtccagacac tcaggatttg tactgcctga atgaaagcag caagaatatt ccctggcaa      1500 acctgcagat acccaattgt ggtttgccat ctgcaaatct ggccgcacct aacctcactg     1560
tggaggaagg aaagtctatc acattatcct gtagtgtggc aggtgatccg gttcctaata     1620
tgtattggga tgttggtaac ctggtttcca acatatgaa tgaaacaagc cacacacagg      1680
gctccttaag gataactaac atttcatccg atgcagtgg gaagcagatc tcttgtgtgg      1740
cggaaaatct tgtaggagaa gatcaagatt ctgtcaacct cactgtgcat tttgcaccaa     1800
ctatcacatt tctcgaatct ccaacctcag accaccactg gtgcattcca ttcactgtga     1860
aaggcaaccc caaaccagcg cttcagtggt tctataacgg ggcaatattg aatgagtcca     1920
aatacatctg tactaaaaata catgttacca atcacacgga gtaccacggc tgcctccagc     1980
tggataatcc cactcacatg aacaatgggg actacactct aatagccaag aatgagtatg     2040
ggaaggatga aaacagatt tctgctcact tcatgggctg gcctggaatt gacgatggtg      2100
caaacccaaa ttatcctgat gtaattatg aagattatgg aactgcagcg aatgacatcg      2160
gggacaccac gaacagaagt aatgaaatcc cttccacaga cgtcactgat aaaaccggtc     2220
gggaacatct ctcggtctat gctgtggtgg tgattgcgtc tgtggtggga ttttgccttt     2280
tggtaatgct gtttctgctt aagttggcaa gacactccaa gtttggcatg aaaggcccag     2340
cctccgttat cagcaatgat gatgactctg ccagcccact ccatcacatc tccaatggga     2400
gtaacactcc atcttcttcg gaaggtggcc cagatgctgt cattattgga atgaccaaga     2460
tccctgtcat tgaaaatccc cagtactttg gcatcaccaa cagtcagctc aagccagaca     2520
catttgttca gcacatcaag cgacataaca ttgttctgaa aagggagcta ggcgaaggag     2580
cctttggaaa agtgttccta gctgaatgct ataacctctg tcctgagcag acaagatct      2640 tggtggcagt gaagacctg aaggatgcca gtgacaatgc acgcaaggac ttccaccgtg      2700
aggccgagct cctgaccaac ctccagcatg agcacatcgt caagttctat ggcgtctgcg     2760
tggagggcga ccccctcatc atggtctttg agtacatgaa gcatgggac ctcaacaagt      2820 tcctcagggc acacggccct gatgccgtgc tgatggctga gggcaacccg cccacggaac     2880
```

```
tgacgcagtc gcagatgctg catatagccc agcagatcgc cgcgggcatg gtctacctgg   2940
cgtcccagca cttcgtgcac cgcgatttgg ccaccaggaa ctgcctggtc ggggagaact   3000
tgctggtgaa aatcggggac tttgggatgt cccgggacgt gtacagcact gactactaca   3060
gggtcggtgg ccacacaatg ctgcccattc gctggatgcc tccagagagc atcatgtaca   3120
ggaaattcac gacggaaagc gacgtctgga gcctggggt cgtgttgtgg gagattttca   3180
cctatggcaa acagccctgg taccagctgt caaacaatga ggtgatagag tgtatcactc   3240
agggccgagt cctgcagcga ccccgcacgt gcccccagga ggtgtatgag ctgatgctgg   3300
ggtgctggca gcgagagccc cacatgagga agaacatcaa gggcatccat accctccttc   3360
agaacttggc caaggcatct ccggtctacc tggacattct aggctagggc cttttcccc   3420
agaccgatcc ttcccaacgt actcctcaga cgggctgaga ggatgaacat cttttaactg   3480
ccgctggagg ccaccaagct gctctccttc actctgacag tattaacatc aaagactccg   3540
agaagctctc gagggaagca gtgtgtactt cttcatccat agacacagta ttgacttctt   3600
tttggcatta tctctttctc tctttccatc tcccttggtt gttccttttt ctttttttaa   3660
attttctttt tcttttttt ttcgtcttcc ctgcttcacg attcttaccc tttcttttga   3720
atcaatctgg cttctgcatt actattaact ctgcatagac aaaggcctta acaaacgtaa   3780
tttgttatat cagcagacac tccagtttgc ccaccacaac taacaatgcc ttgttgtatt   3840
cctgcctttg atgtggatga aaaaaggga aacaaatat ttcacttaaa ctttgtcact   3900
tctgctgtac agatatcgag agtttctatg gattcacttc tatttattta ttattattac   3960
tgttcttatt gttttggat ggcttaagcc tgtgtataaa aagaaaact tgtgttcaat   4020
ctgtgaagcc tttatctatg ggagattaaa accagagaga aagaagattt attatgaacc   4080
gcaatatggg aggaacaaag acaaccactg ggatcagctg gtgtcagtcc ctacttagga   4140
aatactcagc aactgttagc tgggaagaat gtattcggca ccttcccctg aggacccttc   4200
tgaggagtaa aaagactact ggcctctgtg ccatggatga ttcttttccc atcaccagaa   4260
atgatagcgt gcagtagaga gcaaagatgg cttccgtgag acacaagatg gcgcatagtg   4320
tgctcggaca cagttttgtc ttcgtaggtt gtgatgatag cactggtttg tttctcaagc   4380
gctatccaca gaacctttgt caacttcagt tgaaagagg tggattcatg tccagagctc   4440
atttcggggt caggtgggaa agccaagaac ttggaaaaga taagacaagc tataaattcg   4500
gaggcaagtt tcttttacaa tgaactttc agatctcact tccctccgac ccctaacttc   4560
catgcccacc cgtcctttta actgtgcaag caaaattgtg catggtcttc gtcgattaat   4620
accttgtgtg cagacactac tgctccagac gtcgtttccc tgataggtag agcagatcca   4680
taaaaggta tgacttatac aattagggga agctaatgga gtttattagc tgagtatcaa   4740
tgtctctgcg ttgtacggtg gtgatgggtt ttaatgaata tggaccctga agcctggaaa   4800
tcctcatcca cgtcgaaccc acaggactgt gggaagggca gaatcaatcc ctaagggaaa   4860
ggaaacctca ccctgagggc atcacatgca ctcatgttca gtgtacacag gtcaagtccc   4920
ttgctctggg ctctagttgg gagagtggtt tcattccaag tgtactccat tgtcagtatg   4980
ctgttttgt ttccttcact ccattcaaaa agtcaaaata caaatttgg cacagcatgc   5040
caacgggagg ctgtgcccag accaagcact ggaagtgtgc ttctaggcat agtcattggt   5100
tttgcaaaaa gagggctcaa atttaaatag aaatttacag ctatttgaat ggtcagatat   5160
accaagaaag aaaaatattt ctgttcctca agaaaacttg ctaccctctg tgagggaat   5220
```

| | |
|---|---:|
| tttgctaaac ttgacatctt tataacatga gccagattga aagggagtga ttttcattca | 5280 |
| tcttaggtca tgttatttca tatttgtttc tgaaggtgcg atagctctgt tttaggtttt | 5340 |
| gcttgcgcct gttaattact ggaacacctt attttcatt aaaggctttg aaagccaatt | 5400 |
| ctcaaaaatt caaagtgca aattaacaga acaaaaggaa atccagtagc aactgcagtc | 5460 |
| aagcgaggga gttgacaaga taaaccttac gtccattcaa gttatatgct ggcctatgag | 5520 |
| agatgagagt tgggtcgttt gttctctttg ttgatgattt | 5560 |

<210> SEQ ID NO 53
<211> LENGTH: 5608
<212> TYPE: DNA
<213> ORGANISM: Homo sapiens

<400> SEQUENCE: 53

| | |
|---|---:|
| aagacggatt ctcagacaag gcttgcaaat gccccgcagc catcatttaa ctgcacccgc | 60 |
| agaatagtta cggtttgtca cccgaccctc ccggatcgcc taatttgtcc ctagtgagac | 120 |
| cccgaggctc tgcccgcgcc tggcttcttc gtagctggat gcatatcgtg ctccgggcag | 180 |
| cgcgggcgca gggcacgcgt tcgcgcacac cctagcacac atgaacacgc gcaagagctg | 240 |
| aaccaagcac ggtttccatt tcaaaaaggg agacagcctc taccgcgatt gtagaagaga | 300 |
| ctgtggtgtg aattagggac cgggaggcgt cgaacggagg aacggttcat cttagagact | 360 |
| aattttctgg agtttctgcc cctgctctgc gtcagccctc acgtcacttc gccagcagta | 420 |
| gcagaggcgg cggcggcggc tcccggaatt gggttggagc aggagcctcg ctggctgctt | 480 |
| cgctcgcgct ctacgcgctc agtccccggc ggtagcagga gcctggaccc aggcgccgcc | 540 |
| ggcgggcgtg aggcgccgga gcccggcctc gaggtgcata ccggaccccc attcgcatct | 600 |
| aacaaggaat ctgcgcccca gagagtcccg ggagcgccgc cggtcggtgc ccggcgcgcc | 660 |
| gggccatgca gcgacggccg ccgcggagct ccgagcagcg gtagcgcccc cctgtaaagc | 720 |
| ggttcgctat gccggggcca ctgtgaaccc tgccgcctgc ggaacactc ttcgctccgg | 780 |
| accagctcag cctctgataa gctggactcg gcacgcccgc aacaagcacc gaggagttaa | 840 |
| gagagccgca agcgcaggga aggcctcccc gcacgggtgg gggaaagcgg ccggtgcagc | 900 |
| gcggggacag gcactcgggc tggcactggc tgctagggat gtcgtcctgg ataaggtggc | 960 |
| atggacccgc catggcgcgg ctctgggggct tctgctggct ggttgtgggc ttctggaggg | 1020 |
| ccgctttcgc ctgtcccacg tcctgcaaat gcagtgcctc tcggatctgg tgcagcgacc | 1080 |
| cttctcctgg catcgtggca tttccgagat tggagcctaa cagtgtagat cctgagaaca | 1140 |
| tcaccgaaat tttcatcgca aaccagaaaa ggttagaaat catcaacgaa gatgatgttg | 1200 |
| aagcttatgt gggactgaga aatctgacaa ttgtggattc tggattaaaa tttgtggctc | 1260 |
| ataaagcatt tctgaaaaac agcaacctgc agcacatcaa ttttacccga acaaactga | 1320 |
| cgagtttgtc taggaaacat ttccgtcacc ttgacttgtc tgaactgatc ctggtgggca | 1380 |
| atccattac atgctcctgt gacattatgt ggatcaagac tctccaagag gctaaatcca | 1440 |
| gtccagacac tcaggatttg tactgcctga atgaaagcag caagaatatt cccctggcaa | 1500 |
| acctgcagat acccaattgt ggtttgccat ctgcaaatct ggccgcacct aacctcactg | 1560 |
| tggaggaagg aaagtctatc acattatcct gtagtgtggc aggtgatccg gttcctaata | 1620 |
| tgtattggga tgttggtaac ctggtttcca acatatgaa tgaaacaagc cacacacagg | 1680 |
| gctcctaag gataactaac attcatccg atgacagtgg gaagcagatc tcttgtgtgg | 1740 |
| cggaaaatct gtaggagaa gatcaagatt ctgtcaacct cactgtgcat tttgcaccaa | 1800 |

```
ctatcacatt tctcgaatct ccaacctcag accaccactg gtgcattcca ttcactgtga   1860
aaggcaaccc caaaccagcg cttcagtggt tctataacgg ggcaatattg aatgagtcca   1920
aatacatctg tactaaaata catgttacca atcacacgga gtaccacggc tgcctccagc   1980
tggataatcc cactcacatg aacaatgggg actacactct aatagccaag aatgagtatg   2040
ggaaggatga gaaacagatt tctgctcact tcatgggctg gcctggaatt gacgatggtg   2100
caaacccaaa ttatcctgat gtaatttatg aagattatgg aactgcagcg aatgacatcg   2160
gggacaccac gaacagaagt aatgaaatcc cttccacaga cgtcactgat aaaaccggtc   2220
gggaacatct ctcggtctat gctgtggtgg tgattgcgtc tgtggtggga ttttgccttt   2280
tggtaatgct gtttctgctt aagttggcaa gacactccaa gtttggcatg aaagatttct   2340
catggtttgg atttgggaaa gtaaaatcaa gacaaggtgt tggcccagcc tccgttatca   2400
gcaatgatga tgactctgcc agcccactcc atcacatctc caatgggagt aacactccat   2460
cttcttcgga aggtggccca gatgctgtca ttattggaat gaccaagatc cctgtcattg   2520
aaaatcccca gtactttggc atcaccaaca gtcagctcaa gccagacaca tttgttcagc   2580
acatcaagcg acataacatt gttctgaaaa gggagctagg cgaaggagcc tttggaaaag   2640
tgttcctagc tgaatgctat aacctctgtc ctgagcagga caagatcttg gtggcagtga   2700
agaccctgaa ggatgccagt gacaatgcac gcaaggactt ccaccgtgag gccgagctcc   2760
tgaccaacct ccagcatgag cacatcgtca gttctatgg cgtctgcgtg gagggcgacc   2820
ccctcatcat ggtctttgag tacatgaagc atggggacct caacaagttc ctcagggcac   2880
acggccctga tgccgtgctg atggctgagg gcaacccgcc cacggaactg acgcagtcgc   2940
agatgctgca tatagcccag cagatcgccg cgggcatggt ctacctggcg tcccagcact   3000
tcgtgcaccg cgatttggcc accaggaact gcctggtcgg ggagaacttg ctggtgaaaa   3060
tcggggactt tgggatgtcc cgggacgtgt acagcactga ctactacagg gtcggtggcc   3120
acacaatgct gcccattcgc tggatgcctc cagagagcat catgtacagg aaattcacga   3180
cggaaagcga cgtctggagc ctgggggtcg tgttgtggga gattttcacc tatggcaaac   3240
agccctggta ccagctgtca aacaatgagg tgatagagtg tatcactcag ggccgagtcc   3300
tgcagcgacc ccgcacgtgc ccccaggagg tgtatgagct gatgctgggg tgctggcagc   3360
gagagcccca catgaggaag aacatcaagg gcatccatac cctccttcag aacttggcca   3420
aggcatctcc ggtctacctg gacattctag gctagggccc ttttccccag accgatcctt   3480
cccaacgtac tcctcagacg ggctgagagg atgaacatct tttaactgcc gctggaggcc   3540
accaagctgc tctccttcac tctgacagta ttaacatcaa agactccgag aagctctcga   3600
gggaagcagt gtgtacttct tcatccatag acacagtatt gacttctttt tggcattatc   3660
tctttctctc tttccatctc ccttggttgt tcctttttct ttttttaaat tttcttttc   3720 ttttttttt cgtcttccct gcttcacgat tcttaccctt tcttttgaat caatctggct   3780
tctgcattac tattaactct gcatagacaa aggccttaac aaacgtaatt tgttatatca   3840
gcagacactc cagtttgccc accacaacta acaatgcctt gttgtattcc tgcctttgat   3900
gtggatgaaa aaagggaaa acaaatattt cacttaaact tgtcacttc tgctgtacag   3960 atatcgagag tttctatgga ttcacttcta tttatttatt attattactg ttcttattgt   4020
ttttggatgg cttaagcctg tgtataaaaa agaaaacttg tgttcaatct gtgaagcctt   4080
tatctatggg agattaaaac cagagagaaa gaagatttat tatgaaccgc aatatgggag   4140
```

| | |
|---|---:|
| gaacaaagac aaccactggg atcagctggt gtcagtccct acttaggaaa tactcagcaa | 4200 |
| ctgttagctg ggaagaatgt attcggcacc ttccctgag gacctttctg aggagtaaaa | 4260 |
| agactactgg cctctgtgcc atggatgatt cttttcccat caccagaaat gatagcgtgc | 4320 |
| agtagagagc aaagatggct tccgtgagac acaagatggc gcatagtgtg ctcggacaca | 4380 |
| gttttgtctt cgtaggttgt gatgatagca ctggtttgtt tctcaagcgc tatccacaga | 4440 |
| acctttgtca acttcagttg aaaagaggtg gattcatgtc cagagctcat ttcgggtca | 4500 |
| ggtgggaaag ccaagaactt ggaaaagata agacaagcta taaattcgga ggcaagtttc | 4560 |
| ttttacaatg aacttttcag atctcacttc cctccgaccc ctaacttcca tgcccacccg | 4620 |
| tccttttaac tgtgcaagca aaattgtgca tggtcttcgt cgattaatac cttgtgtgca | 4680 |
| gacactactg ctccagacgt cgtttccctg ataggtagag cagatccata aaaaggtatg | 4740 |
| acttatacaa ttaggggaag ctaatggagt ttattagctg agtatcaatg tctctgcgtt | 4800 |
| gtacggtggt gatgggtttt aatgaatatg daccctgaag cctggaaatc ctcatccacg | 4860 |
| tcgaacccac aggactgtgg gaagggcaga atcaatccct aagggaaagg aaacctcacc | 4920 |
| ctgagggcat cacatgcact catgttcagt gtacacaggt caagtcccct gctctgggct | 4980 |
| ctagttggga gagtggtttc attccaagtg tactccattg tcagtatgct gttttgttt | 5040 |
| ccttcactcc attcaaaaag tcaaaataca aaatttggca cagcatgcca acgggaggct | 5100 |
| gtgcccagac caagcactgg aagtgtgctt ctaggcatag tcattggttt tgcaaaaaga | 5160 |
| gggctcaaat ttaaatagaa atttacagct atttgaatgg tcagatatac caagaaagaa | 5220 |
| aaatatttct gttcctcaag aaaacttgct accctctgtg aggggaattt tgctaaactt | 5280 |
| gacatcttta taacatgagc cagattgaaa gggagtgatt ttcattcatc ttaggtcatg | 5340 |
| ttatttcata tttgtttctg aaggtgcgat agctctgttt taggttttgc ttgcgcctgt | 5400 |
| taattactgg aacaccttat ttttcattaa aggctttgaa agccaattct caaaaattca | 5460 |
| aaagtgcaaa ttaacagaac aaaaggaaat ccagtagcaa ctgcagtcaa gcagggagt | 5520 |
| tgacaagata aaccttacgt ccattcaagt tatatgctgg cctatgagag atgagagttg | 5580 |
| ggtcgtttgt tctctttgtt gatgattt | 5608 |

<210> SEQ ID NO 54
<211> LENGTH: 3600
<212> TYPE: DNA
<213> ORGANISM: Homo sapiens

<400> SEQUENCE: 54

| | |
|---|---:|
| gaagagactc agggcagagg gaggaaggac agcagaccag acagtcacag cagccttgac | 60 |
| aaaacgttcc tggaactcaa gctcttctcc acagaggagg acagagcaga cagcagagac | 120 |
| catggagtct ccctcggccc ctccccacag atggtgcatc cctggcaga ggctcctgct | 180 |
| cacagcctca cttctaacct tctggaaccc gcccaccact gccaagctca ctattgaatc | 240 |
| cacgccgttc aatgtcgcag aggggaagga ggtgcttcta cttgtccaca atctgcccca | 300 |
| gcatctttt ggctacagct ggtacaaagg tgaaagagtg gatggcaacc gtcaaattat | 360 |
| aggatatgta ataggaactc aacaagctac cccaggcccc gcatacagtg gtcgagagat | 420 |
| aatataccc aatgcatccc tgctgatcca gaacatcatc agaatgaca caggattcta | 480 |
| caccctacac gtcataaagt cagatcttgt gaatgaagaa gcaactggcc agttccgggt | 540 |
| atacccggag ctgcccaagc cctccatctc cagcaacaac tccaaacccg tggaggacaa | 600 |
| ggatgctgtg gccttcacct gtgaacctga gactcaggac gcaacctacc tgtggtgggt | 660 |

```
aaacaatcag agcctcccgg tcagtcccag gctgcagctg tccaatggca acaggaccct    720
cactctattc aatgtcacaa gaaatgacac agcaagctac aaatgtgaaa cccagaaccc    780
agtgagtgcc aggcgcagtg attcagtcat cctgaatgtc ctctatggcc cggatgcccc    840
caccatttcc cctctaaaca catcttacag atcaggggaa aatctgaacc tctcctgcca    900
cgcagcctct aacccacctg cacagtactc ttggtttgtc aatgggactt tccagcaatc    960
cacccaagag ctctttatcc ccaacatcac tgtgaataat agtggatcct atacgtgcca   1020
agcccataac tcagacactg gcctcaatag gaccacagtc acgacgatca cagtctatgc   1080
agagccaccc aaacccttca tcaccagcaa caactccaac cccgtggagg atgaggatgc   1140
tgtagcctta acctgtgaac ctgagattca gaacacaacc tacctgtggt gggtaaataa   1200
tcagagcctc ccggtcagtc ccaggctgca gctgtccaat gacaacagga ccctcactct   1260
actcagtgtc acaaggaatg atgtaggacc ctatgagtgt ggaatccaga acaaattaag   1320
tgttgaccac agcgacccag tcatcctgaa tgtcctctat ggcccagacg accccaccat   1380
ttccccctca tacacctatt accgtccagg ggtgaacctc agcctctcct gccatgcagc   1440
ctctaaccca cctgcacagt attcttggct gattgatggg aacatccagc aacacacaca   1500
agagctcttt atctccaaca tcactgagaa gaacagcgga ctctatacct gccaggccaa   1560
taactcagcc agtggccaca gcaggactac agtcaagaca atcacagtct ctgcggagct   1620
gcccaagccc tccatctcca gcaacaactc caaacccgtg gaggacaagg atgctgtggc   1680
cttcacctgt gaacctgagg ctcagaacac aacctacctg tggtgggtaa atggtcagag   1740
cctcccagtc agtcccaggc tgcagctgtc caatggcaac aggaccctca ctctattcaa   1800
tgtcacaaga aatgacgcaa gagcctatgt atgtggaatc cagaactcag tgagtgcaaa   1860
ccgcagtgac ccagtcaccc tggatgtcct ctatgggccg acaccccca tcatttcccc   1920 cccagactcg tcttaccttt cgggagcgaa cctcaacctc tcctgccact cggcctctaa   1980
cccatccccg cagtattctt ggcgtatcaa tgggatacog cagcaacaca cacaagttct   2040
ctttatcgcc aaaatcacgc caaataataa cgggacctat gcctgttttg tctctaactt   2100
ggctactggc cgcaataatt ccatagtcaa gagcatcaca gtctctgcat ctggaacttc   2160
tcctggtctc tcagctgggg ccactgtcgg catcatgatt ggagtgctgg ttggggttgc   2220
tctgatatag cagccctggt gtagtttctt catttcagga agactgacag ttgttttgct   2280
tcttccttaa agcatttgca acagctacag tctaaaattg cttctttacc aaggatattt   2340
acagaaaaga ctctgaccag agatcgagac catcctagcc aacatcgtga aacccatctct  2400 ctactaaaaa tacaaaaatg agctgggctt ggtggcgcgc acctgtagtc ccagttactc   2460
gggaggctga ggcaggagaa tcgcttgaac ccgggaggtg gagattgcag tgagcccaga   2520
tcgcaccact gcactccagt ctggcaacag agcaagactc catctcaaaa agaaaagaaa   2580
agaagactct gacctgtact cttgaataca agtttctgat accactgcac tgtctgagaa   2640
tttccaaaac tttaatgaac taactgacag cttcatgaaa ctgtccacca agatcaagca   2700
gagaaaataa ttaatttcat gggactaaat gaactaatga ggataatatt ttcataattt   2760
tttatttgaa attttgctga ttctttaaat gtcttgtttc ccagatttca ggaaactttt   2820
tttcttttaa gctatccaca gcttacagca atttgataaa atatactttt gtgaacaaaa   2880
attgagacat ttcactttc tccctatgtg gtcgctccag acttgggaaa ctattcatga   2940
atatttatat tgtatggtaa tatagttatt gcacaagttc aataaaaatc tgctctttgt   3000
```

```
atgacagaat acatttgaaa acattggtta tattaccaag actttgacta gaatgtcgta    3060
tttgaggata taaacccata ggtaataaac ccacaggtac tacaaacaaa gtctgaagtc    3120
agccttggtt tggcttccta gtgtcaatta aacttctaaa agtttaatct gagattcctt    3180
ataaaaactt ccagcaaagc aactttaaaa agtctgtgt gggccgggcg cggtggctca    3240
cgcctgtaat cccagcactt tgatccgccg aggcgggcgg atcacgaggt caggagatcc    3300
agaccatcct ggctaacaca gtgaaacccc gtctctacta aaatacaaa aaagttagc    3360 cgggcgtggt ggtgggggcc tgtagtccca gctactcagg aggctgaggc aggagaacgg    3420
catgaacccg ggaggcaggg cttgcagtga gccaagatca tgccgctgca ctccagcctg    3480
ggagacaaag tgagactccg tcaaaaaaaa aaaaagtct atgtggtcag tcactactct    3540
tgctgcagtt atgaaagaa tgaggccaag tctgatgaaa ataaacttat tttgaaaaca    3600
```

<210> SEQ ID NO 55
<211> LENGTH: 3095
<212> TYPE: DNA
<213> ORGANISM: Homo sapiens

<400> SEQUENCE: 55

```
attgctgatg gatcagtgag cctgtgttca tgccagtgag ctgctgtggc tcagatactg      60
atactttctt tccaaacagc ataagaagtg attgagccac aagtatactg aaggaagggc     120
tccctcgagt tctggtgtga agagataaat caccagtcac agactatgca cccgactgct     180
gctgttcagt ccagggaaaa tgaaagttgg agtgctgtgg ctcatttctt tcttcacctt     240
cactgacggc cacggtggct tcctggggaa aaatgatggc atcaaaacaa aaaagaact     300 cattgtgaat aagaaaaaac atctaggccc agtcgaagaa tatcagctgc tgcttcaggt     360
gacctataga gattccaagg agaaaagaga tttgagaaat tttctgaagc tcttgaagcc     420
tccattatta tggtcacatg ggctaattag aattatcaga gcaaaggcta ccacagactg     480
caacagcctg aatggagtcc tgcagtgtac ctgtgaagac agctacacct ggtttcctcc     540
ctcatgcctt gatccccaga actgctacct tcacacggct ggagcactcc caagctgtga     600
atgtcatctc aacaacctca gccagagtgt caatttctgt gagagaacaa agatttgggg     660 cacttttcaaa attaatgaaa ggtttacaaa tgaccttttg aattcatctt ctgctatata     720
ctccaaatat gcaaatggaa ttgaaattca acttaaaaaa gcatatgaaa gaattcaagg     780
ttttgagtcg gttcaggtca cccaatttcg aaatggaagc atcgttgctg ggtatgaagt     840
tgttggctcc agcagtgcat ctgaactgct gtcagccatt gaacatgttg ccgagaaggc     900
taagacagcc cttcacaagc tgtttccatt agaagacggc tctttcagag tgttcggaaa     960
agcccagtgt aatgacattg tctttggatt tgggtccaag gatgatgaat atacccctgcc    1020 ctgcagcagt ggctacaggg gaaacatcac agccaagtgt gagtcctctg ggtggcaggt    1080
catcagggag acttgtgtgc tctctctgct gaagaactg aacaagaatt tcagtatgat    1140
tgtaggcaat gccactgagg cagctgtgtc atccttcgtg caaaatcttt ctgtcatcat    1200
tcggcaaaac ccatcaacca cagtggggaa tctggcttcg gtggtgtcga ttctgagcaa    1260
tatttcatct ctgtcactgg ccagccattt cagggtgtcc aattcaacaa tggaggatgt    1320
catcagtata gctgacaata tccttaattc agcctcagta accaactgga cagtcttact    1380
gcgggaagaa aagtatgcca gctcacggtt actagagaca ttagaaaaca tcagcactct    1440
ggtgcctccg acagctcttc ctctgaattt ttctcggaaa ttcattggact ggaaagggat    1500 tccagtgaac aaaagccaac tcaaaagggg ttacagctat cagattaaaa tgtgtcccca    1560
```

| | |
|---|---|
| aaatacatct attcccatca gaggccgtgt gttaattggg tcagaccaat tccagagatc | 1620 |
| ccttccagaa actattatca gcatggcctc gttgactctg gggaacattc tacccgtttc | 1680 |
| caaaaatgga aatgctcagg tcaatggacc tgtgatatcc acggttattc aaaactattc | 1740 |
| cataaatgaa gttttcctat ttttttccaa gatagagtca aacctgagcc agcctcattg | 1800 |
| tgtgttttgg gatttcagtc atttgcagtg gaacgatgca ggctgccacc tagtgaatga | 1860 |
| aactcaagac atcgtgacgt gccaatgtac tcacttgacc tccttctcca tattgatgtc | 1920 |
| accttttgtc ccctctacaa tcttccccgt tgtaaaatgg atcacctatg tgggactggg | 1980 |
| tatctccatt ggaagtctca ttttatgcct gatcatcgag ctttgtttt ggaagcagat | 2040 |
| taaaaaagc caaacctctc acacacgtcg tatttgcatg gtgaacatag ccctgtccct | 2100 |
| cttgattgct gatgtctggt ttattgttgg tgccacagtg dacaccacgg tgaacccttc | 2160 |
| tggagtctgc acagctgctg tgttctttac acacttcttc tacctctctt tgttcttctg | 2220 |
| gatgctcatg cttggcatcc tgctggctta ccggatcatc ctcgtgttcc atcacatggc | 2280 |
| ccagcatttg atgatggctg ttggattttg cctgggttat gggtgccctc tcattatatc | 2340 |
| tgtcattacc attgctgtca cgcaacctag caatacctac aaaaggaaag atgtgtgttg | 2400 |
| gcttaactgg tccaatggaa gcaaaccact cctggctttt gttgtccctg cactggctat | 2460 |
| tgtggctgtg aacttcgttg tggtgctgct agttctcaca aagctctgga ggccgactgt | 2520 |
| tggggaaaga ctgagtcggg atgacaaggc caccatcatc cgcgtgggga agagcctcct | 2580 |
| cattctgacc cctctgctag ggctcacctg gggctttgga ataggaacaa tagtggacag | 2640 |
| ccagaatctg gcttggcatg ttattttgc tttactcaat gcattccagg gattttttat | 2700 |
| cttatgcttt ggaatactct tggacagtaa gctgcgacaa cttctgttca acaagttgtc | 2760 |
| tgccttaagt tcttggaagc aaacagaaaa gcaaaactca tcagatttat ctgccaaacc | 2820 |
| caaattctca aagcctttca acccactgca aacaaaggc cattatgcat tttctcatac | 2880 |
| tggagattcc tccgacaaca tcatgctaac tcagtttgtc tcaaatgaat aaggcaagga | 2940 |
| atcataaaat caagaaaaaa tttccagaac aacttgacat ttagagacaa atgtcaatga | 3000 |
| agaaattatg ctcagtattc gatcgggttt tctgatttag gggtctggga ataaaacaag | 3060 |
| aatgtctcag tggcttcaaa aaaaaaaaaa aaaaa | 3095 |

<210> SEQ ID NO 56
<211> LENGTH: 4071
<212> TYPE: DNA
<213> ORGANISM: Homo sapiens

<400> SEQUENCE: 56

| | |
|---|---|
| tgattcgagc gggaagaggg gggtgggtgg gatcggtggg ggagaccatg acctccagct | 60 |
| acgggcacgt tctggagcgg caaccggcgc tgggcggccg cttggacagc ccgggcaacc | 120 |
| tcgacaccct gcaggcgaaa aagaacttct ccgtcagtca cctgctagac ctggaggaag | 180 |
| ccggggacat ggtggcggca caggcggatg agaacgtggg cgaggctggc cggagcctgc | 240 |
| tggagtcgcc gggactcacc agcggcagcg cacccccgca gcaggacaat gaccagctga | 300 |
| actcagaaga aaaaagaag agaaagcagc gaaggaatag acaaccttc aatagcagcc | 360 |
| agctgcaggc tttggagcgt gtctttgagc ggacacacta tcctgatgct tttgtgcgag | 420 |
| aagaccttgc ccgccgggtg aacctcaccg aggcgagagt gcaggtgtgg tttcagaacc | 480 |
| gaagagccaa gttccgcagg aatgagagag ccatgctagc caataaaaac gcttccctcc | 540 |

```
tcaaatccta ctcaggagac gtgactgctg tggagcagcc catcgtacct cgtcctgctc    600
cgagacccac cgattatctc tcctggggga cagcgtctcc gtacagatcc tcgtccctcc    660
caagatgttg tttacacgag gggcttcata acggattcta acggaagaca ctgaaaagcg    720
ccatggctac ttattctgcc acatgtgcca acaatagccc tgcacagggc atcaacatgg    780
ccaacagcat tgccaacctg agactgaagg ccaaggaata tagtttacag aggaaccagg    840
tgccaacagt caactgagga aaaaaaataa ttaaacaggc taagaagaa  atcaaaaacc    900 ataagacacc tatcctgctc tgttatttct tcatctgctg gggggaaaaa gtaaattaca    960
aacaaacaaa caaagcagaa ctaaaatatt gggaccatgg cagagaaaag caggagagga   1020
gcaaaatgaa aattagttaa caaatgttcc tcctccctct gggataccac caccacttgt   1080
ttctgtgtgt gtttattttg tttttctttc attcatgctt tgcttaatgt actccaggct   1140
tcttcagata ggttcagccc acccacccc  atgattgtat gaagttttaa aaaaaactac   1200
agcagccaaa gaaactatat atatatatat atatatatat atccagaatg attgcctcta   1260
ctgtcctcat tgacttgttt gaaccttagt gccttaccct gtcctcttcc cagttctctt   1320
tatagaagct ctaggagctt tcgaaaagcc aaagtctttc tgaagaatct gtgctggaca   1380
gacataattc cctttctcat tgtctccatc tttgttggtc atggtaaggt ttttccatca   1440
gcctctgaaa aaatagttgt gcacaacatc tgctcactgg actgtctgat ccaatgtaat   1500
tggctgcgtc tggctaattc taagcactaa agtctcatc  taagctatag atttaagctt   1560
gaagctacag attatatcac tatcaccacc accctcacc  ctatgcaatc aatcaatcaa   1620
tcatcttaag ttaaagatat ttgttgtctt tgaatgattt gctgtcacag actatttggt   1680
agaagaaata tttttcacct gagagaggaa gagaaatttc tctagtaaca caagagtga    1740 gttctaaaag gcatgccac  atctctttcg tgccttaagg atagtgagat gcacacttat   1800
atatatactg tatatatttta tatatttata tatatatttc atatatatat ataatattgc   1860
aagcttaagt ttgcaatttc ccaaacaata caaaaagcaa attacacacc ctcaccactg   1920
ttcttatctc tatagtgatg aaacattaat tagggatctt gctgcttttc ttttttctaca   1980 cgaagttttc attaaagcca cagaataatt gatagggcag ctgtttgaga acaggtccca   2040
ttttcacatt agggctttaa atgaattaga aactatttga ggctataaaa atgtccttga   2100
gtttggagcc tgagctctgg tgaaatgctg atacatctga tctatcatgg gaattgcagt   2160
tagagagagt aaggaatacc atttagtcat ctatccgttc ttcacttagc aggaatatga   2220
aagaaaggca catgtttaag aggaatacct aaaggttttt ctaaattcca acatttaaaa   2280
ggcaattgtg ggctattttt attttttaat attttgaaat aaagtttagt gtctagggct   2340
gggagccagg actgatcttc catttctttt tctttgttcc cagccatgct tttgtaactt   2400
gccaggtgga cttgaccaac tacattacca tgctgtgcct cagtttaccc atttgtaaaa   2460
tgggattaat aatacttacc tacctcacag gggtgttgtg aggctctatt catttgctcc   2520
tttattcttt cctgtattct ctgtatgtcc agcactttgt agccatggga ggaaagggac   2580
tataaaagtg tacaatgtta atggaatgat acggtacctg aaagccttgt tttctagtaa   2640
gaaaatgcta cctttgctgta catacttata accttgtatt tggaaatgag aaataggttt   2700
atattttcag atctctcaaa aatcacatca tttgaccaaa gaataattta agacacatag   2760
aacagatttt tttaatttat attttcatcc tgaccagctt agttctaata atttttagtt   2820
gtgagtgatt aaaaaacttt ggatcaattt tggtcaaaca tgccaacttt gtagtctgag   2880
tgacaggcaa ggattttttgg gtttaagatg cacttttagc acacatttgt atttcccttg   2940
```

| | | | | |
|---|---|---|---|---|
| gcatatcaga | ttgagctaat | ggtgatgtta | tttcaatcta | acagccacca atctgaaatt | 3000 |
| gtatttcaaa | tgttgattct | gtagttcttt | aataataat | gaagctcatc ttatacattt | 3060 |
| tgctttcacc | aattgattcc | ttcttctttt | agcccactat | taaaacatttt cttactgaat | 3120 |
| ggttcatgta | ggcttgctga | acagcacgca | ttacttgctt | cctgaagagt tcccccattc | 3180 |
| atccatttgt | cccattagtt | gctgtggatt | atcaagtttt | gaaggaactg tacatcccaa | 3240 |
| cagactgaaa | cattcaagt | gaaatgagta | taatccaagt | aactggtgaa ctttggaggt | 3300 |
| ttggagcttg | aagagaatgg | ctaagaagat | ttgaattata | gggagggaac agaaatcata | 3360 |
| catgaaaagg | ttttactgag | aagggggaaaa | ccttagatag | agggacatgt gaaacaaaat | 3420 |
| catttgaaat | tttgattcag | acatccatttt | ccagtggcaa | acagcaaagc ctgaacccat | 3480 |
| aaacccaaat | gataggtgaa | gttgggtggt | tttatccaat | gtctcaagca agcaatgtct | 3540 |
| gggaatatca | tagagtaaca | agtgctggtc | agccaaagaa | acattcactg ctggtgaacc | 3600 |
| aataccataa | gcatgtatta | tctaagcact | tgatcaagaa | atatacatgt tgtacaagct | 3660 |
| ctcaattttg | ttcattttatt | atcaaattttt | taaaatacaa | gtttggtatg tgatttggaa | 3720 |
| aagatgcctt | ctggatctta | agccagttgt | cagtggaggt | cctcagggct gcaaatgtca | 3780 |
| agacataacc | ctgttcctca | ccatcatgat | accagataca | ggtgaataca taggaactat | 3840 |
| ctgcctgtgt | cctcaatctc | ccttcaaaca | agatgctgat | ttgtagggta cttggcaggt | 3900 |
| taaattaaac | cagaagaggt | gacttaataa | aaaagggaat | gacatttagg gtataaagat | 3960 |
| ctcataagaa | atgtaatatg | taaattatat | cttgctttat | gttgtaaaat atacattgtt | 4020 |
| tgcgctagaa | tagaaatgat | ttcttttcaa | taaaagaaa | gaaggactct a | 4071 |

<210> SEQ ID NO 57
<211> LENGTH: 3999
<212> TYPE: DNA
<213> ORGANISM: Homo sapiens

<400> SEQUENCE: 57

| | | | | |
|---|---|---|---|---|
| tgattcgagc | gggaagaggg | gggtgggtgg | gatcggtggg | ggagaccatg acctccagct | 60 |
| acgggcacgt | tctggagcgg | caaccggcgc | tgggcggccg | cttggacagc ccgggcaacc | 120 |
| tcgacaccct | gcaggcgaaa | aagaacttct | ccgtcagtca | cctgctagac ctggaggaag | 180 |
| ccggggacat | ggtggcggca | caggcggatg | agaacgtggg | cgaggctggc cggagcctgc | 240 |
| tggagtcgcc | gggactcacc | agcggcagcg | acaccccgca | gcaggacaat gaccagctga | 300 |
| actcagaaga | aaaaagaag | agaaagcagc | gaaggaatag | gacaaccttc aatagcagcc | 360 |
| agctgcaggc | tttggagcgt | gtctttgagc | ggacacacta | tcctgatgct tttgtgcgag | 420 |
| aagaccttgc | ccgccgggtg | aacctcaccg | aggcgagagt | gcaggtgtgg ttcagaaacc | 480 |
| gaagagccaa | gttccgcagg | aatgagagag | ccatgctagc | caataaaaac gcttccctcc | 540 |
| tcaaatccta | ctcaggagac | gtgactgctg | tggagcagcc | catcgtacct cgtcctgctc | 600 |
| cgagacccac | cgattatctc | tcctggggga | cagcgtctcc | gtacagcgcc atggctactt | 660 |
| attctgccac | atgtgccaac | aatagccctg | cacagggcat | caacatggcc aacagcattg | 720 |
| ccaacctgag | actgaaggcc | aaggaatata | gtttacagag | gaaccaggtg ccaacagtca | 780 |
| actgaggaaa | aaaataatt | aaacaggcct | aagaagaaat | caaaaaccat aagcaccta | 840 |
| tcctgctctg | ttatttcttc | atctgctggg | gggaaaaagt | aaattacaaa caacaaaca | 900 |
| aagcagaact | aaaatattgg | gaccatggca | gagaaaagca | ggagaggagc aaaatgaaaa | 960 |

-continued

```
ttagttaaca aatgttcctc ctccctctgg gataccacca ccacttgttt ctgtgtgtgt    1020
ttattttgtt tttctttcat tcatgctttg cttaatgtac tccaggcttc ttcagatagg    1080
ttcagcccac ccacccccat gattgtatga agttttaaaa aaaactacag cagccaaaga    1140
aactatatat atatatatat atatatatat ccagaatgat tgcctctact gtcctcattg    1200
acttgtttga accttagtgc cttaccctgt cctcttccca gttctcttta tagaagctct    1260
aggagctttc gaaaagccaa agtctttctg aagaatctgt gctggacaga cataattccc    1320
tttctcattg tctccatctt tgttggtcat ggtaaggttt ttccatcagc ctctgaaaaa    1380
atagttgtgc acaacatctg ctcactggac tgtctgatcc aatgtaattg gctgcgtctg    1440
gctaattcta agcactaaag tctacatcta agctatagat ttaagcttga agctacagat    1500
tatatcacta tcaccaccac ccctcaccct atgcaatcaa tcaatcaatc atcttaagtt    1560
aaagatattt gttgtctttg aatgatttgc tgtcacagac tatttggtag aagaaatatt    1620
tttcacctga gagaggaaga gaaatttctc tagtaacaca aagagtgagt tctaaaaggc    1680
atgcccacat ctctttcgtg ccttaaggat agtgagatgc acactatat atatactgta    1740 tatatttata tatttatata tatatttcat atatatatat aatattgcaa gcttaagttt    1800
gcaatttccc aaacaataca aaaagcaaat tacacaccct caccactgtt cttatctcta    1860
tagtgatgaa acattaatta gggatcttgc tgcttttctt tttctacacg aagttttcat    1920
taaagccaca gaataattga tagggcagct gtttgagaac aggtcccatt ttcacattag    1980
ggctttaaat gaattagaaa ctatttgagg ctataaaaat gtccttgagt ttggagcctg    2040
agctctggtg aaatgctgat acatctgatc tatcatggga attgcagtta gagagagtaa    2100
ggaataccat ttagtcatct atccgttctt cacttagcag gaatatgaaa gaaaggcaca    2160
tgtttaagag gaatacctaa aggttttttct aaattccaac atttaaaagg caattgtggg    2220
ctatttttat tttttaatat tttgaaataa agtttagtgt ctagggctgg gagccaggac    2280
tgatcttcca tttctttttc tttgttccca gccatgcttt tgtaacttgc caggtggact    2340
tgaccaacta cattaccatg ctgtgcctca gtttacccat ttgtaaaatg ggattaataa    2400
tacttaccta cctcacaggg gtgttgtgag gctctattca tttgctcctt tattctttcc    2460
tgtattctct gtatgtccag cactttgtag ccatgggagg aaagggacta taaaagtgta    2520
caatgttaat ggaatgatac ggtacctgaa agccttgttt tctagtaaga aaatgctacc    2580
ttgctgtaca tacttataac cttgtatttg gaaatgagaa ataggtttat attttcagat    2640
ctctcaaaaa tcacatcatt tgaccaaaga ataatttaag acacatagaa cagattttt    2700 taatttatat tttcatcctg accagcttag ttctaataat ttttagttgt gagtgattaa    2760
aaaactttgg atcaattttg gtcaaacatg ccaactttgt agtctgagtg acaggcaagg    2820 attttttgggt ttaagatgca cttttagcac acatttgtat ttcccttggc atatcagatt    2880
gagctaatgg tgatgttatt tcaatctaac agccaccaat ctgaaattgt atttcaaatg    2940
ttgattctgt agttctttaa ataataatga agctcatctt atacattttg ctttcaccaa    3000
ttgattcctt cttcttttag cccactatta aaacatttct tactgaatgg ttcatgtagg    3060
cttgctgaac agcacgcatt acttgcttcc tgaagagttc ccccattcat ccatttgtcc    3120
cattagttgc tgtggattat caagttttga aggaactgta catcccaaca gactgaaaca    3180
ttctaagtga aatgagtata atccaagtaa ctggtgaact ttggaggttt ggagcttgaa    3240
gagaatggct aagaagattt gaattatagg gagggaacag aaatcataca tgaaaaggtt    3300
ttactgagaa ggggaaaacc ttagatagag ggacatgtga aacaaaatca tttgaaattt    3360
```

| | |
|---|---|
| tgattcagac atccatttcc agtggcaaac agcaaagcct gaacccataa acccaaatga | 3420 |
| taggtgaagt tgggtggttt tatccaatgt ctcaagcaag caatgtctgg gaatatcata | 3480 |
| gagtaacaag tgctggtcag ccaaagaaac attcactgct ggtgaaccaa taccataagc | 3540 |
| atgtattatc taagcacttg atcaagaaat atacatgttg tacaagctct caattttgtt | 3600 |
| catttattat caaatttta aaatacaagt ttggtatgtg atttggaaaa gatgccttct | 3660 |
| ggatcttaag ccagttgtca gtggaggtcc tcagggctgc aaatgtcaag acataaccct | 3720 |
| gttcctcacc atcatgatac cagatacagg tgaatacata ggaactatct gcctgtgtcc | 3780 |
| tcaatctccc ttcaaacaag atgctgattt gtagggtact tggcaggtta aattaaacca | 3840 |
| gaagaggtga cttaataaaa aagggaatga catttagggt ataaagatct cataagaaat | 3900 |
| gtaatatgta aattatatct tgctttatgt tgtaaaatat acattgtttg cgctagaata | 3960 |
| gaaatgattt cttttcaata aaagaaaga aggactcta | 3999 |

<210> SEQ ID NO 58
<211> LENGTH: 2466
<212> TYPE: DNA
<213> ORGANISM: Homo sapiens

<400> SEQUENCE: 58

| | |
|---|---|
| ggctgagtgg tttgctcctt cccctctctc tgggaggctg agcaggggtg ccgggttgct | 60 |
| caggccatgg gagccacacc tgttattgct gcctctgatt tgtgtgacac tgagaagccc | 120 |
| acaggcctgt ccctccaact cggtggaccc tctctgtgtg catttggtgt gtgagccagc | 180 |
| tctgagaagg gttcagaagc cactggaggc atctggggac ctcagcttcc atgccatctc | 240 |
| tgcctcactc ccacagggta atgttggact cggtgacaca cagcaccttc ctgcctaatg | 300 |
| catccttctg cgatcccctg atgtcgtgga ctgatctgtt cagcaatgaa gagtactacc | 360 |
| ctgcctttga gcatcagaca gcctgtgact catactggac atcagtccac cctgaatact | 420 |
| ggactaagcg ccatgtgtgg gagtggctcc agttctgctg cgaccagtac aagttggaca | 480 |
| ccaattgcat ctccttctgc aacttcaaca tcagtggcct gcagctgtgc agcatgacac | 540 |
| aggaggagtt cgtcgaggca gctggcctct gcggcgagta cctgtacttc atcctccaga | 600 |
| acatccgcac acaaggttac tcctttttta atgacgctga agaaagcaag gccaccatca | 660 |
| aagactatgc tgattccaac tgcttgaaaa caagtggcat caaaagtcaa gactgtcaca | 720 |
| gtcatagtag aacaagcctc caaagttctc atctatggga atttgtacga gacctgcttc | 780 |
| tatctcctga gaaaactgt ggcattctgg aatgggaaga tagggaacaa ggaattttc | 840 |
| gggtggttaa atcggaagcc ctggcaaaga tgtggggaca aggaagaaa atgacagaa | 900 |
| tgacatatga aaagttgagc agagccctga gatactacta taaaacagga attttggagc | 960 |
| gggttgaccg aaggttagtg tacaaatttg gaaaaaatgc acacgggtgg caggaagaca | 1020 |
| agctatgatc tgctccaggc atcaagctca ttttatggat ttctgtcttt taaaacaatc | 1080 |
| agattgcaat agacattcga aaggcttcat tttcttctct tttttttaa cctgcaaaca | 1140 |
| tgctgataaa atttctccac atctcagctt acatttggat tcagagttgt tgtctacgga | 1200 |
| gggtgagagc agaaactctt aagaaatcct ttcttctccc taaggggatg aggggatgat | 1260 |
| cttttgtggt gtcttgatca aactttattt tcctagagtt gtggaatgac aacagcccat | 1320 |
| gccattgatg ctgatcagag aaaaactatt caattctgcc attagagaca catccaatgc | 1380 |
| tcccatccca aaggttcaaa agttttcaaa taactgtggc agctcaccaa aggtggggga | 1440 |

| | |
|---|---:|
| aagcatgatt agtttgcagg ttatggtagg agagggtgag atataagaca tacatacttt | 1500 |
| agattttaaa ttattaaagt caaaaatcca tagaaaagta tcccttttt ttttttgag | 1560 |
| acgggttctc actatgttgc ccagggctgg tcttgaactc ctatgctcaa gtgatcctcc | 1620 |
| cacctcggcc tcccaaagta ctgtgattac aagcgtgagc cacggcacct gggcagaaaa | 1680 |
| gtatcttaat taatgaaaga gctaagccat caagctggga cttaattgga tttaacatag | 1740 |
| gttcacagaa agtttcctaa ccagagcatc tttttgacca ctcagcaaaa cttccacaga | 1800 |
| catccttctg gacttaaaca cttaacatta accacattat taattgttgc tgagtttatt | 1860 |
| ccccttcta actgatggct ggcatctgat atgcagagtt agtcaacaga cactggcatc | 1920 |
| aattacaaaa tcactgctgt ttctgtgatt caagctgtca acacaataaa atcgaaattc | 1980 |
| attgattcca tctctggtcc agatgttaaa cgtttataaa accggaaatg tcctaacaac | 2040 |
| tctgtaatgg caaattaaat tgtgtgtctt ttttgttttg tctttctacc tgatgtgtat | 2100 |
| tcaagcgcta taacacgtat ttccttgaca aaaatagtga cagtgaattc acactaataa | 2160 |
| atgttcatag gttaaagtct gcactgacat tttctcatca atcactggta tgtaagttat | 2220 |
| cagtgactga cagctaggtg gactgcccct aggacttctg tttcaccaga gcaggaatca | 2280 |
| agtggtgagg cactgaatcg ctgtacaggc tgaagacctc cttattagag ttgaacttca | 2340 |
| aagtaacttg ttttaaaaaa tgtgaattac tgtaaaataa tctattttgg attcatgtgt | 2400 |
| tttccaggtg gatatagttt gtaaacaatg tgaataaagt atttaacatg taaaaaaaaa | 2460 |
| aaaaaa | 2466 |

<210> SEQ ID NO 59
<211> LENGTH: 3127
<212> TYPE: DNA
<213> ORGANISM: Homo sapiens

<400> SEQUENCE: 59

| | |
|---|---:|
| gaagctccac accagccatt acaaccctgc caatctcaag cacctgcctc tacagttggt | 60 |
| acagatggca ttgtcccagt ctgttccctt ctcggccaca gagcttctcc tggcctctgc | 120 |
| catcttctgc ctggtattct gggtgctcaa gggtttgagg cctcgggtcc caaaggcct | 180 |
| gaaaagtcca ccagagccat ggggctggcc cttgctcggg catgtgctga ccctggggaa | 240 |
| gaacccgcac ctggcactgt caaggatgag ccagcgctac ggggacgtcc tgcagatccg | 300 |
| cattggctcc acgcccgtgc tggtgctgag ccgcctggac accatccggc aggccctggt | 360 |
| gcggcagggc gacgatttca agggccggcc tgacctctac acctccaccc tcatcactga | 420 |
| tggccagagc ttgaccttca gcacagactc tggaccggtg tgggctgccc gccggcgcct | 480 |
| ggcccagaat gccctcaaca ccttctccat cgcctctgac ccagcttcct catcctcctg | 540 |
| ctacctggag gagcatgtga gcaaggaggc taaggccctg atcagcaggt tgcaggagct | 600 |
| gatggcaggg cctgggcact tcgacccctta caatcaggtg gtggtgtcag tggccaacgt | 660 |
| cattggtgcc atgtgcttcg acagcacctt ccctgagagt agcgatgaga tgctcagcct | 720 |
| cgtgaagaac actcatgagt tcgtggagac tgcctcctcc gggaaccccc tggacttctt | 780 |
| ccccatcctt cgctacctgc ctaaccctgc cctgcagagg ttcaaggcct tcaaccagag | 840 |
| gttcctgtgg ttcctgcaga aaacagtcca ggagcactat caggactttg acaagaacag | 900 |
| tgtccgggac atcacggtg ccctgttcaa gcacagcaag aaggggccta gagccagcgg | 960 |
| caacctcatc ccacaggaga agattgtcaa ccttgtcaat gacatctttg agcaggatt | 1020 |
| tgacacagtc accacagcca tctcctggag cctcatgtac cttgtgacca gcctgagat | 1080 |

```
acagaggaag atccagaagg agctggacac tgtgattggc agggagcggc ggccccggct    1140
ctctgacaga ccccagctgc cctacttgga ggccttcatc ctggagacct tccgacactc    1200
ctccttcttg cccttcacca tcccccacag cacaacaagg gacacaacgc tgaatggctt    1260
ctacatcccc aagaaatgct gtgtcttcgt aaaccagtgg caggtcaacc atgacccaga    1320
gctgtgggag gacccctctg agttccggcc tgagcggttc ctcaccgccg atggcactgc    1380
cattaacaag cccttgagtg agaagatgat gctgtttggc atgggcaagc gccggtgtat    1440
cggggaagtc ctggccaagt gggagatctt cctcttcctg gccatcctgc tacagcaact    1500
ggagttcagc gtgccgccgg gcgtgaaagt cgacctgacc cccatctacg ggctgaccat    1560
gaagcacgcc cgctgtgaac atgtccaggc gcggctgcgc ttctccatca attgaagaag    1620
acaccaccat tctgaggcca gggagcgagt gggggccagc cacggggact cagcccttgt    1680
ttctcttcct ttcttttttt aaaaaatagc agctttagcc aagtgcaggg cctgtaatcc    1740
cagcatttta ggaggccaag gttggaggat catttgagcc caggaattgg aaagcagcct    1800
ggccaacata gtgggaccct gtctctacaa aaaaaaaatt tgccaagagc ctgagtgaca    1860
gagcaagacc ccatctcaaa aaaaaaaaca aacaaacaaa aaaaaaacca tatatataca    1920
tatatatata gcagctttat ggagatataa ttcttatgcc atataattca ccttcttttt    1980 tttttttgt ctgagacaga atctcagtct gtcacccagg ttggagtgca gtggcgtgat    2040
ctcagctcac tgcaacctcc acctcgcagg ttcaagcaat cctcccactt cagcctccca    2100
agcacctggg attacaagca tgagtcacta cgcctggctg attttttgtag ttttagtgga    2160 gatgggtttt caccatgttg gccaggcttg tctcgaactc ctgaccccaa gttatccacc    2220
tgccttggct tcccaaagtc ctgggattac aggtgtgagc caccacatcc agcctaactt    2280
acattcttaa agtgtcgaat gacttctagt gtagaattgt gcaaccatca ccagaattaa    2340
ttttattatt cttattattt ttgagacaga gtcttactct gttgccaggc tggagtgcag    2400
tggcgcgatc tcagctcact acaacctccg cctcccatgt tcaagcgatt ctcctgcctc    2460
agcctcccga gtagctggga ctataggcat gcgccaccat ggccagctaa tttttgtatt    2520
tttagtagag acgaggtttc actgtgttgg ccaggatggt ctccatctct tgacctcgtg    2580
atccacccgc ctcagcctcc caaagtgctg ggattaacag gtatgaacca ccgcgcccag    2640 ccttttttgtt tttttttttt ttgagacaga gtcttcctct gtctcctaag ctggagtgca    2700
gtggcatcat ctcagctcac tgcaacctct gcctcccagg ttcaagtgct tctccagcct    2760
cagcctccca agtagctgag actacaggca cacaccacca cgcctggcta ttttttgtat    2820
ttttagtaga cgggtttc accatgttgg ctagactagt ctcaaactcc tgacctcaag    2880
tgatctgccc gcctcgacct ctctcaaagt gctggcatta caggtgtgag ccacggtgcc    2940
cggcccacaa ttaattttag aacatttttca tcacccctaa aagaaaccct gcacccatta    3000
gcagtccctc cacatttccc cctagcctgc ctcccctgcc tcaccagccc tggcaactgc    3060
taatctactt tctgtgtcta tggatttgcc ttctctaaac atttcatata aatggaatta    3120
cacaatg                                                              3127
```

METHODS OF DIAGNOSING CHRONIC OBSTRUCTIVE PULMONARY DISEASE (COPD) USING NOVEL MOLECULAR BIOMARKERS

This application is a national phase application under 35 U.S.C. § 371 of International Application No. PCT/EP2015/062426, filed Jun. 3, 2015, which claims benefit of European Application No. 14171390.9, filed Jun. 5, 2014, the entire contents of each of which are hereby incorporated by reference.

The present invention relates to in vitro methods for the diagnosis of chronic obstructive pulmonary disease (COPD), wherein the expression of the marker gene TMSB15A is determined. In particular, the invention relates to an in vitro diagnostic method of assessing the susceptibility of a subject to develop progressive COPD involving the appearance of irreversible lung damage, wherein the expression of the marker gene TMSB15A and optionally one or more further marker genes selected from DMBT1, KIAA1199, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL is determined. The invention also relates to an in vitro method of diagnosing stable COPD or assessing the susceptibility of a subject to develop stable COPD, wherein the expression of TMSB15A and optionally one or more further marker genes selected from DMBT1, KIAA1199, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL is determined. Furthermore, the invention relates to the use of primers for transcripts of the aforementioned marker genes, the use of nucleic acid probes to transcripts of these marker genes, the use of microarrays comprising nucleic acid probes to transcripts of these marker genes, and the use of antibodies against the proteins expressed from these marker genes in corresponding in vitro methods. In vitro methods of monitoring the progression of COPD are also provided, in which the expression of marker genes according to the invention is determined.

COPD represents one of the leading pathologies of the world's elderly population. Triggered by long-term exposure to combustion products, climatic conditions and repeated infections, COPD has become the fourth-leading cause of mortality in aged individuals. During the last decades, the worldwide prevalence of COPD has risen by more than 10%, particularly in active smokers beyond the age of 55 (Murray et al., 1997). Given the increasing number of elderly people in the world's population and the world-wide increase of inhalative hazards, both occupational and personal, COPD must be regarded as one of the most challenging threats to the world's health systems (Halbert et al., 2006; US Burden of Disease Collaborators, 2013). However, although the impact of COPD on health conditions is increasingly understood, the mechanisms that cause and maintain the progression of the disease are largely unknown. Based on clinical experience and results of controlled studies, COPD is regarded as a largely inflammatory disease. However, while long-term anti-inflammatory treatment may improve the outcome in COPD, its impact on the overall pathology of the disease is less clear. The TORCH (TOwards a Revolution in COPD Health) study has clearly shown that this unilateral view upon the pathophysiology of COPD is not entirely correct as patients who were under continuous treatment with inhaled corticosteroids did not have a better outcome than those without. In line with this, several well-defined clinical trials have tried to stratify patients according to relevant clinical phenotypes, the ECLIPSE (Evaluation of COPD Longitudinally to Identify Predictive Surrogate Endpoints) study being the latest and most important attempt thus far (Vestbo et al., 2011). While these attempts have proven the remarkable heterogeneity of the clinical manifestations of COPD, they unfortunately failed to improve the understanding of the disease's central driving forces, their mediators, and their hierarchy in evoking the clinical phenotypes of COPD.

Until recently, COPD has been largely defined by the limitation of the maximum volume of air exhaled in one second during forced expiration ($FEV_1$), as well as by the total amount of air exhaled (forced [expiratory] vital capacity, FVC), and their respective relationship (Wedzicha J A, 2000). However, the variability of the clinical presentation of COPD regardless of any individual degree of airflow limitation suggested that the disease comprises different mechanisms related to bronchial and peribronchial pathologies (Hurst et al., 2010; Han et al., 2010). As a consequence, further clinical measures have been added to the diagnostic process in COPD, such as the intensity of bronchial inflammation, the frequency of disease exacerbations or the presence of comorbidities (Vestbo et al., 2013).

Not surprisingly, $FEV_1$ does not correlate well with symptom development. However, many studies have clearly demonstrated that $FEV_1$ is a strong predictor of mortality and morbidity in COPD, suggesting a relevant correlation between the (morphologically fixed) obstruction of the peripheral airways and the pathophysiology of the disease. Given the probability that the morphology of the small airways is going to reflect the pathologic net result of all metabolic events within this lung compartment, including chronic inflammatory and regenerative activities, this is more than plausible. Based on these facts, it still seems appropriate to apply the symptoms of the most established clinical manifestations of COPD, i.e. fixed bronchial obstruction and intensity of bronchitis as the main clinical indicators for a first attempt to delineate mechanisms and mediators capable of driving the pathology of COPD. In view of the well-documented long-term history of COPD often covering periods of more than two decades, any attempt to delineate the pathology of the disease ought to a) cover the earliest phase of pathologic development, the establishment of chronic bronchitis (COPD "at risk" according to the GOLD (Global Initiative on Obstructive Lung Disease) criteria) likely to precede the first manifestation of "irreversible" bronchial obstruction, b) to include both long-term development of the disease preceding the controlled phase of clinical assessment and c) to span a period long enough to allow for the identification of important short-range effects on COPD pathology. Lastly, as the pathology of COPD is focused in the small airways (Hogg J C, et al., 2004 (a)), the initial biological assessment ought to be performed in this compartment, regardless of the fact that some characteristic symptoms, such as the production of phlegm as a sign of intensified bronchitis, will also reflect the metabolic activity of the more central airways.

COPD progressively debilitates patients, resulting in an increasing disability and worsening impact of exacerbations. In particular, the development of irreversible damage to the lungs commences and then gradually worsens when a patient suffering from COPD advances from the stable early disease stage into the progressive stage of COPD. Unfortunately, many patients with COPD remain undiagnosed and potentially unknown to healthcare providers until the more advanced stages of the disease. In such cases, the delayed diagnosis of COPD results in patients suffering from symptoms and limitations that could otherwise be alleviated by treatment (Price et al., 2011). It would therefore be highly desirable to be able to diagnose COPD at an early disease stage and, in particular, to identify patients who are at risk of developing progressive COPD in order to be able to prevent these patients from suffering significant irreversible damage.

It is therefore an object of the present invention to provide novel and/or improved methods that allow to diagnose COPD at an early disease stage or to assess the risk or susceptibility of a subject to develop COPD. It is furthermore an object of the invention to provide novel and/or improved methods that allow to assess the susceptibility of a subject to develop progressive COPD.

The present invention is based on the unexpected finding that the gene TMSB15A as well as the genes DMBT1, KIAA1199, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL are differentially expressed in samples from subjects suffering from progressive COPD or subjects at risk/prone to develop progressive COPD on the one hand, and in control samples from healthy subjects on the other hand. In particular, and as also described in Example 1, it has been found that the expression of the genes DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and COMP is upregulated in samples from patients suffering from progressive COPD or at risk of developing progressive COPD, while the expression of the genes TMSB15A, DPP6, SLC51B, NUDT11, PLA1A, HYAL2, CST6, ITGA10, CTHRC1, TAL1, FIBIN, BEX5, BEX1, ESM1 and GHRL is downregulated in samples from patients suffering from progressive COPD or at risk of developing progressive COPD, as compared to the expression of the corresponding genes in control samples from healthy patients. Therefore, in accordance with the present invention, these novel molecular biomarkers can advantageously be used for assessing the susceptibility/proneness of a subject to develop progressive COPD. It has further been surprisingly found that the genes TMSB15A, DMBT1, KIAA1199, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL are differentially expressed in samples from subjects suffering from stable COPD or subjects at risk/prone to develop stable COPD on the one hand, and in control samples from healthy subjects on the other hand. In this connection, it has particularly been found that the expression of the genes TMSB15A, KIAA1199, DPP6, SLC51B, NUDT11, PLA1A, HYAL2, CST6, ITGA10, CTHRC1, TAL1, FIBIN, BEX5, BEX1, ESM1 and GHRL is downregulated in samples from patients having stable COPD or at risk of developing stable COPD, while the expression of the genes DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and COMP is upregulated in samples from patients having stable COPD or at risk of developing stable COPD, as compared to the expression of the corresponding genes in control samples from healthy patients. In accordance with the present invention, these novel molecular biomarkers can thus be used for diagnosing stable COPD and/or assessing the susceptibility/proneness of a subject to develop stable COPD. Moreover, the biomarkers provided herein have excellent sensitivity and/or specificity.

Accordingly, in a first aspect the present invention provides an in vitro method for the diagnosis of COPD, the method comprising determining the level of expression of the gene TMSB15A in a sample obtained from a subject.

In accordance with this first aspect, the invention also relates to the use of TMSB15A as a marker for the in vitro diagnosis of COPD.

In a second aspect, the present invention provides an in vitro diagnostic method of assessing the susceptibility of a subject to develop progressive COPD involving the appearance of irreversible lung damage, the method comprising:
  determining the level of expression of the gene TMSB15A in a sample obtained from the subject;
  comparing the level of expression of TMSB15A in the sample from the subject to a control expression level of TMSB15A in a healthy subject; and
  determining whether or not the subject is prone to develop progressive COPD involving the appearance of irreversible lung damage, wherein a decrease in the level of expression of TMSB15A in the sample from the subject as compared to the control expression level of TMSB15A is indicative of a proneness to develop progressive COPD.

It is preferred that in this second aspect the method further comprises:
  determining the level of expression of one or more further genes selected from DMBT1, KIAA1199, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in the sample obtained from the subject;
  comparing the level of expression of the one or more further genes to a control expression level of the corresponding gene(s) in a healthy subject; and
  determining whether or not the subject is prone to develop progressive COPD involving the appearance of irreversible lung damage,
wherein an increase in the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject as compared to the control expression level of the corresponding gene(s) is indicative of a proneness to develop progressive COPD, and wherein a decrease in the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject as compared to the control expression level of the corresponding gene(s) is indicative of a proneness to develop progressive COPD.

In a third aspect, the invention provides an in vitro method of diagnosing stable COPD in a subject or assessing the susceptibility of a subject to develop stable COPD, the method comprising:
  determining the level of expression of the gene TMSB15A in a sample obtained from the subject;

comparing the level of expression of TMSB15A in the sample from the subject to a control expression level of TMSB15A in a healthy subject; and determining whether or not the subject suffers from stable COPD or is prone to suffer from stable COPD, wherein a decrease in the level of expression of TMSB15A in the sample from the subject as compared to the control expression level of TMSB15A is indicative of stable COPD or a proneness to stable COPD.

The method according to this third aspect preferably further comprises:

determining the level of expression of one or more further genes selected from DMBT1, KIAA1199, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in the sample obtained from the subject;

comparing the level of expression of the one or more further genes to a control expression level of the corresponding gene(s) in a healthy subject; and determining whether or not the subject suffers from stable COPD or is prone to suffer from stable COPD, wherein an increase in the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject as compared to the control expression level of the corresponding gene(s) is indicative of stable COPD or a proneness to stable COPD, and wherein a decrease in the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject as compared to the control expression level of the corresponding gene(s) is indicative of stable COPD or a proneness to stable COPD.

In a fifth aspect, the invention relates to the use of (i) a pair of primers for a transcript of the gene TMSB15A, (ii) a nucleic acid probe to a transcript of the gene TMSB15A, (iii) a microarray comprising a nucleic acid probe to the transcript of TMSB15A and optionally comprising nucleic acid probes to the transcripts of one or more further genes selected from DMBT1, KIAA1199, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL, or (iv) an antibody against the protein TMSB15A, in an in vitro diagnostic method of assessing the susceptibility of a subject to develop progressive COPD involving the appearance of irreversible lung damage.

In a sixth aspect, the invention relates to a drug against COPD for use in treating COPD in a subject that has been identified in a method according to the second aspect of the invention as being prone to develop progressive COPD involving the appearance of irreversible lung damage.

The invention further relates to the use of a drug against COPD in the preparation of a pharmaceutical composition for treating COPD in a subject that has been identified in a method according to the second aspect of the invention as being prone to develop progressive COPD involving the appearance of irreversible lung damage.

Moreover, in accordance with this sixth aspect, the invention also provides a method of treating COPD, the method comprising administering a drug against COPD to a subject that has been identified in a method according to the second aspect of the invention as being prone to develop progressive COPD involving the appearance of irreversible lung damage.

In a seventh aspect, the invention relates to the use of (i) a pair of primers for a transcript of the gene TMSB15A, (ii) a nucleic acid probe to a transcript of the gene TMSB15A, (iii) a microarray comprising a nucleic acid probe to the transcript of TMSB15A and optionally comprising nucleic acid probes to the transcripts of one or more further genes selected from DMBT1, KIAA1199, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL, or (iv) an antibody against the protein TMSB15A, in an in vitro method of diagnosing stable COPD in a subject or assessing the susceptibility of a subject to develop stable COPD.

In an eighth aspect, the invention relates to a drug against COPD for use in treating or preventing COPD in a subject that has been identified in a method according to the third aspect of the invention as suffering from stable COPD or as being prone to suffer from stable COPD.

The invention also relates to the use of a drug against COPD in the preparation of a pharmaceutical composition for treating or preventing COPD in a subject that has been identified in a method according to the third aspect of the invention as suffering from stable COPD or as being prone to suffer from stable COPD.

In this aspect, the invention likewise relates to a method of treating or preventing COPD, the method comprising administering a drug against COPD to a subject that has been identified in a method according to the third aspect of the invention as suffering from stable COPD or as being prone to suffer from stable COPD.

In an eleventh aspect, the present invention provides an in vitro method of monitoring the progression of COPD in a subject, the method comprising:

determining the level of expression of one or more genes selected from NTRK2 and RASGRF2 in a first sample obtained from the subject;

determining the level of expression of the one or more genes in a second sample obtained from the subject at a later point in time than the first sample;

comparing the level of expression of the one or more genes in the second sample to the level of expression of the corresponding gene(s) in the first sample; and assessing the progression of COPD in the subject, wherein a decrease in the level of expression of NTRK2 and/or RASGRF2 in the second sample as compared to the level of expression of the corresponding gene(s) in the first sample is indicative of an amelioration of COPD in the subject, and wherein an increase in the level of expression of NTRK2 and/or RASGRF2 in the second sample as compared to the level of expression of the corresponding gene(s) in the first sample is indicative of a worsening of COPD in the subject.

The following description of general and preferred features and embodiments relates to each one of the methods, uses and drugs against COPD provided in the present specification, including in particular those according to the above-described first, second, third, fifth, sixth, seventh, eighth and eleventh aspects of the invention, unless explicitly indicated otherwise.

Chronic obstructive pulmonary disease (COPD) is a lung disease characterized by persistent airflow limitation that is usually progressive and associated with an enhanced chronic inflammatory response in the airways and the lung to noxious particles or gases. COPD is typically classified into four different stages based on the extent of non-reversible pulmonary obstruction to be determined by spirometry, as specified by the Global Initiative for Obstructive Lung Disease (GOLD) (see, e.g., Vestbo et al., 2013; and Pauwels et al., 2001). COPD stage I ("mild COPD") is characterized by an $FEV_1/FVC$ ratio of <70% and an $FEV_1$ of ≥80%. At stage I, the patient may not be aware that his/her lung function is abnormal. COPD stage II ("moderate COPD") is characterized by an $FEV_1/FVC$ ratio of <70% and an $FEV_1$ of ≥50% and <80%. This is the stage at which patients typically seek medical attention because of chronic respiratory symptoms or an exacerbation of their disease. COPD stage III ("severe COPD") is characterized by an $FEV_1/FVC$ ratio of <70% and an $FEV_1$ of ≥30% and <50%. COPD stage IV ("very severe COPD") is characterized by an $FEV_1/FVC$ ratio of <70% and an $FEV_1$ of <30%, or chronic respiratory failure and an $FEV_1$ of <50%. The pathological development of COPD may be preceded by chronic respiratory symptoms (particularly chronic bronchitis) without airways obstruction ($FEV_1/FVC$ ratio of ≥70%), which is also referred to as "stage 0" or "at risk for COPD". The terms "stage I", "stage II", stage "III", "stage IV", and "stage 0" as used in the present specification refer to the corresponding GOLD stages, i.e., the corresponding COPD stages according to the above-described GOLD criteria.

As used herein, the term "stable COPD" (used synonymously with "stable early-stage COPD") refers to the initial stages of COPD that precede the development of irreversible lung damage. In particular, "stable COPD" refers to the initial COPD stages from the earliest signs for the onset of the disease through to mild airflow limitation characterized by an $FEV_1/FVC$ ratio of <70% and an $FEV_1$ of ≥80%. "Stable COPD" thus preferably refers to COPD stage 0 (i.e., the COPD "at risk" stage) and COPD stage I (according to GOLD criteria), and more preferably refers to COPD stage I.

The terms "progressive COPD" and "progressive COPD involving the appearance of irreversible lung damage" are used herein synonymously/interchangeably, and refer to the disease stage of COPD in which irreversible damage to the lungs occurs and progressively worsens. In particular, "progressive COPD" refers to the COPD disease stage characterized by moderate airflow limitation, i.e., an $FEV_1/FVC$ ratio of <70% and an $FEV_1$ of ≥50% and <80%. Accordingly, it is particularly preferred that "progressive COPD" refers to COPD stage II (according to GOLD criteria).

As used herein, the terms "KIAA1199", "DMBT1", "TMSB15A", "DPP6", "SLC51B", "NUDT11", "ITGA10", "CST6", "TAL1", "FIBIN", "BEX5", "BEX1", "ESM1", "GHRL", "NTRK2", "SFN", "GPR110", "FGG", "CEACAM5", "AZGP1", "COMP", "PRRX1", "AHRR", "CYP1A1", "CYP1A2", "CYP1B1", "GDF15", "ELF5", "AQP3", "RASGRF2", "PLA1A", "HYAL2", "CTHRC1", "RND1" and "CXCL3" each refer to the respective human gene, the corresponding mRNA (including all possible transcripts/splice variants), and the corresponding protein (including all possible isoforms). These terms also refer to homologs and/or orthologs of the corresponding human genes that are found in other (non-human) species, particularly other mammalian species, as well as their corresponding mRNAs and their corresponding proteins. It is to be understood that, if the subject to be tested in the methods of the present invention is a non-human animal (particularly a non-human mammal), then the one or more marker genes (the level of expression of which is to be determined) will be the homologs/orthologs of the indicated human genes that are found in the non-human animal to be tested. Preferably, the subject is a human and, accordingly, the above-mentioned terms preferably refer to the respective human genes and the corresponding mRNAs and proteins.

The full names of the human forms of the above-mentioned marker genes, their Entrez Gene ID, and NCBI reference sequences of their mRNAs and proteins are listed in the following Table 1:

TABLE 1

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
|---|---|---|---|---|
| KIAA1199 | KIAA1199 | 57214 | NM_018689.1 (preferably as indicated in SEQ ID NO: 38) | NP_061159.1 |
| DMBT1 | deleted in malignant brain tumors 1 | 1755 | NM_004406.2 (preferably as indicated in SEQ ID NO: 26) NM_007329.2 (preferably as indicated in SEQ ID NO: 32) NM_017579.2 (preferably as indicated in SEQ ID NO: 35) | NP_004397.2 NP_015568.2 NP_060049.2 |
| TMSB15A | thymosin beta 15a | 11013 | NM_021992.2 (preferably as indicated in SEQ ID NO: 41) | NP_068832.1 |

TABLE 1-continued

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
|---|---|---|---|---|
| DPP6 | dipeptidyl-peptidase 6 | 1804 | NM_001039350.1 (preferably as indicated in SEQ ID NO: 45) NM_001936.3 (preferably as indicated in SEQ ID NO: 46) NM_130797.2 (preferably as indicated in SEQ ID NO: 47) | NP_001034439.1 NP_001927.3 NP_570629.2 |
| SLC51B | solute carrier family 51, beta subunit | 123264 | NM_178859.3 (preferably as indicated in SEQ ID NO: 48) | NP_849190.2 |
| NUDT11 | nudix (nucleoside diphosphate linked moiety X)-type motif 11 | 55190 | NM_018159.3 (preferably as indicated in SEQ ID NO: 36) | NP_060629 |
| ITGA10 | integrin, alpha 10 | 8515 | NM_003637.3 (preferably as indicated in SEQ ID NO: 24) | NP_003628.2 |
| CST6 | cystatin E/M | 1474 | NM_001323.3 (preferably as indicated in SEQ ID NO: 21) | NP_001314.1 |
| TAL1 | T-cell acute lymphocytic leukemia 1 | 6886 | NM_003189.2 (preferably as indicated in SEQ ID NO: 49) | NP_003180.1 |
| FIBIN | fin bud initiation factor homolog (zebrafish) | 387758 | NM_203371.1 (preferably as indicated in SEQ ID NO: 50) | NP_976249.1 |
| BEX5 | brain expressed, X-linked 5 | 340542 | NM_001012978.2 (preferably as indicated in SEQ ID NO: 5) NM_001159560.1 (preferably as indicated in SEQ ID NO: 13) | NP_001012996.1 NP_001153032.1 |
| BEX1 | brain expressed, X-linked 1 | 55859 | NM_018476.3 (preferably as indicated in SEQ ID NO: 37) | NP_060946.3 |
| ESM1 | endothelial cell-specific molecule 1 | 11082 | NM_001135604.1 (preferably as indicated in SEQ ID NO: 12) NM_007036.4 (preferably as indicated in SEQ ID NO: 31) | NP_001129076.1 NP_008967.1 |
| GHRL | ghrelin/obestatin prepropeptide | 51738 | NM_001134941.1 (preferably as indicated in SEQ ID NO: 8) NM_001134944.1 (preferably as indicated in SEQ ID NO: 9) NM_001134945.1 (preferably as indicated in SEQ ID NO: 10) | NP_001128413.1 NP_001128416.1 NP_001128417.1 NP_001128418.1 NP_001128418.1 |

TABLE 1-continued

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
|---|---|---|---|---|
| NTRK2 | neurotrophic tyrosine kinase, receptor, type 2 | 4915 | NM_001134946.1 (preferably as indicated in SEQ ID NO: 11) NM_001007097.1 (preferably as indicated in SEQ ID NO: 51) NM_001018064.1 (preferably as indicated in SEQ ID NO: 52) NM_001018065.2 (preferably as indicated in SEQ ID NO: 6) NM_001018066.2 (preferably as indicated in SEQ ID NO: 7) NM_006180.3 (preferably as indicated in SEQ ID NO: 53) | NP_001007098.1 NP_001018074.1 NP_001018075.1 NP_001018076.1 NP_006171.2 |
| SFN | stratifin | 2810 | NM_006142.3 (preferably as indicated in SEQ ID NO: 29) | NP_006133.1 |
| GPR110 | G protein-coupled receptor 110 | 266977 | NM_025048.2 (preferably as indicated in SEQ ID NO: 42) NM_153840.2 (preferably as indicated in SEQ ID NO: 55) | NP_079324.2 NP_722582.2 |
| CYP1B1 | cytochrome P450, family 1, subfamily B, polypeptide 1 | 1545 | NM_000104.3 (preferably as indicated in SEQ ID NO: 2) | NP_000095.2 |
| FGG | fibrinogen gamma chain | 2266 | NM_000509.4 (preferably as indicated in SEQ ID NO: 4) NM_021870.2 (preferably as indicated in SEQ ID NO: 40) | NP_000500.2 NP_068656.2 |
| CEACAM5 | carcinoembryonic antigen-related cell adhesion molecule 5 | 1048 | NM_004363.2 (preferably as indicated in SEQ ID NO: 54) | NP_004354.2 |
| AZGP1 | alpha-2-glycoprotein 1, zinc-binding | 563 | NM_001185.3 (preferably as indicated in SEQ ID NO: 14) | NP_001176.1 |
| COMP | cartilage oligomeric matrix protein | 1311 | NM_000095.2 (preferably as indicated in SEQ ID NO: 1) | NP_000086.2 |
| PRRX1 | paired related homeobox 1 | 5396 | NM_006902.3 (preferably as indicated in SEQ ID NO: 56) NM_022716.2 (preferably as indicated in SEQ ID NO: 57) | NP_008833.1 NP_073207.1 |

TABLE 1-continued

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
| --- | --- | --- | --- | --- |
| AHRR | aryl-hydrocarbon receptor represser | 57491 | NM_001242412.1 (preferably as indicated in SEQ ID NO: 17) NM_020731.4 (preferably as indicated in SEQ ID NO: 39) | NP_001229341.1 NP_065782.2 |
| GDF15 | growth differentiation factor 15 | 9518 | NM_004864.2 (preferably as indicated in SEQ ID NO: 27) | NP_004855.2 |
| ELF5 | E74-like factor 5 (ets domain transcription factor) | 2001 | NM_001243080.1 (preferably as indicated in SEQ ID NO: 18) NM_001243081.1 (preferably as indicated in SEQ ID NO: 19) NM_001422.3 (preferably as indicated in SEQ ID NO: 22) NM_198381.1 (preferably as indicated in SEQ ID NO: 58) | NP_001230009.1 NP_001230010.1 NP_001413.1 NP_938195.1 |
| AQP3 | aquaporin 3 (Gill blood group) | 360 | NM_004925.4 (preferably as indicated in SEQ ID NO: 28) | NP_004916.1 |
| RASGRF2 | Ras protein-specific guanine nucleotide-releasing factor 2 | 5924 | NM_006909.2 (preferably as indicated in SEQ ID NO: 30) | NP_008840.1 |
| PLA1A | phospholipase A1 member A | 51365 | NM_001206960.1 (preferably as indicated in SEQ ID NO: 15) NM_001206961.1 (preferably as indicated in SEQ ID NO: 16) NM_015900.3 (preferably as indicated in SEQ ID NO: 34) | NP_001193889.1 NP_001193890.1 NP_056984.1 |
| HYAL2 | hyaluronoglucosaminidase 2 | 8692 | NM_003773.4 (preferably as indicated in SEQ ID NO: 25) NM_033158.4 (preferably as indicated in SEQ ID NO: 43) | NP_003764.3 NP_149348.2 |
| CTHRC1 | collagen triple helix repeat containing 1 | 115908 | NM_001256099.1 (preferably as indicated in SEQ ID NO: 20) NM_138455.3 (preferably as indicated in SEQ ID NO: 44) | NP_001243028.1 NP_612464.1 |
| RND1 | Rho family GTPase 1 | 27289 | NM_014470.3 (preferably as indicated in SEQ ID NO: 33) | NP_055285.1 |

TABLE 1-continued

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
| --- | --- | --- | --- | --- |
| CXCL3 | chemokine (C-X-C motif) ligand 3 | 2921 | NM_002090.2 (preferably as indicated in SEQ ID NO: 23) | NP_002081.2 |
| CYP1A1 | cytochrome P450, family 1, subfamily A, polypeptide 1 | 1543 | NM_000499.3 (preferably as indicated in SEQ ID NO: 3) | NP_000490.1 |
| CYP1A2 | cytochrome P450, family 1, subfamily A, polypeptide 2 | 1544 | NM_000761.4 (preferably as indicated in SEQ ID NO: 59) | NP_000752.2 |

In the methods according to the present invention, including in particular the methods according to the first, second, third and eleventh aspect of the invention, the level of expression of one or more genes is determined in a sample obtained from the subject to be tested.

The level of expression can be determined, e.g., by determining the level of transcription or the level of translation of the corresponding marker gene(s). Thus, the amount of mRNA of these gene(s) in the sample can be measured or the amount of the corresponding protein(s) can be measured in order to determine the level of expression of the respective genes. This can be accomplished using methods known in the art, as described, e.g., in Green et al., 2012. The level of transcription of these gene(s) can, for example, be determined using a quantitative (real-time) reverse transcriptase polymerase chain reaction ("qRT-PCR") or using a microarray (see, e.g., Ding et al., 2004). The use of a microarray can be advantageous, e.g., if the level of transcription of a number of different marker genes is to be determined. Using a microarray can also be advantageous if various different diseases/disorders or the susceptibility to various diseases/disorders is to be tested or diagnosed simultaneously. If the level of transcription is to be determined, it may further be advantageous to include one or more RNase inhibitors in the sample from the subject. The level of translation of the corresponding marker gene(s) can, for example, be determined using antibody-based assays, such as an enzyme-linked immunosorbent assay (ELISA) or a radioimmunoassay (RIA), wherein antibodies directed specifically against the protein(s) to be quantified are employed, or mass spectrometry, a gel-based or blot-based assay, or flow cytometry (e.g., FACS). If the level of translation is to be determined, it may be advantageous to include one or more protease inhibitors in the sample from the subject. Since mRNA can be isolated and quantified more easily and in a more cost-effective manner than proteins, it is preferred in the methods of the present invention that the level of expression of the one or more genes is determined by determining the level of transcription of the corresponding gene(s). The level of transcription is preferably determined using qRT-PCR or a microarray.

The subject to be tested in accordance with the present invention may be an animal and is preferably a mammal. The mammal to be tested in accordance with the invention may be, e.g., a rodent (such as, e.g., a guinea pig, a hamster, a rat or a mouse), a murine (such as, e.g., a mouse), a canine (such as, e.g., a dog), a feline (such as, e.g., a cat), a porcine (such as, e.g., a pig), an equine (such as, e.g., a horse), a primate, a simian (such as, e.g., a monkey or an ape), a monkey (such as, e.g., a marmoset or a baboon), an ape (such as, e.g., a gorilla, a chimpanzee, an orangutan or a gibbon), or a human. It is particularly envisaged that non-human mammals are to be tested, which are economically, agronomically or scientifically important. Scientifically important mammals include, e.g., mice, rats and rabbits. Non-limiting examples of agronomically important mammals are sheep, cattle and pigs. Economically important mammals include, e.g., cats and dogs. Most preferably, the subject to be tested in accordance with the present invention is a human.

In the second aspect of the invention, it is furthermore preferred that the subject to be tested is a subject (preferably a human) that has been diagnosed as suffering from stable COPD or is suspected of suffering from stable COPD.

In accordance with the third aspect of the invention, it is preferred that the subject to be tested is a subject (preferably a human) that is suspected to suffer from stable COPD or a subject (preferably a human) suspected to be prone to suffer from stable COPD.

The sample obtained from the subject to be tested can, in principle, be any tissue sample or serum from the subject. Preferably, the sample is a lung tissue sample. More preferably, the sample is a transbronchial lung biopsy sample or a bronchoalveolar lavage (BAL) sample.

In some of the methods provided herein, including in particular the methods according to the second and the third aspect of the invention, the level of expression of one or more specific genes is compared to a control expression level of the corresponding gene(s) in a healthy subject. Such control expression levels can be established as part of the respective methods of the invention, which may thus include a further step of determining the level of expression of the corresponding gene(s) in a sample obtained from a healthy subject (i.e., a subject that does not suffer from COPD and does not have an increased risk of developing COPD) or in a mixture of samples from several healthy subjects (e.g., about 10, about 20, about 50, about 100, or about 500 healthy subjects). It is to be understood that the healthy subject(s) will be of the same species as the subject to be tested and should preferably have the same age, gender and ethnicity as the subject to be tested. Alternatively, these control expression levels can also be derived from the medical literature or from experiments conducted before carrying out the methods of the invention. It will be understood that the conditions under which the control expression levels are or were obtained (regardless of whether they are derived from the literature or earlier experiments or whether they are determined in the course of carrying out the methods of the invention), including also the type/origin of the sample (or mixture of samples) from the healthy subject, should be identical or at least similar/comparable to the conditions used for determining the level of expression of the one or more genes in the sample obtained from the subject to be tested.

In the methods according to the second and third aspect of the present invention, the level of expression of TMSB15A and optionally of one or more further marker genes is determined. Preferably, the level of expression of TMSB15A and at least one of the corresponding further marker genes is determined, more preferably the level of expression of TMSB15A and at least two of these further marker genes is determined, and even more preferably the level of expression of TMSB15A and at least three of the corresponding further marker genes is determined, whereby the reliability of the diagnosis or assessment can be further improved. In general, the greater the number of marker genes the expression of which is altered (as defined in the corresponding aspect of the invention), and also the more pronounced the upregulation or downregulation of the expression of each of these marker genes, the more likely it will be that the subject tested is prone to develop progressive COPD (in the method of the second aspect) or that the subject tested suffers from stable COPD or is prone to suffer from stable COPD (in the method of the third aspect of the invention).

Thus, both (i) the number of tested marker genes showing an altered expression level as described above and (ii) the extent of alteration of the expression level of each one of the marker genes tested can be taken into consideration when determining whether or not the subject is prone to develop progressive COPD (in accordance with the second aspect) or whether or not the subject suffers from stable COPD or is prone to suffer from stable COPD (in accordance with the third aspect of the invention). Further factors, signs and symptoms indicative of COPD, such as, e.g., airflow limitation (as determined, e.g., by spirometry), coughing, expiratory wheezing, further respiratory symptoms, the subject's smoking history, bronchial inflammation and/or further biomarkers (including molecular biomarkers), can additionally be taken into account in order to further improve the accuracy of the determination whether or not the subject is prone to develop progressive COPD (in accordance with the second aspect) or whether or not the subject suffers from stable COPD or is prone to suffer from stable COPD (in accordance with the third aspect).

In one embodiment of the method according to the second aspect of the invention, it is preferred that the level of expression of TMSB15A and at least one further gene selected from FGG, CYP1A1, CEACAM5, CTHRC1, NTRK2 and RASGRF2 is determined in the sample obtained from the subject. In this embodiment, it is furthermore preferred that the level of expression of at least two of the aforementioned further genes is determined. For example, the level of expression of TMSB15A, FGG and CYP1A1 may be determined, or the level of expression of TMSB15A, FGG and CEACAM5 may be determined, or the level of expression of TMSB15A, FGG and CTHRC1 may be determined, or the level of expression of TMSB15A, FGG and NTRK2 may be determined, or the level of expression of TMSB15A, FGG and RASGRF2 may be determined, or the level of expression of TMSB15A, CYP1A1 and CEACAM5 may be determined, or the level of expression of TMSB15A, CYP1A1 and CTHRC1 may be determined, or the level of expression of TMSB15A, CYP1A1 and NTRK2 may be determined, or the level of expression of TMSB15A, CYP1A1 and RASGRF2 may be determined, or the level of expression of TMSB15A, CEACAM5 and CTHRC1 may be determined, or the level of expression of TMSB15A, CEACAM5 and NTRK2 may be determined, or the level of expression of TMSB15A, CEACAM5 and RASGRF2 may be determined, or the level of expression of TMSB15A, CTHRC1 and NTRK2 may be determined, or the level of expression of TMSB15A, CTHRC1 and RASGRF2 may be determined, or the level of expression of TMSB15A, NTRK2 and RASGRF2 may be determined. In addition thereto, the level of expression of at least one further gene selected from ELF5, AZGP1, PRRX1, AQP3, SFN, GPR110, GDF15, RASGRF2 and RND1 and/or the level of expression of at least one further gene selected from DMBT1, KIAA1199, DPP6, SLC51B and NUDT11 (particularly DMBT1 and/or KIAA1199) may also be determined.

In a further embodiment of the method according to the second aspect of the invention, it is preferred that the level of expression of TMSB15A and at least one further gene selected from ELF5, AZGP1, PRRX1, AQP3, SFN, GPR110, GDF15, RASGRF2 and RND1 is determined in the sample obtained from the subject. In this embodiment, it is furthermore preferred that the level of expression of at least two of the aforementioned further genes is determined. For example, the level of expression of TMSB15A, ELF5 and AZGP1 may be determined, or the level of expression of TMSB15A, ELF5 and PRRX1 may be determined, or the level of expression of TMSB15A, ELF5 and AQP3 may be determined, or the level of expression of TMSB15A, ELF5 and SFN may be determined, or the level of expression of TMSB15A, ELF5 and GPR110 may be determined, or the level of expression of TMSB15A, ELF5 and GDF15 may be determined, or the level of expression of TMSB15A, ELF5 and RASGRF2 may be determined, or the level of expression of TMSB15A, ELF5 and RND1 may be determined, or the level of expression of TMSB15A, AZGP1 and PRRX1 may be determined, or the level of expression of TMSB15A, AZGP1 and AQP3 may be determined, or the level of expression of TMSB15A, AZGP1 and SFN may be determined, or the level of expression of TMSB15A, AZGP1 and GPR110 may be determined, or the level of expression of TMSB15A, AZGP1 and GDF15 may be determined, or the level of expression of TMSB15A, AZGP1 and RASGRF2 may be determined, or the level of expression of TMSB15A, AZGP1 and RND1 may be determined, or the level of expression of TMSB15A, PRRX1 and AQP3 may be determined, or the level of expression of TMSB15A, PRRX1 and SFN may be determined, or the level of expression of TMSB15A, PRRX1 and GPR110 may be determined, or the level of expression of TMSB15A, PRRX1 and GDF15 may be determined, or the level of expression of TMSB15A, PRRX1 and RASGRF2 may be determined, or the level of expression of TMSB15A, PRRX1 and RND1 may be determined, or the level of expression of TMSB15A, AQP3 and SFN may be determined, or the level of expression of TMSB15A, AQP3 and GPR110 may be determined, or the level of expression of TMSB15A, AQP3 and GDF15 may be determined, or the level of expression of TMSB15A, AQP3 and RASGRF2 may be determined, or the level of expression of TMSB15A, AQP3 and RND1 may be determined, or the level of expression of TMSB15A, SFN and GPR110 may be determined, or the level of expression of TMSB15A, SFN and GDF15 may be determined, or the level of expression of TMSB15A, SFN and RASGRF2 may be determined, or the level of expression of TMSB15A, SFN and RND1 may be determined, or the level of expression of TMSB15A, GPR110 and GDF15 may be determined, or the level of expression of TMSB15A, GPR110 and RASGRF2 may be determined, or the level of expression of TMSB15A, GPR110 and RND1 may be determined, or the level of expression of TMSB15A, GDF15 and RASGRF2 may be determined, or the level of expression of TMSB15A, GDF15 and RND1 may be determined, or the level of expression of TMSB15A, RASGRF2 and RND1 may be determined. In addition thereto, the level of expression of at least one further gene selected from FGG, CYP1A1, CEACAM5, CTHRC1, NTRK2 and RASGRF2 and/or the level of expression of at least one further gene selected from DMBT1, KIAA1199, DPP6, SLC51B and NUDT11 (particularly DMBT1 and/or KIAA1199) may also be determined.

In a further embodiment of the method according to the second aspect of the invention, it is preferred that the level of expression of TMSB15A and at least one further gene selected from DMBT1, KIAA1199, DPP6, SLC51B and NUDT11 is determined in the sample obtained from the subject. In this embodiment, it is furthermore preferred that the level of expression of at least two of the aforementioned further genes is determined. For example, the level of expression of KIAA1199, DMBT1 and TMSB15A may be determined, or the level of expression of KIAA1199, TMSB15A and DPP6 may be determined, or the level of expression of KIAA1199, TMSB15A and SLC51B may be determined, or the level of expression of KIAA1199, TMSB15A and NUDT11 may be determined, or the level of expression of DMBT1, TMSB15A and DPP6 may be determined, or the level of expression of DMBT1, TMSB15A and SLC51B may be determined, or the level of expression of DMBT1, TMSB15A and NUDT11 may be determined, or the level of expression of TMSB15A, DPP6 and SLC51B may be determined, or the level of expression of TMSB15A, DPP6 and NUDT11 may be determined, or the level of expression of TMSB15A, SLC51B and NUDT11 may be determined. In addition thereto, the level of expression of at least one further gene selected from FGG, CYP1A1, CEACAM5, CTHRC1, NTRK2 and RASGRF2 and/or the level of expression of at least one further gene selected from ELF5, AZGP1, PRRX1, AQP3, SFN, GPR110, GDF15, RASGRF2 and RND1 may also be determined.

In the method according to the second aspect of the invention, it is particularly preferred that the level of expression of TMSB15A and at least one further gene selected from DMBT1 and KIAA1199 is determined in the sample obtained from the subject. Accordingly, it is preferred that the level of expression of TMSB15A and KIAA1199 is determined, or that the level of expression of DMBT1 and TMSB15A is determined. Most preferably, the level of expression of DMBT1, KIAA1199 and TMSB15A is determined in the sample obtained from the subject. For example, the level of expression of DMBT1, KIAA1199, TMSB15A and at least one further gene selected from FGG, CYP1A1, CEACAM5, CTHRC1, NTRK2, RASGRF2, ELF5, AZGP1, PRRX1, AQP3, SFN, GPR110, GDF15, RASGRF2, RND1, DPP6, SLC51B and NUDT11 may be determined.

In one embodiment of the method according to the third aspect of the invention, it is preferred that the level of expression of TMSB15A and at least one further gene selected from FGG, CYP1A1, CEACAM5, CTHRC1, NTRK2 and RASGRF2 is determined in the sample obtained from the subject. In this embodiment, it is furthermore preferred that the level of expression of at least two of the aforementioned further genes is determined. For example, the level of expression of TMSB15A, FGG and CYP1A1 may be determined, or the level of expression of TMSB15A, FGG and CEACAM5 may be determined, or the level of expression of TMSB15A, FGG and CTHRC1 may be determined, or the level of expression of TMSB15A, FGG and NTRK2 may be determined, or the level of expression of TMSB15A, FGG and RASGRF2 may be determined, or the level of expression of TMSB15A, CYP1A1 and CEACAM5 may be determined, or the level of expression of TMSB15A, CYP1A1 and CTHRC1 may be determined, or the level of expression of TMSB15A, CYP1A1 and NTRK2 may be determined, or the level of expression of TMSB15A, CYP1A1 and RASGRF2 may be determined, or the level of expression of TMSB15A, CEACAM5 and CTHRC1 may be determined, or the level of expression of TMSB15A, CEACAM5 and NTRK2 may be determined, or the level of expression of TMSB15A, CEACAM5 and RASGRF2 may be determined, or the level of expression of TMSB15A, CTHRC1 and NTRK2 may be determined, or the level of expression of TMSB15A, CTHRC1 and RASGRF2 may be determined, or the level of expression of TMSB15A, NTRK2 and RASGRF2 may be determined. In addition thereto, the level of expression of at least one further gene selected from ELF5, AZGP1, PRRX1, AQP3, SFN, GPR110, GDF15, RASGRF2 and RND1 and/or the level of expression of at least one further gene selected from DMBT1, KIAA1199, DPP6, SLC51B and NUDT11 (particularly DMBT1 and/or KIAA1199) may also be determined.

In a further embodiment of the method according to the third aspect of the invention, it is preferred that the level of expression of TMSB15A and at least one further gene selected from ELF5, AZGP1, PRRX1, AQP3, SFN, GPR110, GDF15, RASGRF2 and RND1 is determined in the sample obtained from the subject. In this embodiment, it is furthermore preferred that the level of expression of at least two of the aforementioned further genes is determined. For example, the level of expression of TMSB15A, ELF5 and AZGP1 may be determined, or the level of expression of TMSB15A, ELF5 and PRRX1 may be determined, or the level of expression of TMSB15A, ELF5 and AQP3 may be determined, or the level of expression of TMSB15A, ELF5 and SFN may be determined, or the level of expression of TMSB15A, ELF5 and GPR110 may be determined, or the level of expression of TMSB15A, ELF5 and GDF15 may be determined, or the level of expression of TMSB15A, ELF5 and RASGRF2 may be determined, or the level of expression of TMSB15A, ELF5 and RND1 may be determined, or the level of expression of TMSB15A, AZGP1 and PRRX1 may be determined, or the level of expression of TMSB15A, AZGP1 and AQP3 may be determined, or the level of expression of TMSB15A, AZGP1 and SFN may be determined, or the level of expression of TMSB15A, AZGP1 and GPR110 may be determined, or the level of expression of TMSB15A, AZGP1 and GDF15 may be determined, or the level of expression of TMSB15A, AZGP1 and RASGRF2 may be determined, or the level of expression of TMSB15A, AZGP1 and RND1 may be determined, or the level of expression of TMSB15A, PRRX1 and AQP3 may be determined, or the level of expression of TMSB15A, PRRX1 and SFN may be determined, or the level of expression of TMSB15A, PRRX1 and GPR110 may be determined, or the level of expression of TMSB15A, PRRX1 and GDF15 may be determined, or the level of expression of TMSB15A, PRRX1 and RASGRF2 may be determined, or the level of expression of TMSB15A, PRRX1 and RND1 may be determined, or the level of expression of TMSB15A, AQP3 and SFN may be determined, or the level of expression of TMSB15A, AQP3 and GPR110 may be determined, or the level of expression of TMSB15A, AQP3 and GDF15 may be determined, or the level of expression of TMSB15A, AQP3 and RASGRF2 may be determined, or the level of expression of TMSB15A, AQP3 and RND1 may be determined, or the level of expression of TMSB15A, SFN and GPR110 may be determined, or the level of expression of TMSB15A, SFN and GDF15 may be determined, or the level of expression of TMSB15A, SFN and RASGRF2 may be determined, or the level of expression of TMSB15A, SFN and RND1 may be determined, or the level of expression of TMSB15A, GPR110 and GDF15 may be determined, or the level of expression of TMSB15A, GPR110 and RASGRF2 may be determined, or the level of expression of TMSB15A, GPR110 and RND1 may be determined, or the level of expression of TMSB15A, GDF15 and RASGRF2 may be determined, or the level of expression of TMSB15A, GDF15 and RND1 may be determined, or the level of expression of TMSB15A, RASGRF2 and RND1 may be determined. In addition thereto, the level of expression of at least one further gene selected from FGG, CYP1A1, CEACAM5, CTHRC1, NTRK2 and RASGRF2 and/or the level of expression of at least one further gene selected from DMBT1, KIAA1199, DPP6, SLC51B and NUDT11 (particularly DMBT1 and/or KIAA1199) may also be determined.

In a further embodiment of the method according to the third aspect of the invention, it is preferred that the level of expression of TMSB15A and at least one further gene selected from DMBT1, KIAA1199, DPP6, SLC51B and NUDT11 is determined in the sample obtained from the subject. In this embodiment, it is furthermore preferred that the level of expression of at least two of the aforementioned further genes is determined. For example, the level of expression of KIAA199, DMBT1 and TMSB15A may be determined, or the level of expression of KIAA1199, TMSB15A and DPP6 may be determined, or the level of expression of KIAA1199, TMSB15A and SLC51B may be determined, or the level of expression of KIAA1199, TMSB15A and NUDT11 may be determined, or the level of expression of DMBT1, TMSB15A and DPP6 may be determined, or the level of expression of DMBT1, TMSB15A and SLC51B may be determined, or the level of expression of DMBT1, TMSB15A and NUDT11 may be determined, or the level of expression of TMSB15A, DPP6 and SLC51B may be determined, or the level of expression of TMSB15A, DPP6 and NUDT11 may be determined, or the level of expression of TMSB15A, SLC51B and NUDT11 may be determined. In addition thereto, the level of expression of at least one further gene selected from FGG, CYP1A1, CEACAM5, CTHRC1, NTRK2 and RASGRF2 and/or the level of expression of at least one further gene selected from ELF5, AZGP1, PRRX1, AQP3, SFN, GPR110, GDF15, RASGRF2 and RND1 may also be determined.

In the method according to the third aspect of the invention, it is particularly preferred that the level of expression of TMSB15A and at least one further gene selected from DMBT1 and KIAA1199 is determined in the sample obtained from the subject. Accordingly, it is preferred that the level of expression of KIAA1199 and TMSB15A is determined, or that the level of expression of DMBT1 and TMSB15A is determined. Most preferably, the level of expression of KIAA1199, DMBT1 and TMSB15A is determined in the sample obtained from the subject.

In the method according to the second aspect of the invention, preferably, it is determined that the subject is prone to develop progressive COPD if the level of expression of a majority of the number of genes tested (i.e., of the number of genes, the expression of which has been tested) is altered in the sense that (i) the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s). If only one marker gene (i.e., TMSB15A) is tested, then the alteration of the level of expression of this marker gene is decisive for determining whether or not the subject is prone to develop progressive COPD. If two or more marker genes are tested, then a decrease or increase in the level of expression of a majority of the number of these marker genes is required for determining that the subject is prone to develop progressive COPD. The term "majority" (as in the expression "majority of the number of genes tested") means more than 50% of the number of the marker genes tested.

In accordance with the second aspect, it is furthermore preferred that an alteration in the level of expression of at least 60%, more preferably at least 70%, even more preferably at least 80%, and still more preferably at least 90% of the number of genes tested—i.e., an alteration in the sense that (i) the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s)—is required for determining that the subject is prone to develop progressive COPD.

The decrease or increase in the level of expression of the marker gene(s) tested which is required for determining that the subject is prone to develop progressive COPD in accordance with the second aspect is preferably at least a 1.5-fold decrease or increase, more preferably at least a 2-fold decrease or increase, even more preferably at least a 3-fold decrease or increase, even more preferably at least a 5-fold decrease or increase, and yet even more preferably at least a 10-fold decrease or increase.

In a preferred embodiment of the method according to the second aspect of the invention, it is determined that the subject to be tested is prone to develop progressive COPD if the level of expression of a majority of the number of genes tested is altered in the sense that (i) the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is at least 3-fold (more preferably at least 5-fold, even more preferably at least 10-fold) increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is at least 3-fold (more preferably at least 5-fold, even more preferably at least 10-fold) decreased as compared to the control expression level of the corresponding gene(s).

In a further preferred embodiment of the method according to the second aspect of the invention, it is determined that the subject to be tested is prone to develop progressive COPD if the level of expression of at least 70% (more preferably at least 80%, and even more preferably at least 90%) of the number of genes tested is altered in the sense that (i) the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s).

In a further preferred embodiment of the method according to the second aspect of the invention, it is determined that the subject to be tested is prone to develop progressive COPD if the level of expression of at least 70% (more preferably at least 80%, and even more preferably at least 90%) of the number of genes tested is altered in the sense that (i) the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is at least 3-fold (more preferably at least 5-fold, even more preferably at least 10-fold) increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is at least 3-fold (more preferably at least 5-fold, even more preferably at least 10-fold) decreased as compared to the control expression level of the corresponding gene(s).

In the method according to the third aspect of the invention, preferably, it is determined that the subject suffers from stable COPD or is prone to suffer from stable COPD if the level of expression of a majority (i.e., more than 50%) of the number of genes tested is altered in the sense that (i) the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s).

In accordance with the third aspect, it is furthermore preferred that an alteration in the level of expression of at least 60%, more preferably at least 70%, even more preferably at least 80%, and still more preferably at least 90% of the number of genes tested—i.e., an alteration in the sense that (i) the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s)—is required for determining that the subject suffers from stable COPD or is prone to suffer from stable COPD.

The decrease or increase in the level of expression of the marker gene(s) tested which is required for determining that the subject suffers from stable COPD or is prone to suffer from stable COPD in accordance with the third aspect is preferably at least a 1.5-fold decrease or increase, more preferably at least a 2-fold decrease or increase, even more preferably at least a 3-fold decrease or increase, even more preferably at least a 5-fold decrease or increase, and yet even more preferably at least a 10-fold decrease or increase.

In a preferred embodiment of the method according to the third aspect of the invention, it is determined that the subject to be tested suffers from stable COPD or is prone to suffer from stable COPD if the level of expression of a majority of the number of genes tested is altered in the sense that (i) the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is at least 3-fold (more preferably at least 5-fold, even more preferably at least 10-fold) increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is at least 3-fold (more preferably at least 5-fold, even more preferably at least 10-fold) decreased as compared to the control expression level of the corresponding gene(s).

In a further preferred embodiment of the method according to the third aspect of the invention, it is determined that the subject to be tested suffers from stable COPD or is prone to suffer from stable COPD if the level of expression of at least 70% (more preferably at least 80%, and even more preferably at least 90%) of the number of genes tested is altered in the sense that (i) the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s).

In a further preferred embodiment of the method according to the third aspect of the invention, it is determined that the subject to be tested suffers from stable COPD or is prone to suffer from stable COPD if the level of expression of at least 70% (more preferably at least 80%, and even more preferably at least 90%) of the number of genes tested is altered in the sense that (i) the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is at least 3-fold (more preferably at least 5-fold, even more preferably at least 10-fold) increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is at least 3-fold (more preferably at least 5-fold, even more preferably at least 10-fold) decreased as compared to the control expression level of the corresponding gene(s).

The present invention furthermore relates to the use of the gene TMSB15A as a marker in an in vitro diagnostic method of assessing the susceptibility of a subject to develop progressive COPD. In particular, in accordance with the fifth aspect, the invention relates to the use of a pair of primers for (i.e., binding to) a transcript of the gene TMSB15A in an in vitro diagnostic method of assessing the susceptibility of a subject to develop progressive COPD. Non-limiting examples of such an in vitro method are the methods according to the second aspect of the present invention. The transcript is preferably an mRNA of the gene TMSB15A (e.g., the specific mRNA of TMSB15A listed in Table 1 above) or a cDNA synthesized from the mRNA of the gene TMSB15A (e.g., a cDNA synthesized from the specific mRNA of TMSB15A listed in Table 1 above). The primers can be designed using methods known in the art (as also described, e.g., in Green et al., 2012) so as to allow the specific amplification/quantification of the transcript of the gene TMSB15A. Furthermore, the primers are preferably DNA primers. The in vitro diagnostic method of assessing the susceptibility of a subject to develop progressive COPD, in which the pair of primers is to be used, preferably comprises a step of determining the expression level of the gene TMSB15A in a sample obtained from the subject. The preferred features/embodiments of the method according to the second aspect of the present invention as described herein, including in particular the preferred embodiments of determining expression levels, the preferred embodiments of the sample, and the preferred embodiments of the subject, also apply to the method in which the pair of primers is to be used.

In accordance with the fifth aspect, the present invention also relates to the use of a nucleic acid probe to (i.e., binding to) a transcript of the gene TMSB15A in an in vitro diagnostic method of assessing the susceptibility of a subject to develop progressive COPD. Non-limiting examples of such an in vitro method are the methods according to the second aspect of the present invention. The transcript is preferably an mRNA of the gene TMSB15A (e.g., the specific mRNA of TMSB15A listed in Table 1 above) or a cDNA synthesized from the mRNA of the gene TMSB15A (e.g., a cDNA synthesized from the specific mRNA of TMSB15A listed in Table 1 above). The nucleic acid probe comprises or consists of a nucleic acid capable of hybridizing with the above-mentioned transcript. The nucleic acid probe is preferably a single-stranded DNA probe or a single-stranded RNA probe, more preferably a single-stranded DNA probe. It is furthermore preferred that the nucleic acid probe (which may be, e.g., a single-stranded DNA or single-stranded RNA, and is preferably a single-stranded DNA) is an oligonucleotide probe having, e.g., 10 to 80 nucleotides, preferably 15 to 60 nucleotides, more preferably 20 to 35 nucleotides, and even more preferably about 25 nucleotides. Such nucleic acid probes can be designed using methods known in the art (as also described, e.g., in Green et al., 2012) so as to allow the specific detection and quantification of the transcript of the corresponding gene. The in vitro diagnostic method of assessing the susceptibility of a subject to develop progressive COPD, in which the nucleic acid probe is to be used, preferably comprises a step of determining the expression level of the gene TMSB15A in a sample obtained from the subject. The preferred features/embodiments of the method according to the second aspect of the invention as described herein, including in particular the preferred embodiments of determining expression levels, the preferred embodiments of the sample, and the preferred embodiments of the subject, also apply to the method in which the nucleic acid probe is to be used.

In the fifth aspect, the invention further relates to the use of a microarray comprising a nucleic acid probe to (i.e., binding to) a transcript of the gene TMSB15A and optionally comprising nucleic acid probes to the transcripts of one or more further genes selected from DMBT1, KIAA1199, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in an in vitro diagnostic method of assessing the susceptibility of a subject to develop progressive COPD. The microarray preferably comprises nucleic acid probes to the transcript of TMSB15A and to the transcripts of at least one, more preferably at least two, even more preferably at least three of the above-mentioned further genes. Each of the transcripts is preferably an mRNA of the corresponding gene (including, e.g., any one of the corresponding specific mRNAs listed in Table 1 above) or a cDNA synthesized from the mRNA of the gene (including, e.g., a cDNA synthesized from any one of the corresponding specific mRNAs listed in Table 1 above). Each of the nucleic acid probes is preferably a single-stranded DNA probe or a single-stranded RNA probe, more preferably a single-stranded DNA probe. It is furthermore preferred that the nucleic acid probes (which may be, e.g., single-stranded DNA or single-stranded RNA, preferably single-stranded DNA) are oligonucleotide probes having, e.g., 10 to 80 nucleotides, preferably 15 to 60 nucleotides, more preferably 20 to 35 nucleotides, and even more preferably about 25 nucleotides. The in vitro diagnostic method of assessing the susceptibility of a subject to develop progressive COPD, in which the microarray is to be used, preferably comprises a step of determining the expression level of the gene TMSB15A and optionally of the one or more further genes in a sample obtained from the subject. The preferred features/embodiments of the method according to the second aspect of the invention as described herein, including in particular the preferred embodiments of determining expression levels, the preferred embodiments of the sample, and the preferred embodiments of the subject, also apply to the method in which the microarray is to be used.

In accordance with the fifth aspect, the invention is also directed to the use of an antibody against (i.e., binding to) the protein TMSB15A in an in vitro diagnostic method of assessing the susceptibility of a subject to develop progressive COPD. The antibody binds specifically to the protein TMSB15A and may be, e.g., a polyclonal antibody or a monoclonal antibody. Preferably, the antibody is a monoclonal antibody. The antibody may further be a full/intact immunoglobulin molecule or a fragment/part thereof (such as, e.g., a separated light or heavy chain, an Fab fragment, an Fab/c fragment, an Fv fragment, an Fab' fragment, or an F(ab')$_2$ fragment), provided that the fragment/part substantially retains the binding specificity of the corresponding full immunoglobulin molecule. The antibody may also be a modified and/or altered antibody, such as a chimeric or humanized antibody, a bifunctional or trifunctional antibody, or an antibody construct (such as a single-chain variable fragment (scFv) or an antibody-fusion protein). The antibody can be prepared using methods known in the art, as also described, e.g., in Harlow et al., 1998. For example, monoclonal antibodies can be prepared by methods such as the hybridoma technique (see, e.g., Köhler et al., 1975), the trioma technique, the human B-cell hybridoma technique (see, e.g., Kozbor et al., 1983) or the EBV-hybridoma technique (see, e.g., Cole et al., 1985). The protein TMSB15A may be, e.g., the specific TMSB15A protein listed in Table 1 above. The in vitro diagnostic method of assessing the susceptibility of a subject to develop progressive COPD, in which the antibody is to be used, preferably comprises a step of determining the amount of the protein TMSB15A in a sample obtained from the subject. The preferred features/embodiments of the method according to the second aspect of the invention as described herein, including in particular the preferred embodiments of determining the amount of a specific protein in a sample (as discussed in connection with the determination of translation levels), the preferred embodiments of the sample, and the preferred embodiments of the subject, also apply to the method in which the antibody is to be used.

Moreover, in accordance with the seventh aspect, the present invention relates to the use of a pair of primers for (i.e., binding to) a transcript of the gene TMSB15A in an in vitro method of diagnosing stable COPD in a subject or assessing the susceptibility of a subject to develop stable COPD. Non-limiting examples of such an in vitro method are the methods according to the third aspect of the present invention. The transcript is preferably an mRNA of the gene TMSB15A (e.g., the specific mRNA of TMSB15A listed in Table 1 above) or a cDNA synthesized from the mRNA of the gene TMSB15A (e.g., a cDNA synthesized from the specific mRNA of TMSB15A listed in Table 1 above). The primers can be designed using methods known in the art (as also described, e.g., in Green et al., 2012) so as to allow the specific amplification/quantification of the transcript of the gene TMSB15A. Furthermore, the primers are preferably DNA primers. The in vitro method of diagnosing stable COPD in a subject or assessing the susceptibility of a subject to develop stable COPD, in which the pair of primers is to be used, preferably comprises a step of determining the expression level of the gene TMSB15A in a sample obtained from the subject. The preferred features/embodiments of the method according to the third aspect of the present invention as described herein, including in particular the preferred embodiments of determining expression levels, the preferred embodiments of the sample, and the preferred embodiments of the subject, also apply to the method in which the pair of primers is to be used.

In accordance with the seventh aspect, the present invention also relates to the use of a nucleic acid probe to (i.e., binding to) a transcript of the gene TMSB15A in an in vitro method of diagnosing stable COPD in a subject or assessing the susceptibility of a subject to develop stable COPD. Non-limiting examples of such an in vitro method are the methods according to the third aspect of the present invention. The transcript is preferably an mRNA of the gene TMSB15A (e.g., the specific mRNA of TMSB15A listed in Table 1 above) or a cDNA synthesized from the mRNA of the gene TMSB15A (e.g., a cDNA synthesized from the specific mRNA of TMSB15A listed in Table 1 above). The nucleic acid probe comprises or consists of a nucleic acid capable of hybridizing with the above-mentioned transcript. The nucleic acid probe is preferably a single-stranded DNA probe or a single-stranded RNA probe, more preferably a single-stranded DNA probe. It is furthermore preferred that the nucleic acid probe (which may be, e.g., a single-stranded DNA or a single-stranded RNA, and is preferably a single-stranded DNA) is an oligonucleotide probe having, e.g., 10 to 80 nucleotides, preferably 15 to 60 nucleotides, more preferably 20 to 35 nucleotides, and even more preferably about 25 nucleotides. Such nucleic acid probes can be designed using methods known in the art (as also described, e.g., in Green et al., 2012) so as to allow the specific detection and quantification of the transcript of the corresponding gene. The in vitro method of diagnosing stable COPD in a subject or assessing the susceptibility of a subject to develop stable COPD, in which the nucleic acid probe is to be used, preferably comprises a step of determining the expression level of the gene TMSB15A in a sample obtained from the subject. The preferred features/embodiments of the method according to the third aspect of the invention as described herein, including in particular the preferred embodiments of determining expression levels, the preferred embodiments of the sample, and the preferred embodiments of the subject, also apply to the method in which the nucleic acid probe is to be used.

In the seventh aspect, the invention further relates to the use of a microarray comprising a nucleic acid probe to (i.e., binding to) a transcript of the gene TMSB15A and optionally comprising nucleic acid probes to the transcripts of one or more further genes selected from DMBT1, KIAA1199, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in an in vitro method of diagnosing stable COPD in a subject or assessing the susceptibility of a subject to develop stable COPD. The microarray preferably comprises nucleic acid probes to the transcript of TMSB15A and to the transcripts of at least one, more preferably at least two, even more preferably at least three of the above-mentioned further genes. Each of the transcripts is preferably an mRNA of the corresponding gene (including, e.g., any one of the corresponding specific mRNAs listed in Table 1 above) or a cDNA synthesized from the mRNA of the gene (including, e.g., a cDNA synthesized from any one of the corresponding specific mRNAs listed in Table 1 above). Each of the nucleic acid probes is preferably a single-stranded DNA probe or a single-stranded RNA probe, more preferably a single-stranded DNA probe. It is furthermore preferred that the nucleic acid probes (which may be, e.g., single-stranded DNA or single-stranded RNA, preferably single-stranded DNA) are oligonucleotide probes having, e.g., 10 to 80 nucleotides, preferably 15 to 60 nucleotides, more preferably 20 to 35 nucleotides, and even more preferably about 25 nucleotides. The in vitro method of diagnosing stable COPD in a subject or assessing the susceptibility of a subject to develop stable COPD, in which the microarray is to be used, preferably comprises a step of determining the expression level of the gene TMSB15A and optionally of the one or more further genes in a sample obtained from the subject.

The preferred features/embodiments of the method according to the third aspect of the invention as described herein, including in particular the preferred embodiments of determining expression levels, the preferred embodiments of the sample, and the preferred embodiments of the subject, also apply to the method in which the microarray is to be used.

In accordance with the seventh aspect, the invention is also directed to the use of an antibody against (i.e., binding to) the protein TMSB15A in an in vitro method of diagnosing stable COPD in a subject or assessing the susceptibility of a subject to develop stable COPD. The antibody binds specifically to the protein TMSB15A and may be, e.g., a polyclonal antibody or a monoclonal antibody. Preferably, the antibody is a monoclonal antibody. The antibody may further be a full/intact immunoglobulin molecule or a fragment/part thereof (such as, e.g., a separated light or heavy chain, an Fab fragment, an Fab/c fragment, an Fv fragment, an Fab' fragment, or an F(ab')$_2$ fragment), provided that the fragment/part substantially retains the binding specificity of the corresponding full immunoglobulin molecule. The antibody may also be a modified and/or altered antibody, such as a chimeric or humanized antibody, a bifunctional or trifunctional antibody, or an antibody construct (such as a single-chain variable fragment (scFv) or an antibody-fusion protein). The antibody can be prepared using methods known in the art, as also described, e.g., in Harlow et al., 1998. For example, monoclonal antibodies can be prepared by methods such as the hybridoma technique (see, e.g., Köhler et al., 1975), the trioma technique, the human B-cell hybridoma technique (see, e.g., Kozbor et al., 1983) or the EBV-hybridoma technique (see, e.g., Cole et al., 1985). The protein TMSB15A may be, e.g., the specific TMSB15A protein listed in Table 1 above. The in vitro method of diagnosing stable COPD in a subject or assessing the susceptibility of a subject to develop stable COPD, in which the antibody is to be used, preferably comprises a step of determining the amount of the protein TMSB15A in a sample obtained from the subject. The preferred features/embodiments of the method according to the third aspect of the invention as described herein, including in particular the preferred embodiments of determining the amount of a specific protein in a sample (as discussed in connection with the determination of translation levels), the preferred embodiments of the sample, and the preferred embodiments of the subject, also apply to the method in which the antibody is to be used.

In accordance with the sixth aspect, the present invention provides a method of treating COPD, the method comprising administering a drug against COPD to a subject that has been identified in a method according to the second aspect of the invention as being prone to develop progressive COPD. The invention likewise provides a drug against COPD for use in treating COPD in a subject that has been identified in a method according to the second aspect as being prone to develop progressive COPD. The invention also relates to the use of a drug against COPD in the preparation of a pharmaceutical composition for treating COPD in a subject that has been identified in a method according to the second aspect as being prone to develop progressive COPD. The subject referred to above is as defined in the methods according to the second aspect of the invention and, accordingly, is preferably a human.

Moreover, in accordance with the eighth aspect, the present invention provides a method of treating or preventing COPD, the method comprising administering a drug against COPD to a subject that has been identified in a method according to the third aspect of the invention as suffering from stable COPD or as being prone to suffer from stable COPD. It will be understood that a subject that has been identified as suffering from stable COPD can be treated by administering a drug against COPD, while a subject that has been identified as being prone to suffer from stable COPD can be prevented from developing COPD by administering a drug against COPD. The invention likewise provides a drug against COPD for use in treating or preventing COPD in a subject that has been identified in a method according to the third aspect as suffering from stable COPD or as being prone to suffer from stable COPD. The invention also relates to the use of a drug against COPD in the preparation of a pharmaceutical composition for treating or preventing COPD in a subject that has been identified in a method according to the third aspect as suffering from stable COPD or as being prone to suffer from stable COPD. The subject referred to above is as defined in the methods according to the third aspect of the invention and, accordingly, is preferably a human.

The drug against COPD to be administered to a subject in accordance with the sixth or eighth aspect of the invention is not particularly limited and may be, for example, a $\beta_2$-agonist (such as, e.g., bitolterol, carbuterol, fenoterol, pirbuterol, procaterol, reproterol, rimiterol, salbutamol, levosalbutamol, terbutaline, tulobuterol, arformoterol, bambuterol, clenbuterol, formoterol, olodaterol, salmeterol, indacaterol, or a pharmaceutically acceptable salt of any of the aforementioned agents), a glucocorticoid (such as, e.g., beclometasone, betamethasone, budesonide, ciclesonide, flunisolide, fluticasone, mometasone, triamcinolone, or a pharmaceutically acceptable salt of any of the aforementioned agents), an anticholinergic or a muscarinic antagonist (such as, e.g., aclidinium bromide, glycopyrronium bromide, ipratropium bromide, oxitropium bromide, tiotropium bromide, or a pharmaceutically acceptable salt of any of the aforementioned agents), a mast cell stabilizer (such as, e.g., cromoglicate, nedocromil, or a pharmaceutically acceptable salt of any of the aforementioned agents), a xanthine derivative (such as, e.g., acefylline, ambuphylline, bamifylline, doxofylline, enprofylline, etamiphylline, proxyphylline, theobromine, theophylline, aminophylline, choline theophyllinate, or a pharmaceutically acceptable salt of any of the aforementioned agents), a leukotriene antagonist (such as, e.g., montelukast, pranlukast, zafirlukast, or a pharmaceutically acceptable salt of any of the aforementioned agents), a lipoxygenase inhibitor (such as, e.g., zileuton or a pharmaceutically acceptable salt thereof), a thromboxane receptor antagonist (such as, e.g., ramatroban, seratrodast, or a pharmaceutically acceptable salt of any of the aforementioned agents) a non-xanthine PDE4 inhibitor (such as, e.g., ibudilast, roflumilast, or a pharmaceutically acceptable salt of any of the aforementioned agents), or any other drug against COPD (such as, e.g., amlexanox, eprozinol, fenspiride, omalizumab, epinephrine, hexoprenaline, isoprenaline, isoproterenol, orciprenaline, metaproterenol, atropine, or a pharmaceutically acceptable salt of any of the aforementioned agents), or any combination thereof. A particularly preferred drug against COPD is roflumilast.

In the eleventh aspect, the present invention provides an in vitro method of monitoring the progression of COPD in a subject, the method comprising:
   determining the level of expression of one or more genes selected from NTRK2 and RASGRF2 in a first sample obtained from the subject;
   determining the level of expression of the one or more genes in a second sample obtained from the subject at a later point in time than the first sample;

comparing the level of expression of the one or more genes in the second sample to the level of expression of the corresponding gene(s) in the first sample; and assessing (or determining) the progression of COPD in the subject, wherein a decrease in the level of expression of NTRK2 and/or RASGRF2 in the second sample as compared to the level of expression of the corresponding gene(s) in the first sample is indicative of an amelioration (i.e., an improvement) of COPD in the subject, and wherein an increase in the level of expression of NTRK2 and/or RASGRF2 in the second sample as compared to the level of expression of the corresponding gene(s) in the first sample is indicative of a worsening of COPD in the subject.

As demonstrated in Example 1 and shown in FIGS. 4A and 8A, a decrease in the level of expression of NTRK2 and/or RASGRF2 is indicative of an amelioration/improvement of COPD whereas an increase in the level of expression of these genes is indicative of a worsening of COPD. Monitoring the progression of COPD in a subject suffering from this disease can be useful, e.g., for assessing the prospects of success of a treatment, of a new medication, or of a new dosing regimen.

In the eleventh aspect, it is preferred that the level of expression of the gene NTRK2 and optionally of the gene RASGRF2 is determined. More preferably, the level of expression of the genes NTRK2 and RASGRF2 is determined.

The level of expression of the above-mentioned marker genes in the first sample and in the second sample according the eleventh aspect of the invention can be determined as described in connection with the methods of the second or third aspects of the invention. For example, the level of transcription or the level of translation of the marker gene(s) NTRK2 and/or RASGRF2 can be determined. It is preferred that the level of expression of the one or more genes selected from NTRK2 and RASGRF2 in the first sample and in the second sample is determined by determining the level of transcription of the corresponding gene(s). The level of transcription is preferably determined using qRT-PCT or a microarray.

The subject to be tested in the method according to the eleventh aspect of the invention is as defined in connection with the methods of the second or third aspects of the invention, and preferably is a human or a non-human mammal, more preferably a human. It is furthermore preferred that the subject to be tested/monitored in accordance with the eleventh aspect is a subject (preferably a human) that has been diagnosed as suffering from COPD (e.g., at the point in time when the first sample was obtained).

While the first sample and the second sample obtained from the subject can, in principle, be any tissue sample or serum from the subject, they should both originate from the same type of tissue of the subject (or should both be serum samples). Preferably, the first sample and the second sample are lung tissue samples. More preferably, the first sample and the second sample are transbronchial lung biopsy samples or they are bronchoalveolar lavage (BAL) samples.

The second sample has been obtained from the subject at a later point in time than the first sample. For instance, the second sample may have been obtained from the subject about 2 months to about 12 months, preferably about 3 months to about 9 months (e.g., about 3 months, or about 4 months, or about 5 months, or about 6 months, or about 7 months, or about 8 months, or about 9 months), and more preferably about 3 months to about 6 months after the first sample was obtained from the subject.

As used herein, the term "about" refers to ±10% of the indicated numerical value, and in particular to ±5% of the indicated numerical value. Whenever the term "about" is used, a specific reference to the exact numerical value indicated is also included. If the term "about" is used in connection with a parameter that is quantified in integers, such as the number of nucleotides in a given nucleic acid, the numbers corresponding to ±10% or ±5% of the indicated numerical value are to be rounded to the nearest integer. For example, the expression "about 25 nucleotides" refers to the range of 23 to 28 nucleotides, in particular the range of 24 to 26 nucleotides, and preferably refers to the specific value of 25 nucleotides.

It is to be understood that the present invention specifically relates to each and every combination of features and embodiments described herein, including any combination of general and/or preferred features/embodiments. In particular, the invention specifically relates to all combinations of preferred features (including all degrees of preference) of the methods and uses provided herein.

In this specification, a number of documents including patent applications, scientific literature and manufacturers' manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention is also described by the following illustrative figures. The appended figures show:

FIG. 1: Study design of the COPD-AUVA study conducted at the Vienna Medical University (see Example 1).

Figure 2:
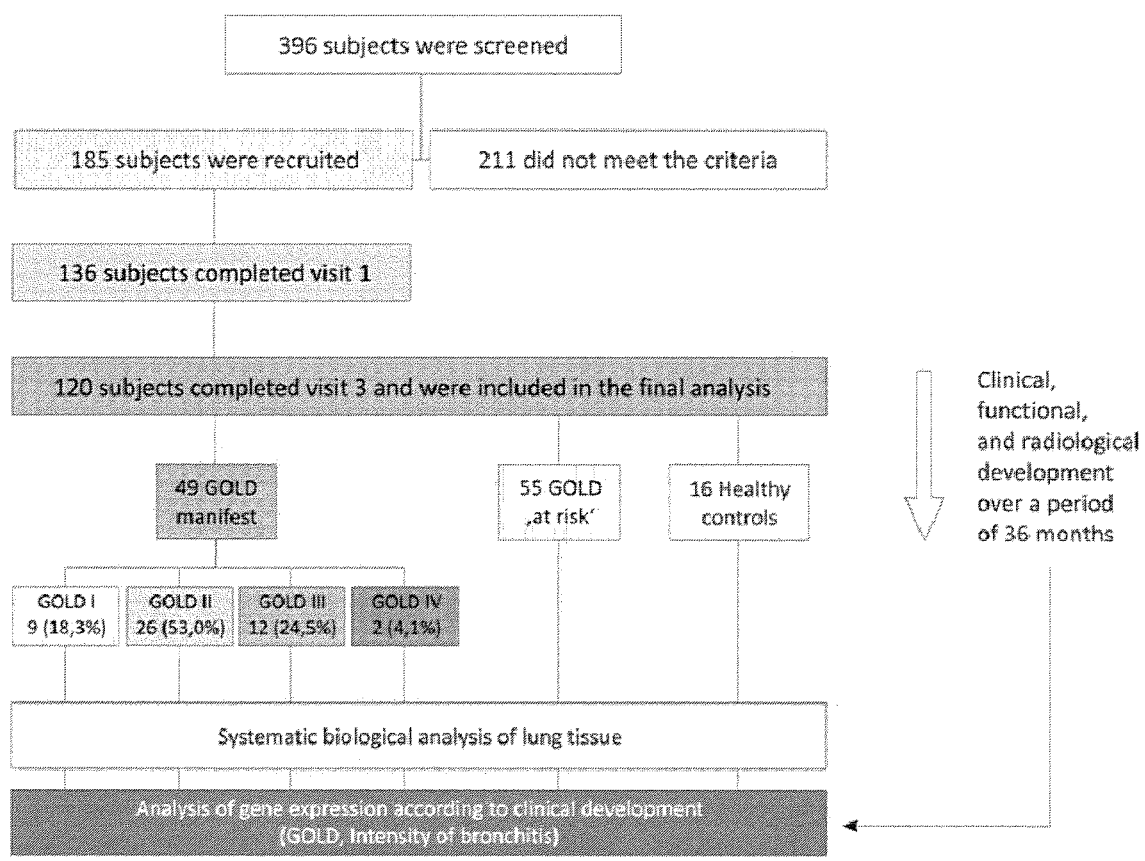

FIG. 2: Overview of the numbers of subjects of different disease states who underwent the COPD-AUVA study.

FIG. 3: Overview of healthy subjects (A) and of subjects with either chronic bronchitis but no signs of pulmonary obstruction (COPD "at risk"; "GOLD 0") at visit 1 (B) or with manifest COPD at visit 1 (C), as well as the development of COPD (severity according to GOLD criteria), bronchitis and smoking habits in these subjects over the period from visit 1 (day 0) to visit 2 (12 months) to visit 3 (36 months). The term "pack years" refers to a person's cigarette consumption calculated as the packs of cigarettes (each pack containing 20 cigarettes) smoked per day, multiplied by the length of cigarette consumption in years. (D) Clinical characteristics of participants in the COPD-AUVA study and changes between baseline and visit 3 (see Example 1).

FIG. 4: COPD Pathology module 1: Development of chronic bronchitis: Progressive inhibition of adaptive motility of mucosal cells caused by the inhibition of coordinated actin cytoskeleton movements.

Chronic bronchitis starts with the significant downregulation of genes that control assembly, polymerization, motility, stabilization and energy supply of F actin-mediated cytoskeleton movements (suppression of thymosin beta 15A (TMSB15A), dipeptidyl-peptidase 6 (DPP6), nudix (nucleoside diphosphate linked moiety X)-type motif 11 (NUDT11), and integrin alpha 10 (ITGA10)). At the same time, expression of the RASGRF2 gene known to inhibit Cdc42-mediated polymerization of actin during cellular movements is progressively increased during advancement of COPD (FIGS. 4A and 4D) indicating that the inhibition of cellular motility is not only a leading mechanism in early stages of COPD development, but also part of the progressive membrane destruction in later stages of COPD.

Of note, reduced expression of these genes is also connected to increasing intensity of bronchial inflammation. This characteristic expression pattern includes the SLC51B gene (FIG. 4D) which is as yet largely known for its capacity to transport steroid-precursor molecules in intestinal cells.

The compensatory activation of the GTPase RND1 (Rho family GTPase 1) best known for its ability to control the organization of the actin cytoskeleton in response to growth factor stimulation is just increased up to COPD GOLD stage II not only indicating a complete failure of actin-dependent cellular cytoskeleton organization in later stages of COPD, but also the loss of the regenerative capacity, as also demonstrated within Module 3 (see FIGS. 6A-6E). This in turn concurs rather well with the progressive downregulation of the cystatin M/E (CST6) gene being annotated with both functional differentiation of epithelial cells and maintenance of surface integrity.

As the coordinated action of these molecules is required for controlled movements of epithelial cells during pivotal processes, such as growth, intercalation and extrusion of cells within a cohesive cell layer system, the loss of these functions causes a profound disturbance of membrane integrity allowing for the development of non-specific bronchial inflammation that basically reflects all constituents of ventilated air including combustion products, such as cigarette smoke or welding fumes.

Figure 5:
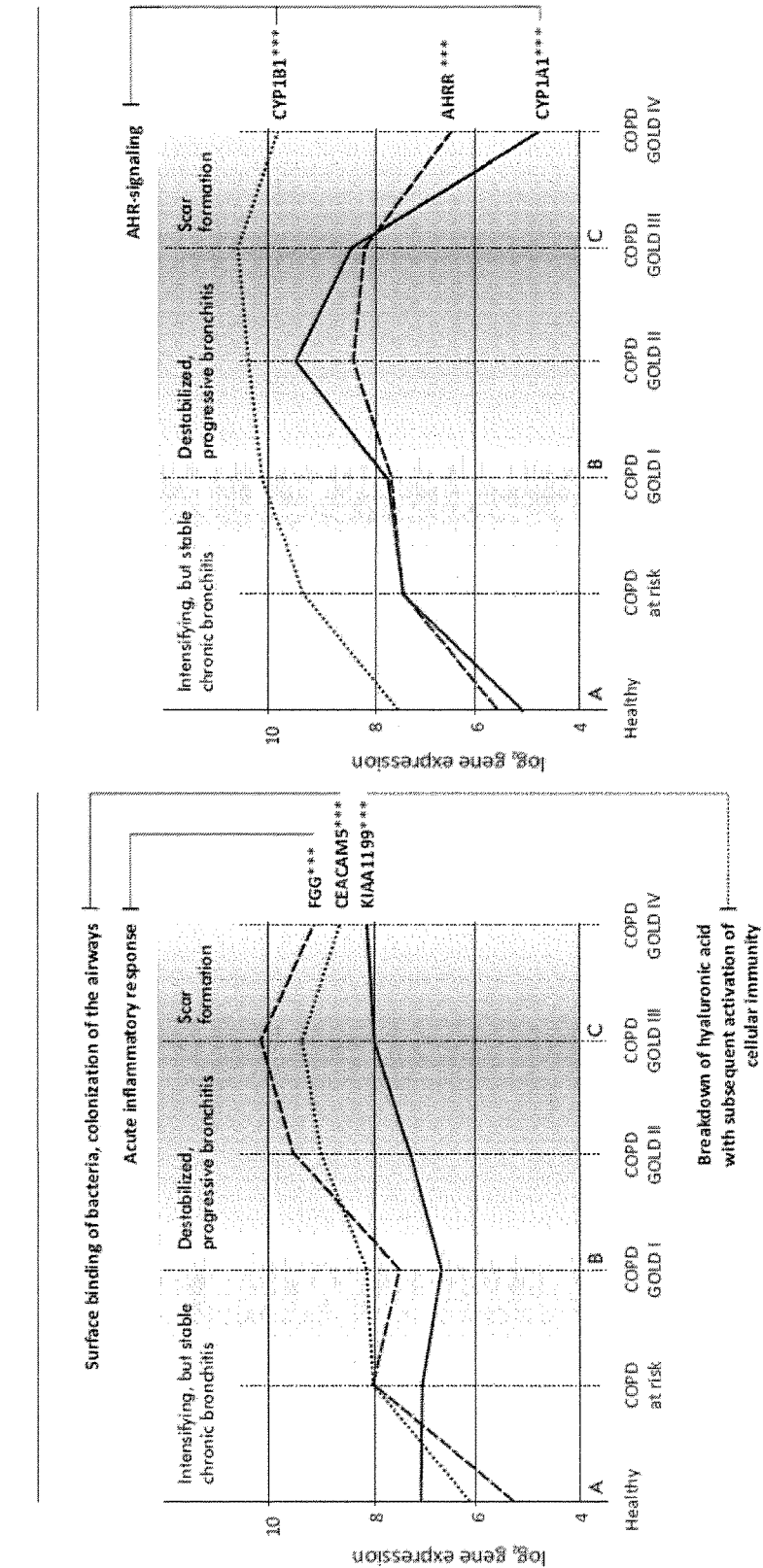
Figure 5:
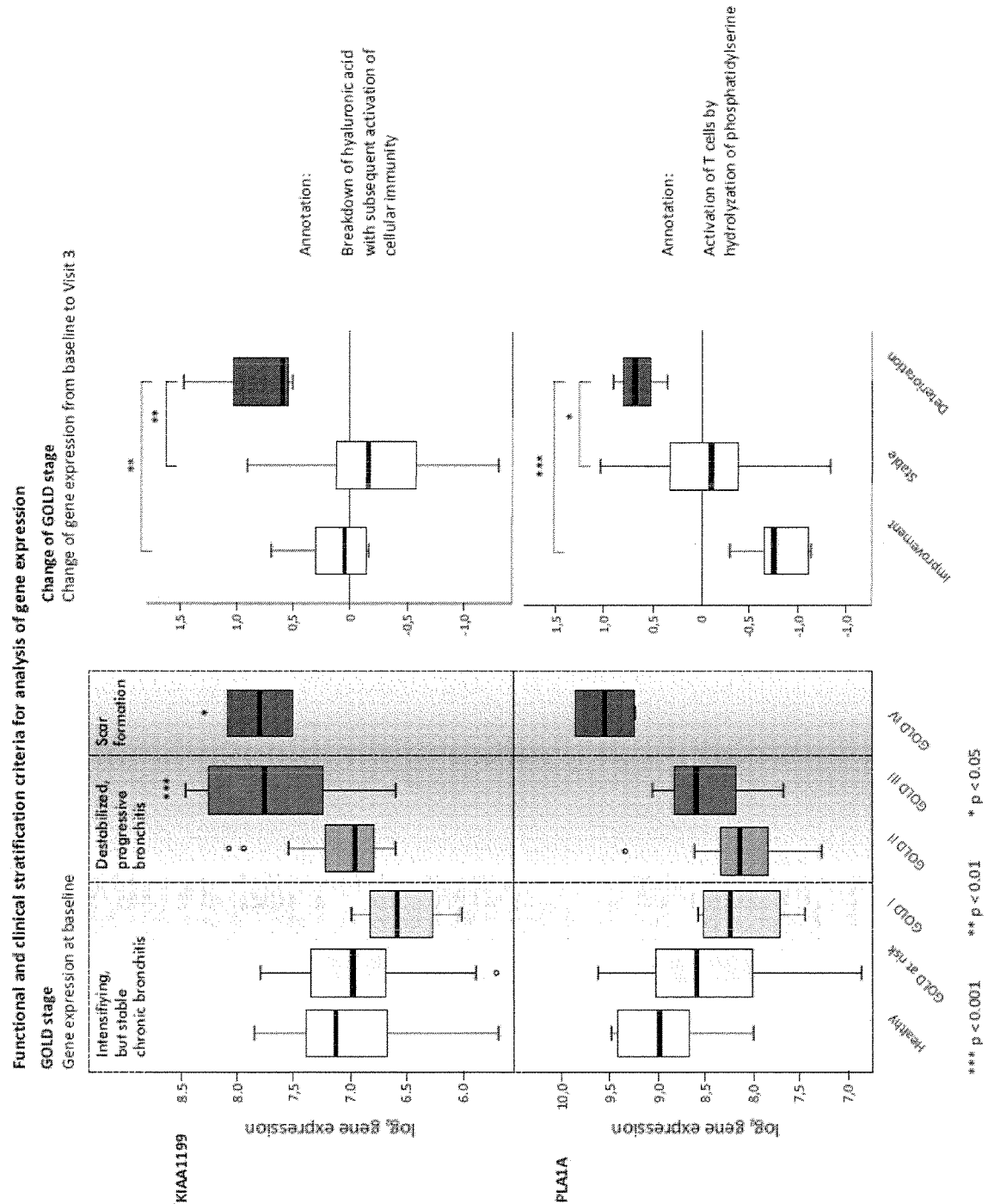
Figure 5:
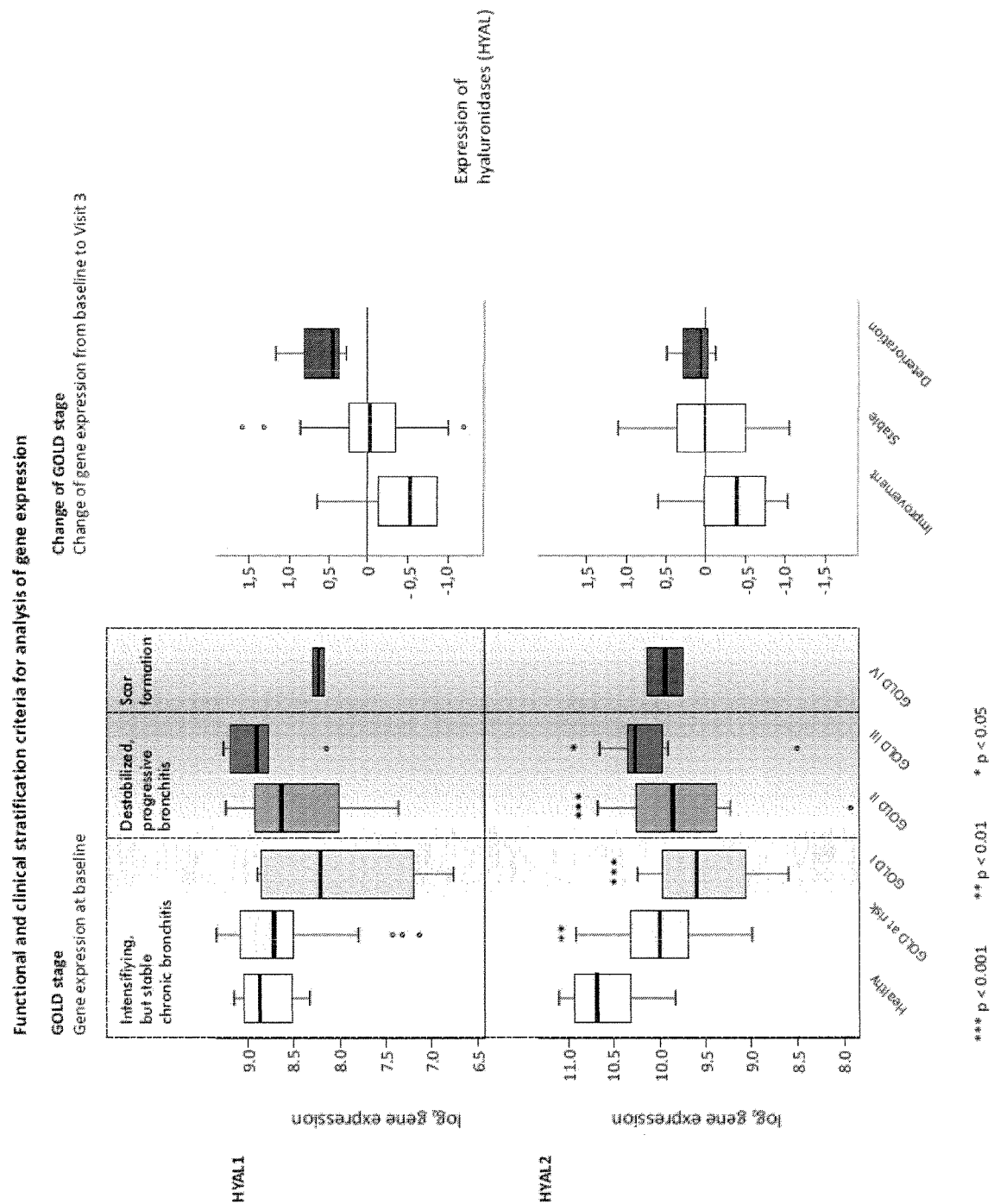
Figure 5:
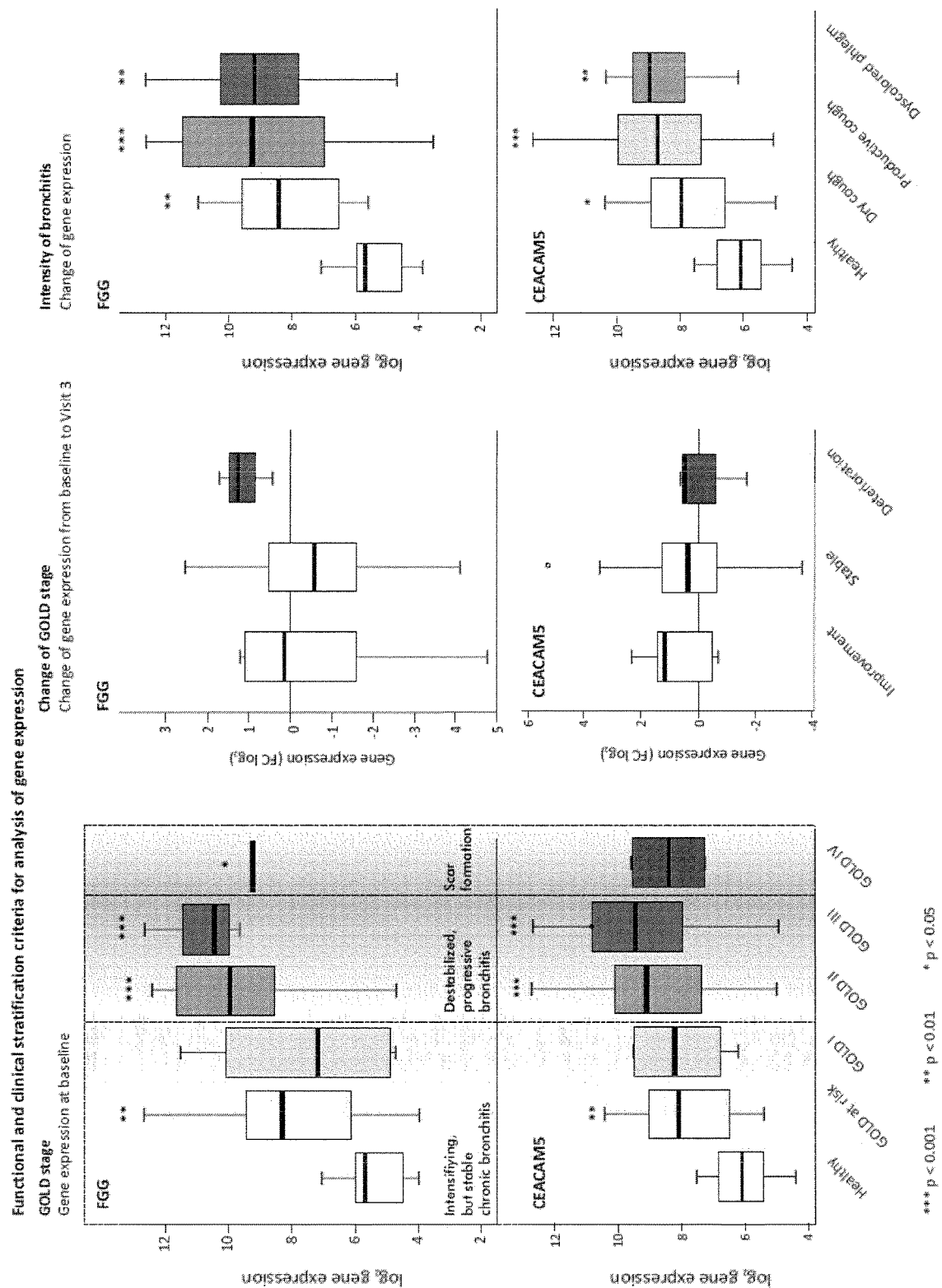
Figure 5:
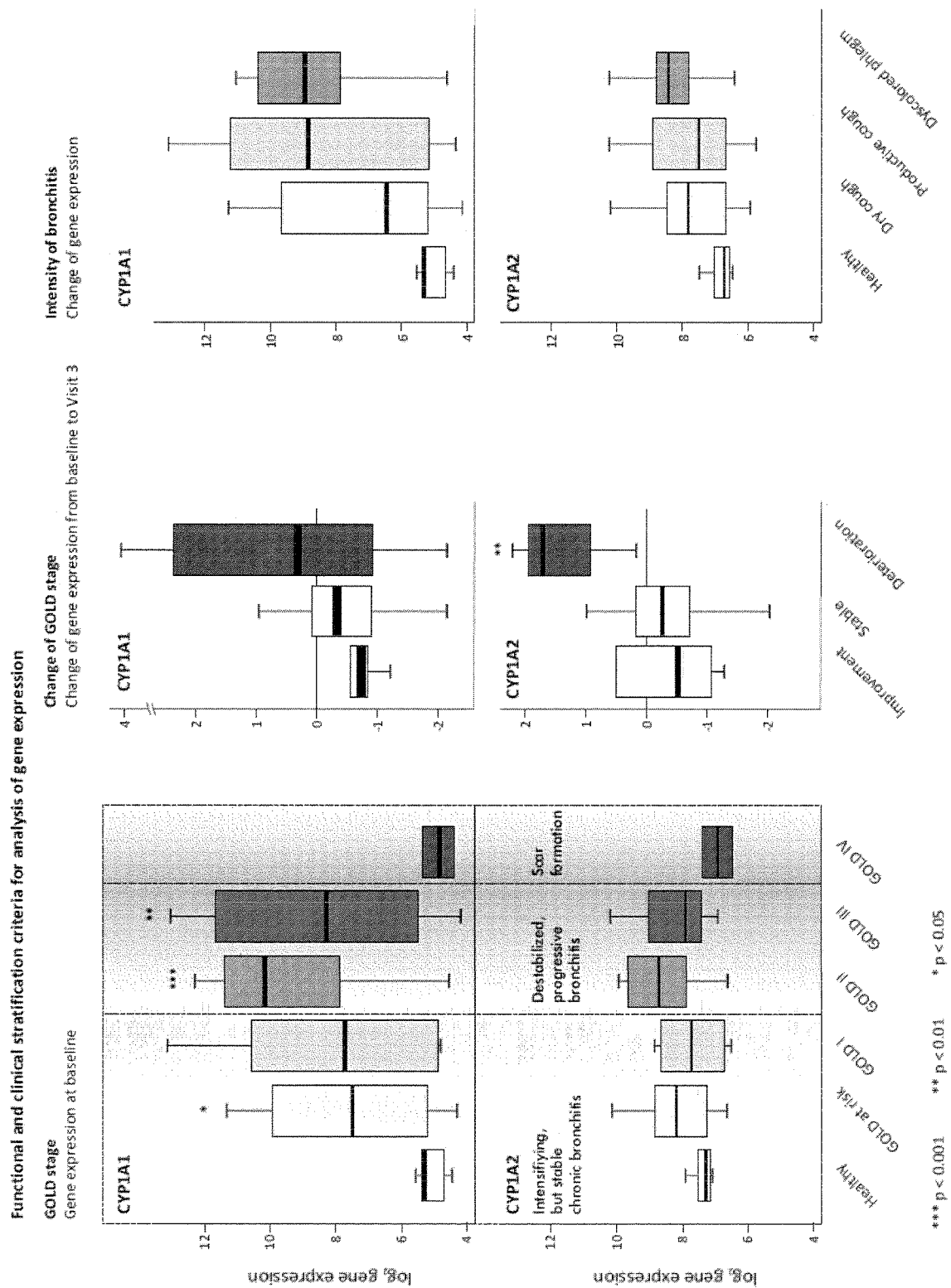
Figure 5:
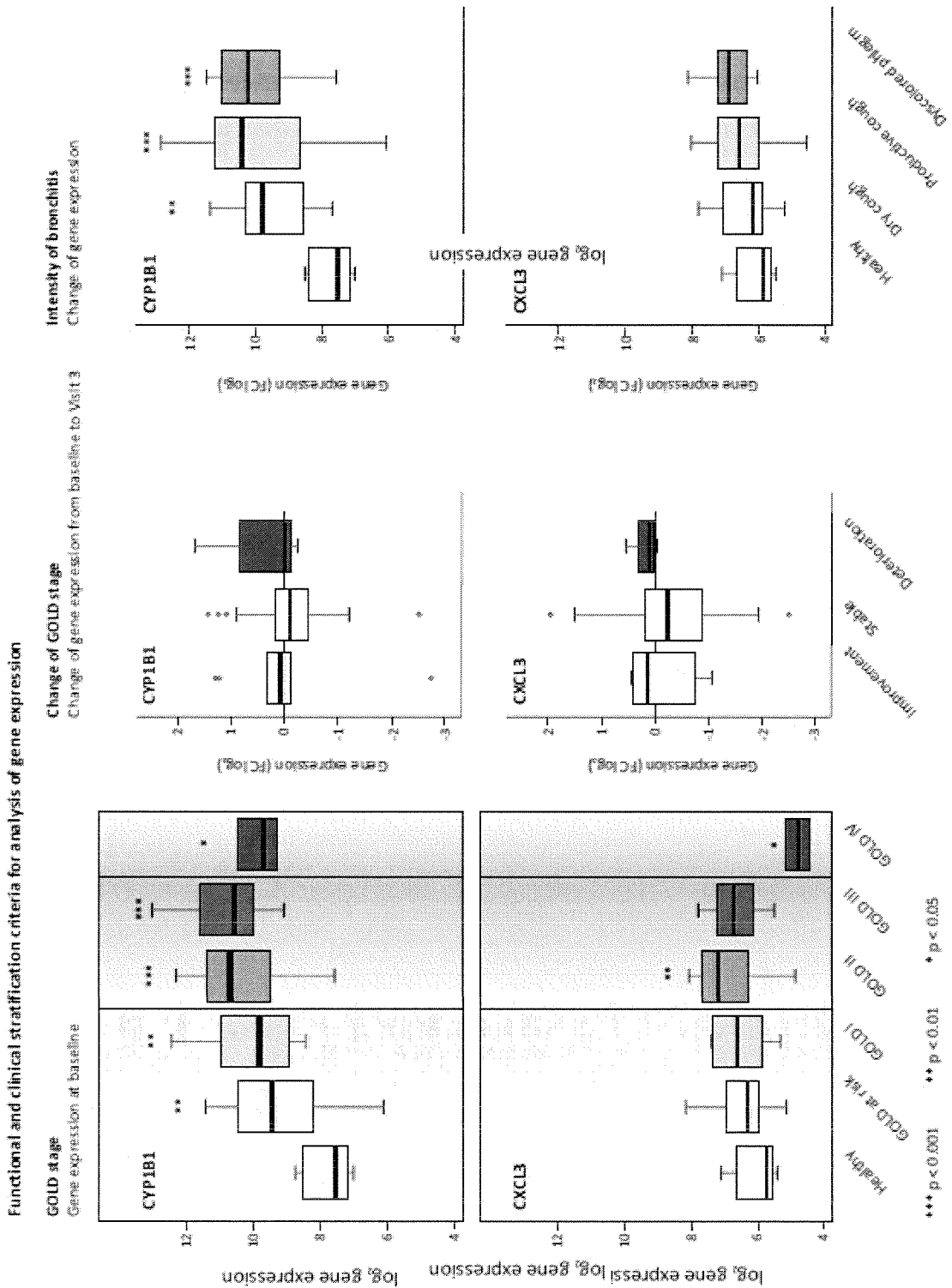
Figure 5:
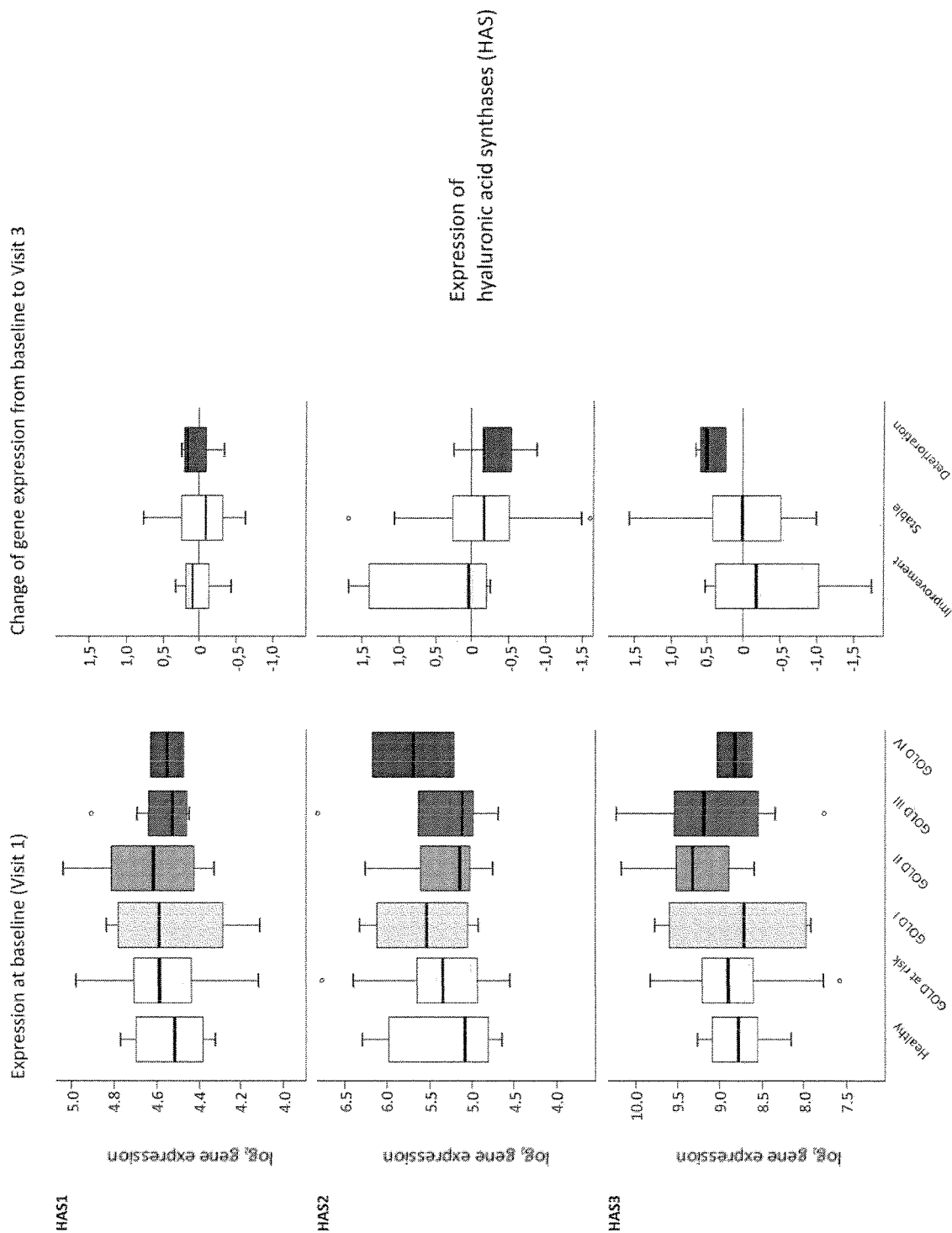
Figure 5:
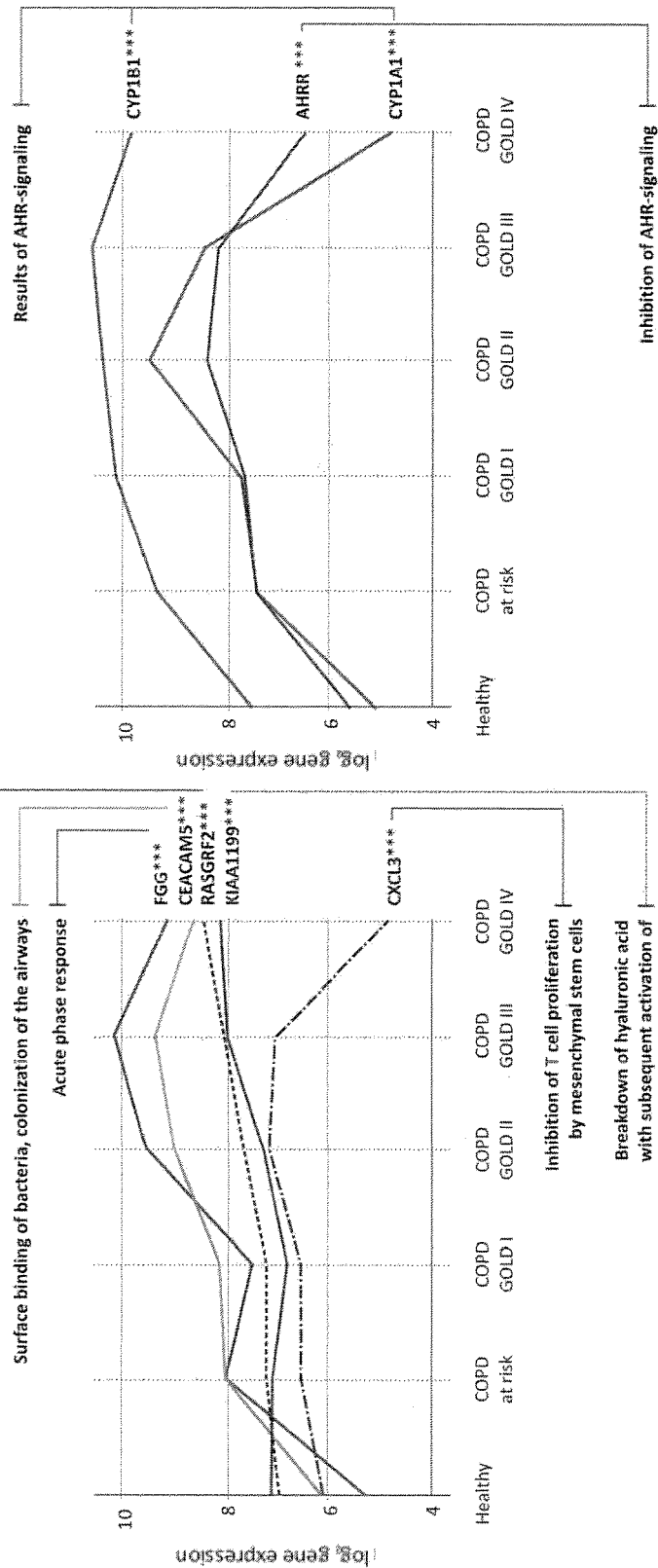

FIG. 5: COPD Pathology module 2: Bi-phasic activation of mucosal immunity.

Driven by this loss of cellular cohesion, the bronchus develops a diverse mucosal immune response that combines mechanisms of acute inflammation, such as the expression of fibrinogen (FGG) (FIGS. 5A and 5D), the upregulation of carcinoembryonic antigen-related cell adhesion molecule 5 (CEACAM 5) (FIGS. 5A and 5D), and aryl hydrocarbon receptor (AHR) signaling, the latter characterized by increased expression of cytochrome P450, family 1, subfamily A polypeptide 1 (CYP1A1) and cytochrome P450, family 1, subfamily B polypeptide 1 (CYP1B1) (FIGS. 5A and 5E, 5F). Intensity of AHR signaling is significant, in spite of the increased compensatory expression of the aryl hydrocarbon receptor repressor gene (AHRR), most likely reflecting the continuous impact of smoke. As CEACAMs have recently been shown to act as surface receptors for gram-negative bacteria such as *Neisseria meningitidis, Haemophilus influenzae* and *Moraxella catarrhalis* being frequently found in progressive bronchitis, this mechanism is prone to contribute to episodes of intensified bronchial inflammation.

Nonetheless, neither FGG nor CEACAM5 expression causes short-term worsening of non-reversible pulmonary obstruction (FIG. 5D, middle panel), although the activation of both genes significantly contributes to the intensity of bronchial inflammation (FIG. 4D, right panel). This differs from CYP1A2, KIAA1199 and phospholipase A1 member A (PLA1A) expression (FIGS. 4b and e) that all correlate with a significant deterioration of pulmonary function. While CYP1A2 expression as part of a smoke-induced AHR signaling response fits well to the current perception of COPD development, the strong correlation of KIAA1199 and PLA1A expression with deterioration of pulmonary function according to GOLD criteria points towards another direction, the complete failure of the bronchial compartment system.

KIAA1199 has recently been demonstrated to activate matrix hyaluronidases while phospholipase A1 member A (PLA1A) is known to activate T cells in response to non-specific inflammatory stimulation. It has presently been found that the significant upregulation of KIAA1199 is characteristic for the second phase of increased bronchial inflammation in GOLD stages III and IV (FIG. 5B) which follows a phase of non-progressive bronchial inflammation characterizing GOLD stage I (FIG. 5A). Notably, during this stabilization phase both the expression of KIAA1199 and of PLA1A is reduced as well (FIG. 5B). Given the strong proinflammatory impact of a degradation of high molecular mass hyaluronan, these observations indicate that the final increase of inflammatory activity in COPD GOLD stage III and IV is the combined result of permanently disturbed epithelial integrity and a secondary destruction of the hyaluronan matrix within the bronchial wall by the activation of matrix hyaluronidases. This view is supported by the expression pattern of matrix hyaluronidase 2 (HYAL2) itself which represents the leading hyaluronan-degrading enzyme in humans (FIG. 5C).

FIG. 6: COPD Pathology module 3: The impact of intensified regenerative repair temporary suspension of progressive bronchial inflammation.

Maintaining the structural integrity of the mucosa as well as upholding essential components of the bronchial wall is part of effective wound healing and as such an indispensable measure to prevent the intrusion of antigens, allergens and infectious agents into submucosal compartments. It is thus not surprising that various genes guiding functions of epithelial repair are upregulated in response to increased inflammation, as demonstrated in FIG. 6A. However, only a small group of these genes is significantly contributing to the temporary suspension of progressive bronchial inflammation in GOLD stage I, genes known to participate in epithelial regeneration and differentiation, bacterial defense and transepithelial water transport (FIGS. 6A-6C): a) deleted in malignant brain tumors 1 (DMBT1), b) zinc-binding alpha-2-glycoprotein 1 (AZGP1), and c) aquaporin 3 (AQP3). However, this regenerative impulse does not last long as expression of these genes decreases again once progression of inflammation resumes stressing the impact of KIAA1199 expression and matrix degradation on bronchial inflammation. Although further genes closely related to epithelial repair, such as stratifin (SFN), the G protein-coupled orphan receptor 110 (GPR110), the smoke-inducible growth differentiation factor 15 (GDF15), and E74-like factor 5 (ELF5) are expressed throughout a much longer period of COPD development (FIG. 6A), the effectiveness of this wound healing approach is evidently not sufficient to maintain bronchial integrity and to balance bronchial inflammation in the presence of epithelial disintegration and progressive hyaluronan breakdown.

As a result, simultaneous measurement of DMBT1 and KIAA1199 gene expression is capable of discerning stable from progressive COPD (according to GOLD criteria), if the difference between DMBT1 and KIAA1199 expression exceeds a value of 3.63 (FIG. 6E). The importance of intensified KIAA1199 expression for progressive epithelial inflammation is further stressed by the fact that in chronic inflammatory wound healing of diabetic skin, expression of KIAA1199 is significantly upregulated, whereas in normal skin repair, KIAA1199 expression is reduced (see FIG. 8). It should also be noted that KIAA1199 expression in aged skin is in general significantly higher than in the skin from younger individuals ($p<0.01$).

Figure 7:
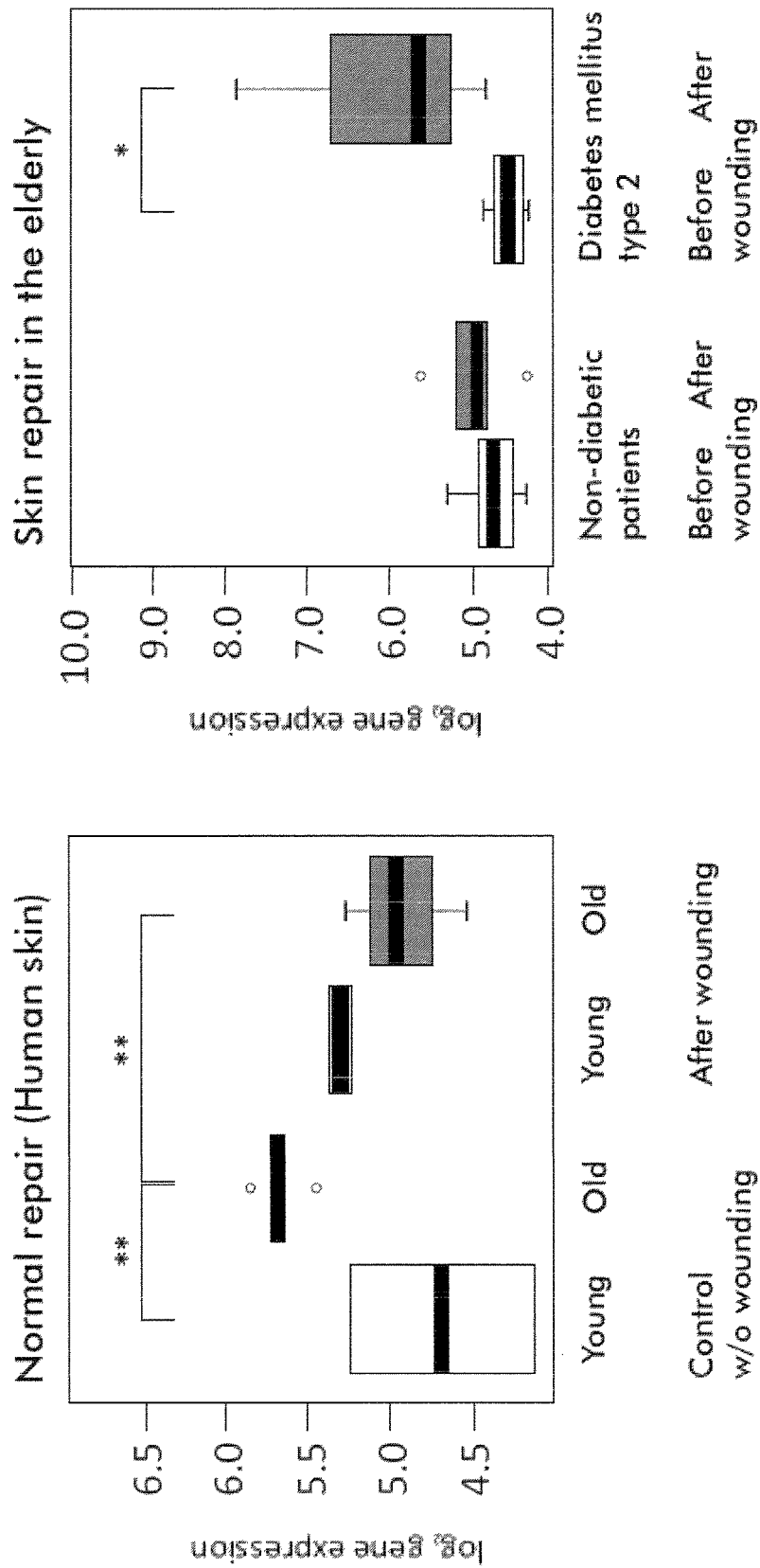

FIG. 7: Expression of KIAA1199 in skin wound healing.

Figure 8:
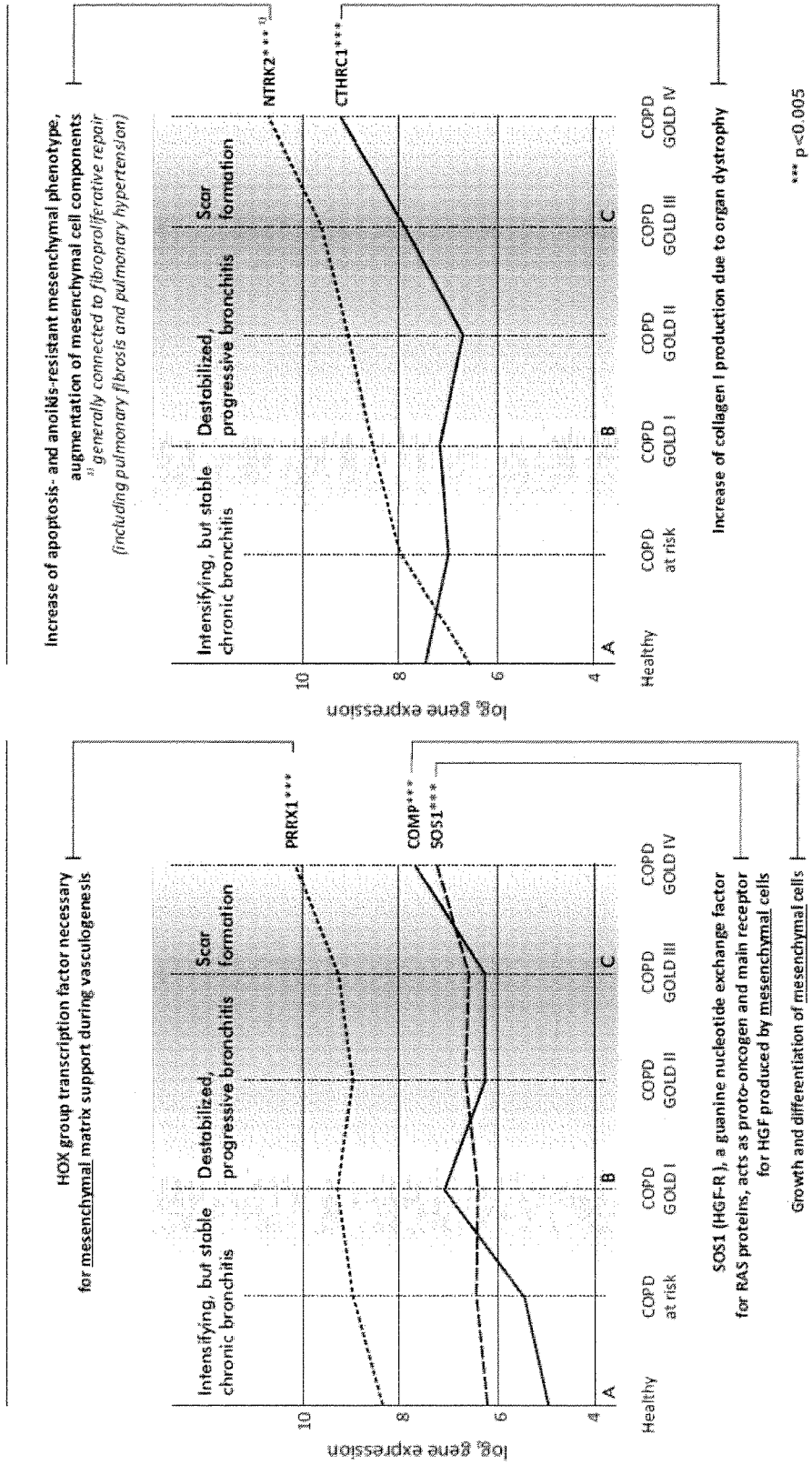
Figure 8:
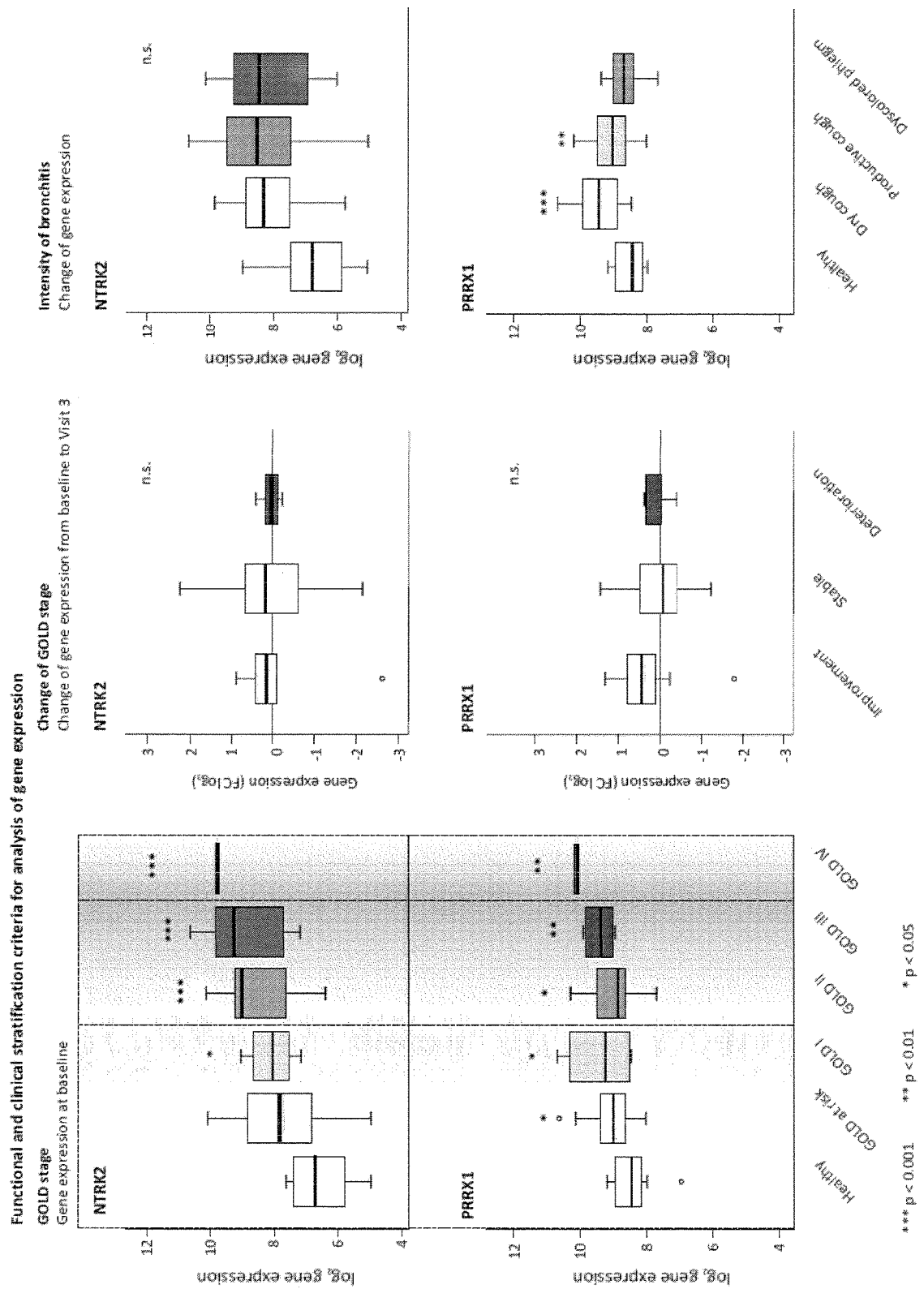
Figure 8:
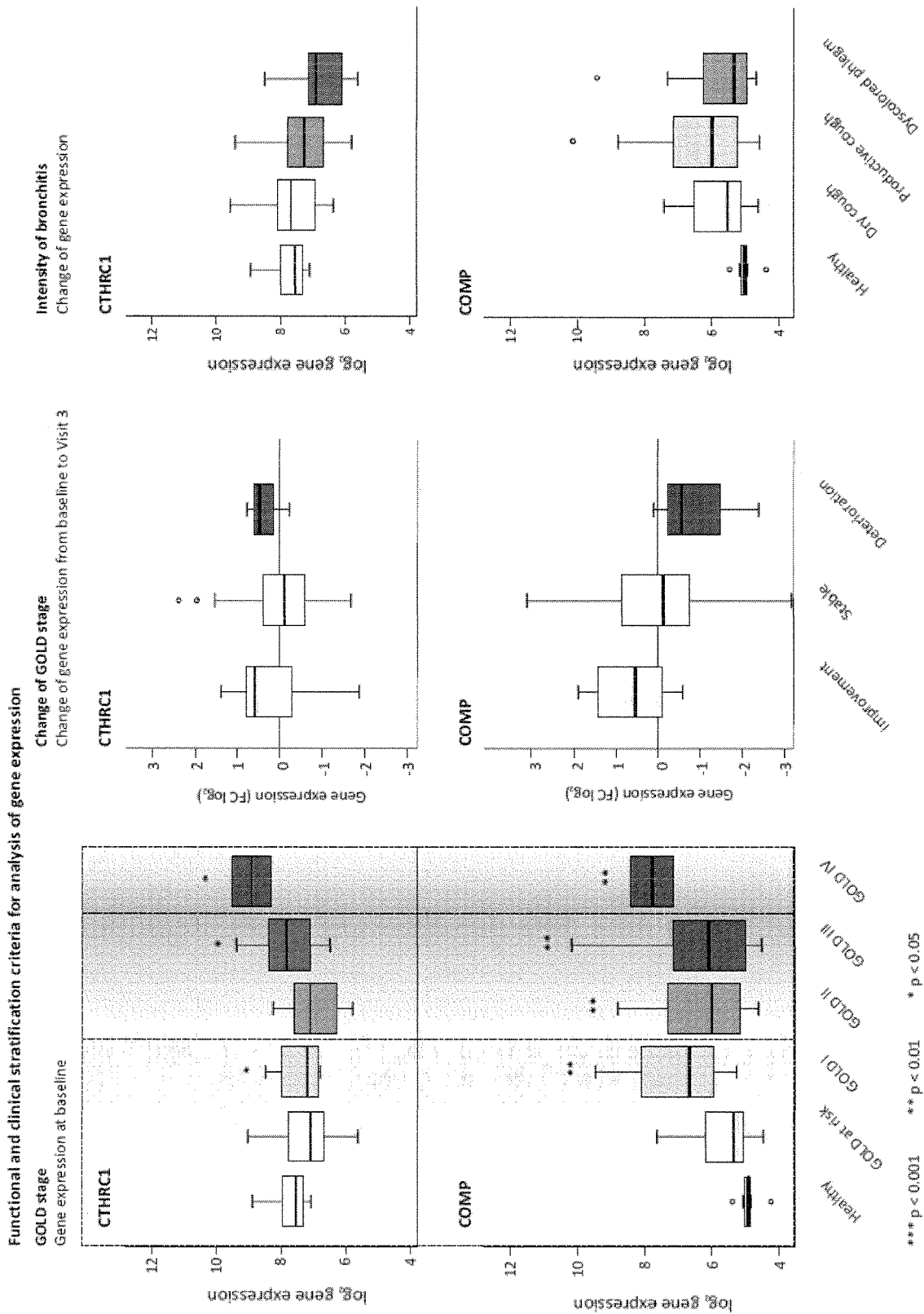
Figure 8:
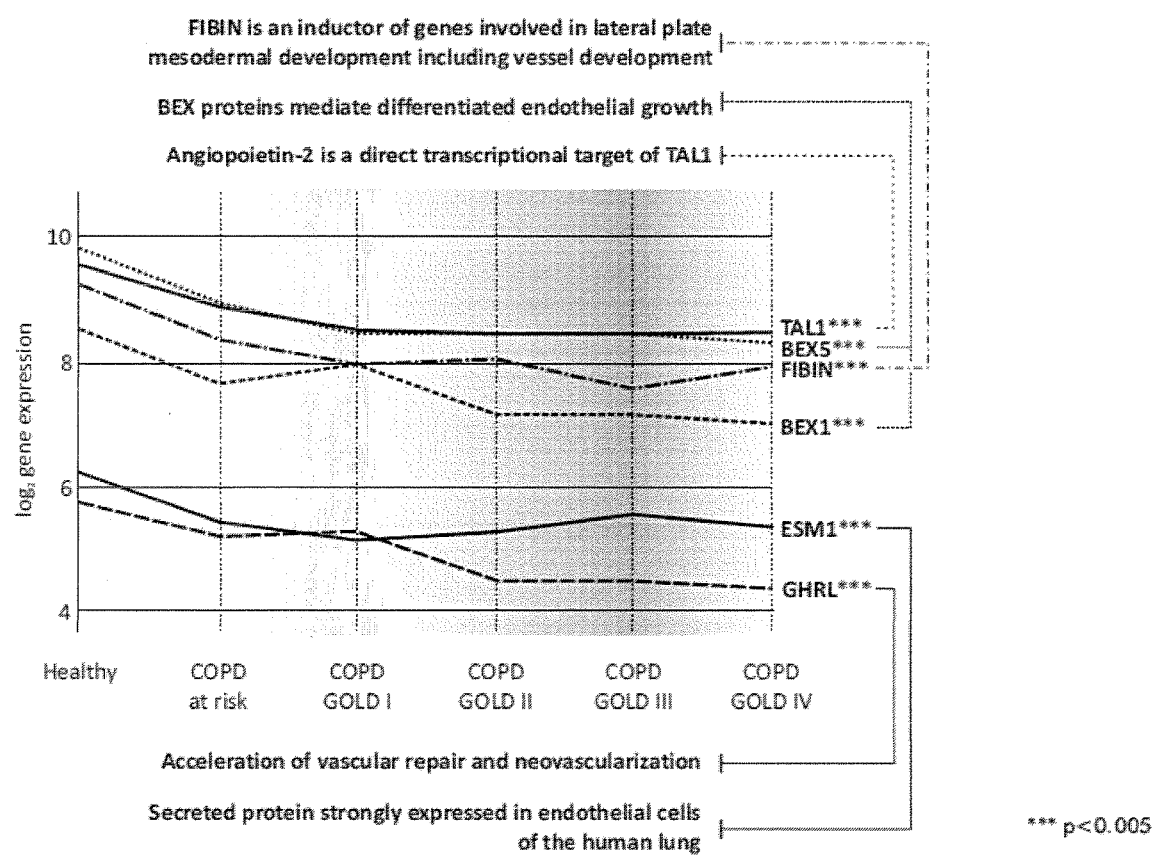

FIG. 8: COPD Pathology module 4: Scar formation by predominant mesenchymal repair as the result of regenerative failure in the presence of a prevailing structural deficit.

As in any situation of prevailing unresolved repair that is not life-threatening, activation of "secondary" mesenchymal repair will serve as the exit strategy to remove the structural deficit and to terminate wound healing. During progression of COPD, coordinated gene activation in this regard can be divided into two categories: a) permanent support of mesenchymal repair (expression of NTRK2 and SOS1 genes) (FIGS. 8A and 8B), b) support of mesenchymal repair during both functional "primary" repair and non-functional "secondary" wound healing (expression of COMP, PRRX1 and CTHRC1 genes) (FIGS. 8A-8C).

As in any form of predominantly mesenchymal repair, expression of genes controlling vascular growth and differentiation is progressively diminished. FIG. 8D provides a synopsis of the expression pattern and relevant annotations for all genes related to vascular outgrowth and repair which are significantly regulated during progression of COPD.

The invention will now be described by reference to the following examples which are merely illustrative and are not to be construed as a limitation of the scope of the present invention.

EXAMPLES

Example 1: Controlled Prospective Pilot Trial Aimed at Identifying Symptom-Based Molecular Metabolic Markers for Progressive COPD (Vienna COPD-AUVA Study)

Introduction

In the context of the present invention, a controlled prospective pilot trial aimed at the identification of symptom-based molecular metabolic markers for progressive COPD was conducted at the Vienna Medical University between 2007 and 2012. The Vienna COPD-AUVA study combined the assessment of validated clinical measures for COPD following in part the overall strategy of the ECLIPSE trial (Vestbo et al., 2011), the largest and most elaborate study addressing progress and variability of COPD.

For stratification of patients, a three-year analysis (day 0, 12 months, and 36 months) of symptom scoring (St. George Respiratory questionnaire, activity and symptom score), assessment of pulmonary function, cardiopulmonary exercise testing, and radiological evaluation by computer-assisted tomography (high-resolution mode) were combined with whole genome transcription analysis plus quantitative RT-PCR assessment and mass spectrometry proteomics. As shown in FIG. 1, the patients were grouped into three strata, two of which presented at the start of the study with regular lung function, either without any sign of a cardiopulmonary disease (healthy volunteers) or with symptoms of chronic bronchitis (COPD "at risk"), and a group of volunteers having symptoms of chronic bronchitis together with deteriorated lung function (COPD at GOLD stages I-IV).

Study visits were performed at base line and after 12 and 36 months, respectively. Each visit was performed on an ambulatory basis and included medical history, physical examination, pulmonary function tests (PFT), cardiopulmonary exercise tests (CPET), radiological assessment by computer-assisted tomography (CAT) scans and a bronchoscopy. On each visit, both personal and occupational history was taken as well as smoking history which comprised onset and duration of symptoms related to COPD, production of phlegm (frequency, quantity, and color), intensity of symptoms measured by the St. George Respiratory Questionnaire (SGRQ; activity and symptom score index) and assessment of life quality using the SF-36 questionnaire. The rate of exacerbations (frequency, number of hospitalizations, use of antibiotics, corticosteroids or combined treatment) and the individual medication were also recorded.

Pulmonary function tests (PFT) were taken at each visit and included blood drawings, body plethysmography, spirometry and quantitative measurement of pulmonary gas exchange at rest and during symptom-limited cardiopulmonary exercise testing (CPET). PFT was performed with an Autobox DL 6200 (Sensor Medics, Vienna, Austria), and CPET on a treadmill using the Sensormedics 2900 Metabolic Measurement Cart. Formulas for calculation of reference values were taken from Hamoncourt et al., 1982. Predicted values were derived from the reference values of the Austrian Society of Pneumology following the recommendations of the European Respiratory Society (Rabe et al., 2007).

Serum samples were analyzed for complete cellular blood count, electrolytes, glucose, C-reactive protein, fibrinogen, and coagulation parameters.

Prior to bronchoscopy, CAT scans encompassing high resolution-computed tomography (HRCT) were performed. Following additional informed consent on each visit, bronchoscopy was performed. During bronchoscopy, both bronchoalveolar lavage (BAL) samples and transbronchial biopsy samples (five per segment in each middle lobe) were taken.

Biological analysis was performed in transbronchial lung biopsies taken during bronchoscopy from two pulmonary localizations (5 each) of the middle-lobe after radiological assessment by computer-assisted tomography (CAT) scans including high-resolution scanning. CAT scans were used for the assessment of emphysema formation as well as for the exclusion of tumor development and infection. During the controlled observational period, combined assessment of clinical and molecular development was finally possible in 120 volunteers. Biomarkers were identified in each case by means of the individual changes of pulmonary function and clinical symptoms characteristic for the progression of COPD. As a result, this approach makes use of the well-known variability of clinical phenotypes in COPD and their variable course of progression while at the same time identifying the very set of biomolecules responsible for this type of disease progression.

Clinical Analysis

The study protocol was approved by the ethical committee of the Medical University of Vienna (ClinicalTrials.gov Identifier: NCT00618137). Following informed consent during screening, individuals were stratified at visit 1 (day 0) if they fulfilled the following criteria:

TABLE 2

Stratification of subjects at visit 1 (day 0).

| | Inclusion criteria | Occupational history |
|---|---|---|
| Healthy Controls | Age 18-70 years<br>No history or clinical findings suggestive of any disease | No occupation with increased exposure towards |

TABLE 2-continued

Stratification of subjects at visit 1 (day 0).

| | Inclusion criteria | Occupational history |
|---|---|---|
| | Never Smoker<br>Normal pulmonary function test at study entry | combustion products, particularly no welding or professional car driving |
| COPD, at risk' | Age 18-70 years<br>Chronic bronchitis according to WHO with repeated episodes of phlegm production<br>No history or clinical findings suggestive of bronchial asthma<br>Normal PFT according to GOLD criteria at study entry<br>Smoking history of at least 10 years<br>No history or clinical findings suggestive of cardiovascular or malign disease | Professional car driver or welder with increased occupational exposure towards combustion products of at least 10 years |
| COPD manifest | Age 18-70 years<br>Chronic bronchitis according to WHO with repeated episodes of phlegm production<br>No history or clinical findings suggestive of bronchial asthma<br>Pathological PFT according to GOLD criteria at study entry<br>Smoking history of at least 10 years<br>No history or clinical findings suggestive of cardiovascular or malign disease | Professional car driver or welder with increased occupational exposure towards combustion products of at least 10 years |

396 individuals were screened, 185 of whom met the study criteria. 136 participants finished visit 2 after 12 months, and 120 completed the final visit after 36 months of controlled observation. Throughout the study, all participants were residing and occupied in the greater Vienna area in order to ensure comparable environmental conditions. The control group consisted of 16 healthy volunteers who had never smoked (7 females and 9 males; mean age 36±12.2 years), as also shown in Table 2 above. None of the healthy participants developed any symptom of pulmonary disease during the study period. At the start of the study, 104 participants presented with clinical symptoms of chronic bronchitis according to WHO definition, 55 of whom did not have signs of non-reversible bronchial obstruction (GOLD "at risk"), while the other 49 participants showed bronchial obstruction ranging from GOLD stage I to IV as determined by PFT (see FIG. 3D). All participants in the COPD and COPD "at risk" groups were active cigarette smokers with a smoking history of more than 10 pack years, except for one welder who in addition to a daily expectoration of phlegm reported about frequent episodes of bronchial infection (>2 per year) without radiological signs of bronchiectasis. 64 participants were working as taxi or bus drivers (53%) and 40 active welders (33%) with a previous exposure to welding fumes of more than 10 years.

At visit 1, the majority of participants with manifest COPD had bronchial obstruction GOLD stage II and III (n=38), while the remaining subjects were in COPD GOLD stage I (n=9) and IV (n=2) (see FIG. 3D). Mean age in GOLD stages I and II was 50±9.5 and 56±10.4 yrs. respectively, compared to 52±9.0 yrs. in GOLD stage III and 63±11 yrs. in GOLD stage IV. 29% of the participants in the GOLD "at risk" group were already presenting with a continuous daily expectoration of sputum, and sputum was frequently discolored (yellow, green, brown) in 27%.

During controlled observation (36 months), 14 participants (12%) had a progression of disease according to GOLD, 7 (13%) in the GOLD "at risk" group, 1 (11%) in GOLD I, 3 (12%) in GOLD II, and 3 (25%) in GOLD III. Improvement of bronchial obstruction according to GOLD was observed in 13 individuals (5 participants in both GOLD stage I and II, and 3 cases in GOLD stage III and IV), mostly connected to a cessation of cigarette smoking.

As part of the observational design of the study, participants were not specifically encouraged to stop smoking. Accordingly, smoking habits changed only slightly: only 5 participants of the "COPD at risk" group (9%) and 2 participants in the "manifest COPD" group (4%) stopped smoking during the observational period, while 31% reduced cigarette smoking (data not shown). These changes did not significantly alter both occurrence and intensity of chronic bronchitis symptoms, as 27 participants (23%) demonstrated improvement and deterioration of cough and sputum production.

Biological/Molecular Analysis (Gene Transcription in Pulmonary Tissue)

RNAlater (Ambion, lifetechnologies) was used for tissue asservation. The lung biopsy material was disrupted using Lysing Matrix D ceramic balls in a Fastprep 24 system (MP Biomedical, Eschwege). A chaotropic lysis buffer (RLT, RNeasy Kit, Qiagen, Hilden) was used, followed by a phenol/chloroform extraction and subsequent clean up using the spin column approach of the RNeasy Mini Kit (Qiagen, Hilden) according to the manufacturer's manual, including a DNase I digestion on the chromatography matrix. RNA quantification was done spectrophotometrically using a NanoDrop 1000 device (Thermo Scientific) and quality control was performed on the Agilent 2100 Bioanalyzer. A cut off for the amount of 1 microgram and a RNA integrity number of 7.0 was chosen.

Total RNA samples were hybridized to Human Genome U133 plus 2.0 array (Affymetrix, St. Clara, Calif.), interrogating 47,000 transcripts with more than 54,000 probe sets.

Array hybridization was performed according to the supplier's instructions using the "GeneChip® Expression 3' Amplification One-Cycle Target Labeling and Control reagents" (Affymetrix, St. Clara, Calif.). Hybridization was carried out overnight (16 h) at 45° C. in the GeneChip® Hybridization Oven 640 (Affymetrix, St. Clara, Calif.). Subsequent washing and staining protocols were performed with the Affymetrix Fluidics Station 450. For signal enhancement, antibody amplification was carried out using a biotinylated anti-streptavidin antibody (Vector Laboratories, U.K.), which was cross-linked by a goat IgG (Sigma, Germany) followed by a second staining with streptavidin-phycoerythrin conjugate (Molecular Probes, Invitrogen).

The scanning of the microarray was done with the GeneChip® Scanner 3000 (Affymetrix, St. Clara, Calif.) at 1.56 micron resolution.

The data analysis was performed with the MAS 5.0 (Microarray Suite statistical algorithm, Affymetrix) probe level analysis using GeneChip Operating Software (GCOS 1.4) and the final data extraction was done with the DataMining Tool 3.1 (Affymetrix, St. Clara, Calif.).

CEL files were imported and processed in R/Bioconductor (Gentleman et al., 2004). Briefly, data was preprocessed using quantile normalization (Gentleman et al., 2004) and combat (Johnson et al., 2007), linear models were calculated using limma (Smyth G K, 2005) and genes with a p-value of the f-statistics<5e-3 were called significant. Those genes were grouped into 20 clusters of co-regulated genes. The procedure of modeling and clustering was repeated for GOLD and phlegm as covariates.

For subsequent Gene Ontology (GO)-analysis it was necessary to separate the effects of GOLD and phlegm on gene expression. To this end, the GOLD classifications were grouped into "no COPD" (healthy and GOLD 0) and "COPD" (GOLD grades I-IV). Similarly, phlegm was reclassified into a "phlegm" group (productive or severe) and a "no phlegm" group (health or no/dry). Based on these reclassifications, gene expression was modeled using a 2×2 factorial design, resulting in five different lists of genes: (1) genes which are regulated with phlegm in the presence of COPD, (2) genes which are regulated with phlegm in the absence of COPD, (3) genes which are regulated with COPD in the presence of COPD, (4) genes which are regulated with COPD in the absence of COPD and finally (5) genes which are regulated differently with COPD, depending on whether there is phlegm or not.

These lists were annotated with respect to their biological functions as catalogued in the Gene Ontology (GO) database using the ClueGO plugin for the Cytoscape framework.

Results of Combined Clinical and Molecular Analysis

Activation of Epithelial Repair Mechanisms

Systematic analysis of the significant changes of gene expression during COPD development reveals a differentiated picture: As shown in FIGS. 6A to 6D, mechanisms of regeneration and repair commence as soon as the chronic inflammatory process in the peripheral bronchial tree is established. This is already the case in persistent or repeatedly manifesting bronchitis (COPD "at risk"). The functions associated with this kind of aberration from the normal equilibrium, in ontological terms still only potential COPD, include mediators involved in the regulation of embryonic epidermal and pulmonary growth, such as ELF5 (E74-like factor 5; ETS domain transcription factor) which confers spatially controlled outgrowth of epithelial structures (Metzger et al., 2008; Yaniw et al., 2005) as well as mucosal immunity of the lung (Lei et al., 2007). Not surprisingly, the expression of ELF5 is accompanied by a significant upregulation of stratifin (SFN) conferring increased epidermal regeneration and differentiation (Medina et al., 2007), yet also reduced deposition of matrix proteins including collagen I (Chavez-Mufioz et al., 2012) and reduced functions of non-specific surface immunity (Butt et al., 2012). This regenerative phase of repair involves not only the G protein-coupled orphan receptor GPR110 and the smoke-inducible growth differentiation factor 15 (GDF15) (Wu et al., 2012), a member of the bone morphogenic protein-transforming growth factor-beta superfamily, but also mediators directing differentiated epithelial repair, such as the zinc-binding alpha-2-glycoprotein 1 (AZGP1), and the DMBT1 gene (deleted in malignant brain tumors 1) which is strongly upregulated during acute but resolving bacterial inflammation in enteral epithelia during appendicitis (Kaemmerer et al., 2012), suggesting a functional relevance for mucosal defense (Diegelmann et al., 2012). The almost identical expression profile of DMBT1 and AZGP1, a mediator capable of inducing a strong epithelial transdifferentiation in tumor cells (Kong et al., 2010), suggests an as yet undefined combinatory effect of both mediators on cellular differentiation during epithelial regeneration. Notably, the expression of these genes is strongly increased in individuals with COPD GOLD I and decreases significantly with progression of COPD, as also shown in FIG. 6A. In line with this observation, all mediators conveying epithelial regeneration and differentiation were found to be significantly downregulated during the transition from COPD stage III to COPD stage IV.

Activation of mediators of regenerative repair was also found in individuals demonstrating significant symptoms of bronchial inflammation, as demonstrated by a uniform increase of gene expression of SFN, GPR110 (see also FIG. 6D), and aquaporin 3 (AQP3) (see FIG. 6A) being an additional mediator known to guide proliferation and differentiation of epithelial cells (Nakahigashi et al., 2011; Kim et al., 2010). However, expression of these factors did not further increase with an increase of severity of bronchial inflammation, much in contrast to mediators capable of intensifying inflammation on epithelial surfaces, such as the carcinoembryonic antigen-related cell adhesion molecule 5 (CEACAM5) (see FIGS. 5A and 5D), or factors being part of the preferentially mesenchymal wound healing response during inflammatory repair (Agarwal et al., 2012; Agarwal et al., 2013), such as the cartilage oligomeric matrix protein (COMP) (see FIGS. 8A and 8C). The study design allowed as well for the measurement of changes of gene expression occurring throughout the study period of 3 years, possibly indicating significant changes of repair during short-term progression of COPD. Here, a significant downregulation of GPR110 and DMBT1 genes correlating with deteriorated lung function according to GOLD was found, as also shown in FIGS. 6B and 6D. This decrease of regenerative gene activity started already in GOLD stage II, where it was accompanied by a striking increase of repair functions related to mesenchymal wound healing (see also FIG. 8).

Progressive Activation of Mesenchymal Repair

During later stages of COPD, expression of mediators favoring mesenchymal repair became increasingly prominent. This did not only relate to the increased expression of the COMP gene (see FIGS. 8A and 8C), but also to the expression of potent activators of mesenchymal stem cells, such as the son of sevenless homolog 1 (SOS1) gene, a guanine nucleotide exchange factor for RAS proteins acting as the cognate receptor for hepatocyte growth factor, and to the paired related homeobox 1 gene (PRRX1), a transcriptional co-activator of RAS transcription factors belonging to the HOX family of early differentiation factors able to induce mesenchymal outgrowth in liver cirrhosis (Jiang et al., 2008) as well as epithelial-to-mesenchymal transition (EMT) during cancer development (Ocafa et al., 2012). While their pattern of expression indicates that both COMP and PRRX1 genes take also part in the regenerative phase of wound healing characterizing GOLD stage I and II, their later increase during transition from GOLD stage III to IV suggests an additional involvement in the progressive scarring of the airways. Increased expression of pro-fibrotic factors is further demonstrated by the striking increase of expression of neurotrophic tyrosine kinase receptor type 2 (or tropomyosin receptor kinase B receptor; TrkB)

(NTRK2). NTRK2/TrkB, thus far known to act as high affinity receptor for various neurotrophic growth factors during nerve development, is also capable of promoting resistance of mesenchymal cells towards apoptosis and anoikis (Frisch et al., 2013). The combined increase of profibrotic mediators includes as well the expression of the collagen triple helix repeat containing 1 gene (CTHRC1) capable of conferring fibrotic organ dystrophy (Spector et al., 2013). Notably, while the increased expression of CTHRC1 starts only at GOLD stage II, cumulative activation of NTRK2/TrkB is a hallmark throughout progression of COPD in general, suggesting a permanent contribution of NTRK2/TrkB signaling to the aberrant repair response in the peripheral airways during COPD development. This view is further supported by the observation that a disturbed TrkB axis may contribute to experimental pulmonary fibrosis (Avcuoglu et al., 2011).

With the exception of COMP expression, where clinical deterioration correlates with worsening of bronchial obstruction according to GOLD (see also FIG. 8C), neither increased long-term expression of NTRK2 (see also FIG. 8B), nor of PRRX1 (see also FIG. 8B) or CTHRC1 genes (see also FIG. 8C) demonstrate a comparable short-term impact on bronchial obstruction during the controlled 3-year observational study period. Corresponding results were obtained when assessing the correlation of gene expression with progressive bronchial inflammation: while the expression of all genes favoring mesenchymal repair is increased as a result of intensified bronchitis, significant changes were only found for the PRRX1 and CTHRC1 genes (see also FIGS. 8B and 8C).

Loss of Structural Integrity of Epithelial Surfaces

Unexpectedly, the present analysis revealed a very significant downregulation of expression of a group of genes which guide movement, distribution and activation of the cellular cytoskeleton and which, as a result, are likely to profoundly influence structural integrity and barrier function of the mucosal surface. The downregulation of these genes takes place already during establishment of chronic bronchitis, well before the establishment of bronchial obstruction according to GOLD, as also shown in FIG. 4A. The genes closely connected to this development are thymosin beta 15 A (TMSB15A), dipeptidyl-peptidase 6 (DPP6), nudix (nucleoside diphosphate linked moiety X)-type motif 11 (NUDT11), integrin alpha 10 (ITGA10), cystatin E/M (CST6), and PRICKLE2 (data not shown). Notably, the two genes most significantly decreased during progression of COPD, TMSB15A and DPP6, are also significantly downregulated in correlation with symptoms of increased bronchial inflammation (see also FIG. 4B). Beta thymosins are controllers of both composition and sequestration of the actin cytoskeleton (Hannappel, 2007; Huff et al., 2001; Malinda et al., 1999), by that influencing membrane structure, surface stability and cellular phenotype (Husson et al., 2010). One of the outcomes of elevated levels of beta thymosins during wound healing seems to be a protection from fibrotic aberrations of repair (De Santis et al., 2011), in part by preventing the expression of α-smooth muscle stress fibers preventing them from a transdifferentiation into myofibroblasts most characteristic for fibrotic tissue development. Currently, little is known about the function of DPP6 in regenerative wound healing. However, DPP6, a member of the S9B family of membrane-bound serine proteases which is lacking any detectable protease activity, has recently been demonstrated to confer membrane stability and controlled outgrowth of cells during nerve development including close control of cell attachment and motility (Lin et al., 2013). Moreover, given its proven association with and control of membrane-bound ion channel expression and activation (Jerng et al., 2012), in particular of voltage-gated potassium channels, expression of DPP6 is also capable of controlling the resting membrane potential (Nadin et al., 2013), thereby controlling both activity and intracellular distribution of the actin cytoskeleton (Mazzochi et al., 2006; Chifflet et al., 2003).

Combined with the striking reduction of TMSB15A gene expression, the significant decrease of DPP6 expression suggests a severe disturbance of regular movement and distribution of the cellular actin skeleton, reducing physico-chemical integrity of the epithelial lipid bilayers. As this occurs already very early in COPD development, this finding could indicate an initiating and possibly predisposing mechanism leading to non-specific surface inflammation.

Cystatin M/E (CST6), on the other side, is an epithelium-specific protease inhibitor belonging to the cystatin family of secreted cysteine protease inhibitors indispensable for the physiological regulation of protease activity during growth and differentiation of epithelial structures. CST6 is expressed both in dermal and bronchial epithelia where it characterizes the status of functional differentiation (Zeeuwen et al., 2009). Significant downregulation of CST6 has already been shown to cause a marked disturbance of both surface integrity and differentiation status in the dermis of mice (Zeeuwen et al., 2010). Progressive downregulation of CST6 as observed during advancement of COPD is thus likely to destabilize the intricate balance between proteases and protease inhibitors, by that contributing to a loss of surface stability as well as cellular adhesion and differentiation in the regenerating bronchial epithelium. Within this context, significant downregulation of two other genes intricately involved in the regulation of cell adhesion and motility has also been observed, namely of integrin α10 (ITGA10) being part of differentiated mesenchymal structures, and the nudix (nucleoside diphosphate linked moiety X)-type motif hydrolase 11 (NUDT11), capable of hydrolyzing diphosphoinositol polyphosphates derived from cellular lipid bilayer structures, and diadenosine polyphosphates, mostly based on adenosine triphosphate (ATP).

The consequence of these changes in gene expression is expected to be a disintegration of the epithelial barrier function, probably starting on the cellular level (continuous shear stress within the cellular lipid bilayer due to uncoordinated accumulation and movements of the actin cytoskeleton attached to it), and aggravated by disintegration of the extracellular matrix composition itself. This is supported by the significant increase of gene expression of the KIAA1199 gene during progression of COPD from GOLD stage I to GOLD stage IV (see FIG. 5B). Increased expression of KIAA1199, in addition to mediating cellular attachment and contact inhibition (Tian et al., 2013), has just recently been demonstrated to cause the leakage of endoplasmatic reticulum (ER) contents into the cytosol of cancer cells (Evensen et al., 2013). Moreover, increased expression of KIAA1199 is capable of activating hyaluronidases (HAase), enzymes capable of degrading high-molecular mass hyaluronic acid (HMM-HA), one of the major constituents of the extracellular matrix (Toole, 2004). Biological responses triggered by hyaluronic acid (HA) depend on the HA polymer length. HMM-HA has strong anti-inflammatory properties (Kothapalli et al., 2007), whereas low-molecular-mass HA promotes inflammation and concomitant cellular proliferation (Puré et al., 2009). In support of this view, degradation of HA has been shown to trigger skin inflammation by generation of low molecular weight fragments of HA (Yoshida et al., 2013).

In line with this, expression of HA synthases (HAS1-3) is not changed during progression of COPD (see FIG. 5G), while the hyaluronidase 2 (HYAL2) gene is upregulated between GOLD stages I and III (see also FIG. 5C). Indeed, the pattern of expression of both HYAL1 and HYAL2 follows the expression pattern of KIAA1199, showing a downregulation during the most intense regenerative phase of repair in COPD progression (chronic bronchitis and COPD GOLD I). Upregulation of KIAA1199 in turn is synchronous to that of the PLA1A gene (see FIG. 5B) which is a phosphatidylserine-specific phospholipase expressed in macrophages stimulated by typical mechanisms of surface immunity, such as toll-like receptor 4 (TLR4) signaling (Wakahara et al., 2007). Both intensified KIAA1199 and PLA1A expression were found to be connected to short-term worsening of pulmonary function according to GOLD criteria (see also FIG. 5B).

Decrease of Pro-Angiogenic Mediators During Progression of COPD

Effective organ repair involves mechanisms concomitantly directing spatially controlled epithelial, mesenchymal and endothelial outgrowth. However, in contrast to gene functions contributing to epithelial and mesenchymal repair, gene expression promoting angiogenesis and vascular differentiation was found to decrease as soon as chronic bronchitis was present. During development of COPD (GOLD stage I and II), this pattern of gene expression proceeded significantly, as also shown in FIG. 8D. Even the increase of Bex1 and Ghrelin (GHRL) gene expression occurring at GOLD stage I is rather small and insignificant compared to gene functions aimed at the regeneration of epithelial outgrowth, such as DMBT1 and AZGP1. Some of the functions, such as FIBIN (fin bud initiation factor homolog), ESM1 (endothelial cell-specific molecule 1) and ghrelin (GHRL) are known to act, in part, as mediators in the early phases of organ development. For instance, FIBIN takes part in mesodermal lateral plate development (Wakahara et al., 2007) which is crucial for early vasculogenesis (Paffett-Lugassy et al., 2013), ESM1 mediates VEGF-A-dependent signaling (Zhang et al., 2012) and is typically expressed in growing vascular tissue which includes tumor angiogenesis (Zhang et al., 2012; Roudnicky et al., 2013; Chen et al., 2010) and regenerative wound healing (Béchard et al., 2001).

Ghrelin, on the other hand, is a typical marker of microvascular development (Li et al., 2007; Wang et al., 2012; Rezaeian et al., 2012) being vital for continuous epithelial oxygen and energy supply preventing excessive apoptosis characteristic for emphysema development (Mimae et al., 2013). BEX1 and BEX5 (Brain Expressed, X-Linked 1 and 5) are genes encoding adapter molecules interfering with p75NTR signaling events. p75NTR is one of the two receptors central to nerve growth factor (NGF) signaling. While BEX1 is known to induce sustained cell proliferation under conditions of growth arrest in response to NGF, much less is known about its possible involvement in angiogenesis and vessel formation, although NGF signaling itself is well-known to promote angiogenesis (Cantarella et al., 2002). One possible interaction could be that reduced BEX1 gene expression would increase p75NTR signaling efficacy causing increased endothelial apoptosis, as the blockade of p75NTR signaling significantly decreases endothelial apoptosis (Han et al., 2008; Caporali et al., 2008). The BEX5 promoter, in turn, contains regulatory binding sites for TAL1 (T-cell acute lymphocytic leukemia 1), a direct transcriptional activator of angiopoietin 2, which is significantly upregulated during angiogenesis (Deleuze et al., 2012). TAL1, however, is downregulated as well during progression of COPD, as also shown in FIG. 8D.

Stage-Dependent Activation of the Immune Response

Based on the significant changes of gene expression measured during progression of COPD, four sequential phases of gene expression were distinguished: Phase 1 is characterized by a rapid increase of genes involved in the acute immune response, such as fibrinogen (FGG) (Duvoix et al., 2013; Cockayne et al., 2012), and products of aryl hydrocarbon receptor (AHR) signaling, such as CYP1A1 (cytochrome P450, family 1, subfamily A, polypeptide 1) and CYP1B1 (cytochrome P450, family 1, subfamily B, polypeptide 1) expression, as also shown in FIGS. 5A to 5E. This includes as well an increased expression of carcinoembryonic antigen (CEA)-related cell adhesion molecules (CEACAMs), particularly of the CEACAM5 gene (see FIGS. 5A and 5D). At this early stage, still representing chronic bronchitis without significant changes of pulmonary function (COPD "at risk"), expression of genes mediating functions of primarily adaptive immunity, such as RAS-GRF2 (Ras protein-specific guanine nucleotide-releasing factor 2), KIAA1199 or CXCL3 was not significantly changed (see also FIGS. 5H and 5F). At phase 2 (representing GOLD stage I), expression of these genes remained stable or even decreased to some extent (see FIGS. 4A and 5A), probably reflecting the stabilizing outcome of regenerative repair efforts which was most intense at GOLD stage I (see also FIG. 6A). However, phase 3 which includes GOLD stages II and III was characterized by a significant increase of expression of all genes related to immunity including genes indicating increased AHR signaling, such as CYP1A1, CYP1A2 and CYP1B1 (see also FIGS. 5A, 5E and 5F). The latter ones most likely reflect the impact of cigarette smoking, all the more as three quarters of the participants were still actives smokers at this stage (see FIG. 3C). Increased gene expression reflecting intensified AHR signaling could be demonstrated in spite of elevated levels of the aryl hydrocarbon receptor repressor (AHRR) gene known to inhibit AHR signaling events, particularly during GOLD stages II and III.

Nonetheless, short-term analysis of gene expression addressing a development of COPD over a period of 3 years (see also FIGS. 5A and 5D, middle) indicates that the overall impact of AHR signaling on the deterioration of pulmonary function is more important than the additional expression of CEACAM5 which, comparable to FGG expression (see also FIG. 5D), seems to reflect the intensity of bronchitis much better. Phase 4 representing GOLD stage IV shows a striking downregulation of the majority of immune-related functions upregulated during earlier phases of COPD development, comparable to the regulation of genes controlling cellular regeneration and differentiation. Interestingly, however, this does not apply to the expression of KIAA1199 and RAS-GRF2 genes which are both upregulated even at GOLD stage IV, the latter one being again capable of influencing cellular movements by inhibition of the actin cytoskeleton (Calvo et al., 2011): RASGRF2 belongs to a group of activators of the GTPase RAS involved as well in the activation of T cells and required for the induction of NF-AT, IL-2 and TNF-α (Ruiz et al., 2007).

Within this context, the slow yet constant and highly significant upregulation of the guanine-nucleotide exchange factor (GEF) son of sevenless homolog 1 (SOS1) (see FIG. 8A), capable of continually activating RAS, could significantly contribute to the chronic inflammatory process facilitating the bronchial wall scarring characteristic for late stage COPD.

Members of the carcinoembryonic antigen-related cell adhesion molecule (CEACAM) family serve as cellular receptors for typical gram-negative bacteria frequently colonizing the surface of the human airways, such as *Neisseria meningitidis, Haemophilus influenzae* and *Moraxella catarrhalis* expressing opacity (Opa) proteins (Muenzner et al., 2010; Bookwalter et al., 2008; Muenzner et al., 2005). It was recently suggested that non-typable *Haemophilus influenzae* and *Moraxella catarrhalis* are able to increase the expression of their respective receptors on host cells (Klaile et al., 2013). However, no correlation between the expression of members of the CEACAM family and COPD was found under the conditions employed in that study. In the present study, only the expression of the CEACAM5 gene was significantly increased up to GOLD stage III, in that following the inflammatory reaction in general, while significantly decreasing afterwards in GOLD stage IV. This does not, however, exclude the aggravation of mucosal inflammation as a result of a persistent upregulation of CEACAM5, all the more as the expression of CEACAM5 was found to be increased in combination with a growing intensity of bronchial inflammation (see FIG. 5D).

CONCLUSIONS

Between 2007 and 2012, a controlled prospective pilot trial was conducted in finally 120 volunteers in order to identify metabolic markers indicative of the progression of COPD. By adopting parts of the design of the ECLIPSE trial (Vestbo et al., 2011), the largest and most elaborate study performed thus far to identify clinical markers describing both progress and variability of COPD, the Vienna COPD study combined controlled assessment of validated clinical measures with unsupervised assessment of genome-wide gene transcription in pulmonary tissue representing the focus of COPD pathology (Hogg J C, 2004 (b)). The correlation of gene expression with clinical development was based a) on the extent of non-reversible pulmonary obstruction at visit 1 (according to the Global Initiative for Obstructive Lung Disease; GOLD), b) on the worsening of non-reversible obstruction according to GOLD between visit 1 and 3 (covering a period of three years), and c) on symptoms indicative of an increasing intensity of bronchitis being recorded during structured clinical history at visits 1 and 3.

This analysis revealed changes of gene expression indicative of six major deviations from regular maintenance of pulmonary structure and defense: (1) Progressive loss of functions guiding epithelial and (2) vascular regeneration combined with (3) persistent and increasing activation of mechanism of fibroproliferative repair, together indicating a transition from regenerative to fibrotic repair during progression of COPD; (4) intensifying bronchial inflammation being antagonized at GOLD stage I when regenerative repair activity is highest, and culminating afterwards at GOLD stages II and III; (5) a complete loss of structural maintenance at GOLD stage IV connected to a finally failing immunity, both suggestive of the formation of scar tissue; and lastly, a rapid and persistent downregulation of functions controlling the intracellular distribution, aggregation and sequestration of actin polymers which form the cytoskeleton (6). The latter finding is of particular interest as the changes in the transcription of the corresponding genes, in particular the downregulation of TMSB15A, DPP6, NUDT11 and PRICKLE2, were already observed at GOLD stage 0 (COPD "at risk"), well before any change of pulmonary function was measurable. This striking loss occurs together with a significant increase of functions determining bronchial inflammation suggesting that these changes might be the first to predispose the bronchi to persistent inflammation. The outcome of such an early and simultaneous downregulation of the TMSB15A, DPP6, NUDT11 and PRICKLE2 genes will be discussed in the following.

Thymosin beta 15A (TMSB15A) belongs to the group of WH2 (WASP-homologue 2) domain binding proteins which are necessary for the depolymerization of actin filaments during cellular movements (Husson et al., 2010; Hertzog et al., 2004). Formation and rapid movement of actin filaments in turn are indispensable for processes such as cell division, intercalation and cellular extrusion. This applies as well to the regulation of apicobasal cell polarity (Nishimura et al., 2012), and even more important, to the formation and maintenance of tight and adherens junctions (Shen et al., 2005; Calautti et al., 2002). These complex membrane dynamics are not only an answer to external and internal stress, but also part of regular tissue growth and as such energy-dependent. The assembly of the actin skeleton is highly dynamic and creates a layer of epidermal cells acting as an impenetrable fluid-like shield composed of the constantly moving lipid border of the cells (Guillot et al., 2013). Thus, a persistent downregulation of TMSB15A is likely to prevent any fast adaptive arrangement of the surface lipid layers during cellular movements causing repeated perturbations of the epithelial barrier function.

DPP6, on the other hand, is known to stabilize the membrane potential by acting on membrane-bound potassium channels, and has also a profound impact on the organization of the actin cytoskeleton (Chifflet et al., 2003), supporting the perception of a failing barrier function. The same applies to the downregulation of NUDT11 gene expression. The nucleoside diphosphate linked moiety X (nudix)-type motif 11 (NUDT11) gene encodes a type 3 diphosphoinositol polyphosphate phosphohydrolase which generates energy-rich phosphates essential for vesicle trafficking, maintenance of cell-wall integrity in *Saccharomyces* and for the mediation of cellular responses to environmental salt stress (Dubois et al., 2002). As the adaptive assembly of F and G actin fibers within the cytoskeleton occurs in seconds, it is easily conceivable that energy-rich diphosphoinositol polyphosphates being integral constituents of any cell membrane will be utilized as rapidly accessible source of energy.

These findings point towards a synchronized dysregulation of genes necessary for upholding the epithelial barrier. Moreover, the downregulation of the PRICKLE2 gene was also shown to be vital for the formation of polarized epithelial layers during mouse embryogenesis (Tao et al., 2012). Decreased expression of all four genes (i.e., TMSB15A, DPP6, NUDT11 and PRICKLE2), however, was associated with significantly increased bronchial inflammation, suggesting a functional correlation between the downregulation of genes that guide functionally interrelated features of cytoskeleton assembly with the activation of bronchitis. This sheds a new light on the progression of bronchial inflammation as it indicates a direct connection between the loss of a protective epithelial shield and the aggravation of chronic bronchitis. Based on the physicochemical nature of such an effect, penetration of the epithelial membranes by any potential antigen or allergen is likely to be enhanced, particularly during intensified repair due to repeated smoke-induced damage or following viral infections. This could not only explain the remarkable heterogeneity of inflammatory conditions characteristic for COPD, but also the observation that the capacity to achieve intense cellular regeneration in spite of ongoing inflammation might be helpful in suppressing pro-inflammatory gene expression.

This view is further supported by the significant downregulation of the protease inhibitor cystatin M/E (CST6) during progression of COPD (see also FIG. 4A). CST6 is known to control the homeostasis of the stratum corneum, its deficiency in mice causing severe ichthyosis and neonatal lethality (Zeeuwen et al., 2009). The progressive loss of a protease inhibitor in later phases of COPD known to preserve the integrity of epithelial structures will most likely contribute to a failure of the protective barrier function, not only by a disintegration of the epithelial layer but also by facilitating the breakdown of the matrix itself.

In this context, the strong upregulation of the KIAA1199 gene which has been demonstrated to significantly increase the activity of matrix hyaluronidases, is probably equally important, as this upregulation is directly associated with a significant worsening of lung function, even within the relatively short observational period of the present study (see also FIG. 5B). It has recently been shown that matrix structures containing large amounts of high molecular mass hyaluronan as well as the inhibition of hyaluronidase activity protect against both inflammation and cancer progression (Tian et al., 2013). In summary, these findings provide the first conclusive evidence for a progressive breakdown of bronchial surface integrity during the course of COPD development causing growing non-specific bronchial inflammation that varies with frequency and intensity of the physicochemical assaults attacking the bronchial surfaces.

According to results described herein, the response to these assaults is a slow progressive scarring process in the peripheral bronchi, whereby the combined upregulation of CTHRC1, SOS1 and NTRK2 genes (see also FIG. 8A) is likely to indicate mechanisms of preferentially mesenchymal wound healing while the stage dependent expression of the PRRX1 and COMP genes suggests their participation in regular organ repair as well demonstrating the ambiguity between regular matrix support during regenerative repair and scar formation as a result of a progressive failure of the organ's regenerative repair capacity.

This fits well to the progressive downregulation of genes mainly controlling functions of regenerative growth of the vascular tree as demonstrated by the concomitant decrease of the expression of FIBIN, TAL1, BEX1/5, and Ghrelin (GHRL) genes (see also FIG. 8D). Here again, the increasing capacity of the peripheral lung to employ mechanisms of preferentially regenerative repair during GOLD stage I becomes evident as BEX1 and GHRL increase at this stage while progressively decreasing during further progression of COPD.

Thus, in the COPD AUVA study, the clinical progression of COPD has been successfully correlated with the biological analysis of gene expression in pulmonary tissue. In particular, it has been demonstrated that the expression of the genes KIAA1199, DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and COMP is increased in pulmonary tissue samples from subjects prone to develop progressive COPD, while the expression of the genes TMSB15A, DPP6, SLC51B, NUDT11, PLA1A, HYAL2, CST6, ITGA10, CTHRC1, TAL1, FIBIN, BEX5, BEX1, ESM1 and GHRL is decreased in pulmonary tissue samples from subjects prone to develop progressive COPD, as compared to the expression of the corresponding genes in pulmonary tissue samples from healthy subjects. These molecular biomarkers can thus be used for assessing the susceptibility/proneness of a subject to develop progressive COPD in accordance with the present invention, particularly in the method of the second aspect of the invention. Moreover, it has also been demonstrated that the expression of the genes DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and COMP is increased in pulmonary tissue samples from subjects suffering from or prone to suffer from stable COPD, while the expression of the genes KIAA1199, TMSB15A, DPP6, SLC51B, NUDT11, PLA1A, HYAL2, CST6, ITGA10, CTHRC1, TAL1, FIBIN, BEX5, BEX1, ESM1 and GHRL is decreased in pulmonary tissue samples from subjects suffering from or prone to suffer from stable COPD, as compared to the expression of the corresponding genes in pulmonary tissue samples from healthy subjects, indicating that these biomarkers are suitable for diagnosing stable COPD or assessing the susceptibility of a subject to develop stable COPD in accordance with the invention, particularly in the method of the third aspect of the invention.

REFERENCES

Agarwal P, et al. *J Biol Chem.* 2012; 287(27):22549-59. doi:10.1074/jbc.M111.335935.

Agarwal P, et al. *Matrix Biol.* 2013; 32(6):325-31. doi: 10.1016/j.matbio.2013.02.010.

Avcuoglu S, et al. *Am J Respir Cell Mol Biol.* 2011; 45(4):768-80. doi:10.1165/rcmb.2010-0195OC.

Béchard D, et al. *J Biol Chem.* 2001; 276(51):48341-9.

Bookwalter J E, et al. *Infect Immun.* 2008; 76(1):48-55.

Butt A Q, et al. *J Biol Chem.* 2012; 287(46):38665-79. doi:10.1074/jbc.M112.367490.

Calautti E, et al. *J Cell Biol.* 2002; 156:137-48.

Calvo F, et al. *Nat Cell Biol.* 2011; 13(7):819-26. doi: 10.1038/ncb2271.

Cantarella G, et al. *FASEB J.* 2002; 16(10):1307-9.

Caporali A, et al. *Circ Res.* 2008; 103(2):e15-26. doi: 10.1161/CIRCRESAHA.108.177386.

Chavez-Mulioz C, et al. *J Cell Biochem.* 2012; 113(8):2622-32. doi:10.1002/jcb.24137.

Chen L Y, et al. *J Int Med Res.* 2010; 38(2):498-510.

Chiffiet S, et al. *Exp Cell Res.* 2003; 282(1):1-13.

Cockayne D A, et al. *PLoS One.* 2012; 7(6):e38629. doi: 10.1371/journal.pone.0038629.

Cole S P C, et al. *Monoclonal Antibodies and Cancer Therapy.* 1985; 27:77-96.

De Santis M, et al. *Respir Res.* 2011; 12:22. doi:10.1186/1465-9921-12-22.

Deleuze V, et al. *PLoS One.* 2012; 7(7):e40484. doi:10.1371/journal.pone.0040484.

Diegelmann J, et al. *J Biol Chem.* 2012; 287(1):286-98. doi:10.1074/jbc.M111.294355.

Ding C, et al. *J Biochem Mol Biol.* 2004; 37(1):1-10.

Dubois E, et al. *J Biol Chem.* 2002; 277:23755-63.

Duvoix A, et al. *Thorax.* 2013; 68(7):670-6. doi:10.1136/thoraxjnl-2012-201871.

Evensen N A, et al. *J Natl Cancer Inst.* 2013; 105(18):1402-16. doi:10.1093/jnci/djt224.

Frisch S M, et al. *J Cell Sci.* 2013; 126(Pt1):21-9. doi: 10.1242/jcs.120907.

Gentleman R, et al. *Genome Biology.* 2004; 5:R80.

Green, M R et al. Molecular Cloning: A Laboratory Manual. Cold Spring Harbor Laboratory Press. Fourth Edition. 2012. ISBN: 978-1936113422.

Guillot C, et al. Science. 2013; 340:1185-9.

Halbert R J, et al. Eur Respir J. 2006; 28:523-32.

Han Y, et al. Biochem Biophys Res Commun. 2008; 366(3): 685-91.

Han M K, et al. Am J Respir Crit Care Med. 2010; 182:598-604.

Hannappel E. Ann NY Acad Sci. 2007; 1112:21-37. doi:10.1196/annals.1415.018.

Harlow E, et al. Using Antibodies: A Laboratory Manual. Cold Spring Harbor Laboratory Press. 1998. ISBN: 978-0879695446.

Hamoncourt K, et al. Osterreich Arzteztg. 1982; 37:1640-2.

Hertzog M, et al. Cell. 2004; 117:611-623.

Hogg J C, et al. N Engl J Med. 2004; 350:2645-2653. (a)

Hogg J C. Lancet. 2004; 364:709-721. (b)

Huff T, et al. Int J Biochem Cell Biol. 2001; 33:205-220. doi:10.1016/S1357-2725(00)00087-X.

Hurst J R, et al. N Engl J Med. 2010; 363:1128-1138.

Husson C, et al. Ann NY Acad Sci. 2010; 1194:44-52. doi:10.1111/j.1749-6632.2010.05473.x.

Jerng H H, et al. PLoS One. 2012; 7(6):e38205. doi:10.1371/journal.pone.0038205.

Jiang F, et al. Exp Biol Med (Maywood). 2008; 233(3):286-96. doi:10.3181/0707-RM-177.

Johnson W E, et al. Biostatistics. 2007; 8(1):118-127.

Kaemmerer E, et al. Histopathology. 2012; 60(4):561-9.doi:10.1111/j.1365-2559.2011.04159.x.

Kim N H, et al. J Invest Dermatol. 2010; 130(9):2231-9. doi:10.1038/jid.2010.99.

Klaile E, et al. Respir Res. 2013; 14:85. doi:10.1186/1465-9921-14-85.

Köhler G, et al. Nature. 1975; 256(5517):495-7.

Kong B, et al. Oncogene. 2010; 29(37):5146-58. doi:10.1038/onc.2010.258.

Kothapalli D, et al. J Cell Biol. 2007; 176:535-44.

Kozbor D, et al. Immunol Today. 1983; 4(3):72-9.

Lei W, et al. Am J Physiol Lung Cell Mol Physiol. 2007; 293(5):L1359-68.

Li A, et al. Biochem Biophys Res Commun. 2007; 353(2): 238-43.

Lin L, et al. Nat Commun. 2013; 4:2270. doi:10.1038/ncomms3270.

Malinda K M, et al. J Invest Dermatol. 1999; 113(3):364-8. doi:10.1046/j.1523-1747.1999.00708.x.

Mazzochi C, et al. Am J Physiol Renal Physiol. 2006; 291(6):F1113-22.

Medina A, et al. Mol Cell Biochem. 2007; 305:255-64.

Metzger D E, et al. Dev Biol. 2008; 320(1):149-60. doi:10.1016/j.ydbio.2008.04.038.

Mimae T, et al. Thorax. 2013. doi:10.1136/thoraxjnl-2013-203867.

Muenzner P, et al. J Cell Biol. 2005; 170(5):825-36. doi:10.1083/jcb.200412151

Muenzner P, et al. Science. 2010; 329(5996):1197-201. doi:10.1126/science.1190892.

Murray C J L, et al. Lancet. 1997; 349:1498-504.

Nadin B M, et al. PLoS One. 2013; 8(4):e60831. doi:10.1371/journal.pone.0060831.

Nakahigashi K, et al. J Invest Dermatol. 2011; 131(4):865-73. doi:10.1038/jid.2010.395.

Nishimura T, et al. Cell. 2012; 149(5):1084-97. doi:10.1016/fj.cell.2012.04.021.

Ocaña O H, et al. Cancer Cell. 2012; 22(6):709-24. doi:10.1016/j.ccr.2012.10.012.

Paffett-Lugassy N, et al. Nat Cell Biol. 2013; 15(11):1362-9. doi:10.1038/ncb2862.

Pauwels, R A et al. Am J Respir Crit Care Med. 2001; 163(5):1256-76.

Price D, et al. Prim Care Respir J. 2011; 20(1):15-22. doi:10.4104/pcrj.2010.00060.

Puré E, et al. Cell Signal. 2009; 21(5):651-5. doi:10.1016/j.cellsig.2009.01.024.

Rabe K F, et al. Am J Respir Crit Care Med. 2007; 176(6):532-55.

Rezaeian F, et al. Am J Physiol Heart Circ Physiol. 2012; 302(3):H603-10. doi: 10.1152/ajpheart.00390.2010.

Roudnicky F, et al. Cancer Res. 2013; 73(3):1097-106. doi:10.1158/0008-5472.CAN-12-1855.

Ruiz S, et al. Mol Cell Biol. 2007; 27(23):8127-42.

Shen L, et al. Mol Bio Cell. 2005; 16:3919-36.

Smyth G K. limma: linear models for microarray data. In: Gentleman R, et al. Bioinformatics and Computational Biology Solutions using R and Bioconductor. 2005. Springer, New York, pages 397-420.

Spector I, et al. Am J Pathol. 2013; 182(3):905-16. doi:10.1016/j.ajpath.2012.11.004.

Tao H, et al. Dev Biol. 2012; 364(2):138-48. doi:10.1016/j.ydbio.2012.01.025.

Tian X, et al. Nature. 2013; 499(7458):346-9. doi:10.1038/nature12234.

Toole B P. Nat Rev Cancer. 2004; 4(7):528-39.

US Burden of Disease Collaborators. JAMA. 2013; 310(6): 591-608.

Vestbo J, et al. N Engl J Med. 2011; 365(13):1184-92.

Vestbo J, et al. Am J Respir Crit Care Med. 2013; 187(4): 347-65. doi:10.1164/rccm.201204-0596PP.

Wang L, et al. Peptides. 2012; 33(1):92-100. doi:10.1016/j.peptides.2011.11.001.

Wakahara T, et al. Dev Biol. 2007; 303(2):527-35.

Wedzicha J A. Thorax. 2000; 55:631-632.

Wu Q, et al. Innate Immun. 2012; 18(4):617-26. doi:10.1177/1753425911429837.

Yaniw D, et al. Cell Res. 2005; 15(6):423-9.

Yoshida H, et al. Proc Natl Acad Sci USA. 2013; 110(14): 5612-7. doi:10.1073/pnas.1215432110.

Zeeuwen P L J M, et al. J Invest Dermatol. 2009; 129:1327-38. doi:10.1038/jid.2009.40.

Zeeuwen P L J M, et al. FASEB J. 2010; 24:3744-55. doi:10.1096/fj.10-155879.

Zhang S M, et al. Biotech Histochem. 2012; 87(3):172-8. doi:10.3109/10520295.2011.577754.

The invention claimed is:

1. A method of treating chronic obstructive pulmonary disease (COPD), in a human subject that is prone to develop progressive COPD involving the appearance of irreversible lung damage, the method comprising:
   a) testing a lung tissue sample obtained from the human subject to determine the level of RNA expression of the gene TMSB15A;
   b) comparing the level of RNA expression of TMSB15A in the lung tissue sample from the human subject to a control RNA expression level of TMSB15A in a healthy human subject;
   c) identifying the human subject as being prone to develop progressive COPD based on detecting a decrease in the level of RNA expression of TMSB15A in the lung tissue sample from the subject as compared to the control RNA expression level of TMSB15A; and
   d) administering a drug against COPD to the human subject identified in step c).

2. The method of claim 1, the drug against COPD being bitolterol, carbuterol, fenoterol, pirbuterol, procaterol, reproterol, rimiterol, salbutamol, levosalbutamol, terbutaline, tulobuterol, arformoterol, bambuterol, clenbuterol, formoterol, olodaterol, salmeterol, indacaterol, beclometasone, betamethasone, budesonide, ciclesonide, flunisolide, fluticasone, mometasone, triamcinolone, aclidinium bromide, glycopyrronium bromide, ipratropium bromide, oxitropium bromide, tiotropium bromide, cromoglicate, nedocromil, acefylline, ambuphylline, bamifylline, doxofylline, enprofylline, etamiphylline, proxyphylline, theobromine, theophylline, aminophylline, choline theophyllinate, montelukast, pranlukast, zafirlukast, zileuton, ramatroban, seratrodast, ibudilast, roflumilast, amlexanox, eprozinol, fenspiride, omalizumab, epinephrine, hexoprenaline, isoprenaline, isoproterenol, orciprenaline, metaproterenol, atropine, or a pharmaceutically acceptable salt of any of the aforementioned agents, or any combination thereof.

3. The method of claim 1, the drug against COPD being roflumilast.

4. A method of treating or preventing chronic obstructive pulmonary disease (COPD), the method comprising administering a drug against COPD to a human subject that has been identified as suffering from stable COPD or as being prone to suffer from stable COPD, the method comprising the steps of:
   a) testing a human lung tissue sample obtained from the human subject to determine the level of RNA expression of the gene TMSB15A;
   b) comparing the level of RNA expression of TMSB15A in the lung tissue sample from the human subject to a control RNA expression level of TMSB15A in a healthy human subject, a decrease in the level of RNA expression of TMSB15A in the lung tissue sample from the human subject as compared to the control RNA expression level of TMSB15A being indicative of stable COPD or a proneness to stable COPD;
   c) identifying the human subject as suffering from stable COPD or as being prone to suffer from stable COPD based on detecting a decrease in the level of RNA expression of TMSB15A in the lung tissue sample from the human subject as compared to the control RNA expression level of TMSB15A; and
   d) administering a drug against COPD to the subject identified in step c).

5. The method of claim 4, the drug against COPD being bitolterol, carbuterol, fenoterol, pirbuterol, procaterol, reproterol, rimiterol, salbutamol, levosalbutamol, terbutaline, tulobuterol, arformoterol, bambuterol, clenbuterol, formoterol, olodaterol, salmeterol, indacaterol, beclometasone, betamethasone, budesonide, ciclesonide, flunisolide, fluticasone, mometasone, triamcinolone, aclidinium bromide, glycopyrronium bromide, ipratropium bromide, oxitropium bromide, tiotropium bromide, cromoglicate, nedocromil, acefylline, ambuphylline, bamifylline, doxofylline, enprofylline, etamiphylline, proxyphylline, theobromine, theophylline, aminophylline, choline theophyllinate, montelukast, pranlukast, zafirlukast, zileuton, ramatroban, seratrodast, ibudilast, roflumilast, amlexanox, eprozinol, fenspiride, omalizumab, epinephrine, hexoprenaline, isoprenaline, isoproterenol, orciprenaline, metaproterenol, atropine, or a pharmaceutically acceptable salt of any of the aforementioned agents, or any combination thereof.

6. The method of claim 1, further comprising:
   a) testing the level of RNA expression of one or more of DMBT1, KIAA1199, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 or GHRL in the lung tissue sample obtained from the human subject;
   b) comparing the level of RNA expression of the one or more genes tested in step a) to a control RNA expression level of the one or more genes in a healthy human subject; and
   c) an increase in the level of RNA expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the lung tissue sample from the human subject as compared to the control RNA expression level of the one or more gene(s) is indicative of a proneness to develop progressive COPD, and
   d) a decrease in the level of RNA expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the lung tissue sample from the human subject as compared to the control RNA expression level of the one or more gene(s) is indicative of a proneness to develop progressive COPD.

7. The method of claim 6, comprising testing the lung tissue sample of the human subject to determine the level of RNA expression of DMBT1 and KIAA1199.

8. The method of claim 6, comprising testing the human lung tissue sample to determine the level of RNA expression of DMBT1, KIAA1199 and at least one of FGG, CYP1A1, CEACAM5, CTHRC1, NTRK2, RASGRF2, ELF5, AZGP1, PRRX1, AQP3, SFN, GPR110, GDF15, RASGRF2, RND1, DPP6, SLC51B or NUDT11.

9. The method of claim 6, comprising testing the human lung tissue sample to determine that the human subject is prone to develop progressive COPD involving the appearance of irreversible lung damage if the level of RNA expression of a majority of the number of genes tested is altered in the sense that (i) the level of RNA expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the lung tissue sample from the human subject is increased as compared to the control RNA expression level of the one or more gene(s) and (ii) the level of RNA expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the lung tissue sample from the human subject is decreased as compared to the control RNA expression level of the one or more gene(s).

10. The method of claim 6, comprising testing the human lung tissue sample to determine that the human subject is prone to develop progressive COPD involving the appearance of irreversible lung damage if the level of RNA expression of a majority of the number of genes tested is altered in the sense that (i) the level of RNA expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the lung tissue sample from the human subject is at least 3-fold increased as compared to the control RNA expression level of the one or more gene(s) and (ii) the level of RNA expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the lung tissue sample from the human subject is at least 3-fold decreased as compared to the control RNA expression level of the one or more gene(s).

11. The method of claim 6, comprising testing the human lung tissue sample to determine that the human subject is prone to develop progressive COPD involving the appearance of irreversible lung damage if the level of RNA expression of at least 70% of the number of genes tested is altered in the sense that (i) the level of RNA expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the lung tissue sample from the human subject is increased as compared to the control RNA expression level of the one or more gene(s) and (ii) the level of RNA expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the lung tissue sample from the human subject is decreased as compared to the control RNA expression level of the one or more gene(s).

12. The method of claim 6, comprising testing the human lung tissue sample to determine that the human subject is prone to develop progressive COPD involving the appearance of irreversible lung damage if the level of RNA expression of at least 70% of the number of genes tested is altered in the sense that (i) the level of RNA expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the lung tissue sample from the human subject is at least 3-fold increased as compared to the control RNA expression level of the one or more gene(s) and (ii) the level of RNA expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the lung tissue sample from the human subject is at least 3-fold decreased as compared to the control RNA expression level of the one or more gene(s).

13. The method of claim 1, the tested human lung tissue sample being a transbronchial lung biopsy lung tissue sample or a bronchoalveolar lavage lung tissue sample.

14. The method of claim 1, the level of RNA expression being determined using a quantitative reverse transcriptase polymerase chain reaction or a microarray.

15. The method of claim 4, comprising:
a) testing the human lung tissue sample to determine the level of RNA expression of one or more of DMBT1, KIAA1199, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1, or GHRL in the lung tissue sample obtained from the human subject;
b) comparing the level of RNA expression of the one or more genes to a control RNA expression level of the one or more gene(s) in a healthy human subject; and
c) testing the human lung tissue sample to determine an increase in the level of RNA expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the lung tissue sample from the human subject as compared to the control RNA expression level of the one or more gene(s) being indicative of stable COPD or a proneness to stable COPD, and
d) a decrease in the level of RNA expression of TMSB15A, KIAA1199, DPP6, SLC51B, NUDT11, PLA1A, HYAL2, CST6, ITGA10, CTHRC1, TAL1, FIBIN, BEX5, BEX1, ESM1 and/or GHRL in the lung tissue sample from the human subject as compared to the control RNA expression level of the one or more gene(s) being indicative of stable COPD or a proneness to stable COPD.

16. The method of claim 15, comprising testing the human lung tissue sample to determine if the human subject suffers from stable COPD or is prone to suffer from stable COPD if the level of RNA expression of a majority of the number of genes tested is altered in the sense that (i) the level of RNA expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the lung tissue sample from the human subject is increased as compared to the control RNA expression level of the gene or genes so tested and (ii) the level of RNA expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the lung tissue sample from the human subject is decreased as compared to the control RNA expression level of the gene or genes tested.

17. The method of claim 15, comprising testing the human lung tissue sample to determine if the human subject suffers from stable COPD or is prone to suffer from stable COPD if the level of RNA expression of at least 70% of the number of genes tested is altered in the sense that (i) the level of RNA expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the lung tissue sample from the human subject is at least 3-fold increased as compared to the control RNA expression level of the gene or genes tested and (ii) the level of RNA expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the lung tissue sample from the human subject is at least 3-fold decreased as compared to the control RNA expression level of the one or more genes tested.

18. The method of claim 4, the lung tissue sample obtained from the human subject being a transbronchial lung biopsy lung tissue sample or a bronchoalveolar lavage lung tissue sample.

19. The method of claim 4, the level of RNA expression being determined using a quantitative reverse transcriptase polymerase chain reaction or a microarray.

\* \* \* \* \*